US012729208B2

(12) United States Patent
Cosford et al.

(10) Patent No.: US 12,729,208 B2
(45) Date of Patent: Sep. 8, 2026

(54) INHIBITOR OF APOPTOSIS (IAP) PROTEIN ANTAGONISTS

(71) Applicant: Sanford Burnham Prebys Medical Discovery Institute, La Jolla, CA (US)

(72) Inventors: Nicholas David Peter Cosford, San Diego, CA (US); Dominik Heimann, Hamm (DE); Peter Teriete, San Diego, CA (US); Sumit Kumar Chanda, La Jolla, CA (US); Lars Pache, San Diego, CA (US); Laurent Jean Stephane De Backer, San Diego, CA (US); Nicole Bata, San Diego, CA (US); Mitchell D. Vamos, Batavia, OH (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 736 days.

(21) Appl. No.: 17/997,461

(22) PCT Filed: Apr. 29, 2021

(86) PCT No.: PCT/US2021/029957
§ 371 (c)(1),
(2) Date: Oct. 28, 2022

(87) PCT Pub. No.: WO2021/222614
PCT Pub. Date: Nov. 4, 2021

(65) Prior Publication Data

US 2023/0295181 A1 Sep. 21, 2023

Related U.S. Application Data

(60) Provisional application No. 63/018,464, filed on Apr. 30, 2020.

(51) Int. Cl.

| | |
|---|---|
| ***C07D 498/04*** | (2006.01) |
| ***A61P 35/00*** | (2006.01) |
| ***C07D 487/04*** | (2006.01) |
| ***C07D 487/22*** | (2006.01) |
| ***C07D 513/04*** | (2006.01) |

(52) U.S. Cl.
CPC ............ *C07D 498/04* (2013.01); *A61P 35/00* (2018.01); *C07D 487/04* (2013.01); *C07D 487/22* (2013.01); *C07D 513/04* (2013.01)

(58) Field of Classification Search
CPC .................................................... C07D 498/04
See application file for complete search history.

(56) References Cited

U.S. PATENT DOCUMENTS

| | | | |
|---|---|---|---|
| 4,107,288 A | 8/1978 | Oppenheim et al. | |
| 5,145,684 A | 9/1992 | Liversidge et al. | |
| 5,455,242 A | 10/1995 | Warshawsky et al. | |
| 5,457,196 A | 10/1995 | Warshawsky et al. | |
| 5,508,272 A | 4/1996 | Robl | |
| 5,635,502 A | 6/1997 | Flynn | |
| 7,244,851 B2 | 7/2007 | Cohen et al. | |
| 7,309,792 B2 | 12/2007 | Harran et al. | |
| 7,345,081 B2 | 3/2008 | Cohen et al. | |
| 7,419,975 B2 | 9/2008 | Palermo et al. | |
| 7,456,209 B2 | 11/2008 | Condon et al. | |
| 7,517,906 B2 | 4/2009 | Condon et al. | |
| 7,547,724 B2 | 6/2009 | Laurent et al. | |
| 7,674,787 B2 | 3/2010 | Wang et al. | |
| 9,546,174 B2 * | 1/2017 | Cosford | A61P 25/00 |
| 10,047,119 B2 * | 8/2018 | Cosford | A61P 13/12 |
| 10,300,074 B2 * | 5/2019 | Pache | A61K 31/18 |
| 10,544,188 B2 * | 1/2020 | Cosford | C07K 5/0806 |
| 10,864,217 B2 * | 12/2020 | Pache | A61K 31/167 |
| 11,111,270 B2 * | 9/2021 | Cosford | A61P 1/16 |
| 11,912,786 B2 * | 2/2024 | Cosford | A61P 35/00 |
| 2008/0132485 A1 | 6/2008 | Wang et al. | |
| 2008/0269140 A1 | 10/2008 | Wang et al. | |
| 2009/0010941 A1 | 1/2009 | Stevenson et al. | |
| 2009/0123480 A1 | 5/2009 | Wang et al. | |
| 2010/0048545 A1 | 2/2010 | Jette et al. | |
| 2010/0190688 A1 | 7/2010 | Chao et al. | |
| 2010/0273812 A1 | 10/2010 | Wang et al. | |
| 2011/0046189 A1 | 2/2011 | Wang et al. | |
| 2014/0057924 A1 | 2/2014 | Wang et al. | |
| 2017/0081362 A1 | 3/2017 | Cosford et al. | |
| 2020/0299309 A1 | 9/2020 | Dunham et al. | |
| 2022/0119444 A1 | 4/2022 | Cosford et al. | |

(Continued)

FOREIGN PATENT DOCUMENTS

| | | |
|---|---|---|
| EP | 0629627 A2 | 12/1994 |
| JP | 2003519629 A | 6/2003 |

(Continued)

OTHER PUBLICATIONS

Darren et.al. (Mol Cancer Ther; 13(1) Jan. 2014, p. 5-15) (Year: 2014).*
Badley et al. Altering cell death pathways as an approach to cure HIV infection. Cell Death Dis 4:e718 (2013).
Baldwin et al. Synthesis of potential β-turn bicyclic dipeptide mimetics.J Chem Soc Chem Commun 9:935-936 (1993).
Bosque et al. Induction of HIV-1 latency and reactivation in primary memory CD4+ T cells. Blood 113:58-65 (2009).
Cai et al. A potent and orally active antagonist (SM-406/AT-406) of multiple inhibitor of apoptosis proteins (IAPs) in clinical development for cancer treatment. J Med Chem 54(8):2714-2726 (2011).
Chiou et al. Highly efficient synthesis of azabicyclo[x.y.0]alkane amino acids and congeners by means of Rh-catalyzed cyclohydrocarbonylation. J Org Chem 72(6):1871-1882 (2007).
Claridge et al. Synthesis and analysis of Leu-enkephalin analogues containing reverse turn peptidomimetics. Bioorg Med Chem Lett 6(4):485-490 (1996).

(Continued)

*Primary Examiner* — John S Kenyon
*Assistant Examiner* — Rehana Ismail
(74) *Attorney, Agent, or Firm* — WILSON SONSINI GOODRICH & ROSATI

(57) ABSTRACT

Provided herein are compounds that modulate the activity of melanoma inhibitor of apoptosis (ML-IAP) protein, compositions comprising the compounds, and methods of using the compounds and compositions comprising the compounds.

22 Claims, 3 Drawing Sheets

(56) References Cited

U.S. PATENT DOCUMENTS

| | | | |
|---|---|---|---|
| 2023/0115837 | A1 | 4/2023 | Cosford et al. |
| 2025/0129099 | A1 | 4/2025 | Cosford et al. |

FOREIGN PATENT DOCUMENTS

| | | | |
|---|---|---|---|
| JP | 2007522116 | A | 8/2007 |
| JP | 2008505976 | A | 2/2008 |
| JP | 2008545780 | A | 12/2008 |
| JP | 2010523722 | A | 7/2010 |
| JP | 2011516581 | A | 5/2011 |
| JP | 2012529482 | A | 11/2012 |
| JP | 2013509429 | A | 3/2013 |
| JP | 2013516422 | A | 5/2013 |
| WO | WO-2004007529 | A2 | 1/2004 |
| WO | WO-2006017295 | A2 | 2/2006 |
| WO | WO-2006069063 | A1 | 6/2006 |
| WO | WO-2007041775 | A1 | 4/2007 |
| WO | WO-2007101347 | A1 | 9/2007 |
| WO | WO-2007130626 | A2 | 11/2007 |
| WO | WO-2008073305 | A1 | 6/2008 |
| WO | WO-2008128121 | A1 | 10/2008 |
| WO | WO-2008128171 | A2 | 10/2008 |
| WO | WO-2008134679 | A1 | 11/2008 |
| WO | WO-2008148202 | A1 | 12/2008 |
| WO | WO-2009060292 | A2 | 5/2009 |
| WO | WO-2009126947 | A2 | 10/2009 |
| WO | WO-2010031735 | A1 | 3/2010 |
| WO | WO-2010120476 | A2 | 10/2010 |
| WO | WO-2010142994 | A1 | 12/2010 |
| WO | WO-2011059763 | A2 | 5/2011 |
| WO | WO-2011067306 | A1 | 6/2011 |
| WO | WO-2011094150 | A1 | 8/2011 |
| WO | WO-2012125622 | A1 | 9/2012 |
| WO | WO-2013182662 | A1 | 12/2013 |
| WO | WO-2014085489 | A1 | 6/2014 |
| WO | WO-2015187998 | A2 | 12/2015 |
| WO | WO-2017143059 | A1 | 8/2017 |
| WO | WO-2020110056 | A1 | 6/2020 |
| WO | WO-2021092500 | A1 | 5/2021 |
| WO | WO-2021222614 | A1 | 11/2021 |
| WO | WO-2023081290 | A1 | 5/2023 |

OTHER PUBLICATIONS

Cohen et al. Antagonists of inhibitor of apoptosis proteins based on thiazole amide isosteres. Bioorg Med Chem Lett. 20(7):2229-2233 (2010).
Cohen et al. Orally bioavailable antagonists of inhibitor of apoptosis proteins based on an azabicyclooctane scaffold. J Med Chem 52(6):1723-1730 (2009).
Cornille et al. Electrochemical Cyclization of Dipeptides toward Novel Bicyclic, Reverse-Turn Peptidomimetics. 1. Synthesis and Conformational Analysis of 7,5-Bicyclic Systems. J Am Chem Soc 117(3):909-917 (1995).
Database Registry 2009 RN 1177797-11-3. Retrieved from STN International on Sep. 20, 2017 (1 pg.).
Finlay et al. Small-molecule IAP antagonists sensitize cancer cells to TRAIL-induced apoptosis: roles of XIAP and cIAPs. Mol Cancer Ther 13(1):5-15 (2014).
Flygare et al. Small-molecule pan-IAP antagonists: a patent review. Expert Opinion on Therapeutic Patents 20(2):251-267 (2010).
Gilley et al. New entry to convertible isocyanides for the Ugi reaction and its application to the stereo-controlled formal total synthesis of the proteasome inhibitor omuralide. J. Org. Lett. 9:3631-3634 (2007).
Gonzalez-Lopez et al. Design, synthesis and evaluation of monovalent Smac mimetics that bind to the BIR2 domain of the anti-apoptotic protein XIAP. Bioorg Med Chem Lett 21(14):4332-4336 (2011).
Griesbaum et al. Difunctional and heterocyclic products from the ozonolysis of conjugated C5-C8-cyclodienes. J Org Chem 55:6024-6027 (1990).
Huang et al. Fragment-based design of small molecule X-linked inhibitor of apoptosis protein inhibitors. J Med Chem 51(22):7111-7118 (2008).
Hyvl et al. Copper-Catalyzed Activation of Disulfides as a Key Step in the Synthesis of Benzothiazole Moieties. Eur. J. Org. Chem. 15:2849-2851 (2010).
Konig et al. Global analysis of host-pathogen interactions that regulate early-stage HIV-1 replication. Cell 135:49-60 (2008).
Li et al. A small molecule Smac mimic potentiates TRAIL- and TNFalpha-mediated cell death. Science 305(5689):1471-1474 (2004).
Ling et al. Theoretical studies on the interactions of XIAP-BIR3 domain with bicyclic and tricyclic core monovalent Smac mimetics. J Mol Graph Model 29(3):354-362 (2010).
Lu et al., SM-164: A novel, bivalent Smac mimetic that induces apoptosis and tumor regression by concurrent removal of the blockade of cIAP-1/2 and XIAP. Cancer Research 68(22):9384-9393 (2008).
Monfardini et al. Screening multicomponent reactions for X-linked inhibitor of apoptosis-baculoviral inhibitor of apoptosis protein repeats domain binder. J Med Chem 54(3):890-900 (2011).
Ndubaku et al. Antagonism of c-IAP and XIAP proteins is required for efficient induction of cell death by small-molecule IAP antagonists. ACS Chem Biol 4(7):577-566 (2009).
Nikolovska-Coleska et al. Development and optimization of a binding assay for the XIAP BIR3 domain using fluorescence polarization. Anal Biochem 332(2):261-273 (2004).
O'Doherty et al. A sensitive, quantitative assay for human immunodeficiency virus type 1 integration. J Virol 76:10942-10950 (2002).
Oost et al. Discovery of potent antagonists of the antiapoptotic protein XIAP for the treatment of cancer. J Med Chem 47(18):4417-4426 (2004).
Orzaez et al. Characterization of dequalinium as a XIAP antagonist that targets the BIR2 domain. Apoptosis 16(5):460-467 (2011).
Park et al. Non-peptidic small molecule inhibitors of XIAP. Bioorg Med Chem Lett. 15(3):771-775 (2005).
PCT/US2013/072064 International Search Report and Written Opinion dated Mar. 31, 2014.
PCT/US2020/059552 International Search Report and Written Opinion dated Feb. 12, 2021.
PCT/US2021/029957 International Search Report and Written Opinion dated Jun. 18, 2021.
Peng et al. Design and synthesis of a 1,5-diazabicyclo[6,3,0] dodecane amino acid derivative as a novel dipeptide reverse-turn mimetic. Tetrahedron Letters 47(27):4769-4770 (2006).
Peng et al. Potent, orally bioavailable diazabicyclic small-molecule mimetics of second mitochondria-derived activator of caspases. J Med Chem 51(24):8158-8162 (2008).
Robl et al. Dual metalloprotease inhibitors: mercaptoacetyl-based fused heterocyclic dipeptide mimetics as inhibitors of angiotensin-converting enzyme and neutral endopeptidase. J Med Chem 40(11):1570-1577 (1997).
Seneci et al. Rational design, synthesis and characterization of potent, non-peptidic Smac mimics/XIAP inhibitors as proapoptotic agents for cancer therapy. Bioorg Med Chem 17(16):5834-5856 (2009).
Slomczynska et al. Electrochemical Cyclization of Dipeptides to Form Novel Bicyclic, Reverse-Turn Peptidomimetics. 2. Synthesis and Conformational Analysis of 6,5-Bicyclic Systems. J Org Chem 61:1198-1204 (1996).
Stoszko et al., A broad drug arsenal to attack a strenuous latent HIV reservoir. Curr Opin Virol. 38:37-53 (2019).
Sun et al. Building functionalized peptidomimetics: use of electroauxiliaries for introducing N-acyliminium ions into peptides. J Am Chem Soc 128(42):13761-13771 (2006).
Sun et al. Cyclopeptide Smac mimetics as antagonists of IAP proteins. Bioorg Med Chem Lett 20(10):3043-3046 (2010).
Sun et al. Design, Synthesis and Characterization of a Potent, Non-Peptide, Cell-Permeable, Bivalent Smac Mimetic that Concurrently Targets both the BIR2 and BIR3 Domains in XIAP. J Am Chem Soc 129(49):15279-15294 (2007).

(56) References Cited

OTHER PUBLICATIONS

Sun et al. Design, synthesis, and evaluation of potent, nonpeptidic mimetics of second mitochondria-derived activator of caspases. J Med Chem 52(3):593-596 (2009).
Sun et al., Potent and Selective Small-Molecule Inhibitors of cIAP1/2 Proteins Reveal That the Binding of Smac Mimetics to XIAP BIR3 Is Not Required for Their Effective Induction of Cell Death in Tumor Cells. ACS Chem. Biol. 9(4): 994-1002 (2014).
Sun et al., Potent Bivalent Smac Mimetics: Effect of the Linker on binding to Inhibitor of Apoptosis Proteins (IAPs) and Anticancer Activity. J Med Chem 54(9):3306-3318 (2011).
Sun et al. Structure-based design, synthesis, evaluation, and crystallographic studies of conformationally constrained Smac mimetics as inhibitors of the X-linked inhibitor of apoptosis protein (XIAP). J Med Chem 51(22):7169-7180 (2008).
Swingler et al. Apoptotic killing of HIV-1-infected macrophages is subverted by the viral envelope glycoprotein. PLoS Pathog 3(9):1281-1290 (2007).
Ueda et al. Efficient entry into 2-substituted tetrahydroquinoline systems through alkylative ring expansion: stereoselective formal synthesis of (+/−)-martinellic acid. J Org Chem 75:914-921 (2010).
U.S. Appl. No. 14/648,435 Office Action dated Feb. 4, 2016.
U.S. Appl. No. 14/648,435 Office Action dated May 23, 2016.
U.S. Appl. No. 15/363,935 Office Action dated Aug. 16, 2017.
U.S. Appl. No. 15/363,935 Office Action dated Dec. 12, 2017.
U.S. Appl. No. 16/031,837 Office Action dated Jul. 8, 2019.
U.S. Appl. No. 16/031,837 Office Action dated Mar. 14, 2019.
U.S. Appl. No. 16/740,240 Office Action dated Jan. 28, 2021.
Vamos et al. Expedient synthesis of highly potent antagonists of inhibitor of apoptosis proteins (IAPs) with unique selectivity for ML-IAP. ACS Chem Biol 8(4):725-732 (2013).
Wang. Design of small-molecule Smac mimetics as IAP antagonists. Curr Top Microbiol Immunol. 348:89-113 (2011).
Yang et al. Importance of Ligand Reorganization Free Energy in Protein-Ligand Binding-Affinity Prediction. J Am Chem Soc 131(38):13709-13721 (2009).
Zbieg et al., Amplification of anti-diastereoselectivity via Curtin-Hammett effects in ruthenium-catalyzed hydrohydroxyalkylation of 1,1-disubstituted allenes: diastereoselective formation of all-carbon quaternary centers. J Am. Chem. Soc. 133(4):1141-1144 (2011).
Zhang et al. A convenient and versatile synthesis of 6,5- and 7,5-fused bicyclic lactams as peptidomimetics. Tetrahedron Letters 42(30):4943-4945 (2001).
Zhang et al. Design, synthesis, and evaluation of tricyclic, conformationally constrained small-molecule mimetics of second mitochondria-derived activator of caspases. J Med Chem 51(23)7352-7355 (2008).
Zobel et al. Design, synthesis, and biological activity of a potent Smac mimetic that sensitizes cancer cells to apoptosis by antagonizing IAPs. ACS Chem Biol. 1(8):525-533 (2006).
Caron, et al. Preparation and utility of trihaloethyl imidates: useful reagents for the synthesis of amidines. J Org Chem 75(3):945-947 (2010).
U.S. Appl. No. 17/389,171 Office Action dated Jun. 23, 2023.
U.S. Appl. No. 17/773,749 Office Action dated Apr. 21, 2025.
Cetraro, Pierina et al. A Review of the Current Impact of Inhibitors of Apoptosis Proteins and Their Repression in Cancer. Cancers 14(7):1671, 1-25 (2022).
Thornber, C.W. Isosterism and molecular modification in drug design. Chemical Society Reviews 8(4):563-580 (1979).
U.S. Appl. No. 17/773,749 Office Action dated Sep. 17, 2025.

* cited by examiner

INHIBITOR OF APOPTOSIS (IAP) PROTEIN ANTAGONISTS

CROSS-REFERENCE TO RELATED APPLICATION

This application is the U.S. National Stage Patent Application of International Application No. PCT/US2021/029957, filed on Apr. 29, 2021; which claims the benefit of U.S. Provisional Patent Application No. 63/018,464, filed Apr. 30, 2020, all of which are incorporated by reference herein in their entirety.

STATEMENT AS TO FEDERALLY SPONSORED RESEARCH

This invention was made with government support under R01CA195227 and R01AI124843 awarded by the National Institutes of Health. The government has certain rights in the invention.

SUMMARY OF THE INVENTION

Described herein are compounds that modulate the activity of certain proteins involved in apoptotic pathways, or signaling pathways associated with inflammation and/or autoimmune diseases and/or cell division and/or angiogenesis. In some embodiments, the compounds described herein are antagonists of inhibitor of apoptosis (IAP) proteins. In some embodiments, the compounds described herein are antagonists of melanoma inhibitor of apoptosis protein (ML-IAP). In some embodiments, the compounds described herein are selective ML-IAP antagonists. In some embodiments, the compounds described herein are useful for the treatment of certain types of cancers as described herein. In some embodiments, the compounds, pharmaceutical compositions, and methods described herein are effective in the treatment of lung cancer. In some embodiments, the compounds, compositions, and methods described herein are effective in the treatment of chemo-resistant cancers.

In some embodiments, the compounds described herein are pan-IAP antagonists. In some embodiments, the compounds described herein are useful for the treatment of cancer, inflammatory diseases, and/or autoimmune diseases as described herein.

In one aspect, provided herein are compounds having the structure of Formula (A-I), or a pharmaceutically acceptable salt, N-oxide, solvate, diastereomeric mixture, or individual enantiomers, or stereoisomer thereof:

Formula (A-I)

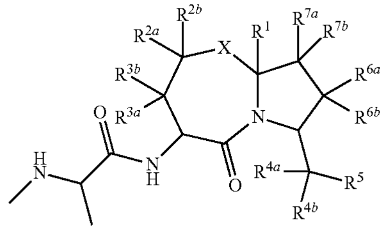

wherein, $R^1$ is hydrogen, $C_1$-$C_6$alkyl, $C_3$-$C_6$cycloalkyl, $C_1$-$C_6$alkyl-($C_3$-$C_6$cycloalkyl), $C_1$-$C_6$alkyl-(phenyl), or $C_1$-$C_6$alkyl-(5- to 6-membered heteroaryl); wherein the $C_1$-$C_6$alkyl, $C_3$-$C_6$cycloalkyl, phenyl, or 5- to 6-membered heteroaryl is optionally substituted with 1, 2, or 3 $R^9$;

X is $NR^4$, O, S, S(O), or $S(O)_2$;

$R^4$ is hydrogen, $C_1$-$C_6$alkyl, C(O)—($C_1$-$C_6$alkyl), C(O)—($C_3$-$C_6$cycloalkyl), C(O)-(phenyl), or C(O)-(5- to 6-membered heteroaryl); wherein each $C_1$-$C_6$alkyl, $C_3$-$C_6$cycloalkyl, phenyl, or 5- to 6-membered heteroaryl is optionally substituted with 1, 2, or 3 $R^9$;

or X is C and taken together with $R^{2a}$, $R^{2b}$, and the carbon atom to which they are attached, forms a phenyl or 5- to 10-membered heteroaryl ring, optionally substituted with 1, 2, or 3 $R^9$;

$R^{2a}$, $R^{2b}$, $R^{3a}$, and $R^{3b}$ are each independently hydrogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, or $C_2$-$C_6$alkynyl is optionally substituted with 1 or 2 $C_3$-$C_{10}$cycloalkyl, 3- to 10-membered heterocycloalkyl, $C_6$-$C_{10}$aryl, or 5- to 10-membered heteroaryl rings; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{2a}$ and $R^{2b}$ together with the carbon atom to which they are attached form a carbonyl;

or $R^{2a}$ and $R^{3a}$, and optionally $R^{2b}$ and $R^{3b}$, together with the carbon atoms to which they are attached form a $C_3$-$C_6$cycloalkyl, 5- to 10-membered heterocycloalkyl, $C_6$-$C_{10}$aryl, or 5- to 10-membered heteroaryl ring; wherein each $C_3$-$C_6$cycloalkyl, 5- to 10-membered heterocycloalkyl, $C_6$-$C_{10}$aryl, or 5- to 10-membered heteroaryl ring is optionally substituted with 1, 2, or 3 $R^9$;

$R^{4a}$ and $R^{4b}$ are each independently hydrogen, halogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, or $C_2$-$C_6$alkynyl is optionally substituted with 1 or 2 $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{4a}$ and $R^{4b}$ together with the carbon atom to which they are attached form a carbonyl;

or $R^{4a}$ and $R^{4b}$ together with the carbon atom to which they are attached form a $C_3$-$C_{10}$cycloalkyl or 3- to 10-membered heterocycloalkyl ring; wherein the $C_3$-$C_{10}$cycloalkyl or 3- to 10-membered heterocycloalkyl ring is optionally substituted with 1, 2, or 3 $R^9$;

$R^5$ is $NHR^8$, $NHS(O)_2R^8$, $OR^8$, $SR^8$, $S(O)_2R^8$, or $S(O)_2NHR^8$;

or $R^5$, $R^{4a}$, and $R^{4b}$, together with the carbon atom to which they are attached, form a $C_6$-$C_{10}$aryl or 5- to 10-membered heteroaryl ring; wherein the $C_6$-$C_{10}$aryl or 5- to 10-membered heteroaryl ring is optionally substituted with 1, 2, or 3 $R^9$;

$R^{6a}$ is hydrogen, halogen, —U, or -G;

$R^{6b}$ is halogen, —U, or -G;

—U is $C_1$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl; wherein each $C_1$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl is optionally substituted with 1, 2, or 3 $R^9$ and/or 1 or 2-G;

-G is $C_3$-$C_{10}$cycloalkyl, 3- to 10-membered heterocycloalkyl, $C_6$-$C_{10}$aryl, or 5- to 10-membered heteroaryl; wherein each $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{6a}$ and $R^{6b}$ together with the carbon atom to which they are attached form a saturated or partially saturated 3- to 7-membered cycloalkyl or a saturated or partially saturated 3- to 7-membered heterocycloalkyl; wherein the cycloalkyl or heterocycloalkyl is optionally substituted with 1, 2, or 3 $R^9$;

$R^{7a}$ is hydrogen, halogen, $C_1$-$C_4$alkyl, or $C_1$-$C_4$haloalkyl;

$R^{7b}$ is hydrogen, halogen, $C_1$-$C_4$alkyl, or $C_1$-$C_4$haloalkyl;

or $R^{7a}$ and $R^{7b}$ together with the carbon atom to which they are attached form a saturated or partially saturated 3- to 7-membered cycloalkyl or a saturated or partially saturated 3- to 7-membered heterocycloalkyl; wherein the cycloalkyl or heterocycloalkyl is optionally substituted with 1, 2, or 3 $R^9$;

or $R^{6b}$ and $R^{7b}$ together with the carbon atoms to which they are attached form a $C_3$-$C_{10}$cycloalkyl or 3- to 10-membered heterocycloalkyl ring; wherein each $C_3$-$C_{10}$cycloalkyl or 3- to 10-membered heterocycloalkyl ring is optionally substituted with 1, 2, or 3 $R^9$;

or $R^{6a}$, $R^{6b}$, $R^{7a}$, and $R^{7b}$ together with the carbon atoms to which they are attached form a 5- to 10-membered heteroaryl ring optionally substituted with 1, 2, or 3 $R^9$;

$R^8$ is Z, $C_2$-$C_6$alkyl, ($C_1$-$C_6$alkylene)-Z, ($C_1$-$C_6$heteroalkylene)-Z, ($C_2$-$C_6$alkenylene)-Z, $CH(Z)_2$, $CH_2CH(Z)_2$, CH($C_1$-$C_6$alkyl)Z, or C(O)Z; wherein each alkyl, alkylene, heteroalkylene, or alkenylene is optionally substituted with 1, 2, or 3 $R^9$;

Z is $C_3$-$C_{10}$cycloalkyl, 3- to 10-membered heterocycloalkyl, $C_6$-$C_{10}$aryl, or 5- to 10-membered heteroaryl; wherein each $C_3$-$C_{10}$cycloalkyl, 3- to 10-membered heterocycloalkyl, $C_6$-$C_{10}$aryl, and 5- to 10-membered heteroaryl is optionally substituted with 1, 2, or 3 $R^9$;

each $R^9$ is independently halogen, $C_1$-$C_4$alkyl, $C_2$-$C_4$alkenyl, $C_2$-$C_4$alkynyl, $C_1$-$C_4$haloalkyl, $C_1$-$C_4$alkoxy, $C_1$-$C_4$haloalkoxy, $C_1$-$C_4$heteroalkyl, —C(O)H, —C(O)OH, —CN, $C_3$-$C_{10}$cycloalkyl, 3- to 10-membered heterocycloalkyl, $C_6$-$C_{10}$aryl, 5- to 10-membered heteroaryl, —C(O)($C_1$-$C_4$alkyl), —C(O)O($C_1$-$C_4$alkyl), —C(O)$NH_2$, —C(O)NH($C_1$-$C_4$alkyl), —C(O)N($C_1$-$C_4$alkyl)$_2$, —$NH_2$, —NH($C_1$-$C_4$alkyl), —N($C_1$-$C_4$alkyl)$_2$, —NH($C_2$-$C_4$alkylene)-OH, —NH($C_2$-$C_4$alkylene)-O—($C_1$-$C_4$alkyl), —OH, —O($C_1$-$C_4$alkyl), —O($C_1$-$C_4$haloalkyl), —O($C_2$-$C_4$alkylene)-$NH_2$, —O($C_2$-$C_4$alkylene)-NH—($C_1$-$C_4$alkyl), —O($C_2$-$C_4$alkylene)-N—($C_1$-$C_4$alkyl)$_2$, —O($C_1$-$C_4$alkylene)-C(O)OH, —O($C_1$-$C_4$alkylene)-C(O)O—($C_1$-$C_4$alkyl), —O($C_2$-$C_4$alkenyl), —O($C_1$-$C_4$alkylene)-($C_6$-$C_{10}$aryl), —O($C_1$-$C_4$alkylene)-(5- to 10-membered heteroaryl), —O($C_6$-$C_{10}$aryl), —SH, $S(O)_2OH$, —$S(O)_2$($C_1$-$C_4$alkyl), —$S(O)_2NH_2$, —$S(O)_2$NH($C_1$-$C_4$alkyl), or —$S(O)_2$N($C_1$-$C_4$alkyl)$_2$;

or two $R^9$ together with the atoms to which they are attached form a $C_3$-$C_{10}$cycloalkyl or a 3- to 10-membered heterocycloalkyl ring; and provided that when $R^{6a}$ and $R^{6b}$ are both $CH_3$ or when $R^{6a}$ and $R^{6b}$ together with the carbon atom to which they are attached form an unsubstituted cyclopentyl or unsubstituted cyclopentenyl, then $R^8$ is not

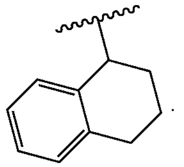 [SMILES: *C1CCCc2ccccc21]

In another aspect, provided herein are compounds having the structure of Formula (B-I), or a pharmaceutically acceptable salt, N-oxide, solvate, diastereomeric mixture, or individual enantiomers, or stereoisomer thereof:

Formula (B-I)

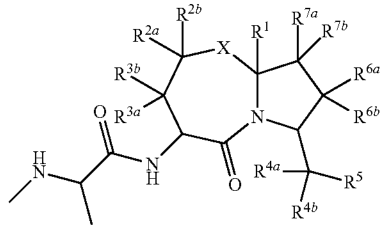

wherein, $R^1$ is hydrogen, $C_1$-$C_6$alkyl, $C_3$-$C_6$cycloalkyl, $C_1$-$C_6$alkyl-($C_3$-$C_6$cycloalkyl), $C_1$-$C_6$alkyl-(phenyl), or $C_1$-$C_6$alkyl-(5- to 6-membered heteroaryl); wherein the $C_1$-$C_6$alkyl, $C_3$-$C_6$cycloalkyl, phenyl, or 5- to 6-membered heteroaryl is optionally substituted with 1, 2, or 3 $R^9$;

X is $NR^A$, O, S, S(O), or $S(O)_2$;

$R^A$ is hydrogen, $C_1$-$C_6$alkyl, C(O)—($C_1$-$C_6$alkyl), C(O)—($C_3$-$C_6$cycloalkyl), C(O)-(phenyl), or C(O)-(5- to 6-membered heteroaryl); wherein each $C_1$-$C_6$alkyl, $C_3$-$C_6$cycloalkyl, phenyl, or 5- to 6-membered heteroaryl is optionally substituted with 1, 2, or 3 $R^9$;

or X is C and taken together with $R^{2a}$, $R^{2b}$, and the carbon atom to which they are attached, forms a phenyl or 5- to 10-membered heteroaryl ring, optionally substituted with 1, 2, or 3 $R^9$;

$R^{2a}$, $R^{2b}$, $R^{3a}$, and $R^{3b}$ are each independently hydrogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, or $C_2$-$C_6$alkynyl is optionally substituted with 1 or 2 $C_3$-$C_{10}$cycloalkyl, 3- to 10-membered heterocycloalkyl, $C_6$-$C_{10}$aryl, or 5- to 10-membered heteroaryl rings; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{2a}$ and $R^{2b}$ together with the carbon atom to which they are attached form a carbonyl;

or $R^{2a}$ and $R^{3a}$, and optionally $R^{2b}$ and $R^{3b}$, together with the carbon atoms to which they are attached form a $C_3$-$C_6$cycloalkyl, 5- to 10-membered heterocycloalkyl, $C_6$-$C_{10}$aryl, or 5- to 10-membered heteroaryl ring; wherein each $C_3$-$C_6$cycloalkyl, 5- to 10-membered heterocycloalkyl, $C_6$-$C_{10}$aryl, or 5- to 10-membered heteroaryl ring is optionally substituted with 1, 2, or 3 $R^9$;

$R^{4a}$ and $R^{4b}$ are each independently hydrogen, halogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, or $C_2$-$C_6$alkynyl is optionally substituted with 1 or 2 $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{4a}$ and $R^{4b}$ together with the carbon atom to which they are attached form a carbonyl;

or $R^{4a}$ and $R^{4b}$ together with the carbon atom to which they are attached form a $C_3$-$C_{10}$cycloalkyl or 3- to 10-membered heterocycloalkyl ring; wherein the $C_3$-$C_{10}$cycloalkyl or 3- to 10-membered heterocycloalkyl ring is optionally substituted with 1, 2, or 3 $R^9$;

$R^5$ is $NHR^8$, $NHS(O)_2R^8$, $OR^8$, $SR^8$, $S(O)_2R^8$, or $S(O)_2NHR^8$;

or $R^5$, $R^{4a}$, and $R^{4b}$, together with the carbon atom to which they are attached, form a $C_6$-$C_{10}$aryl or 5- to 10-membered heteroaryl ring; wherein the $C_6$-$C_{10}$aryl or 5- to 10-membered heteroaryl ring is optionally substituted with 1, 2, or 3 $R^9$;

$R^{6a}$ is hydrogen, halogen, —$U^a$, or -G;

$R^{6b}$ is halogen, —$U^b$, or -G;

—$U^a$ is $C_2$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl; wherein each $C_1$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl is optionally substituted with 1, 2, or 3 $R^9$ and/or 1 or 2-G;

—$U^b$ is $C_1$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl; wherein each $C_1$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl is optionally substituted with 1, 2, or 3 $R^9$ and/or 1 or 2-G;

-G is $C_3$-$C_{10}$cycloalkyl, 3- to 10-membered heterocycloalkyl, $C_6$-$C_{10}$aryl, or 5- to 10-membered heteroaryl; wherein each $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

$R^{7a}$ is hydrogen, halogen, $C_1$-$C_4$alkyl, or $C_1$-$C_4$haloalkyl;

$R^{7b}$ is hydrogen, halogen, $C_1$-$C_4$alkyl, or $C_1$-$C_4$haloalkyl;

$R^8$ is Z, $C_2$-$C_6$alkyl, ($C_1$-$C_6$alkylene)-Z, ($C_1$-$C_6$heteroalkylene)-Z, ($C_2$-$C_6$alkenylene)-Z, $CH(Z)_2$, $CH_2CH(Z)_2$, $CH(C_1$-$C_6alkyl)Z$, or C(O)Z; wherein each alkyl, alkylene, heteroalkylene, or alkenylene is optionally substituted with 1, 2, or 3 $R^9$;

Z is $C_3$-$C_{10}$cycloalkyl, 3- to 10-membered heterocycloalkyl, $C_6$-$C_{10}$aryl, 5- to 10-membered heteroaryl; wherein each $C_3$-$C_{10}$cycloalkyl, 3- to 10-membered heterocycloalkyl, $C_6$-$C_{10}$aryl, 5- to 10-membered heteroaryl is optionally substituted with 1, 2, or 3 $R^9$;

each $R^9$ is independently halogen, $C_1$-$C_4$alkyl, $C_2$-$C_4$alkenyl, $C_2$-$C_4$alkynyl, $C_1$-$C_4$haloalkyl, $C_1$-$C_4$alkoxy, $C_1$-$C_4$haloalkoxy, $C_1$-$C_4$heteroalkyl, —C(O)H, —C(O)OH, —CN, $C_3$-$C_{10}$cycloalkyl, 3- to 10-membered heterocycloalkyl, $C_6$-$C_{10}$aryl, 5- to 10-membered heteroaryl, —C(O)($C_1$-$C_4$alkyl), —C(O)O($C_1$-$C_4$alkyl), —C(O)$NH_2$, —C(O)NH($C_1$-$C_4$alkyl), —C(O)N($C_1$-$C_4$alkyl)$_2$, —$NH_2$, —NH($C_1$-$C_4$alkyl), —N($C_1$-$C_4$alkyl)$_2$, —NH($C_2$-$C_4$alkylene)-OH, —NH($C_2$-$C_4$alkylene)-O—($C_1$-$C_4$alkyl), —OH, —O($C_1$-$C_4$alkyl), —O($C_1$-$C_4$haloalkyl), —O($C_2$-$C_4$alkylene)-$NH_2$, —O($C_2$-$C_4$alkylene)-NH—($C_1$-$C_4$alkyl), —O($C_2$-$C_4$alkylene)-N—($C_1$-$C_4$alkyl)$_2$, —O($C_1$-$C_4$alkylene)-C(O)OH, —O($C_1$-$C_4$alkylene)-C(O)O—($C_1$-$C_4$alkyl), —O($C_2$-$C_4$alkenyl), —O($C_1$-$C_4$alkylene)-($C_6$-$C_{10}$aryl), —O($C_1$-$C_4$alkylene)-(5- to 10-membered heteroaryl), —O($C_6$-$C_{10}$aryl), —SH, $S(O)_2OH$, —$S(O)_2$($C_1$-$C_4$alkyl), —$S(O)_2NH_2$, —$S(O)_2$NH($C_1$-$C_4$alkyl), or —$S(O)_2$N($C_1$-$C_4$alkyl)$_2$;

or two $R^9$ together with the atoms to which they are attached form a $C_3$-$C_{10}$cycloalkyl or a 3- to 10-membered heterocycloalkyl ring.

In another aspect, provided herein are compounds having the structure of Formula (C-I), or a pharmaceutically acceptable salt, N-oxide, solvate, diastereomeric mixture, or individual enantiomers, or stereoisomer thereof:

Formula (C-I)

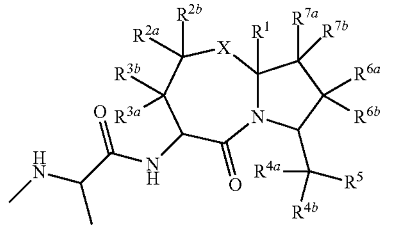

wherein, $R^1$ is hydrogen, $C_1$-$C_6$alkyl, $C_3$-$C_6$cycloalkyl, $C_1$-$C_6$alkyl-($C_3$-$C_6$cycloalkyl), $C_1$-$C_6$alkyl-(phenyl), or $C_1$-$C_6$alkyl-(5- to 6-membered heteroaryl); wherein the $C_1$-$C_6$alkyl, $C_3$-$C_6$cycloalkyl, phenyl, or 5- to 6-membered heteroaryl is optionally substituted with 1, 2, or 3 $R^9$;

X is $NR^A$, O, S, S(O), or $S(O)_2$;

$R^A$ is hydrogen, $C_1$-$C_6$alkyl, C(O)—($C_1$-$C_6$alkyl), C(O)—($C_3$-$C_6$cycloalkyl), C(O)-(phenyl), or C(O)-(5- to 6-membered heteroaryl); wherein each $C_1$-$C_6$alkyl, $C_3$-$C_6$cycloalkyl, phenyl, or 5- to 6-membered heteroaryl is optionally substituted with 1, 2, or 3 $R^9$;

or X is C and taken together with $R^{2a}$, $R^{2b}$, and the carbon atom to which they are attached, forms a phenyl or 5- to 10-membered heteroaryl ring, optionally substituted with 1, 2, or 3 $R^9$;

$R^{2a}$, $R^{2b}$, $R^{3a}$, and $R^{3b}$ are each independently hydrogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, or $C_2$-$C_6$alkynyl is optionally substituted with 1 or 2 $C_3$-$C_{10}$cycloalkyl, 3- to 10-membered heterocycloalkyl, $C_6$-$C_{10}$aryl, or 5- to 10-membered heteroaryl rings; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{2a}$ and $R^{2b}$ together with the carbon atom to which they are attached form a carbonyl;

or $R^{2a}$ and $R^{3a}$, and optionally $R^{2b}$ and $R^{3b}$, together with the carbon atoms to which they are attached form a $C_3$-$C_6$cycloalkyl, 5- to 10-membered heterocycloalkyl, $C_6$-$C_{10}$aryl, or 5- to 10-membered heteroaryl ring; wherein each $C_3$-$C_6$cycloalkyl, 5- to 10-membered heterocycloalkyl, $C_6$-$C_{10}$aryl, or 5- to 10-membered heteroaryl ring is optionally substituted with 1, 2, or 3 $R^9$;

$R^{4a}$ and $R^{4b}$ are each independently hydrogen, halogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, or $C_2$-$C_6$alkynyl is optionally substituted with 1 or 2 $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{4a}$ and $R^{4b}$ together with the carbon atom to which they are attached form a carbonyl;

or $R^{4a}$ and $R^{4b}$ together with the carbon atom to which they are attached form a $C_3$-$C_{10}$cycloalkyl or 3- to 10-membered heterocycloalkyl ring; wherein the $C_3$-$C_{10}$cycloalkyl or 3- to 10-membered heterocycloalkyl ring is optionally substituted with 1, 2, or 3 $R^9$;

$R^5$ is $NHR^B$, $NHS(O)_2R^8$, $OR^B$, $SR^8$, $S(O)_2R^8$, or $S(O)_2NHR^8$;

or $R^5$, $R^{4a}$, and $R^{4b}$, together with the carbon atom to which they are attached, form a $C_6$-$C_{10}$aryl or 5- to 10-membered heteroaryl ring; wherein the $C_6$-$C_{10}$aryl or 5- to 10-membered heteroaryl ring is optionally substituted with 1, 2, or 3 $R^9$;

$R^{6a}$ is hydrogen, halogen, —U, or -G;

$R^{6b}$ is halogen, —U, or -G;

—U is $C_1$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl; wherein each $C_1$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl is optionally substituted with 1, 2, or 3 $R^9$ and/or 1 or 2-G;

G is $C_3$-$C_{10}$cycloalkyl, 3- to 10-membered heterocycloalkyl, $C_6$-$C_{10}$aryl, or 5- to 10-membered heteroaryl; wherein each $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{6a}$ and $R^{6b}$ together with the carbon atom to which they are attached form a saturated or partially saturated 3- to 7-membered cycloalkyl or a saturated or partially saturated 3- to 7-membered heterocycloalkyl; wherein the cycloalkyl or heterocycloalkyl is optionally substituted with 1, 2, or 3 $R^9$;

$R^{7a}$ is hydrogen, halogen, $C_1$-$C_4$alkyl, or $C_1$-$C_4$haloalkyl;

$R^{7b}$ is hydrogen, halogen, $C_1$-$C_4$alkyl, or $C_1$-$C_4$haloalkyl;

or $R^{7a}$ and $R^{7b}$ together with the carbon atom to which they are attached form a saturated or partially saturated 3- to 7-membered cycloalkyl or a saturated or partially saturated 3- to 7-membered heterocycloalkyl; wherein the cycloalkyl or heterocycloalkyl is optionally substituted with 1, 2, or 3 $R^9$;

or $R^{6b}$ and $R^{7b}$ together with the carbon atoms to which they are attached form a $C_3$-$C_{10}$cycloalkyl or 3- to 10-membered heterocycloalkyl ring; wherein each $C_3$-$C_{10}$cycloalkyl or 3- to 10-membered heterocycloalkyl ring is optionally substituted with 1, 2, or 3 $R^9$;

or $R^{6a}$, $R^{6b}$, $R^{7a}$, and $R^{7b}$ together with the carbon atoms to which they are attached form a 5- to 10-membered heteroaryl ring optionally substituted with 1, 2, or 3 $R^9$;

$R^8$ is Z, $C_2$-$C_6$alkyl, ($C_1$-$C_6$alkylene)-Z, ($C_1$-$C_6$heteroalkylene)-Z, ($C_2$-$C_6$alkenylene)-Z, $CH(Z)_2$, $CH_2CH(Z)_2$, $CH(C_1$-$C_6alkyl)Z$, or $C(O)Z$; wherein each alkyl, alkylene, heteroalkylene, or alkenylene is optionally substituted with 1, 2, or 3 $R^9$;

Z is $C_3$-$C_9$cycloalkyl, 3- to 10-membered heterocycloalkyl, $C_6$-$C_{10}$aryl, 5- to 10-membered heteroaryl; wherein each $C_3$-$C_9$cycloalkyl, 3- to 10-membered heterocycloalkyl, $C_6$-$C_{10}$aryl, 5- to 10-membered heteroaryl is optionally substituted with 1, 2, or 3 $R^9$;

or Z is a substituted $C_{10}$cycloalkyl substituted with 1, 2, or 3 $R^9$; and each $R^9$ is independently halogen, $C_1$-$C_4$alkyl, $C_2$-$C_4$alkenyl, $C_2$-$C_4$alkynyl, $C_1$-$C_4$haloalkyl, $C_1$-$C_4$alkoxy, $C_1$-$C_4$haloalkoxy, $C_1$-$C_4$heteroalkyl, —C(O)H, —C(O)OH, —CN, $C_3$-$C_{10}$cycloalkyl, 3- to 10-membered heterocycloalkyl, $C_6$-$C_{10}$aryl, 5- to 10-membered heteroaryl, —C(O)($C_1$-$C_4$alkyl), —C(O)O($C_1$-$C_4$alkyl), —$C(O)NH_2$, —C(O)NH($C_1$-$C_4$alkyl), —C(O)N($C_1$-$C_4alkyl)_2$, —$NH_2$, —NH($C_1$-$C_4$alkyl), —N($C_1$-$C_4alkyl)_2$, —NH($C_2$-$C_4$alkylene)-OH, —NH($C_2$-$C_4$alkylene)-O—($C_1$-$C_4$alkyl), —OH, —O($C_1$-$C_4$alkyl), —O($C_1$-$C_4$haloalkyl), —O($C_2$-$C_4$alkylene)-$NH_2$, —O($C_2$-$C_4$alkylene)-NH—($C_1$-$C_4$alkyl), —O($C_2$-$C_4$alkylene)-N—($C_1$-$C_4alkyl)_2$, —O($C_1$-$C_4$alkylene)-C(O)OH, —O($C_1$-$C_4$alkylene)-C(O)O—($C_1$-$C_4$alkyl), —O($C_2$-$C_4$alkenyl), —O($C_1$-$C_4$alkylene)-($C_6$-$C_{10}$aryl), —O($C_1$-$C_4$alkylene)-(5- to 10-membered heteroaryl), —O($C_6$-$C_{10}$aryl), —SH, $S(O)_2OH$, —$S(O)_2$($C_1$-$C_4$alkyl), —$S(O)_2NH_2$, —$S(O)_2$NH($C_1$-$C_4$alkyl), or —$S(O)_2$N($C_1$-$C_4alkyl)_2$; or two $R^9$ together with the atoms to which they are attached form a $C_3$-$C_{10}$cycloalkyl or a 3- to 10-membered heterocycloalkyl ring.

DETAILED DESCRIPTION OF THE INVENTION

Figure 1:
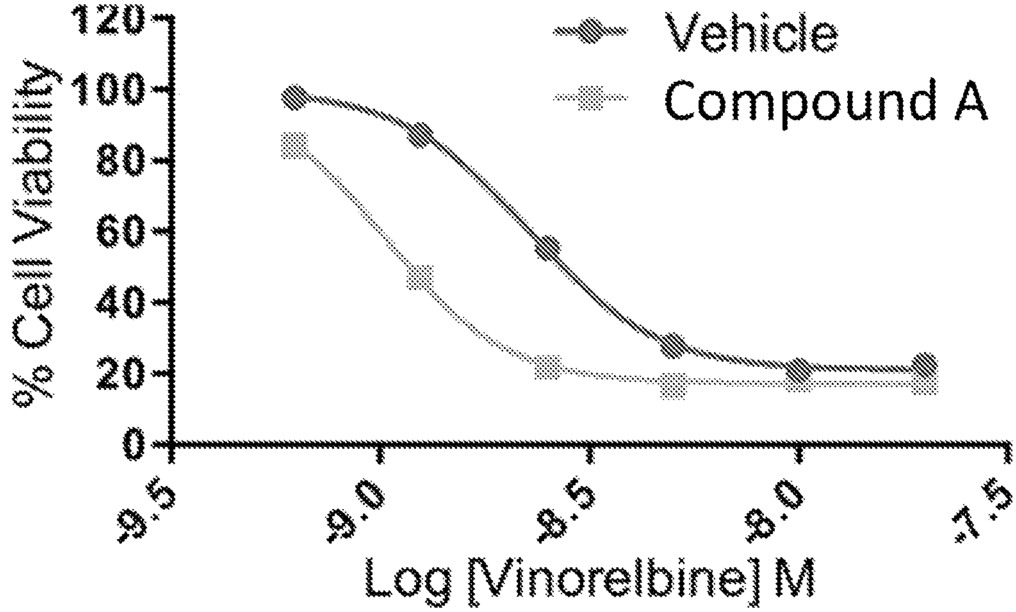
FIG. 1 illustrates the sensitizing effect of a selective ML-IAP antagonist (Compound A) on lung cancer cells.

Provided herein are compounds of utility in the treatment of cancer, among other medical conditions. Compounds of the present disclosure may be, in many cases, potent, selective antagonists of melanoma inhibitor of apoptosis protein (ML-IAP). As discussed herein, ML-IAP is a viable therapeutic target for treating conditions such as lung cancer. To date, studies of ML-IAP have primarily utilized genetic silencing or knock-down mutants in order to study the effects of this protein on cancer progression. The current lack of selective antagonists of ML-IAP has stifled the ability to research and treat conditions wherein ML-IAP is overexpressed or hyperactive, such as may be the case in many cancers. By advancing the development of selective ML-IAP antagonists such as those disclosed herein, the survival of cancer patients including lung cancer patients will be increased.

Cancer is a persistent and growing cause of death throughout the world. Based on the GLOBOCAN 2012 estimates, about 14.1 million cancer cases and 8.2 million cancer deaths are estimated to have occurred in 2012 worldwide. Lung cancer has the highest incidence rate of all cancers and is the leading cause of cancer-induced mortality in all populations worldwide. With a mortality rate of more than double that of any other cancer lung cancer is among the deadliest cancers.

Apoptosis, a form of programmed cell death, is often dysregulated in malignant cells, and the evasion of apoptosis is a hallmark of cancer. As cancer cells divide and proliferate, normal control of cell death is impaired and tumor formation occurs. Disruption of normal cell death processes is a hallmark of cancer leading to escape of tumorigenic cells from apoptotic stimuli as well as substantially increased resistance to chemotherapies and radiation therapies. Cancer cells often display aberrant upregulation of pathways which inhibit apoptosis, allowing the cancer cells to proliferate. One such pathway which is upregulated in cancer cells is the inhibitor of apoptosis (IAP) pathway.

The IAP protein family is involved in blocking and attenuating programmed cell death pathways, predominantly through modulation of the caspase cascade. The members of the IAP family are functionally and structurally related proteins that inhibit apoptosis. Proteins are ascribed to the IAP family if they possess a Baculovirus Inhibitor of apoptosis protein Repeat (BIR) domain. IAPs have been identified as potential therapeutic targets for the treatment of cancer. One member of the IAP family, ML-IAP, stands out as a particularly viable target. This is supported by studies on ML-IAP's function within the apoptotic signaling network as well as its role as a biomarker for disease prognosis. Furthermore, ML-IAP has been identified as an attractive target in lung cancer. Inhibition of ML-IAP in this malignancy leads to a substantial reduction in tumor growth as well as sensitization to traditional standard of care (SOC) therapies.

ML-IAP is upregulated in various cancers and is believed to underlie the resistance of many malignant cells to chemotherapeutics. Ablation or antagonism of ML-IAP is therefore an attractive therapeutic strategy for the treatment of cancer. In certain instances, novel, selective ML-IAP antagonists as disclosed herein may be particularly advantageous in the treatment of treatment-resistant cancers.

ML-IAP, also known as Livin or KIAP, was first identified as a member of the IAP protein family due to its single BIR domain. The ML-IAP BIR domain is also responsible for apoptosis inhibition, and small molecule antagonists have significant potential for development as therapeutic agents. The RING domain of ML-IAP has been shown to function as an E3 ligase, facilitating the ubiquitination and subsequent degradation of itself and, more importantly, the natural caspase antagonist that modulates apoptotic signaling—the second mitochondria-derived activator of caspases (SMAC). SMAC is a mitochondrial protein that negatively regulates apoptosis, also known as programmed cell death. When a cell is primed for apoptosis by the final execution step of caspase activation, SMAC binds to IAPs, preventing IAPs from binding to and deactivating caspases. Thus, SMAC promotes apoptosis by activating caspases.

Thus, inhibition of ML-IAP leads to a direct increase of SMAC and a re-sensitization of cells to apoptotic stimuli. Importantly, both protein and mRNA levels of ML-IAP are low to undetectable in most adult tissues but are highly expressed in a number of cancers such as melanoma and lung cancer. ML-IAP maps to chromosome 20q13, a region frequently implicated in the mutagenic etiology of lung cancers. ML-IAP levels have been shown to be highly relevant as a prognostic biomarker in lung cancer and other cancers. As expected, high ML-IAP expression results in a poor outcome whilst lower levels are more favorable. There exists considerable therapeutic potential of ML-IAP inhibition to treat cancer. A wealth of data has been reported in cellular contexts as well as xenograft studies. In some instances, gene ablation of ML-IAP in a xenograft model of lung cancer results in substantial benefit. However, study of the effect of ML-IAP and its blockade has been limited by the absence of safe, selective, and efficacious antagonists of ML-IAP.

Alterations in IAP proteins are found in many types of human cancer and are associated with chemoresistance, disease progression and poor prognosis. When the IAP pathway is upregulated, the IAP proteins bind to and prevent initiator and effector caspases from cleaving downstream cellular proteins. The proteolytic action of caspases is required to allow the cell death cascade to progress normally. Accordingly, provided herein are compounds that bind and inhibit the upregulated ML-IAP. The compounds provided herein, in some embodiments, bind to ML-IAP and prevent it from suppressing caspase action, thereby allowing the cell death cascade to progress normally. Functionally, compounds described herein are able to inhibit the action of ML-IAP, thereby inducing apoptosis in cells. In addition to facilitating or stimulating cell dead pathways through direct action, the antagonists of ML-IAP offer additional utility as adjuvant therapies in the treatment of cancer. As an example, a tumor that may otherwise avoid apoptosis in response to standard of care (SOC) chemotherapy, immunotherapy, radiation therapy, etc., will often become responsive or sensitized to those therapies following treatment with an ML-IAP antagonist. As such, these compounds may derive additional benefit from use in a combination therapy with other known cancer agents.

In some embodiments, the compounds described herein are nonpeptidic second mitochondria-derived activator of caspase (SMAC) mimetics and induce apoptosis (e.g., in cancer cells). In some embodiments, the compounds described herein are ML-IAP antagonists. In certain preferred embodiments, the compounds described herein are ML-IAP antagonists with selectivity for ML-IAP over other members of the IAP family.

Almost all studies on ML-IAP to date have been based on gene ablation studies using RNA interference, because no selective ML-IAP antagonists were available. Disclosed herein are various highly potent and selective ML-IAP antagonists. In some embodiments, selective ML-IAP antagonists are generated utilizing a rational design approach mimicking the SMAC-IAP interaction. In some embodiments disclosed herein are potent and highly selective inhibitors of ML-IAP in vitro. In some embodiments, a compound disclosed herein blocks resistance to chemotherapeutics in whole cells, halts tumor cell proliferation, and is non-toxic in normal cells.

In some embodiments, disclosed herein are treatments for lung cancer. In some embodiments, a compound, composition, or method of treatment disclosed herein facilitates a subject's ability to overcome resistance to current first-line therapies. In some embodiments, a compound or method of treatment disclosed herein reduces the burden that chemotherapy and radiotherapy exerts on the patient by sensitizing the cancer to much lower doses of SOC therapies. In some embodiments, elevated levels of ML-IAP in bronchial aspiration and other tumor sampling methods are identified as valuable prognostic markers of disease staging and progression. In some embodiments, compounds disclosed herein are useful for the further characterization of the role of ML-IAP as a biomarker in lung cancer.

Aberrant and uncontrolled cell growth due to apoptosis suppression is a hallmark of cancer cells. Cancer cells often display aberrant upregulation of pathways which inhibit apoptosis, allowing the cancer cells to proliferate. One such pathway which is upregulated in cancer cells is the inhibitor of apoptosis (IAP) pathway. The members of the IAP family are functionally and structurally related proteins, which inhibit apoptosis. IAPs share a baculovirus IAP repeat (BIR) domain, each having one to three copies. Eight members of the IAP protein family have currently been identified, in both baculovirus and humans. Five human members of the IAP protein family include: XIAP, cIAP1 (also, BIRC2), cIAP2 (also, BIRC3), NAIP, and survivin. In certain instances, XIAP inhibits apoptosis by binding to and inhibiting the activity of caspase-9, caspase-3 and caspase 7.

Alterations in IAP proteins are found in many types of human cancer and are associated with chemoresistance, disease progression and poor prognosis. When the IAP pathway is upregulated, the IAP proteins bind to and prevent initiator and effector caspases from cleaving downstream cellular proteins.

The proteolytic action of caspases is required to allow the cell death cascade to progress normally. Accordingly, provided herein are compounds that bind the upregulated IAP proteins. The compounds provided herein, in some embodiments, bind to IAP proteins and prevent them from suppressing caspase action, thereby allowing the cell death cascade to progress normally. In other words, provided herein are compounds that inhibit the action of IAP proteins, thereby inducing apoptosis in cells.

One protein implicated in binding with IAPs is SMAC. SMAC is a mitochondrial protein that negatively regulates apoptosis, also known as programmed cell death. When a cell is primed for apoptosis by the final execution step of caspase activation, SMAC binds to IAP, which prevents IAP from binding to, and deactivating caspases. Thus, SMAC promotes apoptosis by activating caspases.

In some embodiments, the compounds described herein are nonpeptidic second mitochondria-derived activator of caspase (SMAC) mimetics and induce apoptosis (e.g., in cancer cells). In some embodiments, the compounds described herein are IAP antagonists.

In certain instances, IAP proteins not only regulate caspases and apoptosis, but also modulate inflammatory signaling and immunity, mitogenic kinase signaling, proliferation and mitosis, as well as cell invasion and metastasis. Inhibitor of apoptosis (IAP) proteins have emerged as regulators of innate immune signaling downstream of Pattern Recognition Receptors (PRRs) such as Toll-like receptor 4 (TLR4), Nucleotide-Binding Oligomerization Domain 1 (NOD1) and NOD2 receptors, and Retinoic Acid-Inducible Gene (RIG)-I Receptor. In certain instances, Cellular Inhibitor of Apoptosis Protein-1 (cIAP1; also Baculoviral IAP Repeat Containing 2 or BIRC2), Cellular Inhibitor of Apoptosis Protein-2 (cIAP2; also, Baculoviral IAP Repeat Containing 3 or BIRC3), and X-linked Inhibitor of Apoptosis (XIAP) facilitate ubiquitin-dependent signaling activated by these PRRs and mediate activation of nuclear factor-kappa B (NF-κB) transcription factors as well as the MAP kinases p38 and JNK. Accordingly, the compounds described herein are also useful in the treatment of non-neoplastic diseases and/or inflammatory diseases and/or autoimmune diseases.

Recent advances in combinatorial antiretroviral therapy (ART) have allowed individuals infected with human immunodeficiency virus (HIV) to live long and otherwise normal lives. However, antiretroviral therapy only targets actively replicating HIV and not the dormant, replication competent HIV that resides in certain types of cells. These dormant HIV viruses can reactivate and trigger new rounds of viral replication upon discontinuation of antiretroviral therapy. In addition to targeting actively replicating HIV, a strategy for improving HIV treatment is to also target the dormant, replication competent HIV virus residing in latently infected cells, which are cells that are infected with HIV but are not actively producing HIV. These latently infected cells are not undergoing active virus replication and the viral genome has been integrated into the host DNA in such a manner that the virus DNA is indistinguishable from the host's DNA. Latently infected cells are not recognized by the immune system and are not susceptible to antiretroviral therapy (ART). Thus, the dormant virus and latently infected cells can remain hidden and persist indefinitely. One approach for targeting latently infected cells is to develop new therapeutic agents or drugs that can reverse latency in infected cells by inducing active HIV replication. Once the dormant HIV virus is "awakened", the infected cells become susceptible to immune system clearance or the effects of additional treatments such as killer agents to eliminate infected cells. Concurrent treatment with antiretroviral drugs will prevent the spread of the reactivated virus and suppress new rounds of HIV infection. The combination of therapeutic agents that can reverse the latency of HIV-infected cells and drugs to eradicate the awakened HIV virus is termed the "shock and kill" or "kick and kill" approach. IAP inhibition has been implicated in the reversal of HIV latency. The IAP antagonists may be used alone or in combination with other therapeutic agents, such as those that are used to treat HIV. In some embodiments, other therapeutic agents that could be used in combination with IAP antagonists include therapeutic agents that activate HIV transcription in latently infected cells, therapeutic agents that inhibit active HIV replication, or any combination thereof. In some embodiments, the additional therapeutic agents that inhibit active HIV replication include antiretroviral therapy drugs. In some embodiments, the pharmaceutical compositions are described comprising IAP antagonists, alone or in combination with one or more additional therapeutics agents that are useful for the treatment of HIV in a mammal. In some embodiments, the mammal is a human.

Definitions

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Oxo" refers to =O.

"Alkyl" refers to an optionally substituted straight-chain, or optionally substituted branched-chain saturated hydrocarbon monoradical having from one to about ten carbon atoms, or from one to six carbon atoms. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_5$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —$CF_3$, —OH, —OMe, —$NH_2$, or —$NO_2$. In some embodiments, the alkyl is optionally substituted with oxo, halogen, —CN, —$CF_3$, —OH, or —OMe. In some embodiments, the alkyl is optionally substituted with halogen.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to, ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —$CF_3$, —OH, —OMe, —$NH_2$, or —$NO_2$. In some embodiments, an alkenyl is optionally substituted with oxo, halogen, —CN, —$CF_3$, —OH, or —OMe. In some embodiments, the alkenyl is optionally substituted with halogen.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to, ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —$CF_3$, —OH, —OMe, —$NH_2$, or —$NO_2$. In some embodiments, an alkynyl is optionally substituted with oxo, halogen, —CN, —$CF_3$, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —$CF_3$, —OH, —OMe, —$NH_2$, or —$NO_2$. In some embodiments, an alkylene is optionally substituted with oxo, halogen, —CN, —$CF_3$, —OH, or —OMe. In some embodiments, the alkylene is optionally substituted with halogen.

"Alkoxy" refers to a radical of the formula —$OR_a$ where $R_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —$CF_3$, —OH, —OMe, —$NH_2$, or —$NO_2$. In some embodiments, an alkoxy is optionally substituted with oxo, halogen, —CN, —$CF_3$, —OH, or —OMe. In some embodiments, the alkoxy is optionally substituted with halogen.

"Aminoalkyl" refers to an alkyl radical, as defined above, that is substituted by one or more amines. In some embodiments, the alkyl is substituted with one amine. In some embodiments, the alkyl is substituted with one, two, or three amines. Hydroxyalkyl include, for example, aminomethyl, aminoethyl, aminopropyl, aminobutyl, or aminopentyl. In some embodiments, the hydroxyalkyl is aminomethyl.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —$CF_3$, —OH, —OMe, —$NH_2$, or —$NO_2$. In some embodiments, an aryl is optionally substituted with halogen, methyl, ethyl, —CN, —$CF_3$, —OH, or —OMe. In some embodiments, the aryl is optionally substituted with halogen.

“Cycloalkyl” refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Some examples of partially saturated bicyclic cycloalkyls include, by way of non-limiting example, include tetrahydronaphthalene, dihydronaphthalene, indane, indene, and dihydroanthracene. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —$CF_3$, —OH, —OMe, —$NH_2$, or —$NO_2$. In some embodiments, a cycloalkyl is optionally substituted with oxo, halogen, methyl, ethyl, —CN, —$CF_3$, —OH, or —OMe. In some embodiments, the cycloalkyl is optionally substituted with halogen.

“Deuteroalkyl” refers to an alkyl radical, as defined above, that is substituted by one or more deuterium atoms. In some embodiments, the alkyl is substituted with one deuterium atom. In some embodiments, the alkyl is substituted with one, two, or three deuterium atoms. In some embodiments, the alkyl is substituted with one, two, three, four, five, or six deuterium atoms. Deuteroalkyl includes, for example, $CD_3$, $CH_2D$, $CHD_2$, $CH_2CD_3$, $CD_2CD_3$, $CHDCD_3$, $CH_2CH_2D$, or $CH_2CHD_2$. In some embodiments, the deuteroalkyl is $CD_3$.

“Haloalkyl” refers to an alkyl radical, as defined above, that is substituted by one or more halogen atoms. In some embodiments, the alkyl is substituted with one, two, or three halogen atoms. In some embodiments, the alkyl is substituted with one, two, three, four, five, or six halogen halogens. Haloalkyl includes, for example, trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. In some embodiments, the haloalkyl is trifluoromethyl.

“Halo” or “halogen” refers to bromo, chloro, fluoro or iodo. In some embodiments, halogen is fluoro or chloro. In some embodiments, halogen is fluoro.

“Heteroalkyl” refers to an alkyl group in which one or more skeletal atoms of the alkyl are selected from an atom other than carbon, e.g., oxygen, nitrogen (e.g., —NH—, —N(alkyl)-), sulfur, or combinations thereof. In some instances, a heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 5 carbon atoms and one or more atoms other than carbon, e.g., oxygen, nitrogen, sulfur, or combinations thereof. In some instances, a carbon atom or heteroatom is optionally oxidized (e.g., —C(O)$OCH_2$—, —$CH_2S(O)_2NHCH_2$—, —NHC(O)$NHCH_2$, —$CH_2$NHC(O)$CH_2$). Further examples of such heteroalkyl are, for example, —$CH_2OCH_3$, —$CH_2CH_2OCH_3$, —$CH_2CH_2OCH_2CH_2OCH_3$, or —$CH(CH_3)OCH_3$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —$CF_3$, —OH, —OMe, —$NH_2$, or —$NO_2$. In some embodiments, a heteroalkyl is optionally substituted with oxo, halogen, methyl, ethyl, —CN, —$CF_3$, —OH, or —OMe. In some embodiments, the heteroalkyl is optionally substituted with halogen.

“Hydroxyalkyl” refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

“Heterocycloalkyl” refers to a stable 3- to 24-membered partially or fully saturated ring radical comprising 2 to 23 carbon atoms and from one to 8 heteroatoms selected from the group consisting of nitrogen, oxygen, phosphorous and sulfur. In some embodiments, the heterocycloalkyl comprises 1 or 2 heteroatoms selected from nitrogen and oxygen. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms ($C_2$-$C_{15}$ heterocycloalkyl), from two to ten carbon atoms ($C_2$-$C_{10}$ heterocycloalkyl), from two to eight carbon atoms ($C_2$-$C_8$ heterocycloalkyl), from two to six carbon atoms ($C_2$-$C_6$ heterocycloalkyl), from two to five carbon atoms ($C_2$-$C_5$ heterocycloalkyl), or two to four carbon atoms ($C_2$-$C_4$ heterocycloalkyl). In some embodiments, the heterocycloalkyl is a 3- to 6-membered heterocycloalkyl. In some embodiments, the cycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to, the monosaccharides, the disaccharides and the oligosaccharides. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —$CF_3$, —OH, —OMe, —$NH_2$, or —$NO_2$. In some embodiments, a heterocycloalkyl is optionally substituted with oxo, halogen, methyl, ethyl, —CN, —$CF_3$, —OH, or —OMe. In some embodiments, the heterocycloalkyl is optionally substituted with halogen.

"Heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl. Unless stated otherwise specifically in the specification, a heteroalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —$CF_3$, —OH, —OMe, —$NH_2$, or —$NO_2$. In some embodiments, a heteroalkyl is optionally substituted with oxo, halogen, methyl, ethyl, —CN, —$CF_3$, —OH, or —OMe. In some embodiments, the heteroalkyl is optionally substituted with halogen.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —$CF_3$, —OH, —OMe, —$NH_2$, or —$NO_2$. In some embodiments, a heteroaryl is optionally substituted with halogen, methyl, ethyl, —CN, —$CF_3$, —OH, or —OMe. In some embodiments, the heteroaryl is optionally substituted with halogen.

An "effective amount" or "therapeutically effective amount" refers to an amount of a compound administered to a subject (e.g. a mammal, such as a human), either as a single dose or as part of a series of doses, which is effective to produce a desired therapeutic effect.

"Therapy" may include any medical intervention to cure, remedy, treat, reverse, halt, delay, or otherwise modulate the effects of a disease or condition. Examples of therapies, by way of non-limiting example, include surgery, radiation, chemotherapy, immunotherapy, blood transfusion, tissue or organ grafting, transplantation. Therapies may comprise small molecules, peptides, peptidomimetics, macromolecules, antibodies, proteins, genetic material (e.g., DNA, RNA, or fragments thereof). Therapies may treat side-effects of a disease or condition, such as inflammation, pain, infection, weight loss/weight gain, depression, anxiety, loss of appetite, sleep loss, nausea, etc. Therapies may be prophylactic, i.e. therapies that prevent, anticipate, slow, or delay the onset of a disease or condition.

"Treatment" of a subject (e.g. a mammal, such as a human) includes any type of intervention used in an attempt to alter the natural course of the subject. In some embodiments, treatment includes administration of a pharmaceutical composition, subsequent to the initiation of a pathologic event or contact with an etiologic agent and includes stabilization of the condition (e.g., condition does not worsen, e.g., cancer does not metastasize and the like) or alleviation of the condition (e.g., reduction in tumor size, remission of cancer, absence of symptoms of autoimmune disease and the like). In other embodiments, treatment also includes prophylactic treatment (e.g., administration of a composition described herein when an individual is suspected to be suffering from a condition described herein).

As used herein, "subject", "individual" and "patient" are used interchangeably. None of the terms imply that a medical professional is required for the administration of the compounds disclosed herein.

ML-IAP Antagonists

In some embodiments, a compound disclosed herein binds to ML-IAP and modulates its function. In some embodiments, the ML-IAP modulator is an inhibitor. In some embodiments, an inhibitor is an antagonist (e.g., a partial antagonist, a full antagonist, an inverse agonist). In some embodiments, the modulator binds at the BIR domain and inhibits SMAC binding. In some embodiments, the modulator binds to an allosteric site. In some embodiments, the modulator interferes with, blocks, prevents, or reduces a protein-protein interaction. In some embodiments, the modulator interferes with, blocks, prevents, or reduces a ligand (e.g., a peptide) from binding. In some embodiments, a ML-IAP antagonist inhibits the ability of SMAC or a fragment thereof from binding to ML-IAP. In some embodiments, the ML-IAP antagonist inhibits a peptide (e.g., SMAC) from binding to a BIR domain. In some embodiments, a compound disclosed herein occupies a ML-IAP BIR domain. In some embodiments, a compound disclosed herein is highly selective for ML-IAP over other IAPs and/or other BIR domains (e.g., XIAP BIR1/2, XIAP BIR3, cIAP1 BIR2, cIAP1 BIR3, cIAP2 BIR2, cIAP2 BIR3). In some embodiments, a compound disclosed herein is 10-fold selective for ML-IAP BIR over another BIR domain. In some embodiments, a compound disclosed herein is 10-fold selective for ML-IAP over all other BIR domains. In some embodiments, a compound disclosed herein exhibits selectivity for ML-IAP BIR over other BIR domains with a selectivity ratio of 2, 5, 10, 20, 50, 100, 1000, or more.

In some embodiments, the ML-IAP antagonist mimics certain features of an endogenous peptide or protein. In some embodiments, the ML-IAP antagonist is conformationally constrained.

In some embodiments, selectivity for ML-IAP over another IAP (e.g., XIAP) results in enhanced anti-cancer effects. In some embodiments, selectivity for ML-IAP over another IAP (e.g., XIAP) results in enhanced effects against lung cancers. In some embodiments, selectivity for ML-IAP over another IAP (e.g., XIAP) results in enhanced induction of cell death in certain cancer cell lines. In some embodiments, ML-IAP selectivity over another IAP (e.g., XIAP) is 50-fold or greater. In some embodiments, ML-IAP selectivity results in an enhanced safety profile (e.g., reduced risk or severity of complications resulting from treatment). In some embodiments, a compound or composition as described herein is synergistic with another form of cancer therapy. In some embodiments, ML-IAP inhibition decreases the effective dose (e.g., $EC_{50}$, $IC_{50}$, $ED_{50}$) needed for another form of therapy to exert anti-cancer effects. In some embodiments, ML-IAP inhibition slows, delays, or reverses tumor development. In some embodiments, the therapeutic window is increased compared to treatment in the absence of an ML-IAP antagonist. In some embodiments, a previously untreatable tumor becomes responsive to SOC therapy.

Compounds

Some embodiments of the present disclosure relate to compounds or pharmaceutically acceptable salt, solvate, diastereomeric mixture, or individual enantiomers thereof, having the structure of Formula (A-I):

Formula (A-I)

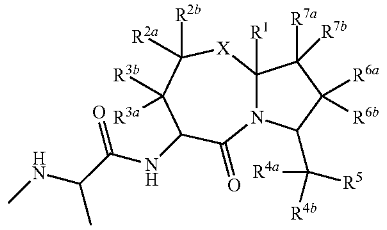

wherein, $R^1$ is hydrogen, $C_1$-$C_6$alkyl, $C_3$-$C_6$cycloalkyl, $C_1$-$C_6$alkyl-($C_3$-$C_6$cycloalkyl), $C_1$-$C_6$alkyl-(phenyl), or $C_1$-$C_6$alkyl-(5- to 6-membered heteroaryl); wherein the $C_1$-$C_6$alkyl, $C_3$-$C_6$cycloalkyl, phenyl, or 5- to 6-membered heteroaryl is optionally substituted with 1, 2, or 3 $R^9$;

X is $NR^A$, O, S, S(O), or $S(O)_2$;

$R^A$ is hydrogen, $C_1$-$C_6$alkyl, C(O)—($C_1$-$C_6$alkyl), C(O)—($C_3$-$C_6$cycloalkyl), C(O)-(phenyl), or C(O)-(5- to 6-membered heteroaryl); wherein each $C_1$-$C_6$alkyl, $C_3$-$C_6$cycloalkyl, phenyl, or 5- to 6-membered heteroaryl is optionally substituted with 1, 2, or 3 $R^9$;

or X is C and taken together with $R^{2a}$, $R^{2b}$, and the carbon atom to which they are attached, forms a phenyl or 5- to 10-membered heteroaryl ring, optionally substituted with 1, 2, or 3 $R^9$;

$R^{2a}$, $R^{2b}$, $R^{3a}$, and $R^{3b}$ are each independently hydrogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, or $C_2$-$C_6$alkynyl is optionally substituted with 1 or 2 $C_3$-$C_{10}$cycloalkyl, 3- to 10-membered heterocycloalkyl, $C_6$-$C_{10}$aryl, or 5- to 10-membered heteroaryl rings; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{2a}$ and $R^{2b}$ together with the carbon atom to which they are attached form a carbonyl;

or $R^{2a}$ and $R^{3a}$, and optionally $R^{2b}$ and $R^{3b}$, together with the carbon atoms to which they are attached form a $C_3$-$C_6$cycloalkyl, 5- to 10-membered heterocycloalkyl, $C_6$-$C_{10}$aryl, or 5- to 10-membered heteroaryl ring; wherein each $C_3$-$C_6$cycloalkyl, 5- to 10-membered heterocycloalkyl, $C_6$-$C_{10}$aryl, or 5- to 10-membered heteroaryl ring is optionally substituted with 1, 2, or 3 $R^9$;

$R^{4a}$ and $R^{4b}$ are each independently hydrogen, halogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, or $C_2$-$C_6$alkynyl is optionally substituted with 1 or 2 $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{4a}$ and $R^{4b}$ together with the carbon atom to which they are attached form a carbonyl;

or $R^{4a}$ and $R^{4b}$ together with the carbon atom to which they are attached form a $C_3$-$C_{10}$cycloalkyl or 3- to 10-membered heterocycloalkyl ring; wherein the $C_3$-$C_{10}$cycloalkyl or 3- to 10-membered heterocycloalkyl ring is optionally substituted with 1, 2, or 3 $R^9$;

$R^5$ is $NHR^8$, $NHS(O)_2R^8$, $OR^8$, $SR^8$, $S(O)_2R^8$, or $S(O)_2NHR^8$;

or $R^5$, $R^{4a}$, and $R^{4b}$, together with the carbon atom to which they are attached, form a $C_6$-$C_{10}$aryl or 5- to 10-membered heteroaryl ring; wherein the $C_6$-$C_{10}$aryl or 5- to 10-membered heteroaryl ring is optionally substituted with 1, 2, or 3 $R^9$;

$R^{6a}$ is hydrogen, halogen, —U, or -G;

$R^{6b}$ is halogen, —U, or -G;

—U is $C_1$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl; wherein each $C_1$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl is optionally substituted with 1, 2, or 3 $R^9$ and/or 1 or 2-G;

G is $C_3$-$C_{10}$cycloalkyl, 3- to 10-membered heterocycloalkyl, $C_6$-$C_{10}$aryl, or 5- to 10-membered heteroaryl; wherein each $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{6a}$ and $R^{6b}$ together with the carbon atom to which they are attached form a saturated or partially saturated 3- to 7-membered cycloalkyl or a saturated or partially saturated 3- to 7-membered heterocycloalkyl; wherein the cycloalkyl or heterocycloalkyl is optionally substituted with 1, 2, or 3 $R^9$;

$R^{7a}$ is hydrogen, halogen, $C_1$-$C_4$alkyl, or $C_1$-$C_4$haloalkyl;

$R^{7b}$ is hydrogen, halogen, $C_1$-$C_4$alkyl, or $C_1$-$C_4$haloalkyl;

or $R^{7a}$ and $R^{7b}$ together with the carbon atom to which they are attached form a saturated or partially saturated 3- to 7-membered cycloalkyl or a saturated or partially saturated 3- to 7-membered heterocycloalkyl; wherein the cycloalkyl or heterocycloalkyl is optionally substituted with 1, 2, or 3 $R^9$;

or $R^{6b}$ and $R^{7b}$ together with the carbon atoms to which they are attached form a $C_3$-$C_{10}$cycloalkyl or 3- to 10-membered heterocycloalkyl ring; wherein each $C_3$-$C_{10}$cycloalkyl or 3- to 10-membered heterocycloalkyl ring is optionally substituted with 1, 2, or 3 $R^9$;

or $R^{6a}$, $R^{6b}$, $R^{7a}$, and $R^{7b}$ together with the carbon atoms to which they are attached form a 5- to 10-membered heteroaryl ring optionally substituted with 1, 2, or 3 $R^9$;

$R^8$ is Z, $C_2$-$C_6$alkyl, ($C_1$-$C_6$alkylene)-Z, ($C_1$-$C_6$heteroalkylene)-Z, ($C_2$-$C_6$alkenylene)-Z, $CH(Z)_2$, $CH_2CH(Z)_2$, $CH(C_1$-$C_6alkyl)Z$, or C(O)Z; wherein each alkyl, alkylene, heteroalkylene, or alkenylene is optionally substituted with 1, 2, or 3 $R^9$;

Z is $C_3$-$C_{10}$cycloalkyl, 3- to 10-membered heterocycloalkyl, $C_6$-$C_{10}$aryl, or 5- to 10-membered heteroaryl; wherein each $C_3$-$C_{10}$cycloalkyl, 3- to 10-membered heterocycloalkyl, $C_6$-$C_{10}$aryl, and 5- to 10-membered heteroaryl is optionally substituted with 1, 2, or 3 $R^9$;

each $R^9$ is independently halogen, $C_1$-$C_4$alkyl, $C_2$-$C_4$alkenyl, $C_2$-$C_4$alkynyl, $C_1$-$C_4$haloalkyl, $C_1$-$C_4$alkoxy, $C_1$-$C_4$haloalkoxy, $C_1$-$C_4$heteroalkyl, —C(O)H, —C(O)OH, —CN, $C_3$-$C_{10}$cycloalkyl, 3- to 10-membered heterocycloalkyl, $C_6$-$C_{10}$aryl, 5- to 10-membered heteroaryl, —C(O)($C_1$-$C_4$alkyl), —C(O)O($C_1$-$C_4$alkyl), —C(O)$NH_2$, —C(O)NH($C_1$-$C_4$alkyl), —C(O)N($C_1$-$C_4$alkyl)$_2$, —$NH_2$, —NH($C_1$-$C_4$alkyl), —N($C_1$-$C_4$alkyl)$_2$, —NH($C_2$-$C_4$alkylene)-OH, —NH($C_2$-$C_4$alkylene)-O—($C_1$-$C_4$alkyl), —OH, —O($C_1$-$C_4$alkyl), —O($C_1$-$C_4$haloalkyl), —O($C_2$-$C_4$alkylene)-$NH_2$, —O($C_2$-$C_4$alkylene)-NH—($C_1$-$C_4$alkyl), —O($C_2$-$C_4$alkylene)-N—($C_1$-$C_4$alkyl)$_2$, —O($C_1$-$C_4$alkylene)-C(O)OH, —O($C_1$-$C_4$alkylene)-C(O)O—($C_1$-$C_4$alkyl), —O($C_2$-$C_4$alkenyl), —O($C_1$-$C_4$alkylene)-($C_6$-$C_{10}$aryl), —O($C_1$-$C_4$alkylene)-(5- to 10-membered heteroaryl), —O($C_6$-$C_{10}$aryl), —SH, $S(O)_2OH$, —$S(O)_2$($C_1$-$C_4$alkyl), —$S(O)_2NH_2$, —$S(O)_2$NH($C_1$-$C_4$alkyl), or —$S(O)_2$N($C_1$-$C_4$alkyl)$_2$;

or two $R^9$ together with the atoms to which they are attached form a $C_3$-$C_{10}$cycloalkyl or a 3- to 10-membered heterocycloalkyl ring; and provided that when $R^{6a}$ and $R^{6b}$ are both $CH_3$ or when $R^{6a}$ and $R^{6b}$ together with the carbon atom to which they are attached form an unsubstituted cyclopentyl or unsubstituted cyclopentenyl, then $R^1$ is not

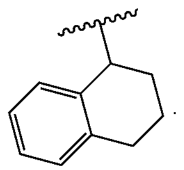 [SMILES: *C1CCCc2ccccc21]

In some embodiments, $R^5$, $R^{4a}$ and $R^{4b}$ together with the carbon atom to which they are attached form a $C_6$-$C_{10}$aryl or 5- to 10-membered heteroaryl ring; wherein the $C_6$-$C_{10}$aryl or 5- to 10-membered heteroaryl ring is optionally substituted with 1, 2, or 3 $R^9$. In some embodiments, $R^5$, $R^{4a}$ and $R^{4b}$ together with the carbon atom to which they are attached form a 5- to 10-membered heteroaryl ring, optionally substituted with 1, 2, or 3 $R^9$. In some embodiments, $R^5$, $R^{4a}$ and $R^{4b}$ together with the carbon atom to which they are attached form a 9- or 10-membered heteroaryl ring, optionally substituted with 1, 2, or 3 $R^9$. In some embodiments, $R^5$, $R^{4a}$ and $R^{4b}$ together with the carbon atom to which they are attached form a 10-membered heteroaryl ring. In some embodiments, $R^5$, $R^{4a}$ and $R^{4b}$ together with the carbon atom to which they are attached form a quinoline, isoquinoline, quinoxaline, quinazoline, quinolizine, naphthyridine. In some embodiments, $R^5$, $R^{4a}$ and $R^{4b}$ together with the carbon atom to which they are attached form a 9-membered heteroaryl ring. In some embodiments, $R^5$, $R^{4a}$ and $R^{4b}$ together with the carbon atom to which they are attached form a 2,3-dihydrobenzo[d]oxazole, benzo[d]oxazole, oxazolo[4,5-b]pyridine, 1H-benzo[d]imidazole, benzo[d]thiazole, benzofuran, indole, aza-indole, 1H-imidazo[4,5-b]pyridine, indolizine, imidazo[1,2-a]pyridine, or an isomer thereof, optionally substituted with 1, 2, or 3 $R^9$. In some embodiments, $R^5$, $R^{4a}$ and $R^{4b}$ together with the carbon atom to which they are attached form a benzo[d]oxazole, optionally substituted with 1, 2, or 3 $R^9$. In some embodiments, the $C_6$-$C_{10}$aryl or 5- to 10-membered heteroaryl ring is unsubstituted.

In some embodiments, $R^5$ is $NHR^8$, $NHS(O)_2R^8$, $OR^8$, $SR^8$, $S(O)_2R^8$, or $S(O)_2NHR^8$. In some embodiments, $R^5$ is $NHR^8$, $NHS(O)_2R^8$, $OR^8$, or $S(O)_2NHR^8$. In some embodiments, R is $NHR^B$, $NHS(O)_2R^8$, or $OR^8$. In some embodiments, $R^5$ is $OR^8$. In some embodiments, $R^5$ is $NHR^8$, or $NHS(O)_2R^8$. In some embodiments, $R^5$ is $NHS(O)_2R^8$. In some embodiments, R is $NHR^8$.

In some embodiments of a compound of Formula (A-I), a compound has one of the following formulae:

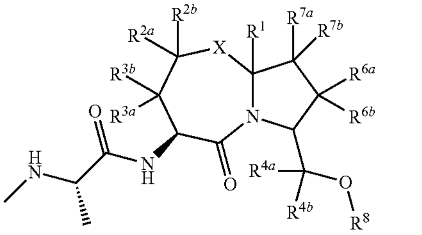

or

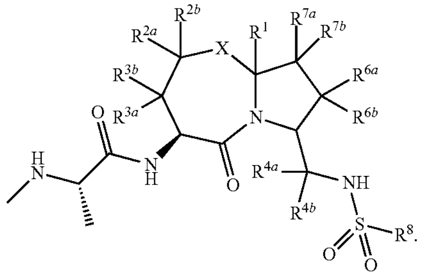

In some embodiments of a compound of Formula (A-I), a compound has the structure of Formula (A-II):

Formula (A-II)

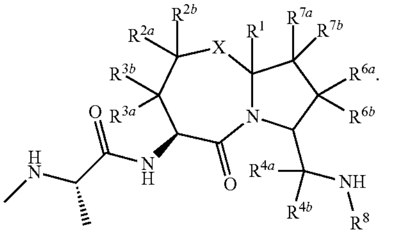

In some embodiments, $R^{4a}$ is H. In some embodiments, $R^{4a}$ is H and $R^{4b}$ is halogen or haloalkyl. In some embodiments, $R^{4b}$ is $CHF_2$ or $CF_3$. In some embodiments, $R^{4a}$ is H and $R^{4b}$ is difluoromethyl or trifluoromethyl. In some embodiments, $R^{4b}$ is difluoromethyl or trifluoromethyl and $R^5$ is $OR^8$. In some embodiments, $R^{4a}$ and $R^{4b}$ are both H.

In some embodiments, $R^{4a}$ and $R^{4b}$ together with the carbon atom to which they are attached form a $C_3$-$C_{10}$cycloalkyl or 3- to 10-membered heterocycloalkyl ring, wherein either of the cycloalkyl or heterocycloalkyl ring is optionally substituted with 1, 2, or 3 $R^9$. In some embodiments, $R^{4a}$ and $R^{4b}$ together with the carbon atom to which they are attached form a $C_3$-$C_6$cycloalkyl, optionally substituted with 1, 2, or 3 $R^9$. In some embodiments, $R^{4a}$ and $R^{4b}$ together with the carbon atom to which they are attached form a $C_3$-$C_5$cycloalkyl, optionally substituted with 1, 2, or 3 $R^9$. In some embodiments, $R^{4a}$ and $R^{4b}$ together with the carbon atom to which they are attached form a cyclopropyl, cyclobutyl, or cyclopentyl ring, optionally substituted with 1, 2, or 3 $R^9$. In some embodiments, $R^{4a}$ and $R^{4b}$ together with the carbon atom to which they are attached form a cyclopropyl, cyclobutyl, or cyclopentyl ring and R is —$OR^8$ or —$NHR^B$. In some embodiments, $R^{4a}$ and $R^{4b}$ are each independently halogen, $C_1$-$C_6$alkyl, $C_1$-$C_6$haloalkyl, $C_1$-$C_6$ alkoxy, or $C_1$-$C_6$heteroalkyl and $R^5$ is $NHR^B$.

In some embodiments, $R^{4a}$ and $R^{4b}$ together with the carbon atom to which they are attached form a carbonyl. In some embodiments, $R^{4a}$ and $R^{4b}$ together with the carbon atom to which they are attached form a carbonyl and $R^5$ is $OR^8$ or $NHR^B$. In some embodiments, $R^{4a}$ and $R^{4b}$ together with the carbon atom to which they are attached form a carbonyl and $R^5$ is $NHR^B$.

In some embodiments, $R^1$ is hydrogen, $C_1$-$C_6$alkyl, $C_3$-$C_6$cycloalkyl, $C_1$-$C_6$alkyl-($C_3$-$C_6$cycloalkyl), wherein each alkyl is optionally substituted with 1, 2, or 3 $R^9$. In some embodiments, $R^1$ is phenethyl. In some embodiments, $R^1$ is hydrogen, methyl, trifluoromethyl, difluoromethyl, fluoromethyl, ethyl, propyl, isopropyl, cyclopropyl, methylenecyclopropyl, or cyclobutyl. In some embodiments, $R^1$ is phenethyl. In some embodiments, $R^1$ is hydrogen, methyl, trifluoromethyl, difluoromethyl, fluoromethyl, or ethyl. In some embodiments, $R^1$ is hydrogen or methyl. In some embodiments, $R^1$ is hydrogen.

In some embodiments of a compound of Formula (A-I), a compound has the structure of Formula (A-III):

Formula (A-III)

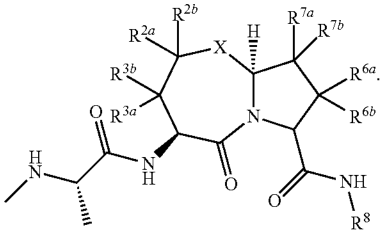

In some embodiments, $R^{2a}$ and $R^{2b}$ are each independently hydrogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, wherein each alkyl, haloalkyl, alkoxy, heteroalkyl, alkenyl, or alkynyl is optionally substituted with 1, 2, or 3 $R^9$. In some embodiments, $R^{2a}$ and $R^{2b}$ are each independently $C_3$-$C_{10}$cycloalkyl, 3- to 10-membered heterocycloalkyl, $C_6$-$C_{10}$aryl, or 5- to 10-membered heteroaryl, wherein each cycloalkyl, heterocycloalkyl, aryl, or heteroaryl is optionally substituted with 1, 2, or 3 $R^9$. In some embodiments, $R^{2a}$ and $R^{2b}$ are each independently hydrogen, $C_1$-$C_6$alkyl, $C_1$-$C_6$haloalkyl, $C_1$-$C_6$ alkoxy, $C_1$-$C_6$heteroalkyl, wherein each alkyl, haloalkyl, alkoxy, or heteroalkyl is optionally substituted with 1 or 2 $C_3$-$C_6$cycloalkyl, 3- to 6-membered heterocycloalkyl, phenyl, or 5- or 6-membered heteroaryl. In some embodiments, $R^{2a}$ is H and $R^{2b}$ is $C_1$-$C_6$alkyl or $C_1$-$C_6$heteroalkyl, wherein each alkyl or heteroalkyl is optionally substituted with a phenyl, or 5- or 6-membered heteroaryl. In some embodiments, $R^{2b}$ is

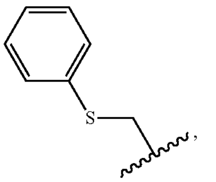

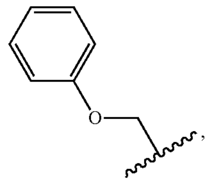

or

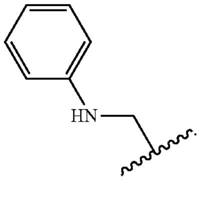

In some embodiments, $R^{2a}$ is hydrogen. In some embodiments, $R^{2a}$ and $R^{2b}$ are each hydrogen.

In some embodiments, $R^{2a}$ and $R^{3a}$, and optionally $R^{2b}$ and $R^{3b}$, together with the carbon atoms to which they are attached form a $C_3$-$C_6$cycloalkyl, 5- to 10-membered heterocycloalkyl, $C_6$-$C_{10}$aryl, or 5- to 10-membered heteroaryl ring; wherein each $C_3$-$C_6$cycloalkyl, 5- to 10-membered heterocycloalkyl, $C_6$-$C_{10}$aryl, or 5- to 10-membered heteroaryl ring is optionally substituted with 1, 2, or 3 $R^9$;

In some embodiments, $R^{2a}$ and $R^{2b}$ together with the atom to which they are attached form a carbonyl. In some embodiments, $R^{2a}$ and $R^{2b}$ together with the atom to which they are attached form a carbonyl and X is NH. In some embodiments, $R^{2a}$ and $R^{2b}$ together with the atom to which they are attached form a carbonyl and X is O.

In some embodiments, $R^{3a}$ and $R^{3b}$ are each independently hydrogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl, any of which is optionally substituted with 1, 2, or 3 $R^9$. In some embodiments, $R^{3a}$ and $R^{3b}$ are each independently hydrogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, or $C_2$-$C_6$alkynyl, wherein each alkyl, haloalkyl, alkoxy, heteroalkyl, alkenyl, or alkynyl is optionally substituted with a cyclopropyl, phenyl, or 5- or 6-membered heteroaryl. In some embodiments, $R^{3a}$ and $R^{3b}$ are each independently hydrogen, methyl, trifluoromethyl, difluoromethyl, ethyl, propyl, isopropyl, cyclopropyl, benzyl, phenethyl, or isobutyl. In some embodiments, $R^{3a}$ and $R^{3b}$ are each methyl. In some embodiments, $R^{3a}$ is hydrogen. In some embodiments, $R^{3a}$ and $R^{3b}$ are each hydrogen.

In some embodiments, $R^{2a}$ and $R^{3a}$, together with the carbon atoms to which they are attached, form a $C_3$-$C_6$cycloalkyl, or 5- to 10-membered heterocycloalkyl. In some embodiments, $R^{2a}$ and $R^{3a}$, together with the carbon atoms to which they are attached, form a cyclopropyl, cyclobutyl, cyclopentyl, cyclohexyl, oxirane, oxetane, tetrahydrofuran, tetrahydropyran, dioxane, aziridine, azetidine, pyrrolidine, piperidine, or morpholine, each of which is optionally substituted with 1 $R^9$. In some embodiments, $R^{2a}$ and $R^{3a}$, together with the carbon atoms to which they are attached, form a cyclopropyl, cyclohexyl, dioxane, piperidine, or morpholine, each of which is optionally substituted with 1 $R^9$. In some embodiments, $R^{2a}$ and $R^{3a}$ together with the carbon atoms to which they are attached form a $C_3$-$C_6$cycloalkyl, optionally substituted with 1, 2, or 3 $R^9$. In some embodiments, $R^{2a}$ and $R^{3a}$, together with the carbon atoms to which they are attached, form a cyclopropyl or cyclohexyl, either of which is optionally substituted with 1, 2, or 3 $R^9$. In some embodiments, $R^{2a}$ and $R^{3a}$, together with the carbon atoms to which they are attached, form a cyclohexyl.

In some embodiments, X is $NR^4$, O, S, S(O), or $S(O)_2$. In some embodiments, X is O. some embodiments, X is S or $S(O)_2$. In some embodiments, X is S. In some embodiments, X is $S(O)_2$. In some embodiments, X is $NR^4$. In some embodiments, $R^4$ is $C_1$-$C_6$alkyl, C(O)—($C_1$-$C_6$alkyl), or C(O)—($C_3$-$C_6$cycloalkyl), wherein each alkyl or cycloalkyl is optionally substituted with 1, 2, or 3 $R^9$. In some embodiments, $R^4$ is hydrogen, methyl, ethyl, $C(O)CH_3$, C(O)cyclopropyl, or C(O)cyclohexyl, wherein each cyclopropyl or cyclohexyl is optionally substituted with 1 or 2 $R^9$. In some embodiments, $R^4$ is hydrogen, methyl, or $C(O)CH_3$. In some embodiments, $R^4$ is hydrogen. In some embodiments of a compound of Formula (A-I), a compound has the structure of Formula (A-IV-a), (A-IV-b), (A-IV-c), or (A-IV-d):

Formula (A-IV-a)

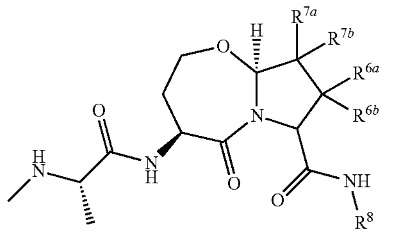

Formula (A-IV-b)

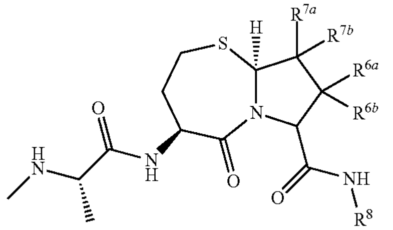

Formula (A-IV-c)

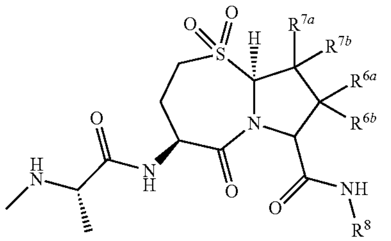

or

Formula (A-IV-d)

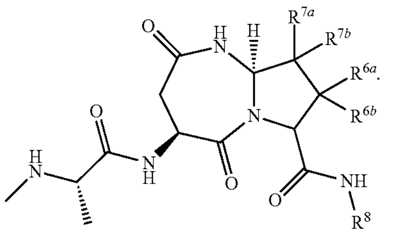

In some embodiments of a compound of Formula (A-I), a compound has the structure of Formula (A-V-a), (A-V-b), (A-V-c), or (A-V-d):

Formula (A-V-a)

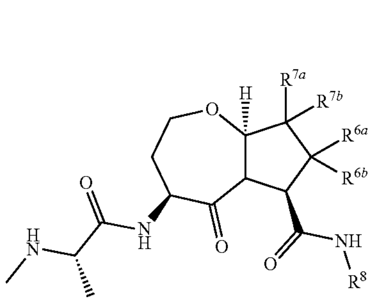

-continued

Formula (A-V-b)

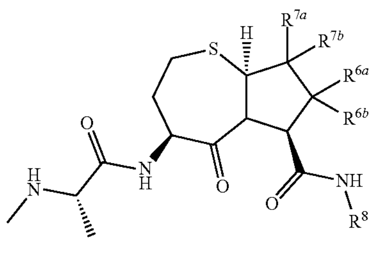

Formula (A-V-c)

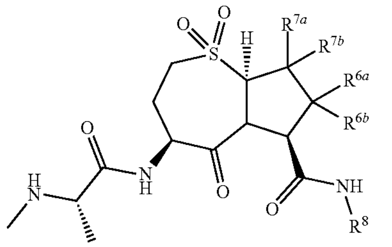

or

Formula (A-V-d)

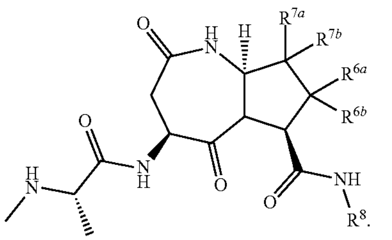

In some embodiments of a compound of Formula (A-I), a compound has the structure of Formula (A-VI-a), (A-VI-b), (A-VI-c), or (A-VI-d):

Formula (A-VI-a)

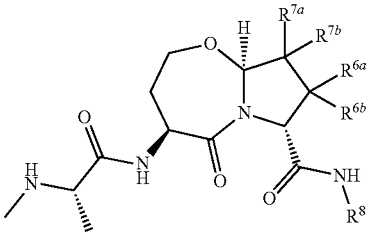

Formula (A-VI-b)

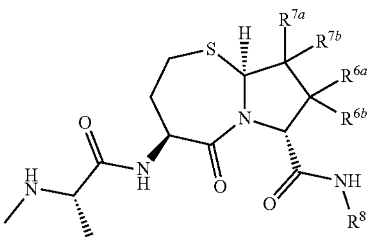

-continued

Formula (A-VI-c)

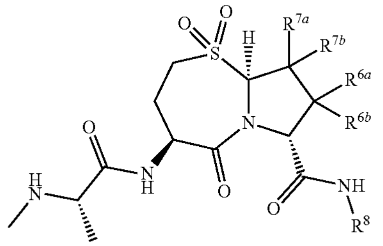

or

Formula (A-VI-d)

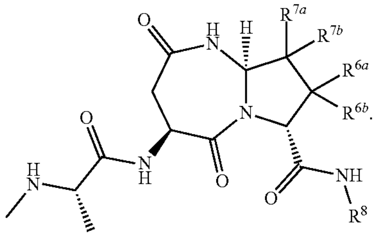

In some embodiments, X is C and taken together with $R^{2a}$, $R^{2b}$, and the carbon atom to which they are attached, forms a phenyl or 5- to 10-membered heteroaryl ring, optionally substituted with 1, 2, or 3 $R^9$. In some embodiments, X is C and taken together with $R^{2a}$, $R^{2b}$, and the carbon atom to which they are attached, forms a phenyl ring, optionally substituted with 1, 2, or 3 $R^9$. In some embodiments, X is C and taken together with $R^{2a}$, $R^{2b}$, and the carbon atom to which they are attached, forms a 5- to 10-membered heteroaryl ring, optionally substituted with 1, 2, or 3 $R^9$. In some embodiments, X is C and taken together with $R^{2a}$, $R^{2b}$, and the carbon atom to which they are attached, forms a 5-membered heteroaryl ring, optionally substituted with 1, 2, or 3 $R^9$. In some embodiments, X is C and taken together with $R^{2a}$, $R^{2b}$, and the carbon atom to which they are attached, forms a 9- or 10-membered heteroaryl ring, optionally substituted with 1, 2, or 3 $R^9$. In some embodiments, X is C and taken together with $R^{2a}$, $R^{2b}$, and the carbon atom to which they are attached, forms a pyrrole, pyrazole, imidazole, indole, or azaindole ring, optionally substituted with 1, 2, or 3 $R^9$. In some embodiments of a compound of Formula (A-I), a compound has the structure of one of the following:

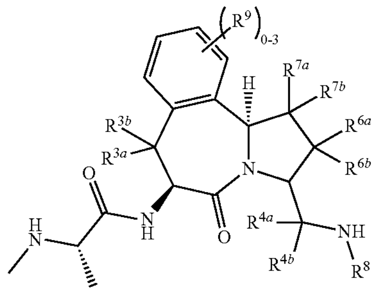

or

-continued

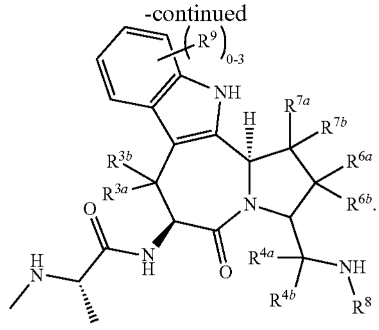

In some embodiments of a compound of Formula (A-I), $R^{6a}$, $R^{6b}$, $R^{7a}$, and $R^{7b}$ together with the carbon atoms to which they are attached form a 5- to 10-membered heteroaryl ring optionally substituted with 1, 2, or 3 $R^9$. In some embodiments of a compound of Formula (A-I), $R^{6a}$, $R^{6b}$, $R^{7a}$, and $R^{7b}$ together with the carbon atoms to which they are attached form a furan, pyrrole, imidazole, pyrazole, triazole, pyridine, pyrimidine, pyridazine, pyrazine, thiophene, oxazole, thiazole, isoxazole, isothiazole, oxepin, azepine, thiepine, triazine, or tetrazine, any of which being optionally substituted with 1, 2, or 3 $R^9$. In some embodiments of a compound of Formula (A-I), $R^{6a}$, $R^{6b}$, $R^{7a}$, and $R^{7b}$ together with the carbon atoms to which they are attached form a furan, pyrrole, imidazole, pyrazole, pyridine, pyrimidine, pyridazine, pyrazine, any of which being optionally substituted with 1, 2, or 3 $R^9$. In some embodiments of a compound of Formula (A-I), $R^{6a}$, $R^{6b}$, $R^{7a}$, and $R^{7b}$ together with the carbon atoms to which they are attached form a furan, pyrrole, pyridine, pyrimidine, pyridazine, pyrazine, any of which being optionally substituted with 1, 2, or 3 $R^9$. In some embodiments of a compound of Formula (A-I), $R^{6a}$, $R^{6b}$, $R^{7a}$, and $R^{7b}$ together with the carbon atoms to which they are attached form a pyridine ring.

In some embodiments of a compound of Formula (A-I), $R^{6b}$ and $R^{7b}$ together with the carbon atoms to which they are attached form a $C_3$-$C_{10}$cycloalkyl or 3- to 10-membered heterocycloalkyl ring; wherein each $C_3$-$C_{10}$cycloalkyl or 3- to 10-membered heterocycloalkyl ring is optionally substituted with 1, 2, or 3 $R^9$. In some embodiments of a compound of Formula (A-I), $R^{6b}$ and $R^{7b}$ together with the carbon atoms to which they are attached form a $C_3$-$C_6$cycloalkyl or 3- to 6-membered heterocycloalkyl ring; wherein each $C_3$-$C_6$cycloalkyl or 3- to 6-membered heterocycloalkyl ring is optionally substituted with 1, 2, or 3 $R^9$. In some embodiments of a compound of Formula (A-I), $R^{6b}$ and $R^{7b}$ together with the carbon atoms to which they are attached form a cyclopropyl, cyclobutyl, cyclopentyl, cyclohexyl, oxirane, aziridine, oxetane, azetidine, oxolane, pyrrolidine, thiolane, oxazolidine, imidazolidine, thiazolidine, isoxazolidine, pyrazolidine, isothiazolidine, dioxolane, dithiolane, oxane, piperidine, thiolane, morpholine, piperazine, thiazine, or dioxane ring, wherein each ring is optionally substituted with 1, 2, or 3 $R^9$. In some embodiments of a compound of Formula (A-I), $R^{6b}$ and $R^{7b}$ together with the carbon atoms to which they are attached form a cyclopropyl, cyclobutyl, cyclopentyl, cyclohexyl, oxolane, oxane, dioxane, morpholine, pyrrolidine, or piperidine ring.

In some embodiments of a compound of Formula (A-I), $R^{7a}$ and $R^{7b}$ together with the carbon atom to which they are attached form a saturated or partially saturated 3- to 7-membered cycloalkyl or a saturated or partially saturated 3- to 7-membered heterocycloalkyl; wherein the cycloalkyl or heterocycloalkyl is optionally substituted with 1, 2, or 3 $R^9$. In some embodiments of a compound of Formula (A-I), $R^{7a}$ and $R^{7b}$ together with the carbon atom to which they are attached form a saturated or partially saturated 3- to 5-membered cycloalkyl or a saturated or partially saturated 3- to 5-membered heterocycloalkyl; wherein the cycloalkyl or heterocycloalkyl is optionally substituted with 1, 2, or 3 $R^9$. In some embodiments of a compound of Formula (A-I), $R^{7a}$ and $R^{7b}$ together with the carbon atom to which they are attached form a cyclopropyl, cyclobutyl, cyclopropenyl, cyclobutenyl, oxirane, aziridine, oxetane, azetidine, cyclopentyl, or cyclopentenyl ring, wherein each ring is optionally substituted with 1, 2, or 3 $R^9$. In some embodiments of a compound of Formula (A-I), $R^{7a}$ and $R^{7b}$ together with the carbon atom to which they are attached form a cyclopropyl ring, optionally substituted with 1, 2, or 3 $R^9$. In some embodiments of a compound of Formula (A-I), $R^{7a}$ and $R^{7b}$ are each independently hydrogen, halogen, $C_1$-$C_4$alkyl, or $C_1$-$C_4$haloalkyl. In some embodiments of a compound of Formula (A-I), $R^{7a}$ and $R^{7b}$ are each independently hydrogen, fluoro, methyl, ethyl, difluoromethyl, or trifluoromethyl. In some embodiments of a compound of Formula (A-I), $R^{7a}$ and $R^{7b}$ are each independently hydrogen, methyl, or ethyl. In some embodiments, $R^{7a}$ and $R^{7b}$ are both hydrogen.

In some embodiments of a compound of Formula (A-I), $R^{6a}$ and $R^{6b}$ together with the carbon atom to which they are attached form a saturated or partially saturated 3- to 7-membered cycloalkyl ring optionally substituted with 1, 2, or 3 $R^9$. In some embodiments of a compound of Formula (A-I), $R^{6a}$ and $R^{6b}$ together with the carbon atom to which they are attached form a cyclopropyl, cyclobutyl, cyclopropenyl, cyclobutenyl, oxirane, aziridine, oxetane, azetidine, or cyclopentyl, or cyclopentenyl ring, wherein each ring is optionally substituted with 1, 2, or 3 $R^9$. In some embodiments of a compound of Formula (A-I), $R^{6a}$ and $R^{6b}$ together with the carbon atom to which they are attached form a saturated or partially saturated 3- to 5-membered cycloalkyl ring, optionally substituted with 1, 2, or 3 $R^9$.

In some embodiments of a compound of Formula (A-I), $R^{6a}$ is hydrogen. In some embodiments of a compound of Formula (A-I), $R^{6a}$ is hydrogen and $R^{6b}$ is halogen, $C_1$-$C_6$alkyl, $C_1$-$C_6$haloalkyl, $C_2$-$C_6$alkenyl, or $C_2$-$C_6$alkynyl; wherein each $C_1$-$C_6$alkyl, $C_1$-$C_6$haloalkyl, $C_2$-$C_6$alkenyl, or $C_2$-$C_6$alkynyl is optionally substituted with 1, 2, or 3 $R^9$ and/or 1 or 2, G. In some embodiments of a compound of Formula (A-I), $R^{6b}$ is halogen, $C_1$-$C_6$alkyl, $C_1$-$C_6$haloalkyl, $C_2$-$C_6$alkenyl, or $C_2$-$C_6$alkynyl; wherein each $C_1$-$C_6$alkyl, $C_1$-$C_6$haloalkyl, $C_2$-$C_6$alkenyl, or $C_2$-$C_6$alkynyl is optionally substituted with 1, 2, or 3 $R^9$ and/or 1 or 2, G. In some embodiments of a compound of Formula (A-I), $R^{6b}$ is $C_1$-$C_6$alkyl, $C_1$-$C_6$haloalkyl, $C_2$-$C_6$alkenyl, or $C_2$-$C_6$alkynyl, wherein each alkyl, haloalkyl, alkenyl, or alkynyl is optionally substituted with a phenyl or 5- or 6-membered heteroaryl ring, wherein each phenyl or heteroaryl ring is optionally substituted with 1, 2, or 3 $R^9$. In some embodiments of a compound of Formula (A-I), $R^{6b}$ is methyl, ethyl, or propyl, wherein the methyl, ethyl, or propyl is optionally substituted with G, and wherein G is a phenyl ring further substituted with 1, 2, or 3 $R^9$. In some embodiments of a compound of Formula (A-I), $R^{6b}$ is ethyl, optionally substituted with phenyl, tolyl, phenolyl, fluorophenyl, chlorophenyl, anilinyl, methoxyphenyl, dimethylphenyl, difluorophenyl, dichlorophenyl, dihydroxyphenyl, dimethoxyphenyl, fluoromethoxyphenyl, or naphthyl. In some embodiments of a compound of Formula (A-I), $R^{6b}$ is $C_1$-$C_6$alkyl, $C_1$-$C_6$haloalkyl, $C_2$-$C_6$alkenyl, or $C_2$-$C_6$alkynyl, wherein each alkyl, haloalkyl, alkenyl, or alkynyl is optionally substituted with a $C_3$-$C_6$cycloalkyl or 3- to 6-membered heterocycloalkyl ring, wherein each cycloalkyl or heterocyclalkyl ring is optionally substituted with 1, 2, or 3 $R^9$. In some embodiments of a compound of Formula (A-I), $R^{6b}$ is methyl, ethyl, 2-propenyl, isopropyl, or phenethyl. In some embodiments of a compound of Formula (A-I), $R^{6b}$ is methyl. In some embodiments, $R^{6b}$ is ethyl. In some embodiments, $R^{6b}$ is 2-propenyl. In some embodiments, $R^{6b}$ is isopropyl. In some embodiments, $R^{6b}$ is phenethyl.

In some embodiments of a compound of Formula (A-I), $R^{6a}$ and $R^{6b}$ are each independently halogen, $C_1$-$C_6$alkyl, $C_1$-$C_6$haloalkyl, $C_2$-$C_6$alkenyl, or $C_2$-$C_6$alkynyl; wherein each $C_1$-$C_6$alkyl, $C_1$-$C_6$haloalkyl, $C_2$-$C_6$alkenyl, or $C_2$-$C_6$alkynyl is optionally substituted with 1, 2, or 3 $R^9$ and/or 1 or 2, G. In some embodiments, $R^{6a}$ and $R^{6b}$ are each independently halogen, $C_2$-$C_6$alkyl, $C_1$-$C_6$haloalkyl, $C_2$-$C_6$alkenyl, or $C_2$-$C_6$alkynyl; wherein each $C_2$-$C_6$alkyl, $C_1$-$C_6$haloalkyl, $C_2$-$C_6$alkenyl, or $C_2$-$C_6$alkynyl is optionally substituted with 1, 2, or 3 $R^9$ and/or 1 or 2, G. In some embodiments of a compound of Formula (A-I), $R^{6a}$ and $R^{6b}$ are each independently $C_1$-$C_6$alkyl, $C_1$-$C_6$haloalkyl, $C_2$-$C_6$alkenyl, or $C_2$-$C_6$alkynyl, wherein each alkyl, haloalkyl, alkenyl, or alkynyl is optionally substituted with a phenyl or 5- or 6-membered heteroaryl ring, wherein each phenyl or heteroaryl ring is optionally substituted with 1, 2, or 3 $R^9$. In some embodiments of a compound of Formula (A-I), $R^{6a}$ and $R^{6b}$ are each independently methyl, ethyl, or propyl, optionally substituted with G, wherein G is a phenyl ring further substituted with 1, 2, or 3 $R^9$. In some embodiments, $R^{6a}$ and $R^{6b}$ are each independently ethyl, optionally substituted with phenyl, tolyl, phenolyl, fluorophenyl, chlorophenyl, anilinyl, methoxyphenyl, dimethylphenyl, difluorophenyl, dichlorophenyl, dihydroxyphenyl, dimethoxyphenyl, fluoromethoxyphenyl, or naphthyl. In some embodiments of a compound of Formula (A-I), $R^{6a}$ and $R^{6b}$ are each independently $C_1$-$C_6$alkyl, $C_1$-$C_6$haloalkyl, $C_2$-$C_6$alkenyl, or $C_2$-$C_6$alkynyl, wherein each alkyl, haloalkyl, alkenyl, or alkynyl is optionally substituted with a $C_3$-$C_6$cycloalkyl or 3- to 6-membered heterocycloalkyl ring, wherein each cycloalkyl or heterocycloalkyl ring is optionally substituted with 1, 2, or 3 $R^9$. In some embodiments of a compound of Formula (A-I), $R^{6a}$ and $R^{6b}$ are each independently methyl, ethyl, 2-propenyl, isopropyl, or phenethyl. In some embodiments, $R^{6a}$ and $R^{6b}$ are each independently ethyl, 2-propenyl, isopropyl, or phenethyl. In some embodiments of a compound of Formula (A-I), $R^{6a}$ and $R^{6b}$ are methyl provided that when $R^{6a}$ and $R^{6b}$ are both methyl, then $R^8$ is not

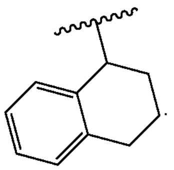 [SMILES: *C1CCCc2ccccc21]

In some embodiments of a compound of Formula (A-I), $R^{6a}$ and $R^{6b}$ are methyl. In some embodiments, $R^{6a}$ and $R^{6b}$ are ethyl. In some embodiments, $R^{6a}$ and $R^{6b}$ are 2-propenyl. In some embodiments, $R^{6a}$ and $R^{6b}$ are isopropyl. In some embodiments, $R^{6a}$ and $R^{6b}$ are phenethyl.

In some embodiments of a compound of Formula (A-I), $R^8$ is Z, $C_2$-$C_6$alkyl, ($C_1$-$C_6$alkylene)-Z, ($C_1$-

$C_6$heteroalkylene)-Z, ($C_2$-$C_6$alkenylene)-Z, $CH(Z)_2$, $CH_2CH(Z)_2$, $CH(C_1$-$C_6alkyl)Z$, or C(O)Z; wherein each alkyl, alkylene, heteroalkylene, or alkenylene is optionally substituted with 1, 2, or 3 $R^9$. In some embodiments of a compound of Formula (A-I), $R^8$ is Z, $C_2$-$C_6$alkyl, $CH(Z)_2$, or C(O)Z. In some embodiments of a compound of Formula (A-I), $R^8$ is Z, $C_2$-$C_6$alkyl, $CH(Z)_2$, or C(O)Z, wherein Z is $C_3$-$C_{10}$cycloalkyl, 3- to 10-membered heterocycloalkyl, $C_6$-$C_{10}$aryl, or 5- to 10-membered heteroaryl. In some embodiments of a compound of Formula (A-I), $R^1$ is Z or $CH(Z)_2$. In some embodiments of a compound of Formula (A-I), R is Z. In some embodiments of a compound of Formula (A-I), $R^8$ is $CH(Z)_2$. In some embodiments of a compound of Formula (A-I), Z is $C_3$-$C_{10}$cycloalkyl, 3- to 10-membered heterocycloalkyl, $C_6$-$C_{10}$aryl, or 5- to 10-membered heteroaryl; wherein each $C_3$-$C_{10}$cycloalkyl, 3- to 10-membered heterocycloalkyl, $C_6$-$C_{10}$aryl, and 5- to 10-membered heteroaryl is optionally substituted with 1, 2, or 3 $R^9$. In some embodiments of a compound of Formula (A-I), Z is $C_6$-$C_{10}$aryl or 5- to 10-membered heteroaryl, wherein each aryl or heteroaryl is optionally substituted with 1, 2, or 3 $R^9$. In some embodiments of a compound of Formula (A-I), Z is $C_3$-$C_{10}$cycloalkyl or 3- to 10-membered heterocycloalkyl; wherein each $C_3$-$C_{10}$cycloalkyl and 3- to 10-membered heterocycloalkyl is optionally substituted with 1, 2, or 3 $R^9$. In some embodiments of a compound of Formula (A-I), Z is $C_3$-$C_{10}$cycloalkyl optionally substituted with 1, 2, or 3 $R^9$. In some embodiments of a compound of Formula (A-I), Z is phenyl or naphthyl, optionally substituted with 1, 2, or 3 $R^9$. In some embodiments of a compound of Formula (A-I), Z is pyridine, pyrimidine, pyridazine, pyrazine, quinoline, naphthyridine, quinoxaline, quinolizine, benzofuran, benzoxazole, or benzothiophene. In some embodiments, Z is tetrahydronaphthalene, tetrahydroquinoline, tetrahydroisoquinoline, chroman, thiochroman, indane, indoline, dihydrobenzofuran, or dihydrobenzothiophene.

In some embodiments of a compound of Formula (A-I), $R^8$ is:

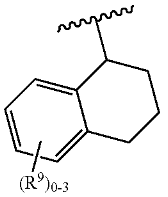,
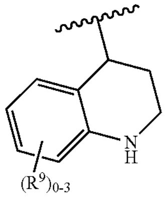,
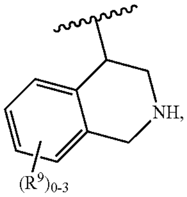,
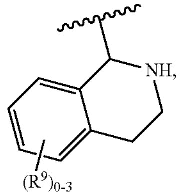,
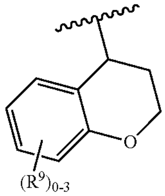,
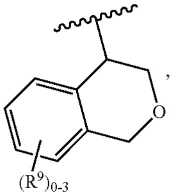,
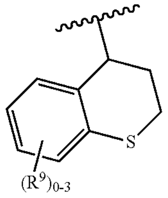,
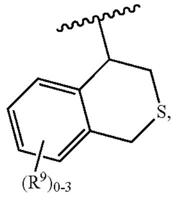,
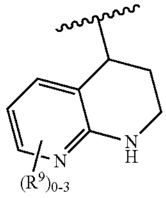, -continued
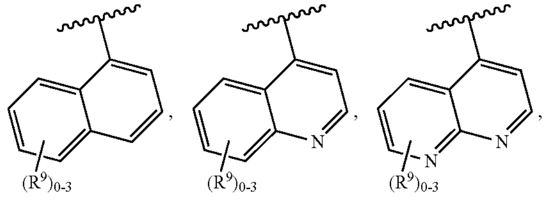
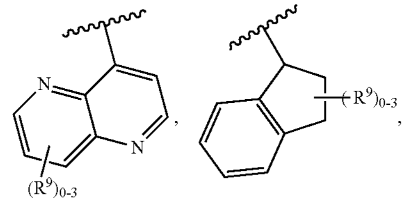
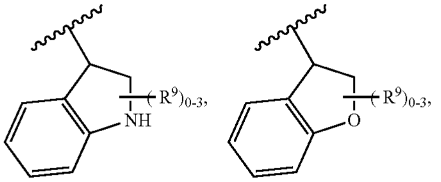
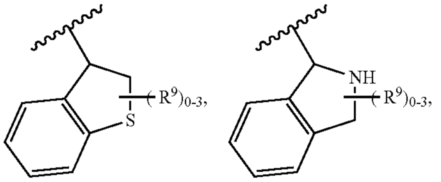
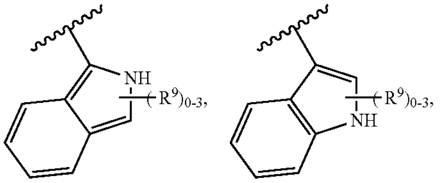
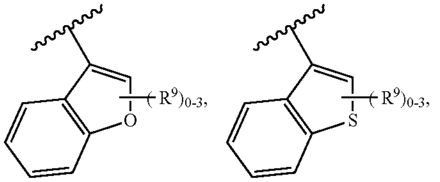
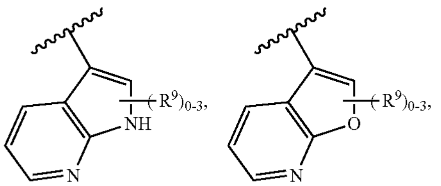
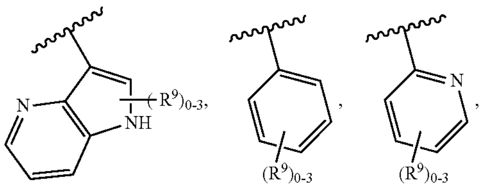
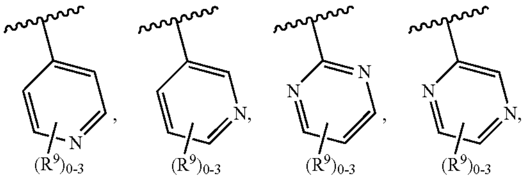
-continued
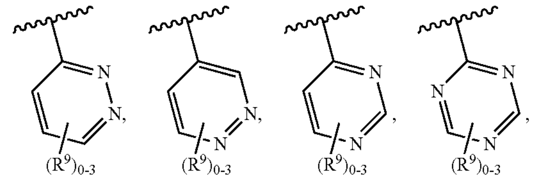
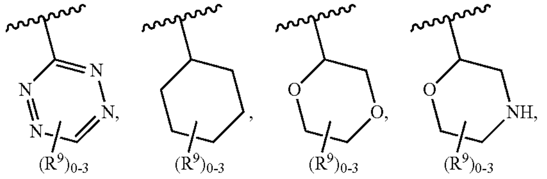
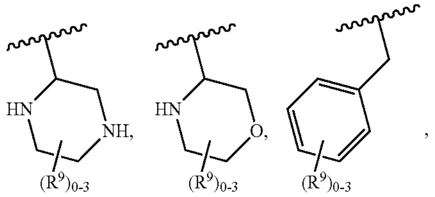
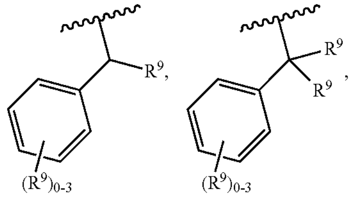
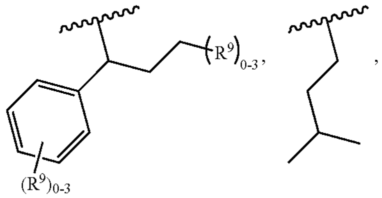
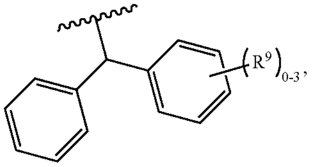
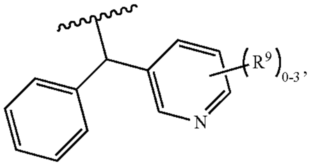
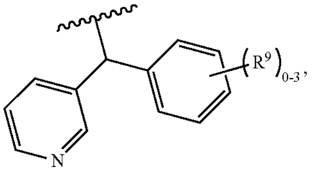
or
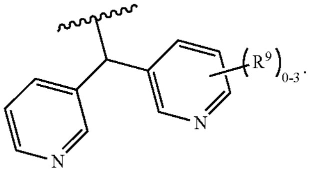
In some embodiments of a compound of Formula (A-I), $R^8$ is:

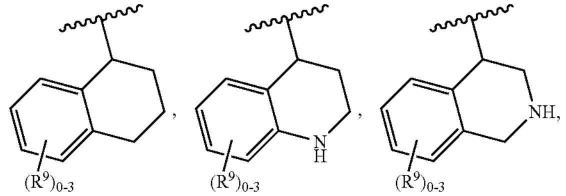
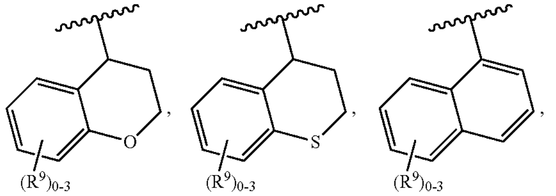
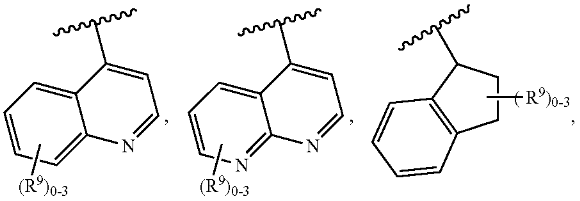
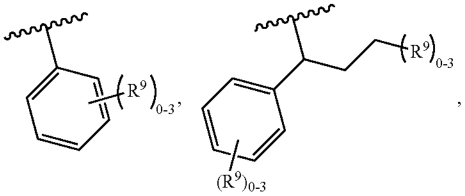
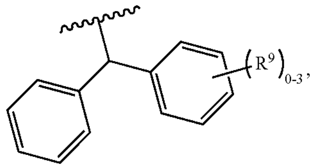
or
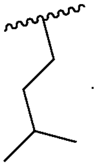
In some embodiments of a compound of Formula (A-I), $R^8$ is:
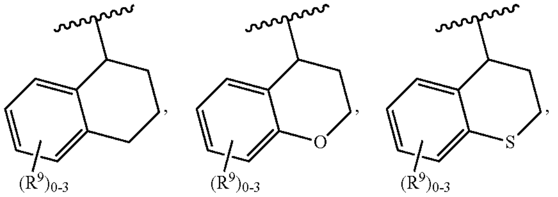
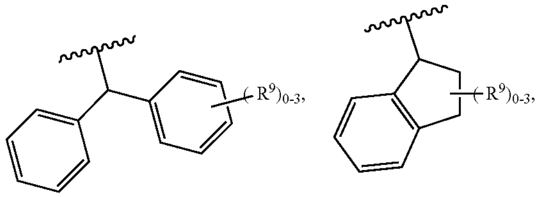
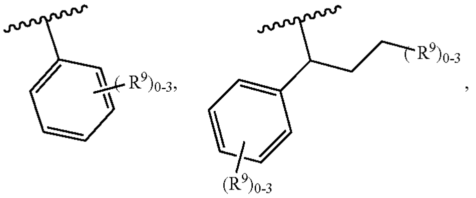
or
-continued
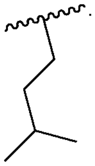
In some embodiments of a compound of Formula (A-I), $R^8$ is:
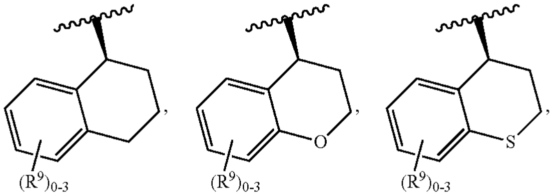
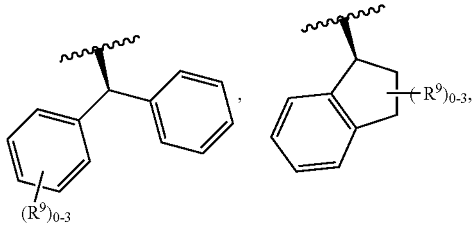
or
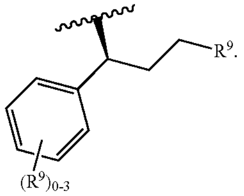
In some embodiments of a compound of Formula (A-I), $R^8$ is:
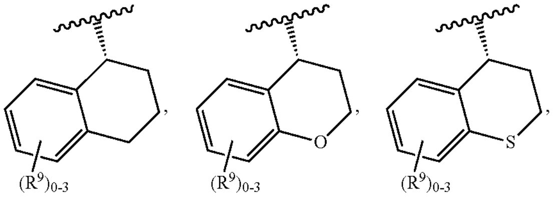
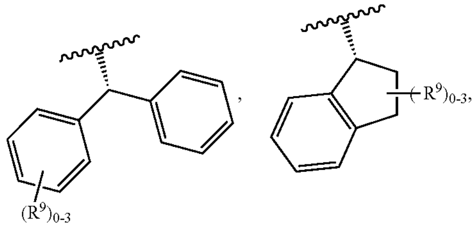
or
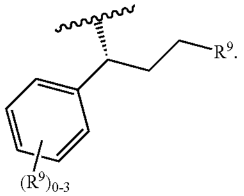

In some embodiments of a compound of Formula (A-I), $R^8$ is:
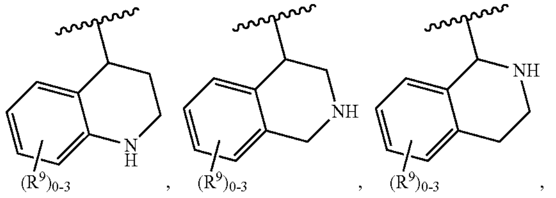
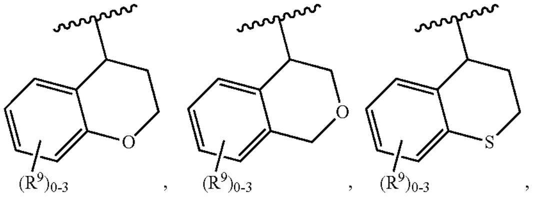
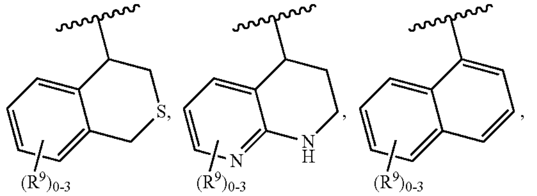
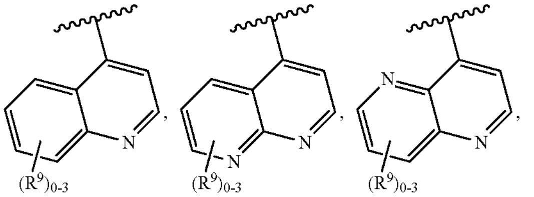
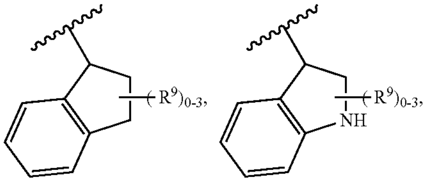
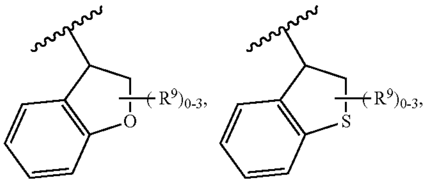
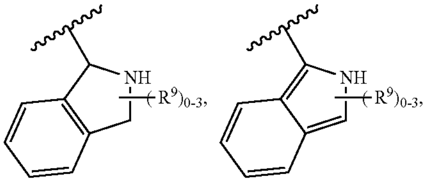
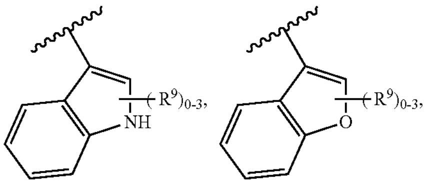
-continued
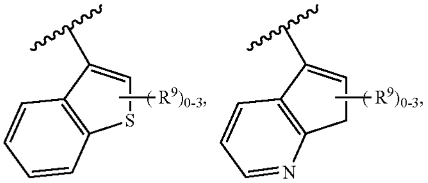
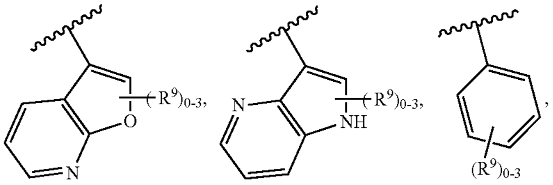
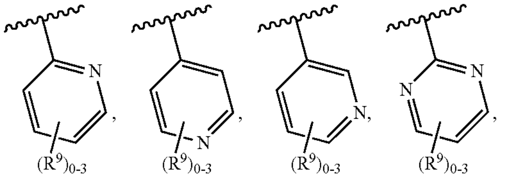
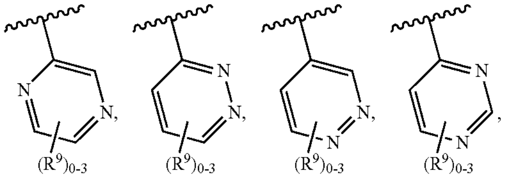
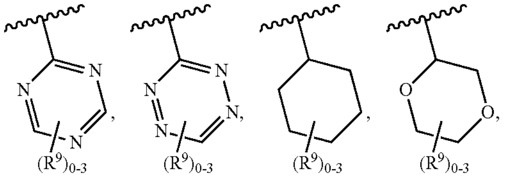
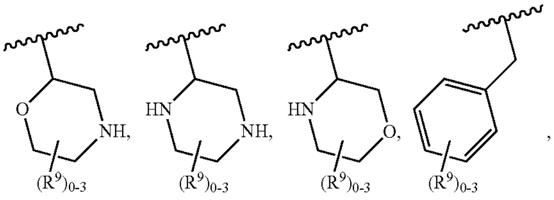
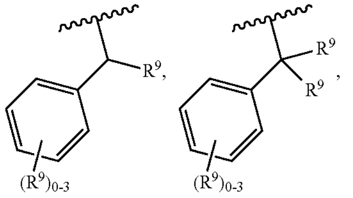
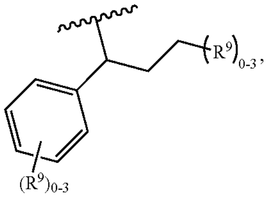
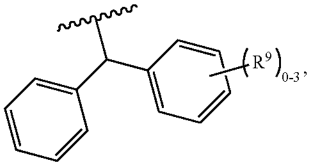

-continued
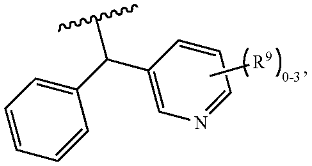
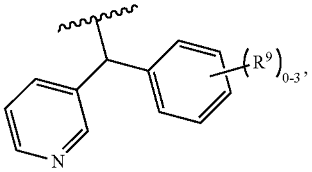
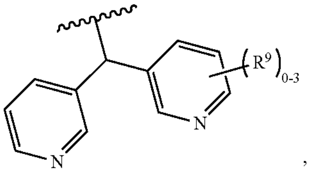
, or
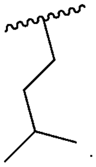
.
In some embodiments of a compound of Formula (A-I), $R^8$ is:
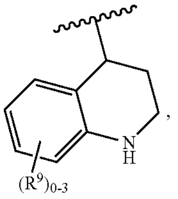
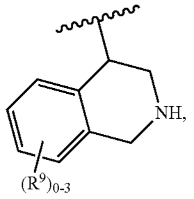
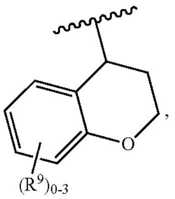
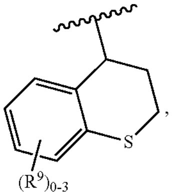
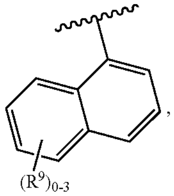
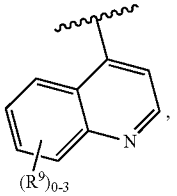
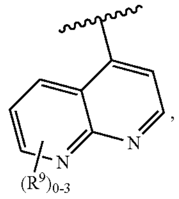
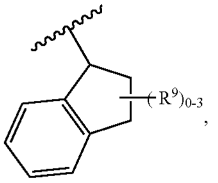
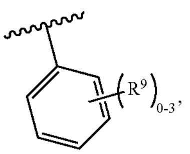
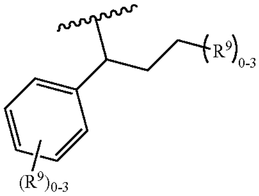
,
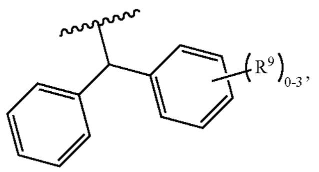
or
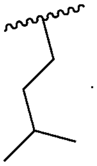
.
In some embodiments of a compound of Formula (A-I), $R^8$ is:
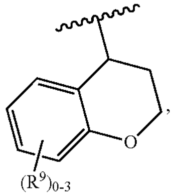
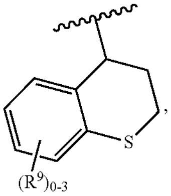
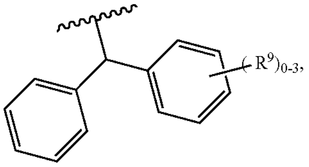
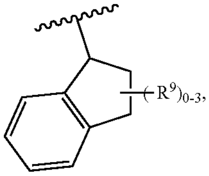
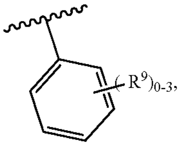
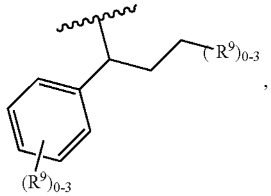
, or
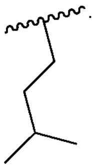
In some embodiments of a compound of Formula (A-I), $R^8$ is:
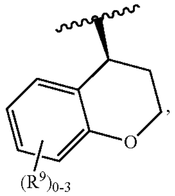
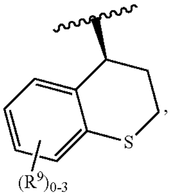
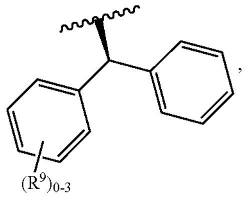
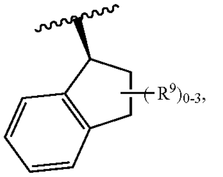
or
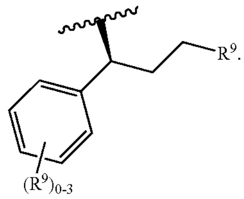
In some embodiments of a compound of Formula (A-I), $R^8$ is:

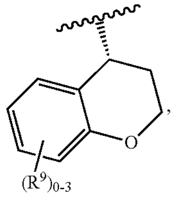,
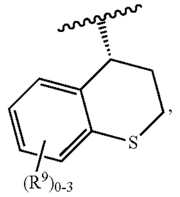,
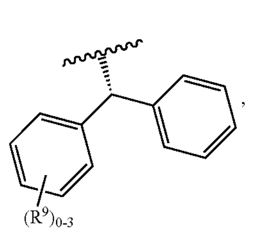,
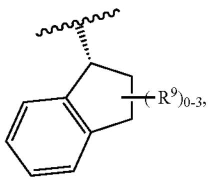, or
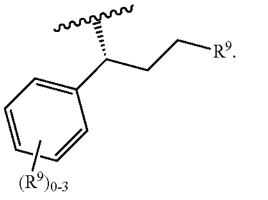.

In some embodiments of a compound of Formula (A-I), $R^8$ is:

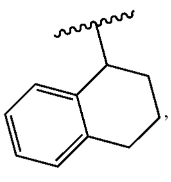,
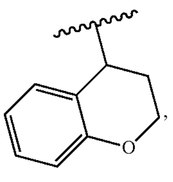,
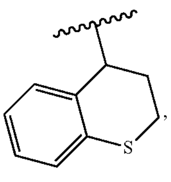,
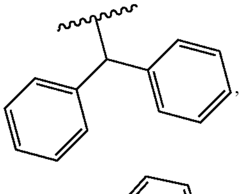,
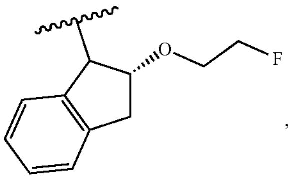,
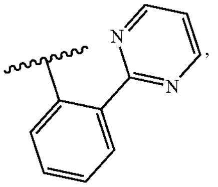,
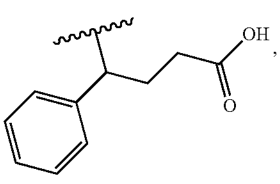, or
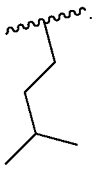.

In some embodiments of a compound of Formula (A-I), $R^8$ is:

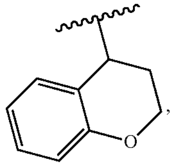,
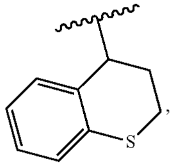,
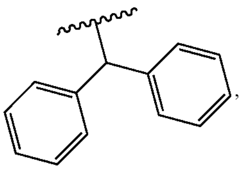,
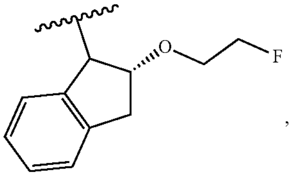,
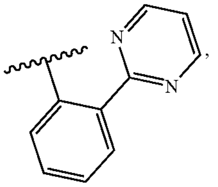,
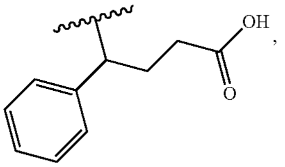, or
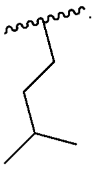.

In some embodiments, each $R^9$ is independently halogen, $C_1$-$C_4$alkyl, $C_2$-$C_4$alkenyl, $C_2$-$C_4$alkynyl, $C_1$-$C_4$haloalkyl, $C_1$-$C_4$alkoxy, $C_1$-$C_4$haloalkoxy, $C_1$-$C_4$heteroalkyl, —C(O)H, —C(O)OH, —CN, $C_3$-$C_{10}$cycloalkyl, 3- to 10-membered heterocycloalkyl, $C_6$-$C_{10}$aryl, 5- to 10-membered heteroaryl, —N($C_1$-$C_4$alkyl)$_2$, —OH, —O($C_1$-$C_4$alkyl), —O($C_1$-$C_4$haloalkyl), —O($C_1$-$C_4$alkylene)-(5- to 10-membered heteroaryl), —O($C_6$-$C_{10}$aryl), —SH, S(O)$_2$OH, —S(O)$_2$($C_1$-$C_4$alkyl), —S(O)$_2$NH$_2$, —S(O)$_2$NH($C_1$-$C_4$alkyl), or —S(O)$_2$N($C_1$-$C_4$alkyl)$_2$. In some embodiments, each $R^9$ is independently halogen, $C_1$-$C_4$alkyl, $C_2$-$C_4$alkenyl, $C_2$-$C_4$alkynyl, $C_1$-$C_4$haloalkyl, $C_1$-$C_4$alkoxy, $C_1$-$C_4$haloalkoxy, $C_1$-$C_4$heteroalkyl, —C(O)H, —C(O)OH, —CN, $C_3$-$C_{10}$cycloalkyl, 3- to 10-membered heterocycloalkyl, $C_6$-$C_{10}$aryl, 5- to 10-membered heteroaryl, —OH, —O($C_1$-$C_4$alkyl), or —O($C_1$-$C_4$haloalkyl). In some embodiments, each $R^9$ is independently halogen, $C_1$-$C_4$alkyl, —C(O)OH, —O($C_1$-$C_4$alkyl), —O($C_1$-$C_4$haloalkyl), or 5- to 10-membered heteroaryl. In some embodiments, each $R^9$ is each independently —C(O)OH, —O($CH_3$), —O($CH_2CH_2F$), or pyrimidine.

Also disclosed herein is a compound or pharmaceutically acceptable salt, solvate, diastereomeric mixture, or individual enantiomers thereof, having the structure of Formula (B-I):

Formula (B-I)

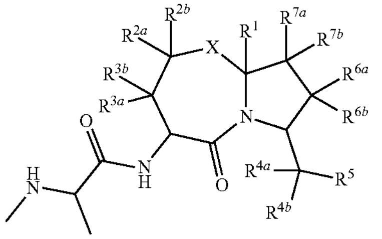

wherein, $R^1$ is hydrogen, $C_1$-$C_6$alkyl, $C_3$-$C_6$cycloalkyl, $C_1$-$C_6$alkyl-($C_3$-$C_6$cycloalkyl), $C_1$-$C_6$alkyl-(phenyl), or $C_1$-$C_6$alkyl-(5- to 6-membered heteroaryl); wherein the $C_1$-$C_6$alkyl, $C_3$-$C_6$cycloalkyl, phenyl, or 5- to 6-membered heteroaryl is optionally substituted with 1, 2, or 3 $R^9$;

X is $NR^A$, O, S, S(O), or $S(O)_2$;

$R^A$ is hydrogen, $C_1$-$C_6$alkyl, C(O)—($C_1$-$C_6$alkyl), C(O)—($C_3$-$C_6$cycloalkyl), C(O)-(phenyl), or C(O)-(5- to 6-membered heteroaryl); wherein each $C_1$-$C_6$alkyl, $C_3$-$C_6$cycloalkyl, phenyl, or 5- to 6-membered heteroaryl is optionally substituted with 1, 2, or 3 $R^9$;

or X is C and taken together with $R^{2a}$, $R^{2b}$, and the carbon atom to which they are attached, forms a phenyl or 5- to 10-membered heteroaryl ring, optionally substituted with 1, 2, or 3 $R^9$;

$R^{2a}$, $R^{2b}$, $R^{3a}$, and $R^{3b}$ are each independently hydrogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, or $C_2$-$C_6$alkynyl is optionally substituted with 1 or 2 $C_3$-$C_{10}$cycloalkyl, 3- to 10-membered heterocycloalkyl, $C_6$-$C_{10}$aryl, or 5- to 10-membered heteroaryl rings; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{2a}$ and $R^{2b}$ together with the carbon atom to which they are attached form a carbonyl;

or $R^{2a}$ and $R^{3a}$, and optionally $R^{2b}$ and $R^{3b}$, together with the carbon atoms to which they are attached form a $C_3$-$C_6$cycloalkyl, 5- to 10-membered heterocycloalkyl, $C_6$-$C_{10}$aryl, or 5- to 10-membered heteroaryl ring; wherein each $C_3$-$C_6$cycloalkyl, 5- to 10-membered heterocycloalkyl, $C_6$-$C_{10}$aryl, or 5- to 10-membered heteroaryl ring is optionally substituted with 1, 2, or 3 $R^9$;

$R^{4a}$ and $R^{4b}$ are each independently hydrogen, halogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, or $C_2$-$C_6$alkynyl is optionally substituted with 1 or 2 $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{4a}$ and $R^{4b}$ together with the carbon atom to which they are attached form a carbonyl;

or $R^{4a}$ and $R^{4b}$ together with the carbon atom to which they are attached form a $C_3$-$C_{10}$cycloalkyl or 3- to 10-membered heterocycloalkyl ring; wherein the $C_3$-$C_{10}$cycloalkyl or 3- to 10-membered heterocycloalkyl ring is optionally substituted with 1, 2, or 3 $R^9$;

$R^5$ is $NHR^B$, $NHS(O)_2R^8$, $OR^8$, $SR^8$, $S(O)_2R^8$, or $S(O)_2NHR^8$;

or $R^5$, $R^{4a}$, and $R^{4b}$, together with the carbon atom to which they are attached, form a $C_6$-$C_{10}$aryl or 5- to 10-membered heteroaryl ring; wherein the $C_6$-$C_{10}$aryl or 5- to 10-membered heteroaryl ring is optionally substituted with 1, 2, or 3 $R^9$;

$R^{6a}$ is hydrogen, halogen, —$U^a$, or -G;

$R^{6b}$ is halogen, —$U^b$, or -G;

—$U^a$ is $C_2$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl; wherein each $C_1$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl is optionally substituted with 1, 2, or 3 $R^9$ and/or 1 or 2-G;

—$U^b$ is $C_1$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl; wherein each $C_1$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl is optionally substituted with 1, 2, or 3 $R^9$ and/or 1 or 2-G;

-G is $C_3$-$C_{10}$cycloalkyl, 3- to 10-membered heterocycloalkyl, $C_6$-$C_{10}$aryl, or 5- to 10-membered heteroaryl; wherein each $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

$R^{7a}$ is hydrogen, halogen, $C_1$-$C_4$alkyl, or $C_1$-$C_4$haloalkyl;

$R^{7b}$ is hydrogen, halogen, $C_1$-$C_4$alkyl, or $C_1$-$C_4$haloalkyl;

$R^8$ is Z, $C_2$-$C_6$alkyl, ($C_1$-$C_6$alkylene)-Z, ($C_1$-$C_6$heteroalkylene)-Z, ($C_2$-$C_6$alkenylene)-Z, $CH(Z)_2$, $CH_2CH(Z)_2$, CH($C_1$-$C_6$alkyl)Z, or C(O)Z; wherein each alkyl, alkylene, heteroalkylene, or alkenylene is optionally substituted with 1, 2, or 3 $R^9$;

Z is $C_3$-$C_{10}$cycloalkyl, 3- to 10-membered heterocycloalkyl, $C_6$-$C_{10}$aryl, 5- to 10-membered heteroaryl; wherein each $C_3$-$C_{10}$cycloalkyl, 3- to 10-membered heterocycloalkyl, $C_6$-$C_{10}$aryl, 5- to 10-membered heteroaryl is optionally substituted with 1, 2, or 3 $R^9$;

each $R^9$ is independently halogen, $C_1$-$C_4$alkyl, $C_2$-$C_4$alkenyl, $C_2$-$C_4$alkynyl, $C_1$-$C_4$haloalkyl, $C_1$-$C_4$alkoxy, $C_1$-$C_4$haloalkoxy, $C_1$-$C_4$heteroalkyl, —C(O)H, —C(O)OH, —CN, $C_3$-$C_{10}$cycloalkyl, 3- to 10-membered heterocycloalkyl, $C_6$-$C_{10}$aryl, 5- to 10-membered heteroaryl, —C(O)($C_1$-$C_4$alkyl), —C(O)O($C_1$-$C_4$alkyl), —C(O)$NH_2$, —C(O)NH($C_1$-$C_4$alkyl), —C(O)N($C_1$-$C_4$alkyl)$_2$, —$NH_2$, —NH($C_1$-$C_4$alkyl), —N($C_1$-$C_4$alkyl)$_2$, —NH($C_2$-$C_4$alkylene)-OH, —NH($C_2$-$C_4$alkylene)-O—($C_1$-$C_4$alkyl), —OH, —O($C_1$-$C_4$alkyl), —O($C_1$-$C_4$haloalkyl), —O($C_2$-$C_4$alkylene)-$NH_2$, —O($C_2$-$C_4$alkylene)-NH—($C_1$-$C_4$alkyl), —O($C_2$-$C_4$alkylene)-N—($C_1$-$C_4$alkyl)$_2$, —O($C_1$-$C_4$alkylene)-C(O)OH, —O($C_1$-$C_4$alkylene)-C(O)O—($C_1$-$C_4$alkyl), —O($C_2$-$C_4$alkenyl), —O($C_1$-$C_4$alkylene)-($C_6$-$C_{10}$aryl), —O($C_1$-$C_4$alkylene)-(5- to 10-membered heteroaryl), —O($C_6$-$C_{10}$aryl), —SH, $S(O)_2OH$, —$S(O)_2$($C_1$-$C_4$alkyl), —$S(O)_2NH_2$, —$S(O)_2$NH($C_1$-$C_4$alkyl), or —$S(O)_2$N($C_1$-$C_4$alkyl)$_2$; or two $R^9$ together with the atoms to which they are attached form a $C_3$-$C_{10}$cycloalkyl or a 3- to 10-membered heterocycloalkyl ring.

In some embodiments, $R^5$, $R^{4a}$ and $R^{4b}$ together with the carbon atom to which they are attached form a $C_6$-$C_{10}$aryl or 5- to 10-membered heteroaryl ring; wherein the $C_6$-$C_{10}$aryl or 5- to 10-membered heteroaryl ring is optionally substituted with 1, 2, or 3 $R^9$. In some embodiments, $R^5$, $R^{4a}$ and $R^{4b}$ together with the carbon atom to which they are attached form a 5- to 10-membered heteroaryl ring, optionally substituted with 1, 2, or 3 $R^9$. In some embodiments, $R^5$, $R^{4a}$ and $R^{4b}$ together with the carbon atom to which they are attached form a 9- or 10-membered heteroaryl ring, optionally substituted with 1, 2, or 3 $R^9$. In some embodiments, $R^5$, $R^{4a}$ and $R^{4b}$ together with the carbon atom to which they are attached form a 10-membered heteroaryl ring. In some embodiments, $R^5$, $R^{4a}$ and $R^{4b}$ together with the carbon atom to which they are attached form a quinoline, isoquinoline, quinoxaline, quinazoline, quinolizine, naphthyridine. In some embodiments, $R^5$, $R^{4a}$ and $R^{4b}$ together with the carbon atom to which they are attached form a 9-membered heteroaryl ring. In some embodiments, $R^5$, $R^{4a}$ and $R^{4b}$ together with the carbon atom to which they are attached form a 2,3-dihydrobenzo[d]oxazole, benzo[d]oxazole, oxazolo[4,5-b]pyridine, 1H-benzo[d]imidazole, benzo[d]thiazole, benzofuran, indole, aza-indole, 1H-imidazo[4,5-b]pyridine, indolizine, imidazo[1,2-a]pyridine, or an isomer thereof, optionally substituted with 1, 2, or 3 $R^9$. In some embodiments, $R^5$, $R^{4a}$ and $R^{4b}$ together with the carbon atom to which they are attached form a benzo[d]oxazole, optionally substituted with 1, 2, or 3 $R^9$. In some embodiments, the $C_6$-$C_{10}$aryl or 5- to 10-membered heteroaryl ring is unsubstituted.

In some embodiments, $R^5$ is $NHR^8$, $NHS(O)_2R^8$, $OR^8$, $SR^B$, $S(O)_2R^8$, or $S(O)_2NHR^8$. In some embodiments, $R^5$ is $NHR^8$, $NHS(O)_2R^8$, $OR^8$, or $S(O)_2NHR^8$. In some embodiments, $R^5$ is $NHR^B$, $NHS(O)_2R^8$, or $OR^8$. In some embodiments, $R^5$ is $OR^8$. In some embodiments, $R^5$ is $NHR^B$, or $NHS(O)_2R^8$. In some embodiments, $R^5$ is $NHS(O)_2R^8$. In some embodiments, $R^5$ is $NHR^8$.

In some embodiments of a compound of Formula (B-I), a compound has any one of the following formulae:

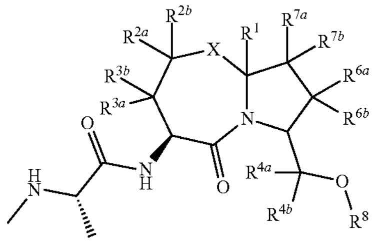

or

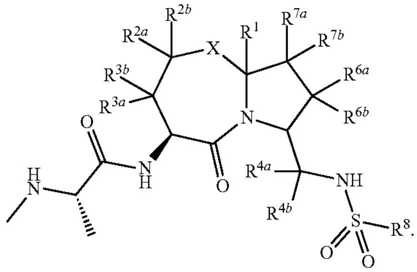

In some embodiments of a compound of Formula (B-I), a compound has the structure of Formula (B-II):

Formula (B-II)

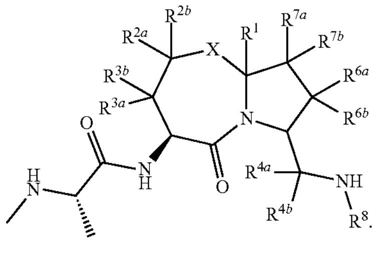

In some embodiments, $R^{4a}$ is H. In some embodiments, $R^{4a}$ is H and $R^{4b}$ is halogen or haloalkyl. In some embodiments, $R^{4b}$ is $CHF_2$ or $CF_3$. In some embodiments, $R^{4a}$ is H and $R^{4b}$ is difluoromethyl or trifluoromethyl. In some embodiments, $R^{4b}$ is difluoromethyl or trifluoromethyl and $R^5$ is $OR^8$. In some embodiments, $R^{4a}$ and $R^{4b}$ are both H.

In some embodiments, $R^{4a}$ and $R^{4b}$ together with the carbon atom to which they are attached form a $C_3$-$C_{10}$cycloalkyl or 3- to 10-membered heterocycloalkyl ring, wherein either of the cycloalkyl or heterocycloalkyl ring is optionally substituted with 1, 2, or 3 $R^9$. In some embodiments, $R^{4a}$ and $R^{4b}$ together with the carbon atom to which they are attached form a $C_3$-$C_6$cycloalkyl, optionally substituted with 1, 2, or 3 $R^9$. In some embodiments, $R^{4a}$ and $R^{4b}$ together with the carbon atom to which they are attached form a $C_3$-$C_5$cycloalkyl, optionally substituted with 1, 2, or 3 $R^9$. In some embodiments, $R^{4a}$ and $R^{4b}$ together with the carbon atom to which they are attached form a cyclopropyl, cyclobutyl, or cyclopentyl ring, optionally substituted with 1, 2, or 3 $R^9$. In some embodiments, $R^{4a}$ and $R^{4b}$ together with the carbon atom to which they are attached form a cyclopropyl, cyclobutyl, or cyclopentyl ring and $R^5$ is —$OR^8$ or —$NHR^8$. In some embodiments, $R^{4a}$ and $R^{4b}$ are each independently halogen, $C_1$-$C_6$alkyl, $C_1$-$C_6$haloalkyl, $C_1$-$C_6$ alkoxy, or $C_1$-$C_6$heteroalkyl and $R^5$ is $NHR^B$.

In some embodiments, $R^{4a}$ and $R^{4b}$ together with the carbon atom to which they are attached form a carbonyl. In some embodiments, $R^{4a}$ and $R^{4b}$ together with the carbon atom to which they are attached form a carbonyl and $R^5$ is $OR^8$ or $NHR^8$. In some embodiments, $R^{4a}$ and $R^{4b}$ together with the carbon atom to which they are attached form a carbonyl and $R^5$ is $NHR^8$.

In some embodiments, $R^1$ is hydrogen, $C_1$-$C_6$alkyl, $C_3$-$C_6$cycloalkyl, $C_1$-$C_6$alkyl-($C_3$-$C_6$cycloalkyl), wherein each alkyl is optionally substituted with 1, 2, or 3 $R^9$. In some embodiments, $R^1$ is phenethyl. In some embodiments, $R^1$ is hydrogen, methyl, trifluoromethyl, difluoromethyl, fluoromethyl, ethyl, propyl, isopropyl, cyclopropyl, methylenecyclopropyl, or cyclobutyl. In some embodiments, $R^1$ is phenethyl. In some embodiments, $R^1$ is hydrogen, methyl, trifluoromethyl, difluoromethyl, fluoromethyl, or ethyl. In some embodiments, $R^1$ is hydrogen or methyl. In some embodiments, $R^1$ is hydrogen.

In some embodiments of a compound of Formula (B-I), a compound has the structure of Formula (B-III):

Formula (B-III)

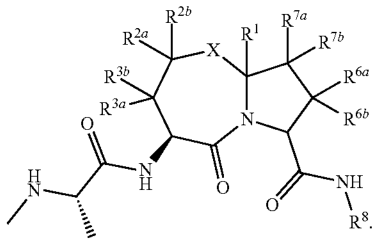

In some embodiments, $R^{2a}$ and $R^{2b}$ are each independently hydrogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, wherein each alkyl, haloalkyl, alkoxy, heteroalkyl, alkenyl, or alkynyl is optionally substituted with 1, 2, or 3 $R^9$. In some embodiments, $R^{2a}$ and $R^{2b}$ are each independently $C_3$-$C_{10}$cycloalkyl, 3- to 10-membered heterocycloalkyl, $C_6$-$C_{10}$aryl, or 5- to 10-membered heteroaryl, wherein each cycloalkyl, heterocycloalkyl, aryl, or heteroaryl is optionally substituted with 1, 2, or 3 $R^9$. In some embodiments, $R^{2a}$ and $R^{2b}$ are each independently hydrogen, $C_1$-$C_6$alkyl, $C_1$-$C_6$haloalkyl, $C_1$-$C_6$ alkoxy, $C_1$-$C_6$heteroalkyl, wherein each alkyl, haloalkyl, alkoxy, or heteroalkyl is optionally substituted with 1 or 2 $C_3$-$C_6$cycloalkyl, 3- to 6-membered heterocycloalkyl, phenyl, or 5- or 6-membered heteroaryl. In some embodiments, $R^{2a}$ is H and $R^{2b}$ is $C_1$-$C_6$alkyl or $C_1$-$C_6$heteroalkyl, wherein each alkyl or heteroalkyl is optionally substituted with a phenyl, or 5- or 6-membered heteroaryl. In some embodiments, $R^{2b}$ is

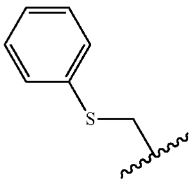,
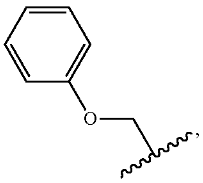, or
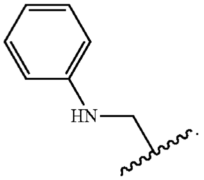.

In some embodiments, $R^{2a}$ is hydrogen. In some embodiments, $R^{2a}$ and $R^{2b}$ are each hydrogen.

In some embodiments, $R^{2a}$ and $R^{3a}$, and optionally $R^{2b}$ and $R^{3b}$, together with the carbon atoms to which they are attached form a $C_3$-$C_6$cycloalkyl, 5- to 10-membered heterocycloalkyl, $C_6$-$C_{10}$aryl, or 5- to 10-membered heteroaryl ring; wherein each $C_3$-$C_6$cycloalkyl, 5- to 10-membered heterocycloalkyl, $C_6$-$C_{10}$aryl, or 5- to 10-membered heteroaryl ring is optionally substituted with 1, 2, or 3 $R^9$;

In some embodiments, $R^{2a}$ and $R^{2b}$ together with the atom to which they are attached form a carbonyl. In some embodiments, $R^{2a}$ and $R^{2b}$ together with the atom to which they are attached form a carbonyl and X is NH. In some embodiments, $R^{2a}$ and $R^{2b}$ together with the atom to which they are attached form a carbonyl and X is O.

In some embodiments, $R^{3a}$ and $R^{3b}$ are each independently hydrogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl, any of which is optionally substituted with 1, 2, or 3 $R^9$. In some embodiments, $R^{3a}$ and $R^{3b}$ are each independently hydrogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, or $C_2$-$C_6$alkynyl, wherein each alkyl, haloalkyl, alkoxy, heteroalkyl, alkenyl, or alkynyl is optionally substituted with a cyclopropyl, phenyl, or 5- or 6-membered heteroaryl. In some embodiments, $R^{3a}$ and $R^{3b}$ are each independently hydrogen, methyl, trifluoromethyl, difluoromethyl, ethyl, propyl, isopropyl, cyclopropyl, benzyl, phenethyl, or isobutyl. In some embodiments, $R^{3a}$ and $R^{3b}$ are each methyl. In some embodiments, $R^{3a}$ is hydrogen. In some embodiments, $R^{3a}$ and $R^{3b}$ are each hydrogen.

In some embodiments, $R^{2a}$ and $R^{3a}$, together with the carbon atoms to which they are attached, form a $C_3$-$C_6$cycloalkyl, or 5- to 10-membered heterocycloalkyl. In some embodiments, $R^{2a}$ and $R^{3a}$, together with the carbon atoms to which they are attached, form a cyclopropyl, cyclobutyl, cyclopentyl, cyclohexyl, oxirane, oxetane, tetrahydrofuran, tetrahydropyran, dioxane, aziridine, azetidine, pyrrolidine, piperidine, or morpholine, each of which is optionally substituted with 1 $R^9$. In some embodiments, $R^{2a}$ and $R^{3a}$, together with the carbon atoms to which they are attached, form a cyclopropyl, cyclohexyl, dioxane, piperidine, or morpholine, each of which is optionally substituted with 1 $R^9$. In some embodiments, $R^{2a}$ and $R^{3a}$ together with the carbon atoms to which they are attached form a $C_3$-$C_6$cycloalkyl, optionally substituted with 1, 2, or 3 $R^9$. In some embodiments, $R^{2a}$ and $R^{3a}$, together with the carbon atoms to which they are attached, form a cyclopropyl or cyclohexyl, either of which is optionally substituted with 1, 2, or 3 $R^9$. In some embodiments, $R^{2a}$ and $R^{3a}$, together with the carbon atoms to which they are attached, form a cyclohexyl.

In some embodiments, X is $NR^A$, O, S, S(O), or $S(O)_2$. In some embodiments, X is O. In some embodiments, X is S or $S(O)_2$. In some embodiments, X is S. In some embodiments, X is $S(O)_2$. In some embodiments, X is $NR^A$. In some embodiments, $R^A$ is $C_1$-$C_6$alkyl, C(O)—($C_1$-$C_6$alkyl), or C(O)—($C_3$-$C_6$cycloalkyl), wherein each alkyl or cycloalkyl is optionally substituted with 1, 2, or 3 $R^9$. In some embodiments, $R^A$ is hydrogen, methyl, ethyl, $C(O)CH_3$, C(O)cyclopropyl, or C(O)cyclohexyl, wherein each cyclopropyl or cyclohexyl is optionally substituted with 1 or 2 $R^9$. In some embodiments, $R^A$ is hydrogen, methyl, or $C(O)CH_3$. In some embodiments, $R^A$ is hydrogen. In some embodiments of a compound of Formula (B-I), a compound has the structure of Formula (B-IV-a), (B-IV-b), (B-IV-c), or (B-IV-d):

Formula (B-IV-a)

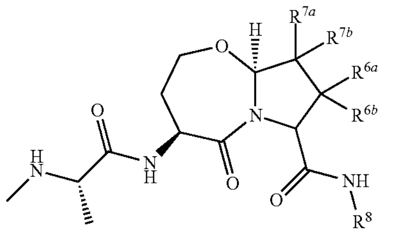

Formula (B-IV-b)

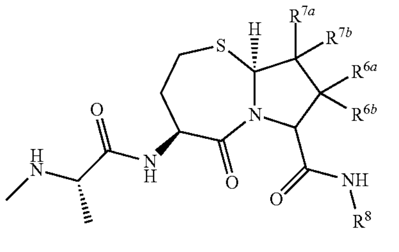

Formula (B-IV-c)

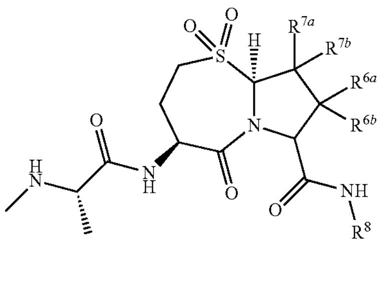 or

-continued

Formula (B-IV-d)

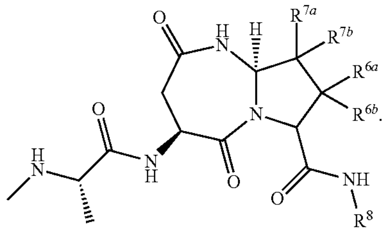

In some embodiments of a compound of Formula (B-I), a compound has the structure of Formula (B-V-a) or (B-V-b):

Formula (B-V-a)

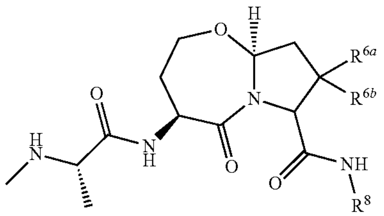

Formula (B-V-b)

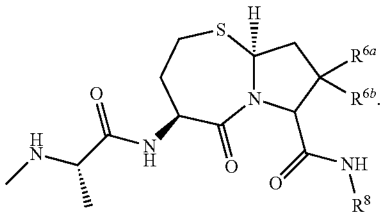

In some embodiments of a compound of Formula (B-I), a compound has the structure of Formula (B-VI-a), (B-VI-b), (B-VI-c), or (B-VI-d):

Formula (B-VI-a)

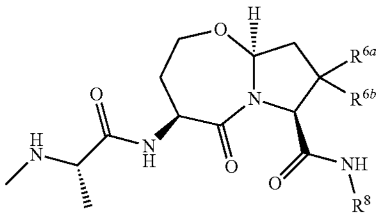

Formula (B-VI-b)

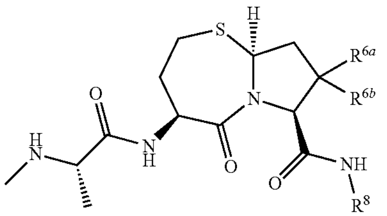

-continued

Formula (B-VI-c)

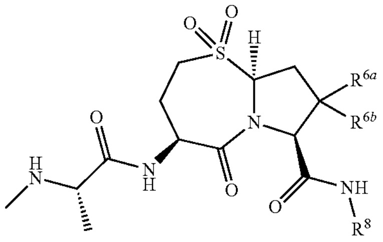

or

Formula (B-VI-d)

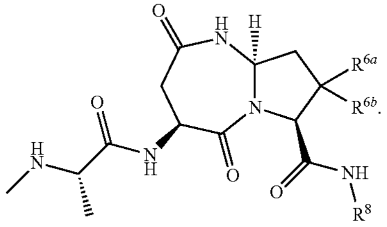

In some embodiments of a compound of Formula (B-I), a compound has the structure of Formula (B-VII-a), (B-VII-b), (B-VII-c), or (B-VII-d):

Formula (B-VII-a)

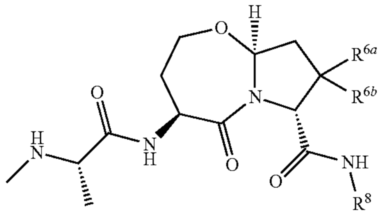

Formula (B-VII-b)

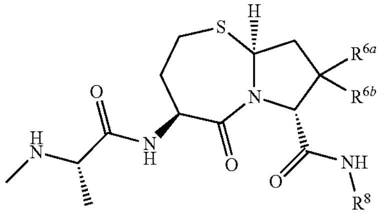

Formula (B-VII-c)

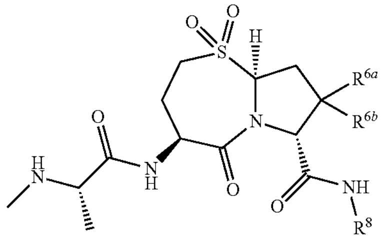

or

Formula (B-VII-d)

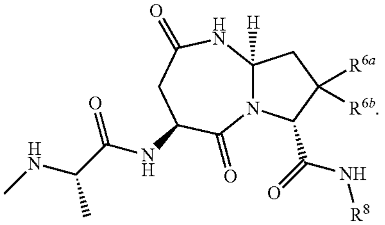

In some embodiments, X is C and taken together with $R^{2a}$, $R^{2b}$, and the carbon atom to which they are attached, forms a phenyl or 5- to 10-membered heteroaryl ring, optionally substituted with 1, 2, or 3 $R^9$. In some embodiments, X is C and taken together with $R^{2a}$, $R^{2b}$, and the carbon atom to which they are attached, forms a phenyl ring, optionally substituted with 1, 2, or 3 $R^9$. In some embodiments, X is C and taken together with $R^{2a}$, $R^{2b}$, and the carbon atom to which they are attached, forms a 5- to 10-membered heteroaryl ring, optionally substituted with 1, 2, or 3 $R^9$. In some embodiments, X is C and taken together with $R^{2a}$, $R^{2b}$, and the carbon atom to which they are attached, forms a 5-membered heteroaryl ring, optionally substituted with 1, 2, or 3 $R^9$. In some embodiments, X is C and taken together with $R^{2a}$, $R^{2b}$, and the carbon atom to which they are attached, forms a 9- or 10-membered heteroaryl ring, optionally substituted with 1, 2, or 3 $R^9$. In some embodiments, X is C and taken together with $R^{2a}$, $R^{2b}$, and the carbon atom to which they are attached, forms a pyrrole, pyrazole, imidazole, indole, or azaindole ring, optionally substituted with 1, 2, or 3 $R^9$. In some embodiments, a compound as disclosed herein has the structure of one of the following:

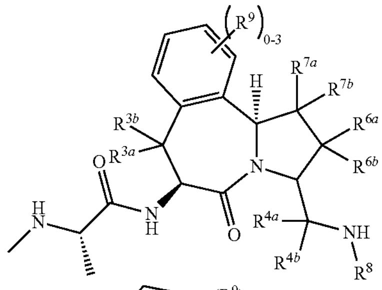

or

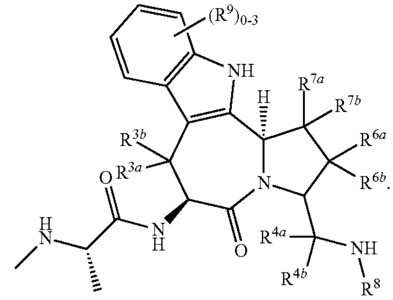

In some embodiments, $R^{7a}$ and $R^{7b}$ are each independently hydrogen, halogen, $C_1$-$C_4$alkyl, or $C_1$-$C_4$haloalkyl. In some embodiments, $R^{7a}$ and $R^{7b}$ are each independently hydrogen, fluoro, methyl, ethyl, difluoromethyl, or trifluoromethyl. In some embodiments, $R^{7a}$ and $R^{7b}$ are each independently hydrogen, methyl, or ethyl. In some embodiments, $R^{7a}$ and $R^{7b}$ are both hydrogen.

In some embodiments of a compound of Formula (B-I), $R^{6a}$ is hydrogen. In some embodiments of a compound of Formula (B-I), $R^{6a}$ is hydrogen and $R^b$ is halogen, $C_1$-$C_6$alkyl, $C_1$-$C_6$haloalkyl, $C_2$-$C_6$alkenyl, or $C_2$-$C_6$alkynyl; wherein each $C_1$-$C_6$alkyl, $C_1$-$C_6$haloalkyl, $C_2$-$C_6$alkenyl, or $C_2$-$C_6$alkynyl is optionally substituted with 1, 2, or 3 $R^9$ and/or 1 or 2, G. In some embodiments of a compound of Formula (B-I), $R^{6b}$ is halogen, $C_1$-$C_6$alkyl, $C_1$-$C_6$haloalkyl, $C_2$-$C_6$alkenyl, or $C_2$-$C_6$alkynyl; wherein each $C_1$-$C_6$alkyl, $C_1$-$C_6$haloalkyl, $C_2$-$C_6$alkenyl, or $C_2$-$C_6$alkynyl is optionally substituted with 1, 2, or 3 $R^9$ and/or 1 or 2, G. In some embodiments of a compound of Formula (B-I), $R^{6b}$ is $C_1$-$C_6$alkyl, $C_1$-$C_6$haloalkyl, $C_2$-$C_6$alkenyl, or $C_2$-$C_6$alkynyl, wherein each alkyl, haloalkyl, alkenyl, or alkynyl is optionally substituted with a phenyl or 5- or 6-membered heteroaryl ring, wherein each phenyl or heteroaryl ring is optionally substituted with 1, 2, or 3 $R^9$. In some embodiments of a compound of Formula (B-I), $R^{6b}$ is methyl, ethyl, or propyl, optionally substituted with G, wherein G is a phenyl ring further substituted with 1, 2, or 3 $R^9$. In some embodiments of a compound of Formula (B-I), $R^{6b}$ is ethyl, optionally substituted with phenyl, tolyl, phenolyl, fluorophenyl, chlorophenyl, anilinyl, methoxyphenyl, dimethylphenyl, difluorophenyl, dichlorophenyl, dihydroxyphenyl, dimethoxyphenyl, fluoromethoxyphenyl, or naphthyl. In some embodiments of a compound of Formula (B-I), $R^{6b}$ is $C_1$-$C_6$alkyl, $C_1$-$C_6$haloalkyl, $C_2$-$C_6$alkenyl, or $C_2$-$C_6$alkynyl, wherein each alkyl, haloalkyl, alkenyl, or alkynyl is optionally substituted with a $C_3$-$C_6$cycloalkyl or 3- to 6-membered heterocycloalkyl ring, wherein each cycloalkyl or heterocycloalkyl ring is optionally substituted with 1, 2, or 3 $R^9$. In some embodiments of a compound of Formula (B-I), $R^{6b}$ is methyl, ethyl, 2-propenyl, isopropyl, or phenethyl. In some embodiments of a compound of Formula (B-I), $R^{6b}$ is methyl, ethyl, 2-propenyl, isopropyl, or phenethyl, and the carbon to which it is attached has the (S) stereochemical configuration. In some embodiments of a compound of Formula (B-I), $R^{6b}$ is methyl, ethyl, 2-propenyl, isopropyl, or phenethyl, and the carbon to which it is attached has the (R) stereochemical configuration. In some embodiments of a compound of Formula (B-I), $R^{6b}$ is methyl. In some embodiments, $R^{6b}$ is ethyl. In some embodiments, $R^{6b}$ is 2-propenyl. In some embodiments, $R^{6b}$ is isopropyl. In some embodiments, $R^{6b}$ is phenethyl.

In some embodiments of a compound of Formula (B-I), $R^{6a}$ and $R^{6b}$ are each independently halogen, $C_2$-$C_6$alkyl, $C_1$-$C_6$haloalkyl, $C_2$-$C_6$alkenyl, or $C_2$-$C_6$alkynyl; wherein each $C_2$-$C_6$alkyl, $C_1$-$C_6$haloalkyl, $C_2$-$C_6$alkenyl, or $C_2$-$C_6$alkynyl is optionally substituted with 1, 2, or 3 $R^9$ and/or 1 or 2, G. In some embodiments of a compound of Formula (B-I), $R^{6a}$ and $R^{6b}$ are each independently $C_2$-$C_6$alkyl, $C_1$-$C_6$haloalkyl, $C_2$-$C_6$alkenyl, or $C_2$-$C_6$alkynyl, wherein each alkyl, haloalkyl, alkenyl, or alkynyl is optionally substituted with a phenyl or 5- or 6-membered heteroaryl ring, wherein each phenyl or heteroaryl ring is optionally substituted with 1, 2, or 3 $R^9$. In some embodiments of a compound of Formula (B-I), $R^{6a}$ and $R^{6b}$ are each independently ethyl or propyl, optionally substituted with G, wherein G is a phenyl ring further substituted with 1, 2, or 3 $R^9$. In some embodiments of a compound of Formula (B-I), $R^{6a}$ and $R^{6b}$ are each independently ethyl, optionally substituted with phenyl, tolyl, phenolyl, fluorophenyl, chlorophenyl, anilinyl, methoxyphenyl, dimethylphenyl, difluorophenyl, dichlorophenyl, dihydroxyphenyl, dimethoxyphenyl, fluoromethoxyphenyl, or naphthyl. In some embodiments of a compound of Formula (B-I), $R^{6a}$ and $R^{6b}$ are each independently $C_2$-$C_6$alkyl, $C_1$-$C_6$haloalkyl, $C_2$-$C_6$alkenyl, or $C_2$-$C_6$alkynyl, wherein each alkyl, haloalkyl, alkenyl, or alkynyl is optionally substituted with a $C_3$-$C_6$cycloalkyl or 3- to 6-membered heterocycloalkyl ring, wherein each cycloalkyl or heterocycloalkyl ring is optionally substituted with 1, 2, or 3 $R^9$. In some embodiments of a compound of Formula (B-I), $R^{6a}$ and $R^{6b}$ are each independently ethyl, 2-propenyl, isopropyl, or phenethyl. In some embodiments, $R^{6a}$ and $R^{6b}$ are ethyl. In some embodiments, $R^{6a}$ and $R^{6b}$ are 2-propenyl. In some embodiments, $R^{6a}$ and Rib are isopropyl. In some embodiments, $R^{6a}$ and $R^{6b}$ are phenethyl. In some embodiments of a compound of Formula (B-I), $R^{6a}$ is halogen, $C_2$-$C_6$alkyl, $C_1$-$C_6$haloalkyl, $C_2$-$C_6$alkenyl, or $C_2$-$C_6$alkynyl; wherein each $C_2$-$C_6$alkyl, $C_1$-$C_6$haloalkyl, $C_2$-$C_6$alkenyl, or $C_2$-$C_6$alkynyl is optionally substituted with 1, 2, or 3 $R^9$ and/or 1 or 2 G; and $R^{6b}$ is methyl. In some embodiments of a compound of Formula (B-I), $R^{6a}$ is $C_2$-$C_6$alkyl, $C_1$-$C_6$haloalkyl, $C_2$-$C_6$alkenyl, or $C_2$-$C_6$alkynyl, wherein each alkyl, haloalkyl, alkenyl, or alkynyl is optionally substituted with a phenyl or 5- or 6-membered heteroaryl ring, wherein each phenyl or heteroaryl ring is optionally substituted with 1, 2, or 3 $R^9$; and $R^{6b}$ is methyl. In some embodiments of a compound of Formula (B-I), $R^{6a}$ is ethyl or propyl, optionally substituted with G, wherein G is a phenyl ring further substituted with 1, 2, or 3 $R^9$; and $R^{6b}$ is methyl. In some embodiments of a compound of Formula (B-I), $R^{6a}$ is ethyl, optionally substituted with phenyl, tolyl, phenolyl, fluorophenyl, chlorophenyl, anilinyl, methoxyphenyl, dimethylphenyl, difluorophenyl, dichlorophenyl, dihydroxyphenyl, dimethoxyphenyl, fluoromethoxyphenyl, or naphthyl; and $R^{6b}$ is methyl. In some embodiments of a compound of Formula (B-I), $R^{6a}$ is $C_2$-$C_6$alkyl, $C_1$-$C_6$haloalkyl, $C_2$-$C_6$alkenyl, or $C_2$-$C_6$alkynyl, wherein each alkyl, haloalkyl, alkenyl, or alkynyl is optionally substituted with a $C_3$-$C_6$cycloalkyl or 3- to 6-membered heterocycloalkyl ring, wherein each cycloalkyl or heterocycloalkyl ring is optionally substituted with 1, 2, or 3 $R^9$; and $R^{6b}$ is methyl. In some embodiments of a compound of Formula (B-I), $R^{6a}$ is ethyl, 2-propenyl, isopropyl, or phenethyl, and $R^{6b}$ is methyl.

In some embodiments of a compound of Formula (B-I), $R^8$ is Z, $C_2$-$C_6$alkyl, ($C_1$-$C_6$alkylene)-Z, ($C_1$-$C_6$heteroalkylene)-Z, ($C_2$-$C_6$alkenylene)-Z, $CH(Z)_2$, $CH_2CH(Z)_2$, CH($C_1$-$C_6$alkyl)Z, or C(O)Z; wherein each alkyl, alkylene, heteroalkylene, or alkenylene is optionally substituted with 1, 2, or 3 $R^9$. In some embodiments of a compound of Formula (B-I), $R^8$ is Z, $C_2$-$C_6$alkyl, $CH(Z)_2$, or C(O)Z. In some embodiments of a compound of Formula (B-I), $R^8$ is Z, $C_2$-$C_6$alkyl, $CH(Z)_2$, or C(O)Z, wherein Z is $C_3$-$C_{10}$cycloalkyl, 3- to 10-membered heterocycloalkyl, $C_6$-$C_{10}$aryl, or 5- to 10-membered heteroaryl. In some embodiments of a compound of Formula (B-I), R is Z or $CH(Z)_2$. In some embodiments of a compound of Formula (B-I), $R^1$ is Z. In some embodiments of a compound of Formula (B-I), R is $CH(Z)_2$. In some embodiments of a compound of Formula (B-I), Z is $C_3$-$C_{10}$cycloalkyl, 3- to 10-membered heterocycloalkyl, $C_6$-$C_{10}$aryl, or 5- to 10-membered heteroaryl; wherein each $C_3$-$C_{10}$cycloalkyl, 3- to 10-membered heterocycloalkyl, $C_6$-$C_{10}$aryl, and 5- to 10-membered heteroaryl is optionally substituted with 1, 2, or 3 $R^9$. In some embodiments of a compound of Formula (B-I), Z is $C_6$-$C_{10}$aryl or 5- to 10-membered heteroaryl, wherein each aryl or heteroaryl is optionally substituted with 1, 2, or 3 $R^9$. In some embodiments of a compound of Formula (B-I), Z is $C_3$-$C_{10}$cycloalkyl or 3- to 10-membered heterocycloalkyl; wherein each $C_3$-$C_{10}$cycloalkyl and 3- to 10-membered heterocycloalkyl is optionally substituted with 1, 2, or 3 $R^9$. In some embodiments of a compound of Formula (B-I), Z is $C_3$-$C_{10}$cycloalkyl optionally substituted with 1, 2, or 3 $R^9$. In some embodiments of a compound of Formula (B-I), Z is phenyl or naphthyl, optionally substituted with 1, 2, or 3 $R^9$. In some embodiments of a compound of Formula (B-I), Z is pyridine, pyrimidine, pyridazine, pyrazine, quinoline, naphthyridine, quinoxaline, quinolizine, benzofuran, benzoxazole, or benzothiophene. In some embodiments of a compound of Formula (B-I), Z is tetrahydronaphthalene, tetrahydroquinoline, tetrahydroisoquinoline, chroman, thiochroman, indane, indoline, dihydrobenzofuran, or dihydrobenzothiophene.

In some embodiments of a compound of Formula (B-I), $R^8$ is:

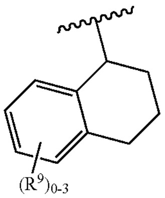, 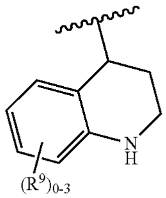, 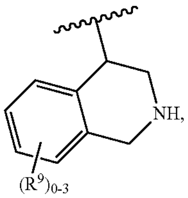

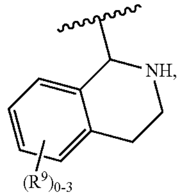 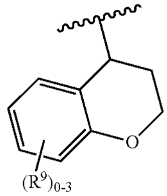, 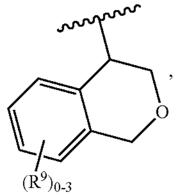,

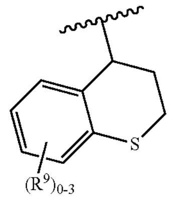, 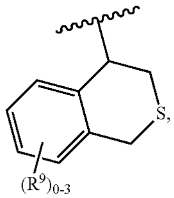 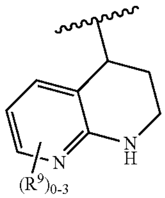,

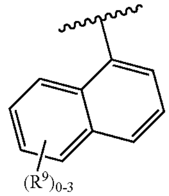, 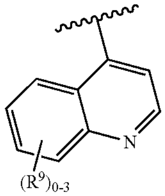, 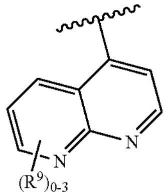,

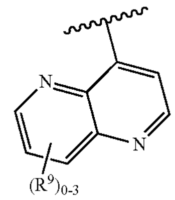, 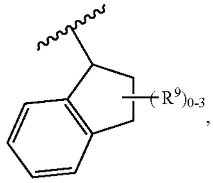,

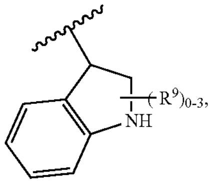 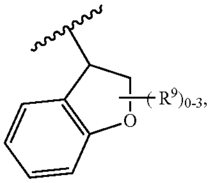

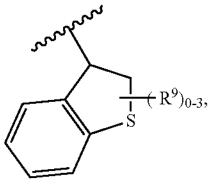 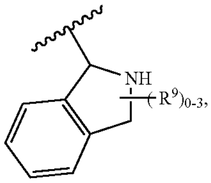

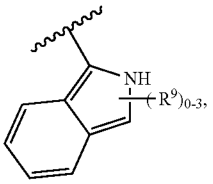 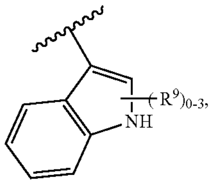

-continued
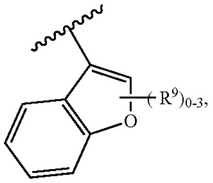 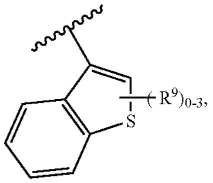
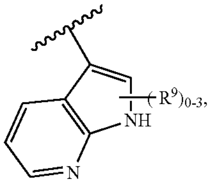 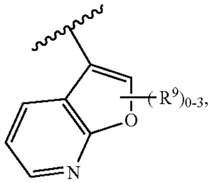
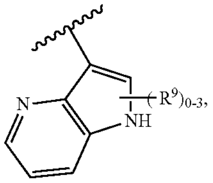 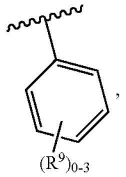 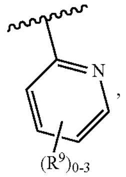
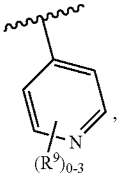 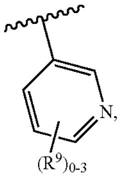 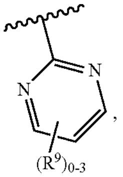 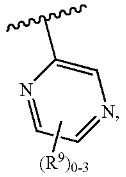
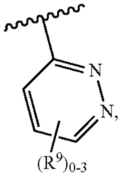 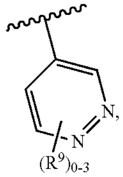 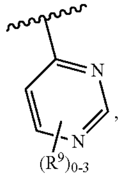 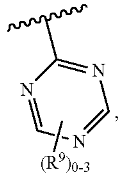
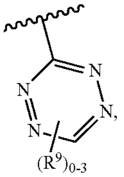 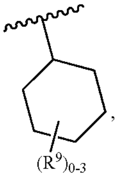 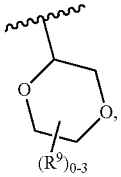 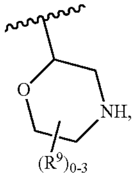
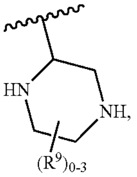 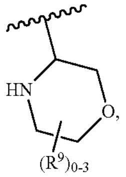 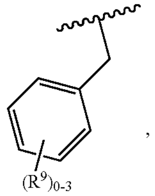
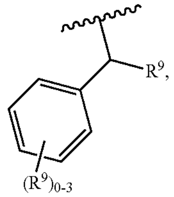 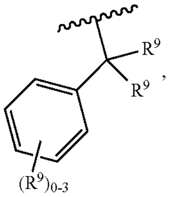
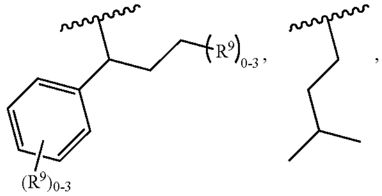
-continued
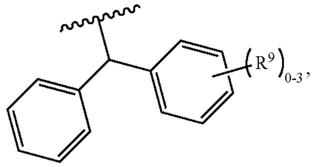
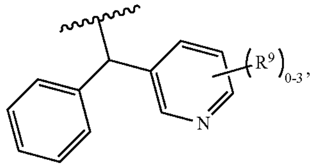
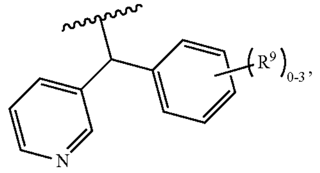 or
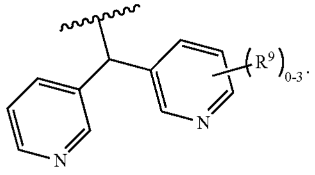
In some embodiments of a compound of Formula (B-I), $R^8$ is:
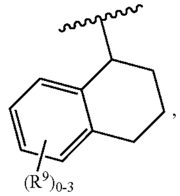 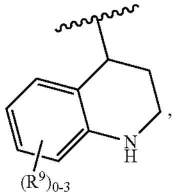 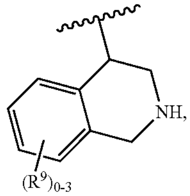
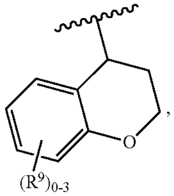 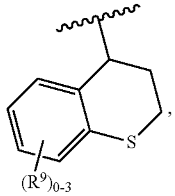 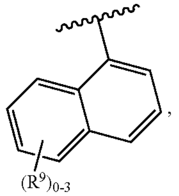
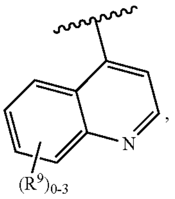 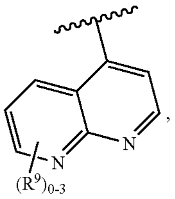 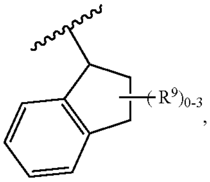
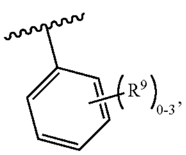 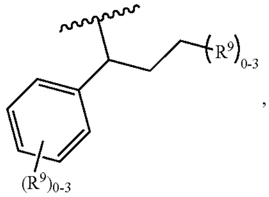

-continued
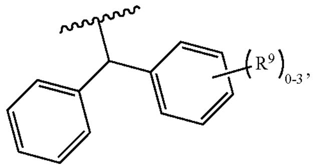, or 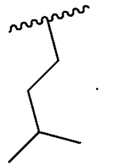.
In some embodiments of a compound of Formula (B-I), $R^8$ is:
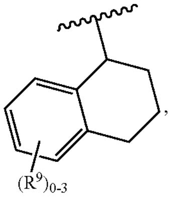, 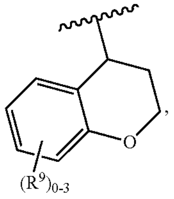, 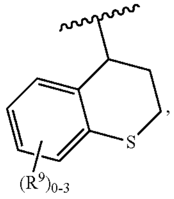, 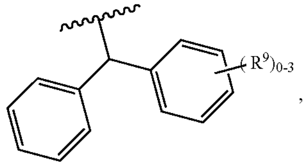, 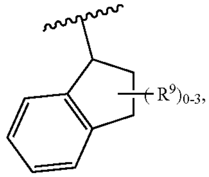, 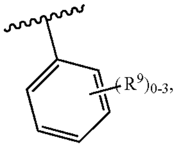, 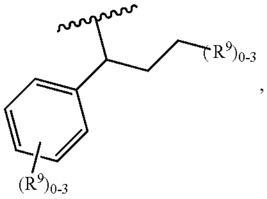, or 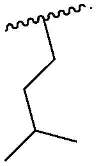.
In some embodiments of a compound of Formula (B-I), $R^8$ is:
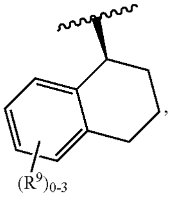, 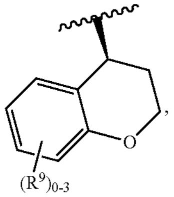, 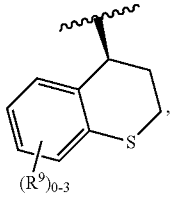, 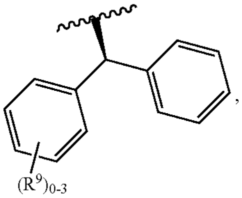, 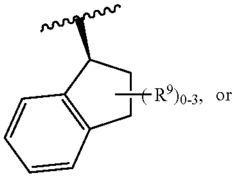, or
-continued
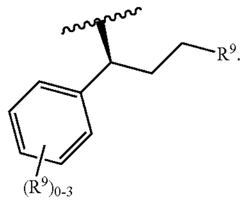.
In some embodiments of a compound of Formula (B-I), $R^8$ is:
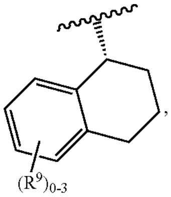, 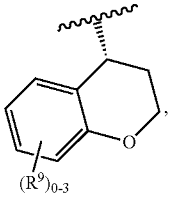, 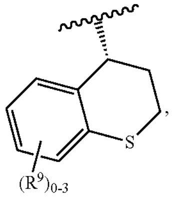, 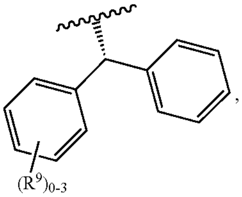, 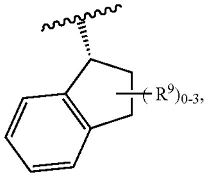, or 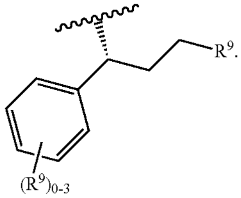.
In some embodiments of a compound of Formula (B-I), $R^8$ is:
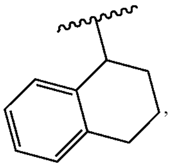, 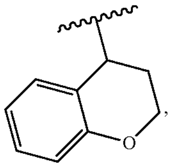, 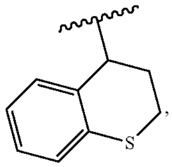, 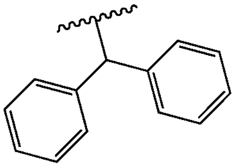, 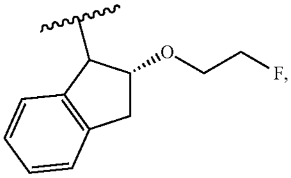, 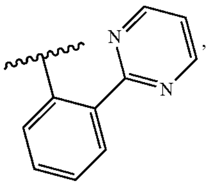, 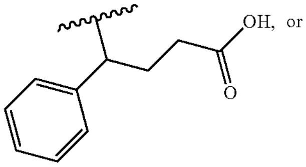, or -continued

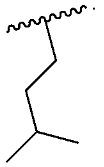

In some embodiments of a compound of Formula (B-I), $R^8$ is:

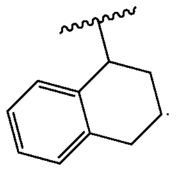 [SMILES: *C1CCCc2ccccc21]

In some embodiments, each $R^9$ is independently halogen, $C_1$-$C_4$alkyl, $C_2$-$C_4$alkenyl, $C_2$-$C_4$alkynyl, $C_1$-$C_4$haloalkyl, $C_1$-$C_4$alkoxy, $C_1$-$C_4$haloalkoxy, $C_1$-$C_4$heteroalkyl, —C(O)H, —C(O)OH, —CN, $C_3$-$C_{10}$cycloalkyl, 3- to 10-membered heterocycloalkyl, $C_6$-$C_{10}$aryl, 5- to 10-membered heteroaryl, —N($C_1$-$C_4$alkyl)$_2$, —OH, —O($C_1$-$C_4$alkyl), —O($C_1$-$C_4$haloalkyl), —O($C_1$-$C_4$alkylene)-(5- to 10-membered heteroaryl), —O($C_6$-$C_{10}$aryl), —SH, $S(O)_2OH$, —$S(O)_2$($C_1$-$C_4$alkyl), —$S(O)_2NH_2$, —$S(O)_2NH$($C_1$-$C_4$alkyl), or —$S(O)_2N$($C_1$-$C_4$alkyl)$_2$. In some embodiments, each $R^9$ is independently halogen, $C_1$-$C_4$alkyl, $C_2$-$C_4$alkenyl, $C_2$-$C_4$alkynyl, $C_1$-$C_4$haloalkyl, $C_1$-$C_4$alkoxy, $C_1$-$C_4$haloalkoxy, $C_1$-$C_4$heteroalkyl, —C(O)H, —C(O)OH, —CN, $C_3$-$C_{10}$cycloalkyl, 3- to 10-membered heterocycloalkyl, $C_6$-$C_{10}$aryl, 5- to 10-membered heteroaryl, —OH, —O($C_1$-$C_4$alkyl), or —O($C_1$-$C_4$haloalkyl). In some embodiments, each $R^9$ is independently halogen, $C_1$-$C_4$alkyl, —C(O)OH, —O($C_1$-$C_4$alkyl), —O($C_1$-$C_4$haloalkyl), or 5- to 10-membered heteroaryl. In some embodiments, each $R^9$ is each independently —C(O)OH, —O($CH_3$), —O($CH_2CH_2F$), or pyrimidine.

Also disclosed herein is a compound or pharmaceutically acceptable salt, solvate, diastereomeric mixture, or individual enantiomers thereof, having the structure of Formula (C-I):

Formula (C-I)

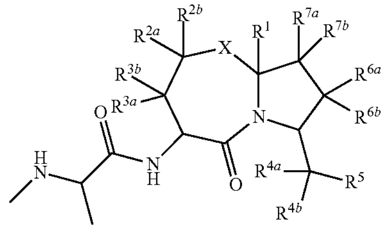

wherein, $R^1$ is hydrogen, $C_1$-$C_6$alkyl, $C_3$-$C_6$cycloalkyl, $C_1$-$C_6$alkyl-($C_3$-$C_6$cycloalkyl), $C_1$-$C_6$alkyl-(phenyl), or $C_1$-$C_6$alkyl-(5- to 6-membered heteroaryl); wherein the $C_1$-$C_6$alkyl, $C_3$-$C_6$cycloalkyl, phenyl, or 5- to 6-membered heteroaryl is optionally substituted with 1, 2, or 3 $R^9$;

X is $NR^A$, O, S, S(O), or $S(O)_2$;

$R^A$ is hydrogen, $C_1$-$C_6$alkyl, C(O)—($C_1$-$C_6$alkyl), C(O)—($C_3$-$C_6$cycloalkyl), C(O)-(phenyl), or C(O)-(5- to 6-membered heteroaryl); wherein each $C_1$-$C_6$alkyl, $C_3$-$C_6$cycloalkyl, phenyl, or 5- to 6-membered heteroaryl is optionally substituted with 1, 2, or 3 $R^9$;

or X is C and taken together with $R^{2a}$, $R^{2b}$, and the carbon atom to which they are attached, forms a phenyl or 5- to 10-membered heteroaryl ring, optionally substituted with 1, 2, or 3 $R^9$;

$R^{2a}$, $R^{2b}$, $R^{3a}$, and $R^{3b}$ are each independently hydrogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, or $C_2$-$C_6$alkynyl is optionally substituted with 1 or 2 $C_3$-$C_{10}$cycloalkyl, 3- to 10-membered heterocycloalkyl, $C_6$-$C_{10}$aryl, or 5- to 10-membered heteroaryl rings; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{2a}$ and $R^{2b}$ together with the carbon atom to which they are attached form a carbonyl;

or $R^{2a}$ and $R^{3a}$, and optionally $R^{2b}$ and $R^{3b}$, together with the carbon atoms to which they are attached form a $C_3$-$C_6$cycloalkyl, 5- to 10-membered heterocycloalkyl, $C_6$-$C_{10}$aryl, or 5- to 10-membered heteroaryl ring; wherein each $C_3$-$C_6$cycloalkyl, 5- to 10-membered heterocycloalkyl, $C_6$-$C_{10}$aryl, or 5- to 10-membered heteroaryl ring is optionally substituted with 1, 2, or 3 $R^9$;

$R^{4a}$ and $R^{4b}$ are each independently hydrogen, halogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, or $C_2$-$C_6$alkynyl is optionally substituted with 1 or 2 $C_3$-$C_{10}$cycloalkyl, 3- to 10-membered heterocycloalkyl, $C_6$-$C_{10}$aryl, or 5- to 10-membered heteroaryl; wherein each $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{4a}$ and $R^{4b}$ together with the carbon atom to which they are attached form a carbonyl;

or $R^{4a}$ and $R^{4b}$ together with the carbon atom to which they are attached form a $C_3$-$C_{10}$cycloalkyl or 3- to 10-membered heterocycloalkyl ring; wherein the $C_3$-$C_{10}$cycloalkyl or 3- to 10-membered heterocycloalkyl ring is optionally substituted with 1, 2, or 3 $R^9$;

$R^5$ is $NHR^B$, $NHS(O)_2R^8$, $OR^B$, $SR^8$, $S(O)_2R^8$, or $S(O)_2NHR^8$;

or $R^5$, $R^{4a}$, and $R^{4b}$, together with the carbon atom to which they are attached, form a $C_6$-$C_{10}$aryl or 5- to 10-membered heteroaryl ring; wherein the $C_6$-$C_{10}$aryl or 5- to 10-membered heteroaryl ring is optionally substituted with 1, 2, or 3 $R^9$;

$R^{6a}$ is hydrogen, halogen, —U, or -G;

$R^{6b}$ is halogen, —U, or -G;

—U is $C_1$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl; wherein each $C_1$-$C_6$alkyl, $C_1$-$C_6$haloalkyl, $C_1$-$C_6$alkoxy, $C_1$-$C_6$heteroalkyl, $C_2$-$C_6$alkenyl, or $C_2$-$C_6$alkynyl is optionally substituted with 1, 2, or 3 $R^9$ and/or 1 or 2-G;

-G is $C_3$-$C_{10}$cycloalkyl, 3- to 10-membered heterocycloalkyl, $C_6$-$C_{10}$aryl, or 5- to 10-membered heteroaryl; wherein each $C_3$-$C_{10}$cycloalkyl, 3- to 10-membered heterocycloalkyl, $C_6$-$C_{10}$aryl, or 5- to 10-membered heteroaryl is optionally substituted with 1, 2, or 3 $R^9$;

or $R^{6a}$ and $R^{6b}$ together with the carbon atom to which they are attached form a saturated or partially saturated 3- to 7-membered cycloalkyl or a saturated or partially saturated 3- to 7-membered heterocycloalkyl; wherein the cycloalkyl or heterocycloalkyl is optionally substituted with 1, 2, or 3 $R^9$;

$R^{7a}$ is hydrogen, halogen, $C_1$-$C_4$alkyl, or $C_1$-$C_4$haloalkyl; $R^{7b}$ is hydrogen, halogen, $C_1$-$C_4$alkyl, or $C_1$-$C_4$haloalkyl;

or $R^{7a}$ and $R^{7b}$ together with the carbon atom to which they are attached form a saturated or partially saturated 3- to 7-membered cycloalkyl or a saturated or partially saturated 3- to 7-membered heterocycloalkyl; wherein the cycloalkyl or heterocycloalkyl is optionally substituted with 1, 2, or 3 $R^9$;

or $R^{6b}$ and $R^{7b}$ together with the carbon atoms to which they are attached form a $C_3$-$C_{10}$cycloalkyl or 3- to 10-membered heterocycloalkyl ring; wherein each $C_3$-$C_{10}$cycloalkyl or 3- to 10-membered heterocycloalkyl ring is optionally substituted with 1, 2, or 3 $R^9$;

or $R^{6a}$, $R^{6b}$, $R^{7a}$, and $R^{7b}$ together with the carbon atoms to which they are attached form a 5- to 10-membered heteroaryl ring optionally substituted with 1, 2, or 3 $R^9$;

$R^8$ is Z, $C_2$-$C_6$alkyl, ($C_1$-$C_6$alkylene)-Z, ($C_1$-$C_6$heteroalkylene)-Z, ($C_2$-$C_6$alkenylene)-Z, $CH(Z)_2$, $CH_2CH(Z)_2$, CH($C_1$-$C_6$alkyl)Z, or C(O)Z; wherein each alkyl, alkylene, heteroalkylene, or alkenylene is optionally substituted with 1, 2, or 3 $R^9$;

Z is $C_3$-$C_9$cycloalkyl, 3- to 10-membered heterocycloalkyl, $C_6$-$C_{10}$aryl, 5- to 10-membered heteroaryl; wherein each $C_3$-$C_9$cycloalkyl, 3- to 10-membered heterocycloalkyl, $C_6$-$C_{10}$aryl, 5- to 10-membered heteroaryl is optionally substituted with 1, 2, or 3 $R^9$;

or Z is a substituted $C_{10}$cycloalkyl substituted with 1, 2, or 3 $R^9$; and each $R^9$ is independently halogen, $C_1$-$C_4$alkyl, $C_2$-$C_4$alkenyl, $C_2$-$C_4$alkynyl, $C_1$-$C_4$haloalkyl, $C_1$-$C_4$alkoxy, $C_1$-$C_4$haloalkoxy, $C_1$-$C_4$heteroalkyl, —C(O)H, —C(O)OH, —CN, $C_3$-$C_{10}$cycloalkyl, 3- to 10-membered heterocycloalkyl, $C_6$-$C_{10}$aryl, 5- to 10-membered heteroaryl, —C(O)($C_1$-$C_4$alkyl), —C(O)O($C_1$-$C_4$alkyl), —C(O)$NH_2$, —C(O)NH($C_1$-$C_4$alkyl), —C(O)N($C_1$-$C_4$alkyl)$_2$, —$NH_2$, —NH($C_1$-$C_4$alkyl), —N($C_1$-$C_4$alkyl)$_2$, —NH($C_2$-$C_4$alkylene)-OH, —NH($C_2$-$C_4$alkylene)-O—($C_1$-$C_4$alkyl), —OH, —O($C_1$-$C_4$alkyl), —O($C_1$-$C_4$haloalkyl), —O($C_2$-$C_4$alkylene)-$NH_2$, —O($C_2$-$C_4$alkylene)-NH—($C_1$-$C_4$alkyl), —O($C_2$-$C_4$alkylene)-N—($C_1$-$C_4$alkyl)$_2$, —O($C_1$-$C_4$alkylene)-C(O)OH, —O($C_1$-$C_4$alkylene)-C(O)O—($C_1$-$C_4$alkyl), —O($C_2$-$C_4$alkenyl), —O($C_1$-$C_4$alkylene)-($C_6$-$C_{10}$aryl), —O($C_1$-$C_4$alkylene)-(5- to 10-membered heteroaryl), —O($C_6$-$C_{10}$aryl), —SH, $S(O)_2OH$, —$S(O)_2$($C_1$-$C_4$alkyl), —$S(O)_2NH_2$, —$S(O)_2$NH($C_1$-$C_4$alkyl), or —$S(O)_2$N($C_1$-$C_4$alkyl)$_2$; or two $R^9$ together with the atoms to which they are attached form a $C_3$-$C_{10}$cycloalkyl or a 3- to 10-membered heterocycloalkyl ring.

In some embodiments, $R^5$, $R^{4a}$ and $R^{4b}$ together with the carbon atom to which they are attached form a $C_6$-$C_{10}$aryl or 5- to 10-membered heteroaryl ring; wherein the $C_6$-$C_{10}$aryl or 5- to 10-membered heteroaryl ring is optionally substituted with 1, 2, or 3 $R^9$. In some embodiments, $R^5$, $R^{4a}$ and $R^{4b}$ together with the carbon atom to which they are attached form a 5- to 10-membered heteroaryl ring, optionally substituted with 1, 2, or 3 $R^9$. In some embodiments, $R^5$, $R^{4a}$ and $R^{4b}$ together with the carbon atom to which they are attached form a 9- or 10-membered heteroaryl ring, optionally substituted with 1, 2, or 3 $R^9$. In some embodiments, $R^5$, $R^{4a}$ and $R^{4b}$ together with the carbon atom to which they are attached form a 10-membered heteroaryl ring. In some embodiments, $R^5$, $R^{4a}$ and $R^{4b}$ together with the carbon atom to which they are attached form a quinoline, isoquinoline, quinoxaline, quinazoline, quinolizine, naphthyridine. In some embodiments, $R^5$, $R^{4a}$ and $R^{4b}$ together with the carbon atom to which they are attached form a 9-membered heteroaryl ring. In some embodiments, $R^5$, $R^{4a}$ and $R^{4b}$ together with the carbon atom to which they are attached form a 2,3-dihydrobenzo[d]oxazole, benzo[d]oxazole, oxazolo[4,5-b]pyridine, 1H-benzo[d]imidazole, benzo[d]thiazole, benzofuran, indole, aza-indole, 1H-imidazo[4,5-b]pyridine, indolizine, imidazo[1,2-a]pyridine, or an isomer thereof, optionally substituted with 1, 2, or 3 $R^9$. In some embodiments, $R^5$, $R^{4a}$ and $R^{4b}$ together with the carbon atom to which they are attached form a benzo[d]oxazole, optionally substituted with 1, 2, or 3 $R^9$. In some embodiments, the $C_6$-$C_{10}$aryl or 5- to 10-membered heteroaryl ring is unsubstituted.

In some embodiments, $R^5$ is $NHR^B$, $NHS(O)_2R^8$, $OR^8$, $SR^8$, $S(O)_2R^8$, or $S(O)_2NHR^8$. In some embodiments, $R^5$ is $NHR^B$, $NHS(O)_2R^8$, $OR^8$, or $S(O)_2NHR^8$. In some embodiments, $R^5$ is $NHR^B$, $NHS(O)_2R^8$, or $OR^8$. In some embodiments, $R^5$ is $OR^8$. In some embodiments, $R^5$ is $NHR^B$, or $NHS(O)_2R^8$. In some embodiments, $R^5$ is $NHS(O)_2R^8$. In some embodiments, $R^5$ is $NHR^8$.

In some embodiments of a compound of Formula (C-I), a compound has the structure of one of the following:

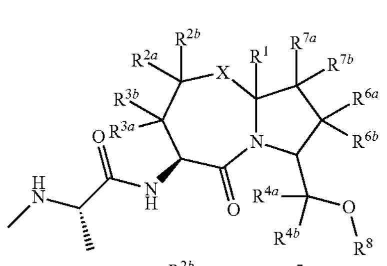

or

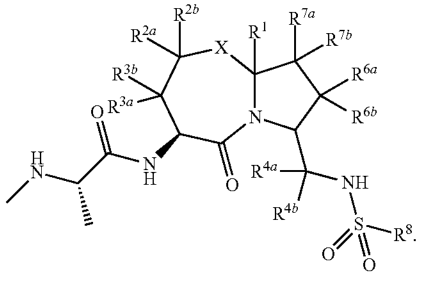

In some embodiments of a compound of Formula (C-I), a compound has the structure of Formula (C-II):

Formula (C-II)

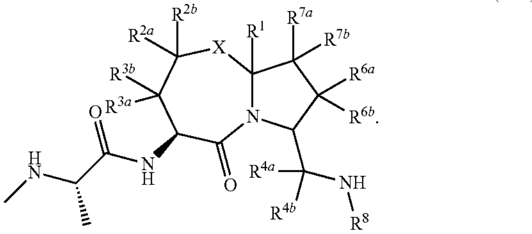

In some embodiments, $R^{4a}$ is H. In some embodiments, $R^{4a}$ is H and $R^{4b}$ is halogen or haloalkyl. In some embodiments, $R^{4b}$ is $CHF_2$ or $CF_3$. In some embodiments, $R^{4a}$ is H and $R^{4b}$ is difluoromethyl or trifluoromethyl. In some embodiments, $R^{4b}$ is difluoromethyl or trifluoromethyl and $R^5$ is $OR^8$. In some embodiments, $R^{4a}$ and $R^{4b}$ are both H.

In some embodiments, $R^{4a}$ and $R^{4b}$ together with the carbon atom to which they are attached form a $C_3$-$C_{10}$cycloalkyl or 3- to 10-membered heterocycloalkyl ring, wherein either of the cycloalkyl or heterocycloalkyl ring is optionally substituted with 1, 2, or 3 $R^9$. In some embodiments, $R^{4a}$ and $R^{4b}$ together with the carbon atom to which they are attached form a $C_3$-$C_6$cycloalkyl, optionally substituted with 1, 2, or 3 $R^9$. In some embodiments, $R^{4a}$ and $R^{4b}$ together with the carbon atom to which they are attached form a $C_3$-$C_5$cycloalkyl, optionally substituted with 1, 2, or 3 $R^9$. In some embodiments, $R^{4a}$ and $R^{4b}$ together with the carbon atom to which they are attached form a cyclopropyl, cyclobutyl, or cyclopentyl ring, optionally substituted with 1, 2, or 3 $R^9$. In some embodiments, $R^{4a}$ and $R^{4b}$ together with the carbon atom to which they are attached form a cyclopropyl, cyclobutyl, or cyclopentyl ring and $R^5$ is —$OR^8$ or —$NHR^B$. In some embodiments, $R^{4a}$ and $R^{4b}$ are each independently halogen, $C_1$-$C_6$alkyl, $C_1$-$C_6$haloalkyl, $C_1$-$C_6$ alkoxy, or $C_1$-$C_6$heteroalkyl and $R^5$ is $NHR^B$.

In some embodiments, $R^{4a}$ and $R^{4b}$ together with the carbon atom to which they are attached form a carbonyl. In some embodiments, $R^{4a}$ and $R^{4b}$ together with the carbon atom to which they are attached form a carbonyl and $R^5$ is $OR^8$ or $NHR^8$. In some embodiments, $R^{4a}$ and $R^{4b}$ together with the carbon atom to which they are attached form a carbonyl and $R^5$ is $NHR^8$.

In some embodiments, $R^1$ is hydrogen, $C_1$-$C_6$alkyl, $C_3$-$C_6$cycloalkyl, $C_1$-$C_6$alkyl-($C_3$-$C_6$cycloalkyl), wherein each alkyl is optionally substituted with 1, 2, or 3 $R^9$. In some embodiments, $R^1$ is phenethyl. In some embodiments, $R^1$ is hydrogen, methyl, trifluoromethyl, difluoromethyl, fluoromethyl, ethyl, propyl, isopropyl, cyclopropyl, methylenecyclopropyl, or cyclobutyl. In some embodiments, $R^1$ is phenethyl. In some embodiments, $R^1$ is hydrogen, methyl, trifluoromethyl, difluoromethyl, fluoromethyl, or ethyl. In some embodiments, $R^1$ is hydrogen or methyl. In some embodiments, $R^1$ is hydrogen.

In some embodiments of a compound of Formula (C-I), a compound has the structure of Formula (C-III):

Formula (C-III)

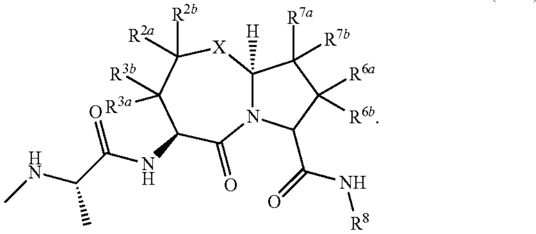

In some embodiments, $R^{2a}$ and $R^{2b}$ are each independently hydrogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, wherein each alkyl, haloalkyl, alkoxy, heteroalkyl, alkenyl, or alkynyl is optionally substituted with 1, 2, or 3 $R^9$. In some embodiments, $R^{2a}$ and $R^{2b}$ are each independently $C_3$-$C_{10}$cycloalkyl, 3- to 10-membered heterocycloalkyl, $C_6$-$C_{10}$aryl, or 5- to 10-membered heteroaryl, wherein each cycloalkyl, heterocycloalkyl, aryl, or heteroaryl is optionally substituted with 1, 2, or 3 $R^9$. In some embodiments, $R^{2a}$ and $R^{2b}$ are each independently hydrogen, $C_1$-$C_6$alkyl, $C_1$-$C_6$haloalkyl, $C_1$-$C_6$ alkoxy, $C_1$-$C_6$heteroalkyl, wherein each alkyl, haloalkyl, alkoxy, or heteroalkyl is optionally substituted with 1 or 2 $C_3$-$C_6$cycloalkyl, 3- to 6-membered heterocycloalkyl, phenyl, or 5- or 6-membered heteroaryl. In some embodiments, $R^{2a}$ is H and $R^{2b}$ is $C_1$-$C_6$alkyl or $C_1$-$C_6$heteroalkyl, wherein each alkyl or heteroalkyl is optionally substituted with a phenyl, or 5- or 6-membered heteroaryl. In some embodiments, $R^{2b}$ is

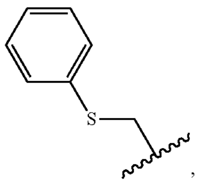

,

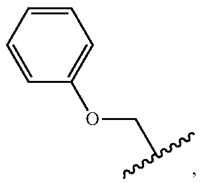

, or

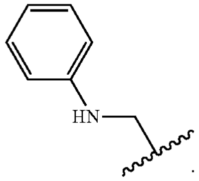

.

In some embodiments, $R^{2a}$ is hydrogen. In some embodiments, $R^{2a}$ and $R^{2b}$ are each hydrogen.

In some embodiments, $R^{2a}$ and $R^{3a}$, and optionally $R^{2b}$ and $R^{3b}$, together with the carbon atoms to which they are attached form a $C_3$-$C_6$cycloalkyl, 5- to 10-membered heterocycloalkyl, $C_6$-$C_{10}$aryl, or 5- to 10-membered heteroaryl ring; wherein each $C_3$-$C_6$cycloalkyl, 5- to 10-membered heterocycloalkyl, $C_6$-$C_{10}$aryl, or 5- to 10-membered heteroaryl ring is optionally substituted with 1, 2, or 3 $R^9$;

In some embodiments, $R^{2a}$ and $R^{2b}$ together with the atom to which they are attached form a carbonyl. In some embodiments, $R^{2a}$ and $R^{2b}$ together with the atom to which they are attached form a carbonyl and X is NH. In some embodiments, $R^{2a}$ and $R^{2b}$ together with the atom to which they are attached form a carbonyl and X is O.

In some embodiments, $R^{3a}$ and $R^{3b}$ are each independently hydrogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, $C_2$-$C_6$alkynyl, $C_3$-$C_{10}$cycloalkyl, 3- to 10-membered heterocycloalkyl, $C_6$-$C_{10}$aryl, or 5- to 10-membered heteroaryl, any of which is optionally substituted with 1, 2, or 3 $R^9$. In some embodiments, $R^{3a}$ and $R^{3b}$ are each independently hydrogen, $C_1$-$C_6$alkyl, $C_1$-$C_6$haloalkyl, $C_1$-$C_6$ alkoxy, $C_1$-$C_6$heteroalkyl, $C_2$-$C_6$alkenyl, or $C_2$-$C_6$alkynyl, wherein each alkyl, haloalkyl, alkoxy, heteroalkyl, alkenyl, or alkynyl is optionally substituted with a cyclopropyl, phenyl, or 5- or 6-membered heteroaryl. In some embodiments, $R^{3a}$ and $R^{3b}$ are each independently hydrogen, methyl, trifluoromethyl, difluoromethyl, ethyl, propyl, isopropyl, cyclopropyl, benzyl, phenethyl, or isobutyl. In some embodiments, $R^{3a}$ and $R^{3b}$ are each methyl. In some embodiments, $R^{3a}$ is hydrogen. In some embodiments, $R^{3a}$ and $R^{3b}$ are each hydrogen.

In some embodiments, $R^{2a}$ and $R^{3a}$, together with the carbon atoms to which they are attached, form a $C_3$-$C_6$cycloalkyl, or 5- to 10-membered heterocycloalkyl. In some embodiments, $R^{2a}$ and $R^{3a}$, together with the carbon atoms to which they are attached, form a cyclopropyl, cyclobutyl, cyclopentyl, cyclohexyl, oxirane, oxetane, tetrahydrofuran, tetrahydropyran, dioxane, aziridine, azetidine, pyrrolidine, piperidine, or morpholine, each of which is optionally substituted with 1 $R^9$. In some embodiments, $R^{2a}$ and $R^{3a}$, together with the carbon atoms to which they are attached, form a cyclopropyl, cyclohexyl, dioxane, piperidine, or morpholine, each of which is optionally substituted with 1 $R^9$. In some embodiments, $R^{2a}$ and $R^{3a}$ together with the carbon atoms to which they are attached form a $C_3$-$C_6$cycloalkyl. In some embodiments, $R^{2a}$ and $R^{3a}$ together with the carbon atoms to which they are attached form a $C_3$-$C_6$cycloalkyl, optionally substituted with 1, 2, or 3 $R^9$. In some embodiments, $R^{2a}$ and $R^{3a}$, together with the carbon atoms to which they are attached, form a cyclopropyl or cyclohexyl, either of which is optionally substituted with 1, 2, or 3 $R^9$. In some embodiments, $R^{2a}$ and $R^{3a}$, together with the carbon atoms to which they are attached, form a cyclohexyl.

In some embodiments, X is $NR^4$, O, S, S(O), or $S(O)_2$. In some embodiments, X is O. In some embodiments, X is S or $S(O)_2$. In some embodiments, X is S. In some embodiments, X is $S(O)_2$. In some embodiments, X is $NR^4$. In some embodiments, $R^4$ is $C_1$-$C_6$alkyl, C(O)—($C_1$-$C_6$alkyl), or C(O)—($C_3$-$C_6$cycloalkyl), wherein each alkyl or cycloalkyl is optionally substituted with 1, 2, or 3 $R^9$. In some embodiments, $R^4$ is hydrogen, methyl, ethyl, $C(O)CH_3$, C(O)cyclopropyl, or C(O)cyclohexyl, wherein each cyclopropyl or cyclohexyl is optionally substituted with 1 or 2 $R^9$. In some embodiments, $R^4$ is hydrogen, methyl, or $C(O)CH_3$. In some embodiments, $R^4$ is hydrogen. In some embodiments of a compound of Formula (C-I), a compound has the structure of Formula (C-IV-a), (C-IV-b), (C-IV-c), or (C-IV-d):

Formula (C-IV-a)

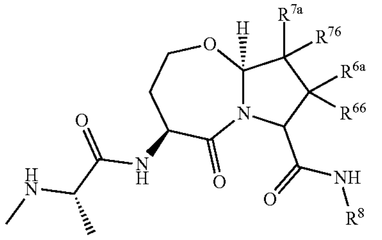

-continued

Formula (C-IV-b)

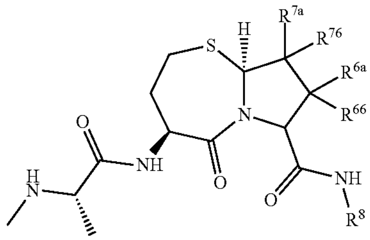

Formula (C-IV-c)

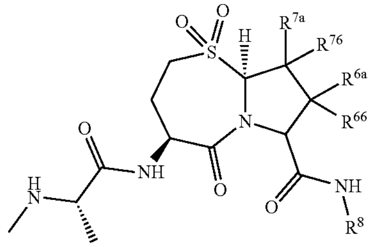

or

Formula (C-IV-d)

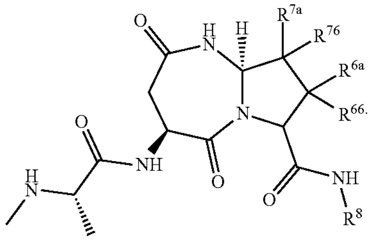

In some embodiments of a compound of Formula (C-I), a compound has the structure of Formula (C-V-a), (C-V-b), (C-V-c), or (C-V-d):

Formula (C-V-a)

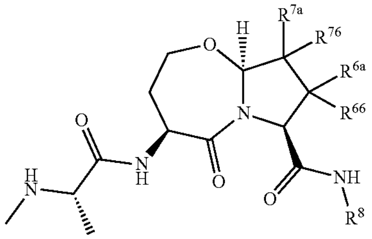

Formula (C-V-b)

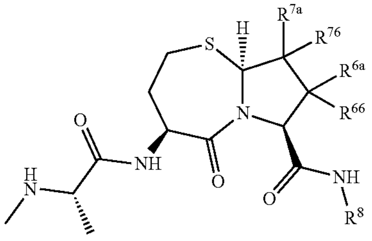

-continued

Formula (C-V-c)

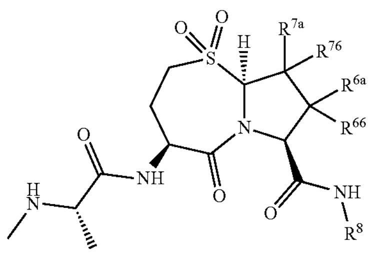

or

Formula (C-V-d)

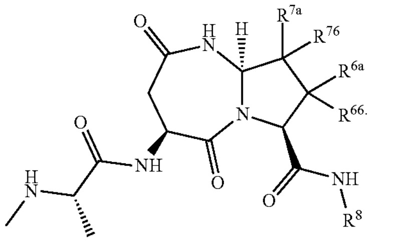

In some embodiments of a compound of Formula (C-I), a compound has the structure of Formula (C-VI-a), (C-VI-b), (C-VI-c), or (C-VI-d):

Formula (C-VI-a)

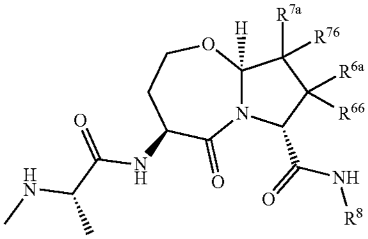

Formula (C-VI-b)

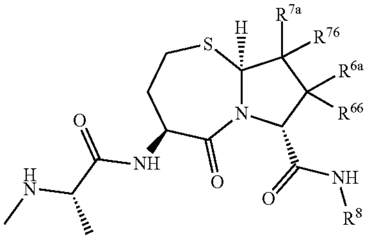

Formula (C-VI-c)

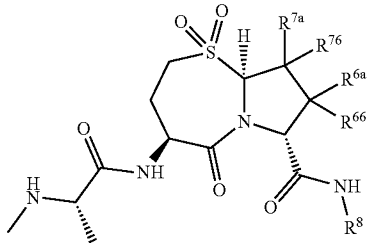

or

-continued

Formula (C-VI-d)

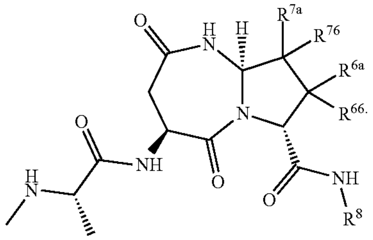

In some embodiments, X is C and taken together with $R^{2a}$, $R^{2b}$, and the carbon atom to which they are attached, forms a phenyl or 5- to 10-membered heteroaryl ring, optionally substituted with 1, 2, or 3 $R^9$. In some embodiments, X is C and taken together with $R^{2a}$, $R^{2b}$, and the carbon atom to which they are attached, forms a phenyl ring, optionally substituted with 1, 2, or 3 $R^9$. In some embodiments, X is C and taken together with $R^{2a}$, $R^{2b}$, and the carbon atom to which they are attached, forms a 5- to 10-membered heteroaryl ring, optionally substituted with 1, 2, or 3 $R^9$. In some embodiments, X is C and taken together with $R^{2a}$, $R^{2b}$, and the carbon atom to which they are attached, forms a 5-membered heteroaryl ring, optionally substituted with 1, 2, or 3 $R^9$. In some embodiments, X is C and taken together with $R^{2a}$, $R^{2b}$, and the carbon atom to which they are attached, forms a 9- or 10-membered heteroaryl ring, optionally substituted with 1, 2, or 3 $R^9$. In some embodiments, X is C and taken together with $R^{2a}$, $R^{2b}$, and the carbon atom to which they are attached, forms a pyrrole, pyrazole, imidazole, indole, or azaindole ring, optionally substituted with 1, 2, or 3 $R^9$. In some embodiments, a compound as disclosed herein has the structure of one of the following:

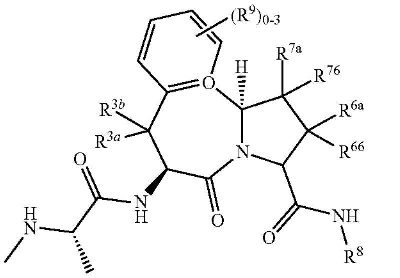

or

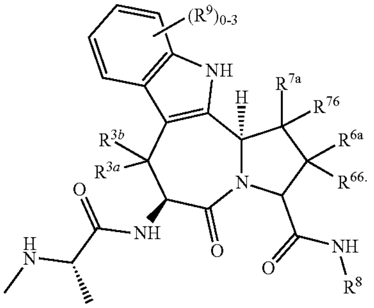

In some embodiments of a compound of Formula (C-I), $R^{6a}$, $R^{6b}$, $R^{7a}$, and $R^{7b}$ together with the carbon atoms to which they are attached form a 5- to 10-membered heteroaryl ring optionally substituted with 1, 2, or 3 $R^9$. In some embodiments of a compound of Formula (C-I), $R^{6a}$, $R^{6b}$, $R^{7a}$, and $R^{7b}$ together with the carbon atoms to which they are attached form a furan, pyrrole, imidazole, pyrazole, triazole, pyridine, pyrimidine, pyridazine, pyrazine, thiophene, oxazole, thiazole, isoxazole, isothiazole, oxepin, azepine, thiepine, triazine, or tetrazine, any of which being optionally substituted with 1, 2, or 3 $R^9$. In some embodiments of a compound of Formula (C-I), $R^{6a}$, $R^{6b}$, $R^{7a}$, and $R^{7b}$ together with the carbon atoms to which they are attached form a furan, pyrrole, imidazole, pyrazole, pyridine, pyrimidine, pyridazine, pyrazine, any of which being optionally substituted with 1, 2, or 3 $R^9$. In some embodiments of a compound of Formula (C-I), $R^{6a}$, $R^{6b}$, $R^{7a}$, and $R^{7b}$ together with the carbon atoms to which they are attached form a furan, pyrrole, pyridine, pyrimidine, pyridazine, pyrazine, any of which being optionally substituted with 1, 2, or 3 $R^9$. In some embodiments of a compound of Formula (C-I), $R^{6a}$, $R^{6b}$, $R^{7a}$, and $R^{7b}$ together with the carbon atoms to which they are attached form a pyridine ring.

In some embodiments of a compound of Formula (C-I), $R^{6b}$ and $R^{7b}$ together with the carbon atoms to which they are attached form a $C_3$-$C_{10}$cycloalkyl or 3- to 10-membered heterocycloalkyl ring; wherein each $C_3$-$C_{10}$cycloalkyl or 3- to 10-membered heterocycloalkyl ring is optionally substituted with 1, 2, or 3 $R^9$. In some embodiments of a compound of Formula (C-I), $R^{6b}$ and $R^{7b}$ together with the carbon atoms to which they are attached form a $C_3$-$C_6$cycloalkyl or 3- to 6-membered heterocycloalkyl ring; wherein each $C_3$-$C_6$cycloalkyl or 3- to 6-membered heterocycloalkyl ring is optionally substituted with 1, 2, or 3 $R^9$. In some embodiments of a compound of Formula (C-I), $R^{6b}$ and $R^{7b}$ together with the carbon atoms to which they are attached form a cyclopropyl, cyclobutyl, cyclopentyl, cyclohexyl, oxirane, aziridine, oxetane, azetidine, oxolane, pyrrolidine, thiolane, oxazolidine, imidazolidine, thiazolidine, isoxazolidine, pyrazolidine, isothiazolidine, dioxolane, dithiolane, oxane, piperidine, thiolane, morpholine, piperazine, thiazine, or dioxane ring, wherein each ring is optionally substituted with 1, 2, or 3 $R^9$. In some embodiments of a compound of Formula (C-I), $R^{6b}$ and $R^{7b}$ together with the carbon atoms to which they are attached form a cyclopropyl, cyclobutyl, cyclopentyl, cyclohexyl, oxolane, oxane, dioxane, morpholine, pyrrolidine, or piperidine ring.

In some embodiments of a compound of Formula (C-I), $R^{7a}$ and $R^{7b}$ together with the carbon atom to which they are attached form a saturated or partially saturated 3- to 7-membered cycloalkyl or a saturated or partially saturated 3- to 7-membered heterocycloalkyl; wherein the cycloalkyl or heterocycloalkyl is optionally substituted with 1, 2, or 3 $R^9$. In some embodiments of a compound of Formula (C-I), $R^{7a}$ and $R^{7b}$ together with the carbon atom to which they are attached form a saturated or partially saturated 3- to 5-membered cycloalkyl or a saturated or partially saturated 3- to 5-membered heterocycloalkyl; wherein the cycloalkyl or heterocycloalkyl is optionally substituted with 1, 2, or 3 $R^9$. In some embodiments of a compound of Formula (C-I), $R^{7a}$ and $R^{7b}$ together with the carbon atom to which they are attached form a cyclopropyl, cyclobutyl, cyclopropenyl, cyclobutenyl, oxirane, aziridine, oxetane, azetidine, or cyclopentyl, or cyclopentenyl ring, wherein each ring is optionally substituted with 1, 2, or 3 $R^9$. In some embodiments of a compound of Formula (C-I), $R^{7a}$ and $R^{7b}$ together with the carbon atom to which they are attached form a cyclopropyl ring, optionally substituted with 1, 2, or 3 $R^9$. In some embodiments of a compound of Formula (C-I), $R^{7a}$ and $R^{7b}$ are each independently hydrogen, halogen, $C_1$-$C_4$alkyl, or $C_1$-$C_4$haloalkyl. In some embodiments of a compound of Formula (C-I), $R^{7a}$ and $R^{7b}$ are each independently hydrogen, fluoro, methyl, ethyl, difluoromethyl, or trifluoromethyl. In some embodiments of a compound of Formula (C-I), $R^{7a}$ and $R^{7b}$ are each independently hydrogen, methyl, or ethyl. In some embodiments of a compound of Formula (C-I), $R^{7a}$ and $R^{7b}$ are each hydrogen.

In some embodiments of a compound of Formula (C-I), $R^{6a}$ and $R^{6b}$ together with the carbon atom to which they are attached form a saturated or partially saturated 3- to 7-membered cycloalkyl ring optionally substituted with 1, 2, or 3 $R^9$. In some embodiments of a compound of Formula (C-I), $R^{6a}$ and $R^{6b}$ together with the carbon atom to which they are attached form a cyclopropyl, cyclobutyl, cyclopropenyl, cyclobutenyl, oxirane, aziridine, oxetane, azetidine, or cyclopentyl, or cyclopentenyl ring, wherein each ring is optionally substituted with 1, 2, or 3 $R^9$. In some embodiments of a compound of Formula (C-I), $R^{6a}$ and $R^{6b}$ together with the carbon atom to which they are attached form a saturated or partially saturated 3- to 5-membered cycloalkyl ring, optionally substituted with 1, 2, or 3 $R^9$.

In some embodiments, $R^{6a}$ is hydrogen. In some embodiments, $R^{6a}$ is hydrogen and $R^{6b}$ is halogen, $C_1$-$C_6$alkyl, $C_1$-$C_6$haloalkyl, $C_2$-$C_6$alkenyl, or $C_2$-$C_6$alkynyl; wherein each $C_1$-$C_6$alkyl, $C_1$-$C_6$haloalkyl, $C_2$-$C_6$alkenyl, or $C_2$-$C_6$alkynyl is optionally substituted with 1, 2, or 3 $R^9$ and/or 1 or 2, G. In some embodiments, $R^{6b}$ is halogen, $C_1$-$C_6$alkyl, $C_1$-$C_6$haloalkyl, $C_2$-$C_6$alkenyl, or $C_2$-$C_6$alkynyl; wherein each $C_1$-$C_6$alkyl, $C_1$-$C_6$haloalkyl, $C_2$-$C_6$alkenyl, or $C_2$-$C_6$alkynyl is optionally substituted with 1, 2, or 3 $R^9$ and/or 1 or 2, G. In some embodiments, $R^{6b}$ is $C_1$-$C_6$alkyl, $C_1$-$C_6$haloalkyl, $C_2$-$C_6$alkenyl, or $C_2$-$C_6$alkynyl, wherein each alkyl, haloalkyl, alkenyl, or alkynyl is optionally substituted with a phenyl or 5- or 6-membered heteroaryl ring, wherein each phenyl or heteroaryl ring is optionally substituted with 1, 2, or 3 $R^9$. In some embodiments, $R^{6b}$ is methyl, ethyl, or propyl, wherein the methyl, ethyl, or propyl is optionally substituted with G, and wherein G is a phenyl ring further substituted with 1, 2, or 3 $R^9$. In some embodiments, $R^{6b}$ is ethyl, optionally substituted with phenyl, tolyl, phenolyl, fluorophenyl, chlorophenyl, anilinyl, methoxyphenyl, dimethylphenyl, difluorophenyl, dichlorophenyl, dihydroxyphenyl, dimethoxyphenyl, fluoromethoxyphenyl, or naphthyl. In some embodiments, $R^{6b}$ is $C_1$-$C_6$alkyl, $C_1$-$C_6$haloalkyl, $C_2$-$C_6$alkenyl, or $C_2$-$C_6$alkynyl, wherein each alkyl, haloalkyl, alkenyl, or alkynyl is optionally substituted with a $C_3$-$C_6$cycloalkyl or 3- to 6-membered heterocycloalkyl ring, wherein each cycloalkyl or heterocyclalkyl ring is optionally substituted with 1, 2, or 3 $R^9$. In some embodiments, $R^{6b}$ is methyl, ethyl, 2-propenyl, isopropyl, or phenethyl. In some embodiments, $R^{6b}$ is methyl. In some embodiments, $R^{6b}$ is ethyl. In some embodiments, $R^{6b}$ is 2-propenyl. In some embodiments, $R^{6b}$ is isopropyl. In some embodiments, $R^{6b}$ is phenethyl.

In some embodiments of a compound of Formula (C-I), $R^{6a}$ and $R^{6b}$ are each independently halogen, $C_1$-$C_6$alkyl, $C_1$-$C_6$haloalkyl, $C_2$-$C_6$alkenyl, or $C_2$-$C_6$alkynyl; wherein each $C_1$-$C_6$alkyl, $C_1$-$C_6$haloalkyl, $C_2$-$C_6$alkenyl, or $C_2$-$C_6$alkynyl is optionally substituted with 1, 2, or 3 $R^9$ and/or 1 or 2, G. In some embodiments of a compound of Formula (C-I), $R^{6a}$ and $R^{6b}$ are each independently halogen, $C_2$-$C_6$alkyl, $C_1$-$C_6$haloalkyl, $C_2$-$C_6$alkenyl, or $C_2$-$C_6$alkynyl; wherein each $C_2$-$C_6$alkyl, $C_1$-$C_6$haloalkyl, $C_2$-$C_6$alkenyl, or $C_2$-$C_6$alkynyl is optionally substituted with 1, 2, or 3 $R^9$ and/or 1 or 2, G. In some embodiments of a compound of Formula (C-I), $R^{6a}$ and $R^{6b}$ are each independently $C_1$-$C_6$alkyl, $C_1$-$C_6$haloalkyl, $C_2$-$C_6$alkenyl, or $C_2$-$C_6$alkynyl, wherein each alkyl, haloalkyl, alkenyl, or alkynyl is optionally substituted with a phenyl or 5- or 6-membered heteroaryl ring, wherein each phenyl or heteroaryl ring is optionally substituted with 1, 2, or 3 $R^9$. In some embodiments of a compound of Formula (C-I), $R^{6a}$ and $R^{6b}$ are each independently methyl, ethyl, or propyl, optionally substituted with G, wherein G is a phenyl ring further substituted with 1, 2, or 3 $R^9$. In some embodiments, $R^{6a}$ and $R^{6b}$ are each independently ethyl, optionally substituted with phenyl, tolyl, phenolyl, fluorophenyl, chlorophenyl, anilinyl, methoxyphenyl, dimethylphenyl, difluorophenyl, dichlorophenyl, dihydroxyphenyl, dimethoxyphenyl, fluoromethoxyphenyl, or naphthyl. In some embodiments of a compound of Formula (C-I), $R^{6a}$ and $R^{6b}$ are each independently $C_1$-$C_6$alkyl, $C_1$-$C_6$haloalkyl, $C_2$-$C_6$alkenyl, or $C_2$-$C_6$alkynyl, wherein each alkyl, haloalkyl, alkenyl, or alkynyl is optionally substituted with a $C_3$-$C_6$cycloalkyl or 3- to 6-membered heterocycloalkyl ring, wherein each cycloalkyl or heterocyclalkyl ring is optionally substituted with 1, 2, or 3 $R^9$. In some embodiments of a compound of Formula (C-I), $R^{6a}$ and $R^{6b}$ are each independently methyl, ethyl, 2-propenyl, isopropyl, or phenethyl. In some embodiments, $R^{6a}$ and $R^{6b}$ are each independently ethyl, 2-propenyl, isopropyl, or phenethyl. In some embodiments of a compound of Formula (C-I), $R^{6a}$ and $R^{6b}$ are methyl. In some embodiments, $R^{6a}$ and $R^{6b}$ are ethyl. In some embodiments, $R^{6a}$ and $R^{6b}$ are 2-propenyl. In some embodiments, $R^{6a}$ and $R^{6b}$ are isopropyl. In some embodiments, $R^{6a}$ and $R^{6b}$ are phenethyl.

In some embodiments, $R^8$ is Z, $C_2$-$C_6$alkyl, ($C_1$-$C_6$alkylene)-Z, ($C_1$-$C_6$heteroalkylene)-Z, ($C_2$-$C_6$alkenylene)-Z, $CH(Z)_2$, $CH_2CH(Z)_2$, $CH(C_1$-$C_6alkyl)Z$, or C(O)Z; wherein each alkyl, alkylene, heteroalkylene, or alkenylene is optionally substituted with 1, 2, or 3 $R^9$. In some embodiments, $R^8$ is Z, $C_2$-$C_6$alkyl, $CH(Z)_2$, or C(O)Z. In some embodiments of a compound of Formula (C-I), $R^8$ is Z, $C_2$-$C_6$alkyl, $CH(Z)_2$, or C(O)Z, wherein Z is $C_3$-$C_9$cycloalkyl, 3- to 10-membered heterocycloalkyl, $C_6$-$C_{10}$aryl, or 5- to 10-membered heteroaryl. In some embodiments, $R^8$ is Z or $CH(Z)_2$. In some embodiments, $R^8$ is Z. In some embodiments, $R^8$ is $CH(Z)_2$. In some embodiments of a compound of Formula (C-I), Z is $C_3$-$C_9$cycloalkyl, 3- to 10-membered heterocycloalkyl, $C_6$-$C_{10}$aryl, or 5- to 10-membered heteroaryl; wherein each $C_3$-$C_9$cycloalkyl, 3- to 10-membered heterocycloalkyl, $C_6$-$C_{10}$ aryl, and 5- to 10-membered heteroaryl is optionally substituted with 1, 2, or 3 $R^9$. In some embodiments, Z is $C_6$-$C_{10}$aryl or 5- to 10-membered heteroaryl, wherein each aryl or heteroaryl is optionally substituted with 1, 2, or 3 $R^9$. In some embodiments of a compound of Formula (C-I), Z is $C_3$-$C_9$cycloalkyl or 3- to 10-membered heterocycloalkyl; wherein each $C_3$-$C_9$cycloalkyl and 3- to 10-membered heterocycloalkyl is optionally substituted with 1, 2, or 3 $R^9$. In some embodiments of a compound of Formula (C-I), Z is $C_{10}$cycloalkyl substituted with 1, 2, or 3 $R^9$. In some embodiments, Z is phenyl or naphthyl, optionally substituted with 1, 2, or 3 $R^9$. In some embodiments, Z is pyridine, pyrimidine, pyridazine, pyrazine, quinoline, naphthyridine, quinoxaline, quinolizine, benzofuran, benzoxazole, or benzothiophene. In some embodiments, Z is tetrahydroquinoline, tetrahydroisoquinoline, chroman, thiochroman, indane, indoline, dihydrobenzofuran, or dihydrobenzothiophene.

In some embodiments of a compound of Formula (C-I), $R^8$ is:

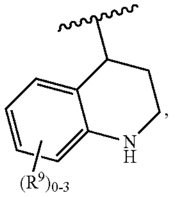
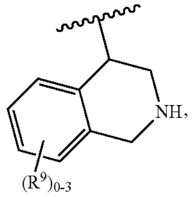
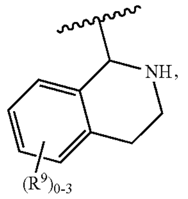
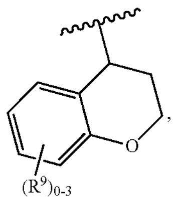
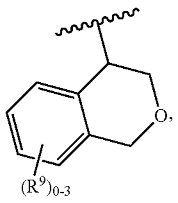
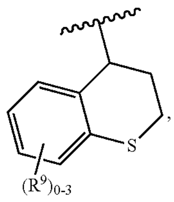
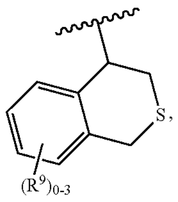
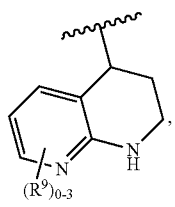
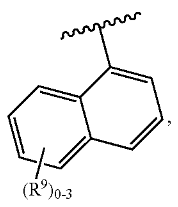
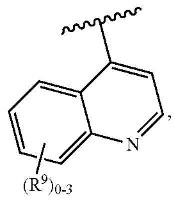
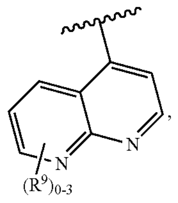
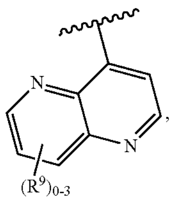
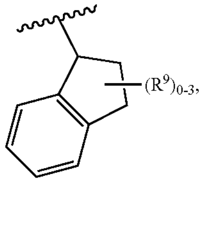

-continued
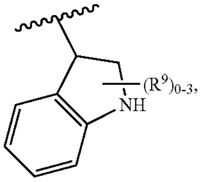,
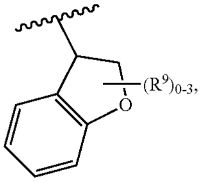,
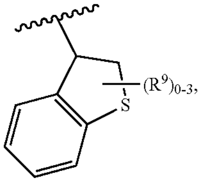,
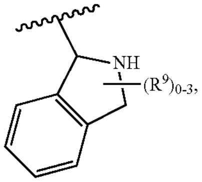,
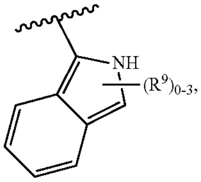,
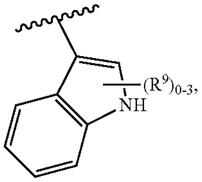,
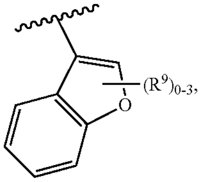,
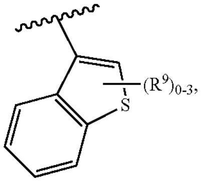,
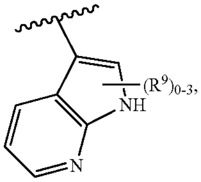,
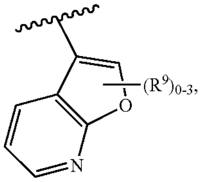,
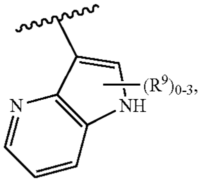,
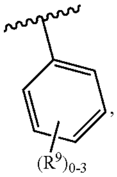,
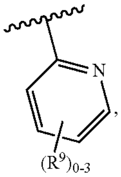,
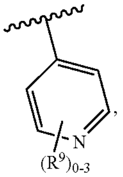,
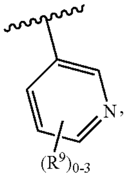,
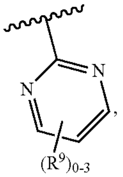,
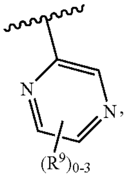,
-continued
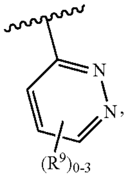,
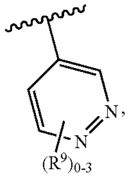,
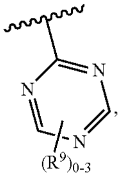,
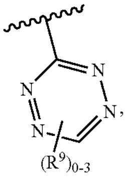,
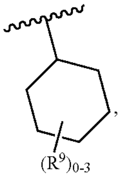,
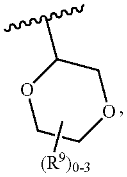,
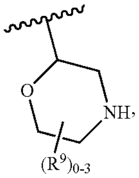,
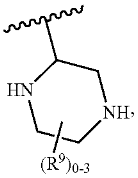,
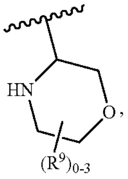,
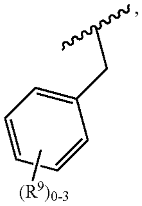,
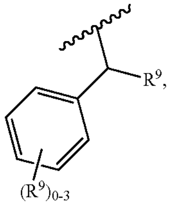,
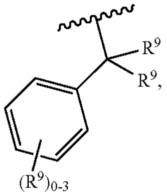,
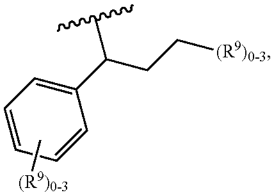, -continued
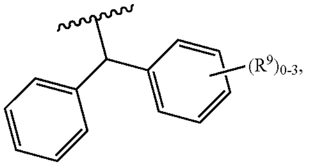
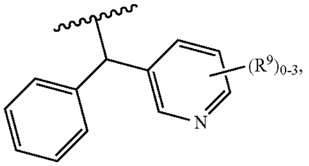
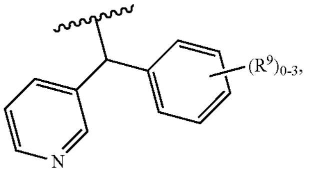
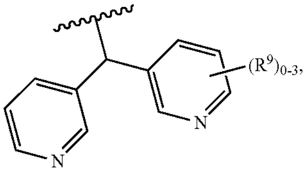
or
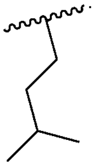
In some embodiments of a compound of Formula (C-I), $R^8$ is:
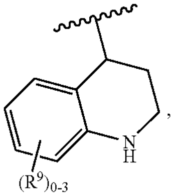
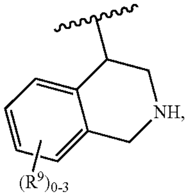
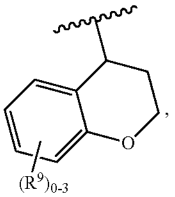
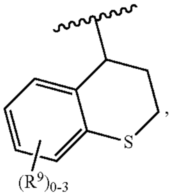
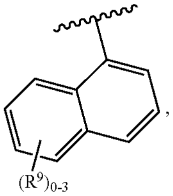
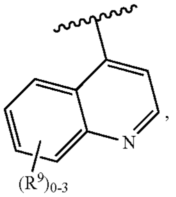
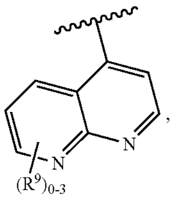
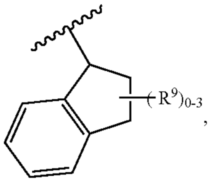
-continued
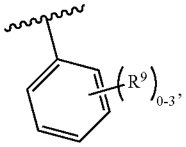
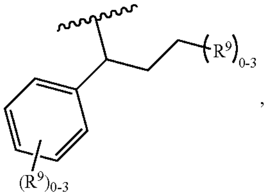
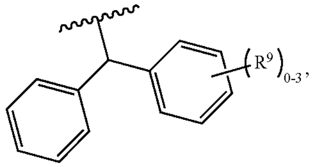
or
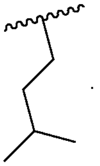
In some embodiments of a compound of Formula (C-I), $R^8$ is:
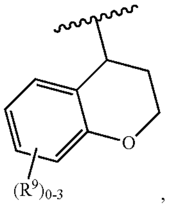
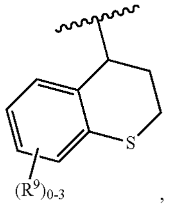
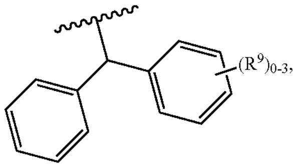
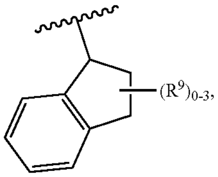
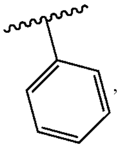
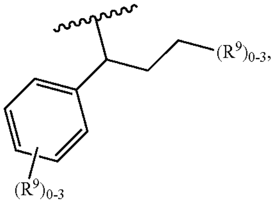
or
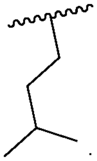
In some embodiments of a compound of Formula (C-I), $R^8$ is:

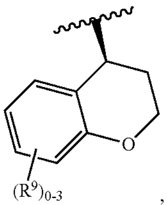
,
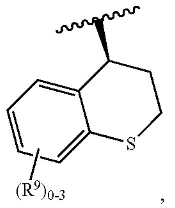
,
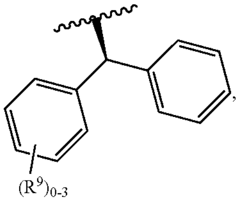
,
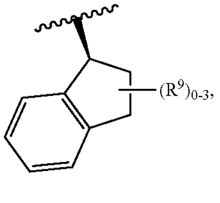
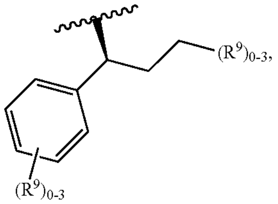
or

In some embodiments of a compound of Formula (C-I), $R^8$ is:

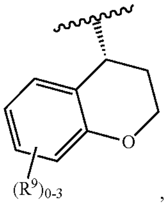
,
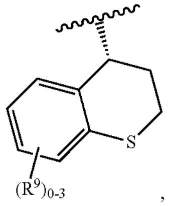
,
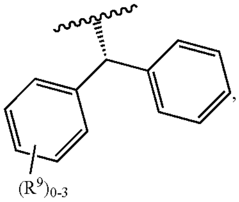
,
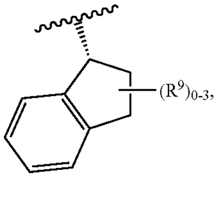
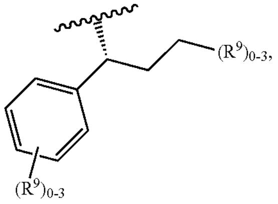
or

In some embodiments of a compound of Formula (C-I), $R^8$ is:

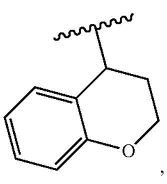
,
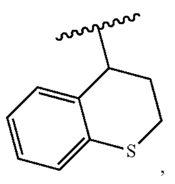
,

-continued

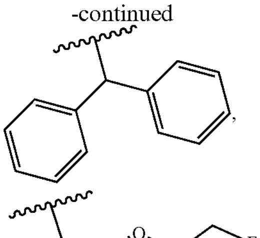
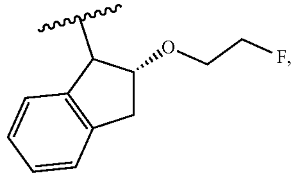
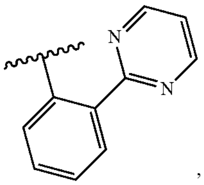
,
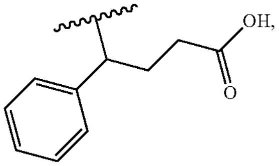
or
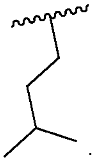
.

In some embodiments of a compound of Formula (C-I), $R^8$ is:

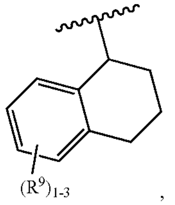
,
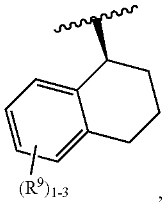
, or
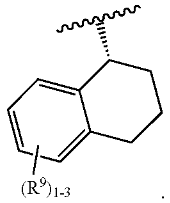
.

In some embodiments, each $R^9$ is independently halogen, $C_1$-$C_4$alkyl, $C_2$-$C_4$alkenyl, $C_2$-$C_4$alkynyl, $C_1$-$C_4$haloalkyl, $C_1$-$C_4$alkoxy, $C_1$-$C_4$haloalkoxy, $C_1$-$C_4$heteroalkyl, —C(O)H, —C(O)OH, —CN, $C_3$-$C_{10}$cycloalkyl, 3- to 10-membered heterocycloalkyl, $C_6$-$C_{10}$aryl, 5- to 10-membered heteroaryl, —N($C_1$-$C_4$alkyl)$_2$, —OH, —O($C_1$-$C_4$alkyl), —O($C_1$-$C_4$haloalkyl), —O($C_1$-$C_4$alkylene)-(5- to 10-membered heteroaryl), —O($C_6$-$C_{10}$aryl), —SH, $S(O)_2OH$, —$S(O)_2$($C_1$-$C_4$alkyl), —$S(O)_2NH_2$, —$S(O)_2NH$($C_1$-$C_4$alkyl), or —$S(O)_2N$($C_1$-$C_4$alkyl)$_2$. In some embodiments, each $R^9$ is independently halogen, $C_1$-$C_4$alkyl, $C_2$-$C_4$alkenyl, $C_2$-$C_4$alkynyl, $C_1$-$C_4$haloalkyl, $C_1$-$C_4$alkoxy, $C_1$-$C_4$haloalkoxy, $C_1$-$C_4$heteroalkyl, —C(O)H, —C(O)OH, —CN, $C_3$-$C_{10}$cycloalkyl, 3- to 10-membered heterocycloalkyl, $C_6$-$C_{10}$aryl, 5- to 10-membered heteroaryl, —OH, —O($C_1$-$C_4$alkyl), or —O($C_1$-$C_4$haloalkyl). In some embodiments, each $R^9$ is independently halogen, $C_1$-$C_4$alkyl, —C(O)OH, —O($C_1$-$C_4$alkyl), —O($C_1$-$C_4$haloalkyl), or 5- to 10-membered heteroaryl. In some embodiments, each $R^9$ is each independently —C(O)OH, —O($CH_3$), —O($CH_2CH_2F$), or pyrimidine.

In some embodiments, a compound of the present disclosure has the structure:

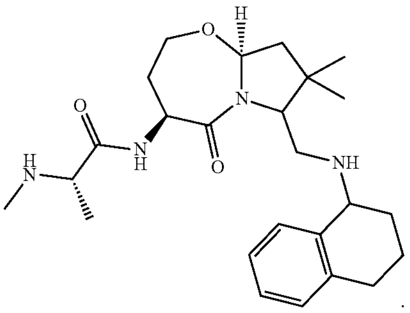 [SMILES: CN[C@@H](C)C(=O)N[C@H]1CCO[C@H]2CC(C)(C)C(CNC3CCCc4ccccc43)N2C1=O]

In some embodiments, a compound of the present disclosure has the structure:

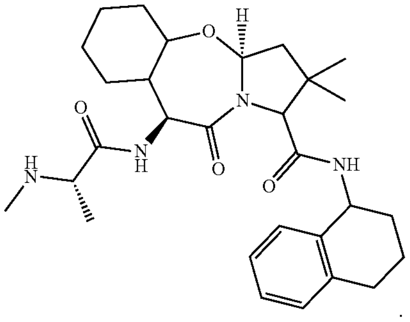 [SMILES: CN[C@@H](C)C(=O)N[C@@H]1C(=O)N2C(C(=O)NC3CCCc4ccccc43)C(C)(C)C[C@@H]2OC2CCCCC21]

In some embodiments, a compound of the present disclosure has the structure:

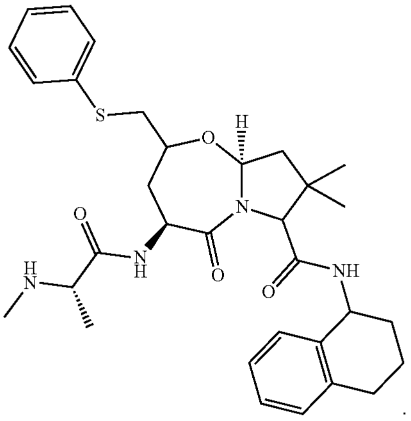 [SMILES: CN[C@@H](C)C(=O)N[C@H]1CC(CSc2ccccc2)O[C@H]2CC(C)(C)C(C(=O)NC3CCCc4ccccc43)N2C1=O]

In some embodiments, a compound of the present disclosure has the structure:

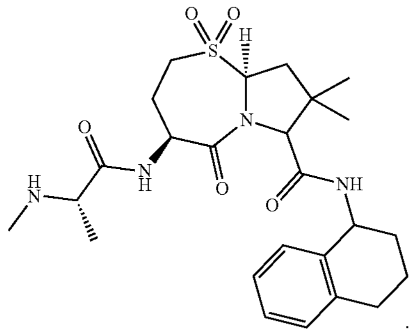 [SMILES: CN[C@@H](C)C(=O)N[C@H]1CCS(=O)(=O)[C@H]2CC(C)(C)C(C(=O)NC3CCCc4ccccc43)N2C1=O]

In some embodiments, a compound of the present disclosure has the structure:

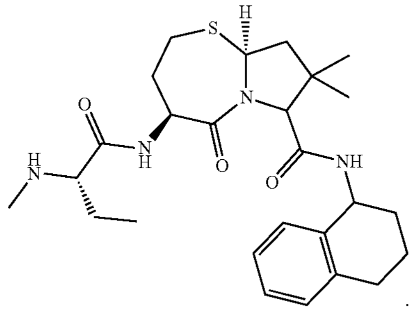 [SMILES: CC[C@H](NC)C(=O)N[C@H]1CCS[C@H]2CC(C)(C)C(C(=O)NC3CCCc4ccccc43)N2C1=O]

In some embodiments, a compound of the present disclosure has the structure:

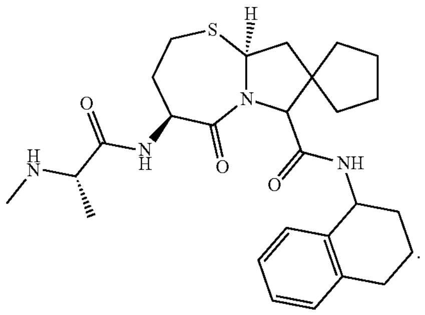 [SMILES: CN[C@@H](C)C(=O)N[C@H]1CCS[C@H]2CC3(CCCC3)C(C(=O)NC3CCCc4ccccc43)N2C1=O]

In some embodiments, a compound of the present disclosure has the structure:

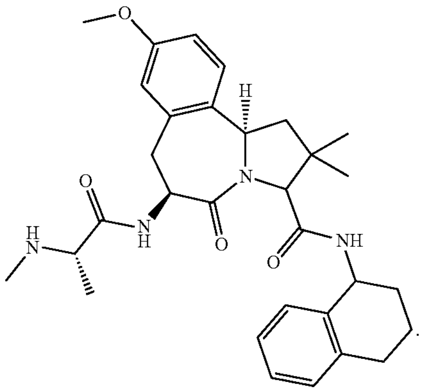 [SMILES: CN[C@@H](C)C(=O)N[C@H]1Cc2cc(OC)ccc2[C@H]2CC(C)(C)C(C(=O)NC3CCCc4ccccc43)N2C1=O]

In some embodiments, a compound of the present disclosure has the structure:

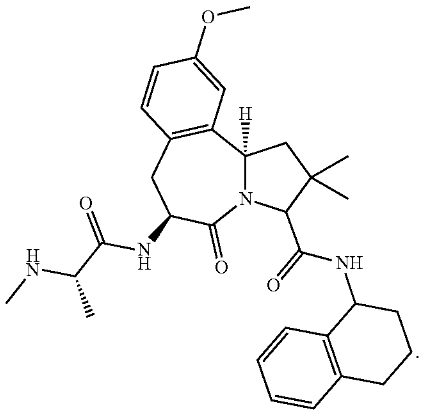 [SMILES: CN[C@@H](C)C(=O)N[C@H]1Cc2ccc(OC)cc2[C@H]2CC(C)(C)C(C(=O)NC3CCCc4ccccc43)N2C1=O]

In some embodiments, a compound of the present disclosure has the structure:

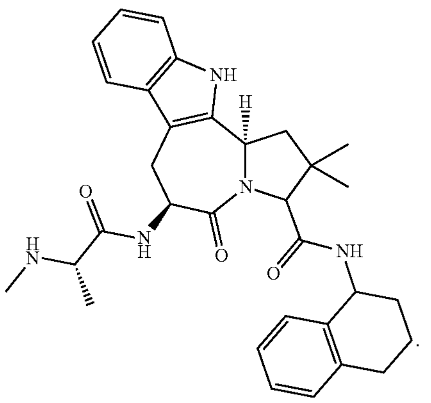 [SMILES: CN[C@@H](C)C(=O)N[C@H]1Cc2c([nH]c3ccccc23)[C@H]2CC(C)(C)C(C(=O)NC3CCCc4ccccc43)N2C1=O]

In some embodiments, a compound of the present disclosure has the structure:

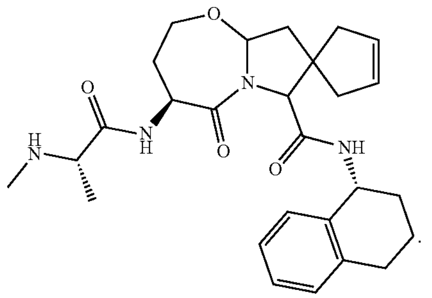 [SMILES: CN[C@@H](C)C(=O)N[C@H]1CCOC2CC3(CC=CC3)C(C(=O)N[C@@H]3CCCc4ccccc43)N2C1=O]

In some embodiments, a compound of the present disclosure has the structure:

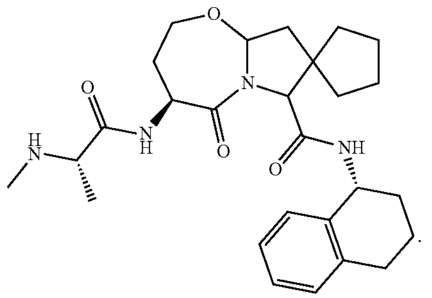 [SMILES: CN[C@@H](C)C(=O)N[C@H]1CCOC2CC3(CCCC3)C(C(=O)N[C@@H]3CCCc4ccccc43)N2C1=O]

In some embodiments, a compound of the present disclosure has the structure:

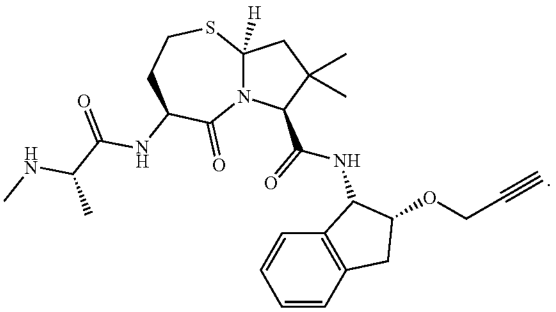

In some embodiments, a compound of the present disclosure has the structure:

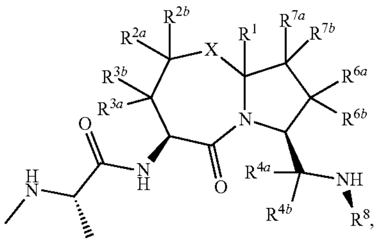

-continued

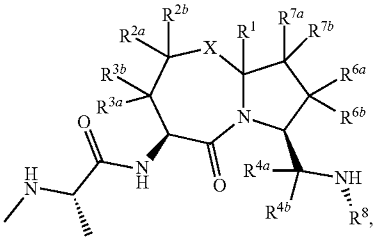

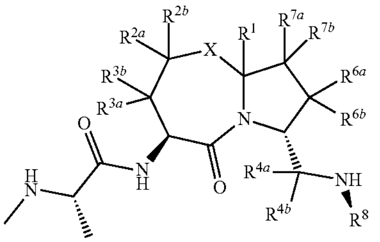

or

-continued

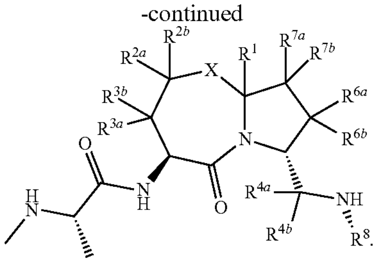

In some embodiments, a compound described herein has the form of any one of the structures found in Table A. Various stereoisomers (e.g., enantiomers, diastereomers) exist for many of the compounds disclosed. All of the possible stereoisomers are contemplated within the context of the present disclosure. In some embodiments, a compound disclosed herein may be a mixture of stereoisomers. In some embodiments, a compound may be a pure isomer. In some embodiments, a compound is a mixture of enantiomers. In some embodiments, a compound is a mixture of diastereomers. In some embodiments, a compound disclosed herein exists as a mixture of various stereoisomers, wherein one or more chiral centers are unresolved or unseparated. In some embodiments, each chiral center is known. In some embodiments, a subset of the total number of chiral centers have known stereochemistry. In some embodiments, a compound may be racemized or contain a mixture of racemates.

TABLE A

| Structure | Compound # |
| --- | --- |
| 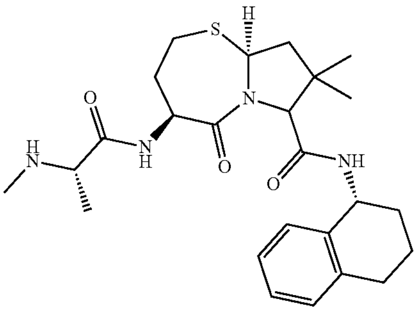 [SMILES: CN[C@@H](C)C(=O)N[C@H]1CCS[C@H]2CC(C)(C)C(C(=O)N[C@@H]3CCCc4ccccc43)N2C1=O] | A |
| 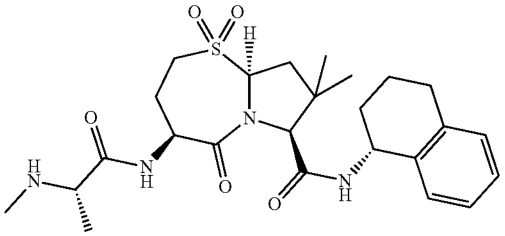 [SMILES: CN[C@@H](C)C(=O)N[C@H]1CCS(=O)(=O)[C@H]2CC(C)(C)[C@@H](C(=O)N[C@@H]3CCCc4ccccc43)N2C1=O] | 1 |
| 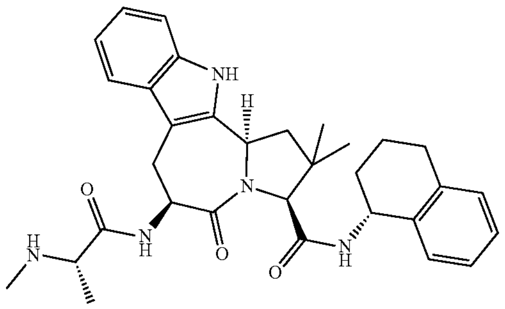 [SMILES: CN[C@@H](C)C(=O)N[C@H]1Cc2c([nH]c3ccccc23)[C@H]2CC(C)(C)[C@@H](C(=O)N[C@@H]3CCCc4ccccc43)N2C1=O] | 2 |

TABLE A-continued
| Structure | Compound # |
|---|---|
| 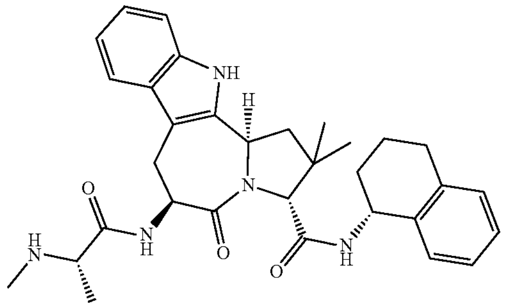 [SMILES: CN[C@@H](C)C(=O)N[C@H]1Cc2c([nH]c3ccccc23)[C@H]2CC(C)(C)[C@H](C(=O)N[C@@H]3CCCc4ccccc43)N2C1=O] | 3 |
| 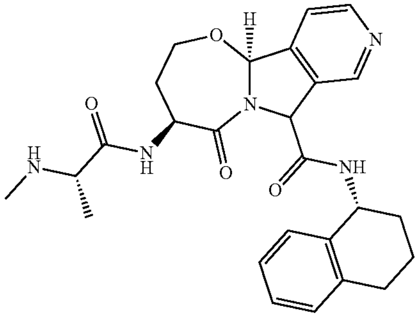 [SMILES: CN[C@@H](C)C(=O)N[C@H]1CCO[C@H]2c3ccncc3C(C(=O)N[C@@H]3CCCc4ccccc43)N2C1=O] | 4 |
| 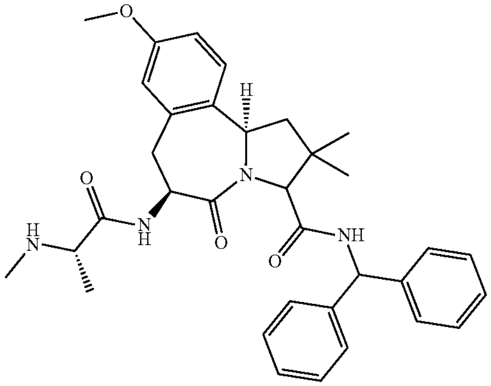 [SMILES: CN[C@@H](C)C(=O)N[C@H]1Cc2cc(OC)ccc2[C@H]2CC(C)(C)C(C(=O)NC(c3ccccc3)c3ccccc3)N2C1=O] | 5 |
| 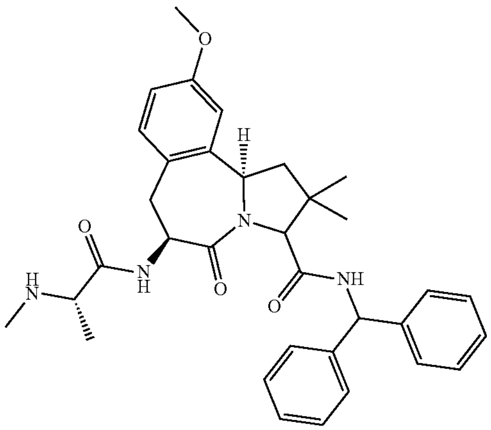 [SMILES: CN[C@@H](C)C(=O)N[C@H]1Cc2ccc(OC)cc2[C@H]2CC(C)(C)C(C(=O)NC(c3ccccc3)c3ccccc3)N2C1=O] | 6 |

TABLE A-continued
| Structure | Compound # |
| --- | --- |
| 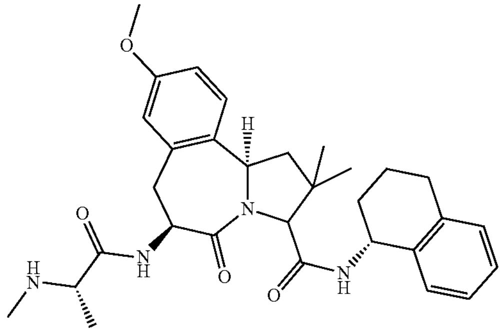 [SMILES: CN[C@@H](C)C(=O)N[C@H]1Cc2cc(OC)ccc2[C@H]2CC(C)(C)C(C(=O)N[C@@H]3CCCc4ccccc43)N2C1=O] | 7 |
| 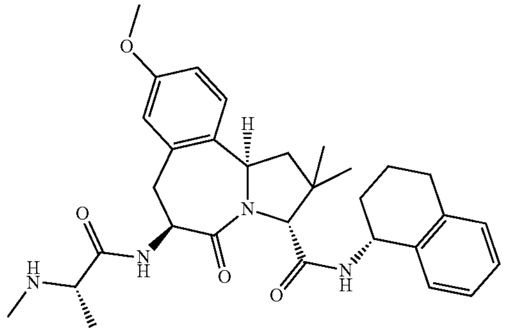 [SMILES: CN[C@@H](C)C(=O)N[C@H]1Cc2cc(OC)ccc2[C@H]2CC(C)(C)[C@H](C(=O)N[C@@H]3CCCc4ccccc43)N2C1=O] | 8 |
| 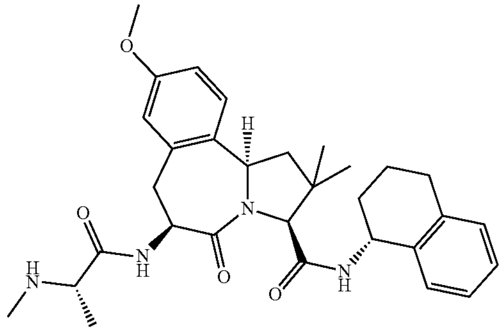 [SMILES: CN[C@@H](C)C(=O)N[C@H]1Cc2cc(OC)ccc2[C@H]2CC(C)(C)[C@@H](C(=O)N[C@@H]3CCCc4ccccc43)N2C1=O] | 9 |
| 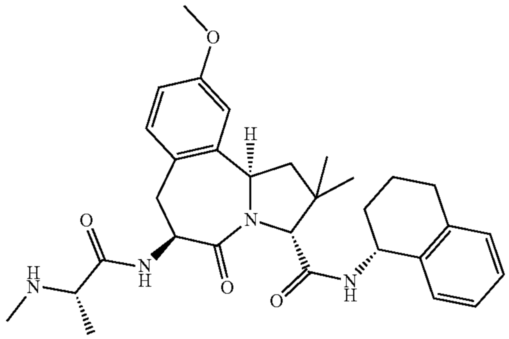 [SMILES: CN[C@@H](C)C(=O)N[C@H]1Cc2ccc(OC)cc2[C@H]2CC(C)(C)[C@H](C(=O)N[C@@H]3CCCc4ccccc43)N2C1=O] | 10 |

TABLE A-continued
| Structure | Compound # |
|---|---|
| 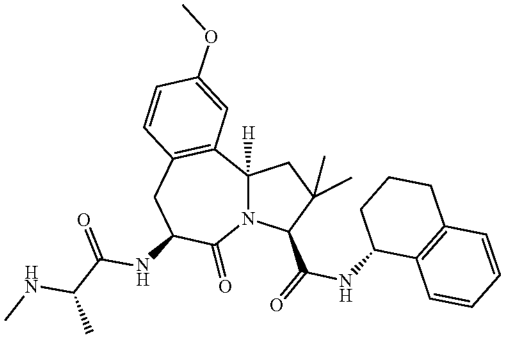 [SMILES: CN[C@@H](C)C(=O)N[C@H]1Cc2ccc(OC)cc2[C@H]2CC(C)(C)[C@@H](C(=O)N[C@@H]3CCCc4ccccc43)N2C1=O] | 11 |
| 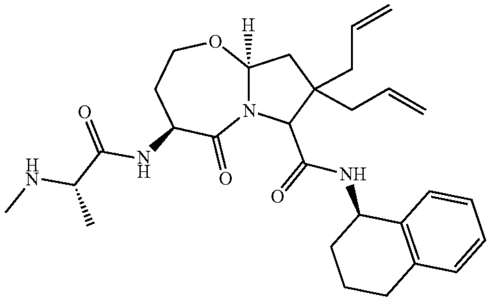 [SMILES: C=CCC1(CC=C)C[C@@H]2OCC[C@H](NC(=O)[C@H](C)NC)C(=O)N2C1C(=O)N[C@@H]1CCCc2ccccc21] | 12 |
| 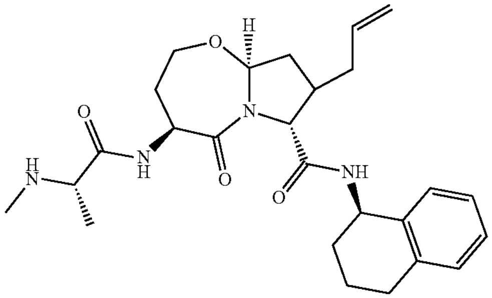 [SMILES: C=CCC1C[C@@H]2OCC[C@H](NC(=O)[C@H](C)NC)C(=O)N2[C@H]1C(=O)N[C@@H]1CCCc2ccccc21] | 13 |
| 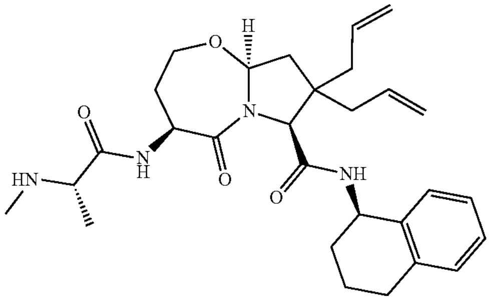 [SMILES: C=CCC1(CC=C)C[C@@H]2OCC[C@H](NC(=O)[C@H](C)NC)C(=O)N2[C@@H]1C(=O)N[C@@H]1CCCc2ccccc21] | 14 |
| 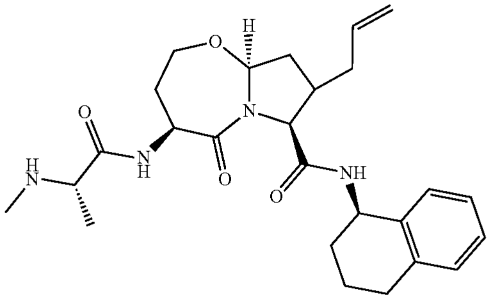 [SMILES: C=CCC1C[C@@H]2OCC[C@H](NC(=O)[C@H](C)NC)C(=O)N2[C@@H]1C(=O)N[C@@H]1CCCc2ccccc21] | 15* |

TABLE A-continued
| Structure | Compound # |
| --- | --- |
| 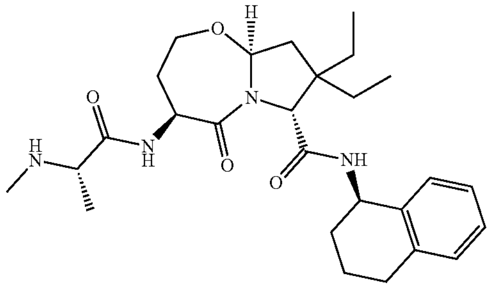 [SMILES: CCC1(CC)C[C@@H]2OCC[C@H](NC(=O)[C@H](C)NC)C(=O)N2[C@H]1C(=O)N[C@@H]1CCCc2ccccc21] | |
| 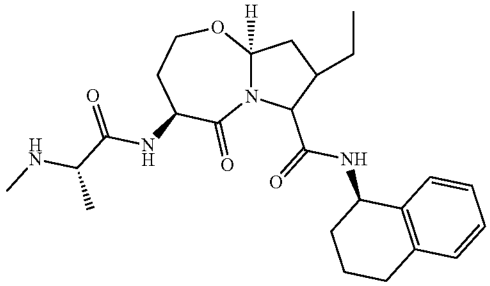 [SMILES: CCC1C[C@@H]2OCC[C@H](NC(=O)[C@H](C)NC)C(=O)N2C1C(=O)N[C@@H]1CCCc2ccccc21] | 20 |
| 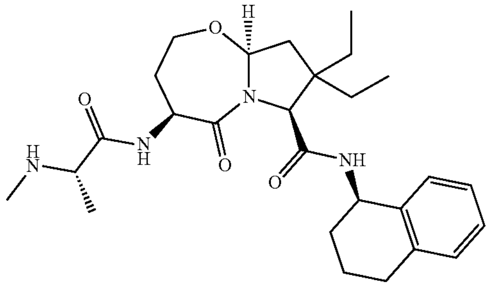 [SMILES: CCC1(CC)C[C@@H]2OCC[C@H](NC(=O)[C@H](C)NC)C(=O)N2[C@@H]1C(=O)N[C@@H]1CCCc2ccccc21] | 21 |
| 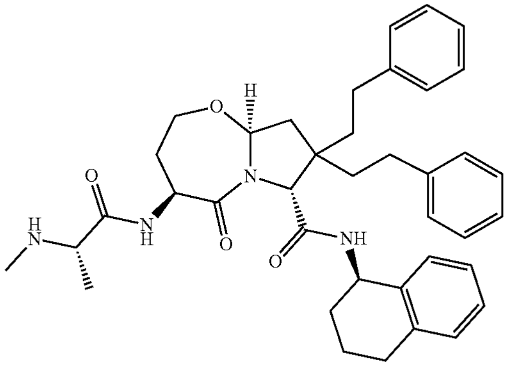 [SMILES: CN[C@@H](C)C(=O)N[C@H]1CCO[C@H]2CC(CCc3ccccc3)(CCc3ccccc3)[C@H](C(=O)N[C@@H]3CCCc4ccccc43)N2C1=O] | 22* |

TABLE A-continued
| Structure | Compound # |
| --- | --- |
| 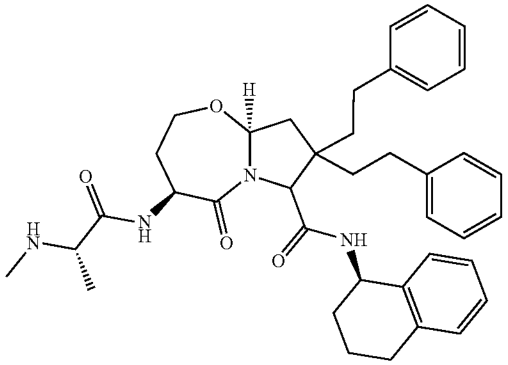 [SMILES: CN[C@@H](C)C(=O)N[C@H]1CCO[C@H]2CC(CCc3ccccc3)(CCc3ccccc3)C(C(=O)N[C@@H]3CCCc4ccccc43)N2C1=O] | 23* |
| 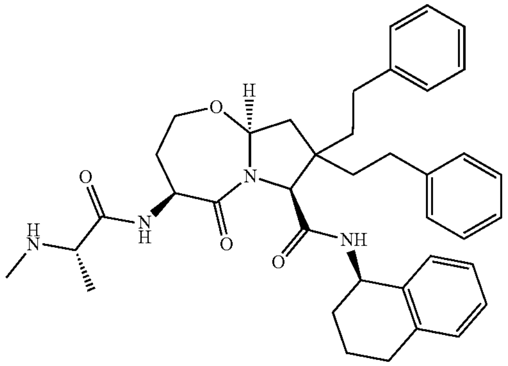 | 24* |
| 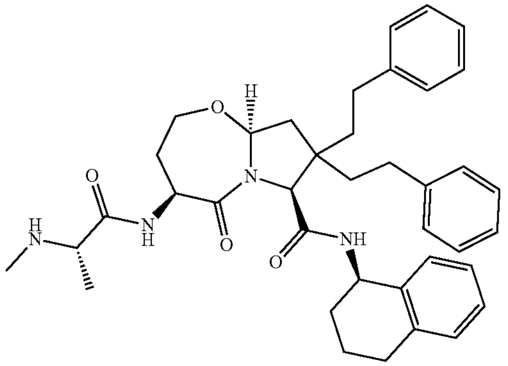 [SMILES: CN[C@@H](C)C(=O)N[C@H]1CCO[C@H]2CC(CCc3ccccc3)(CCc3ccccc3)[C@@H](C(=O)N[C@@H]3CCCc4ccccc43)N2C1=O] | 25* |
| 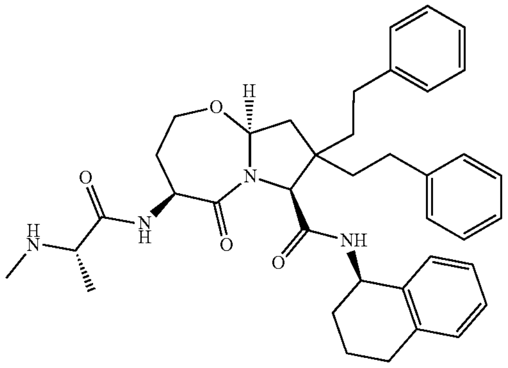 [SMILES: CN[C@@H](C)C(=O)N[C@H]1CCO[C@H]2CC(CCc3ccccc3)(CCc3ccccc3)[C@@H](C(=O)N[C@@H]3CCCc4ccccc43)N2C1=O] | 26* |

TABLE A-continued
| Structure | Compound # |
|---|---|
| 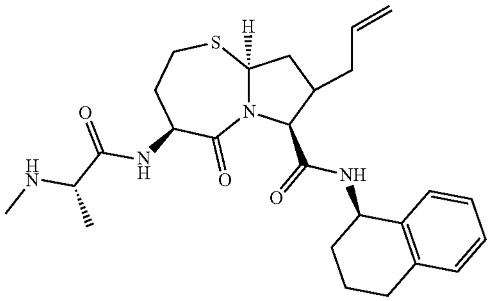 [SMILES: C=CCC1C[C@@H]2SCC[C@H](NC(=O)[C@H](C)NC)C(=O)N2[C@@H]1C(=O)N[C@@H]1CCCc2ccccc21] | 27* |
| 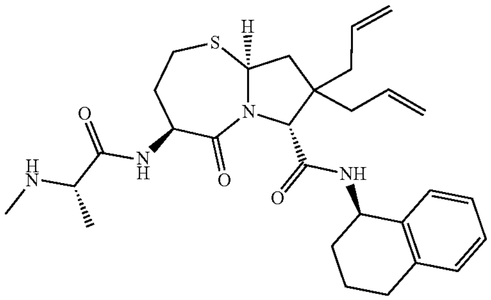 [SMILES: C=CCC1(CC=C)C[C@@H]2SCC[C@H](NC(=O)[C@H](C)NC)C(=O)N2[C@H]1C(=O)N[C@@H]1CCCc2ccccc21] | 28* |
| 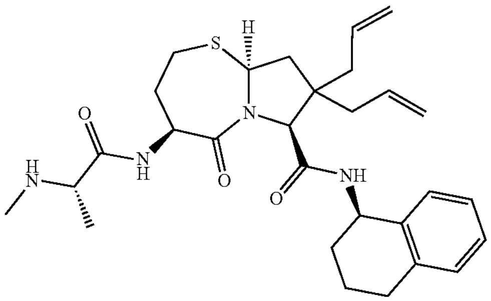 [SMILES: C=CCC1(CC=C)C[C@@H]2SCC[C@H](NC(=O)[C@H](C)NC)C(=O)N2[C@@H]1C(=O)N[C@@H]1CCCc2ccccc21] | 29* |
| 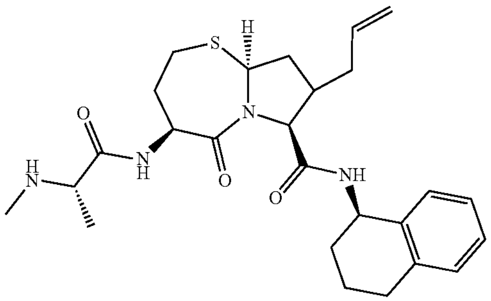 [SMILES: C=CCC1C[C@@H]2SCC[C@H](NC(=O)[C@H](C)NC)C(=O)N2[C@@H]1C(=O)N[C@@H]1CCCc2ccccc21] | 30* |
| 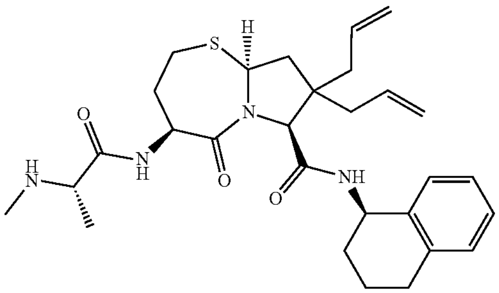 [SMILES: C=CCC1(CC=C)C[C@@H]2SCC[C@H](NC(=O)[C@H](C)NC)C(=O)N2[C@@H]1C(=O)N[C@@H]1CCCc2ccccc21] | 31* |

TABLE A-continued
| Structure | Compound # |
| --- | --- |
| 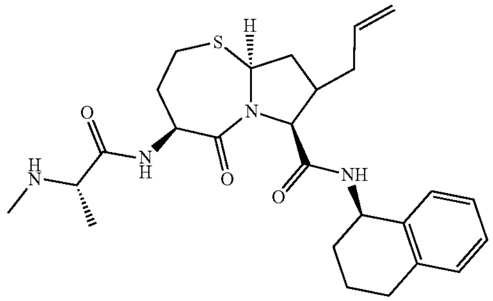 [SMILES: C=CCC1C[C@@H]2SCC[C@H](NC(=O)[C@H](C)NC)C(=O)N2[C@@H]1C(=O)N[C@@H]1CCCc2ccccc21] | 32* |
| 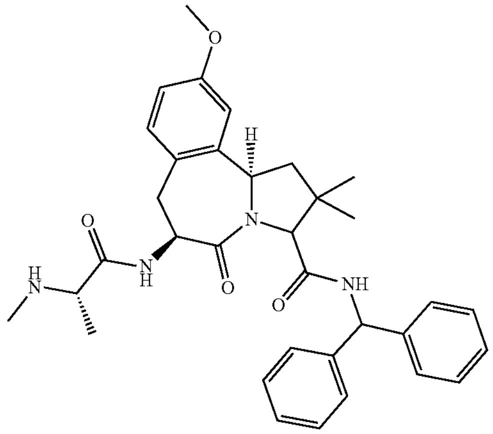 [SMILES: CN[C@@H](C)C(=O)N[C@H]1Cc2ccc(OC)cc2[C@H]2CC(C)(C)C(C(=O)NC(c3ccccc3)c3ccccc3)N2C1=O] | 33 |
| 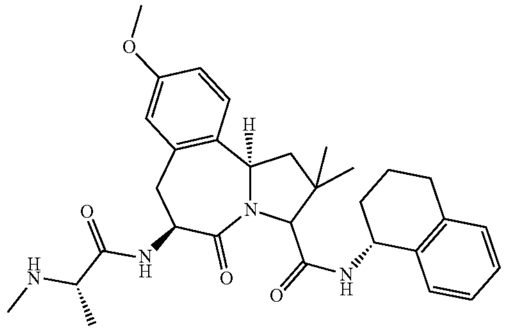 [SMILES: CN[C@@H](C)C(=O)N[C@H]1Cc2cc(OC)ccc2[C@H]2CC(C)(C)C(C(=O)N[C@@H]3CCCc4ccccc43)N2C1=O] | 34 |
| 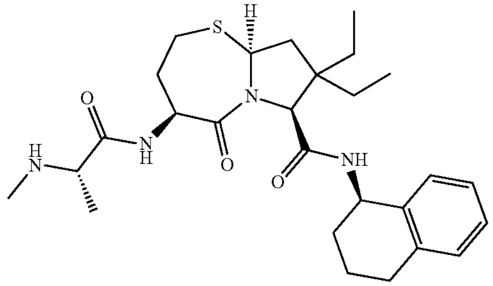 [SMILES: CCC1(CC)C[C@@H]2SCC[C@H](NC(=O)[C@H](C)NC)C(=O)N2[C@@H]1C(=O)N[C@@H]1CCCc2ccccc21] | 35* |

TABLE A-continued
| Structure | Compound # |
| --- | --- |
| 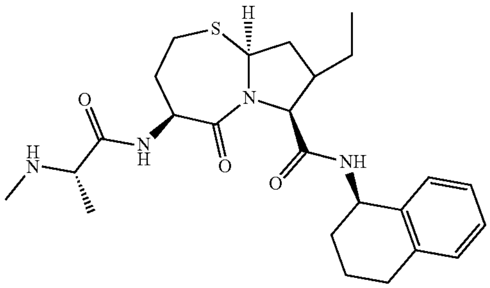 [SMILES: CCC1C[C@@H]2SCC[C@H](NC(=O)[C@H](C)NC)C(=O)N2[C@@H]1C(=O)N[C@@H]1CCCc2ccccc21] | 36* |
| 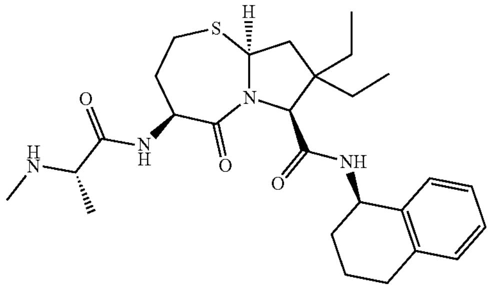 [SMILES: CCC1(CC)C[C@@H]2SCC[C@H](NC(=O)[C@H](C)NC)C(=O)N2[C@@H]1C(=O)N[C@@H]1CCCc2ccccc21] | 37* |
| 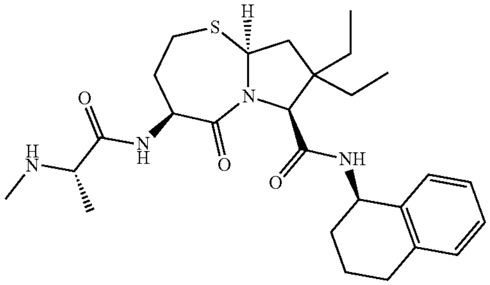 [SMILES: CCC1(CC)C[C@@H]2SCC[C@H](NC(=O)[C@H](C)NC)C(=O)N2[C@@H]1C(=O)N[C@@H]1CCCc2ccccc21] | 38* |
| 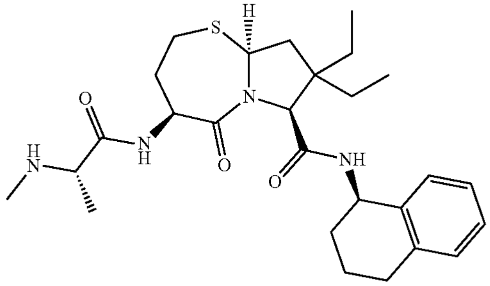 [SMILES: CCC1(CC)C[C@@H]2SCC[C@H](NC(=O)[C@H](C)NC)C(=O)N2[C@@H]1C(=O)N[C@@H]1CCCc2ccccc21] | 39* |
| 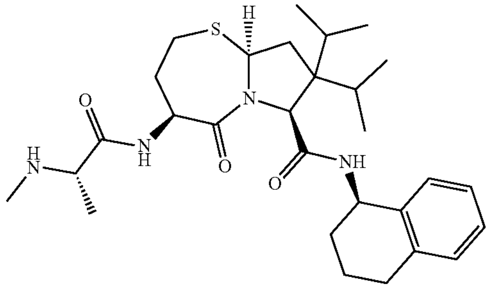 [SMILES: CN[C@@H](C)C(=O)N[C@H]1CCS[C@H]2CC(C(C)C)(C(C)C)[C@@H](C(=O)N[C@@H]3CCCc4ccccc43)N2C1=O] | 40* |

TABLE A-continued
| Structure | Compound # |
| --- | --- |
| 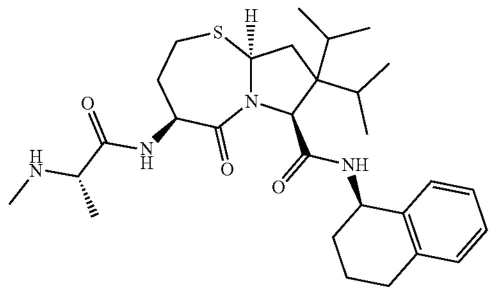 [SMILES: CN[C@@H](C)C(=O)N[C@H]1CCS[C@H]2CC(C(C)C)(C(C)C)[C@@H](C(=O)N[C@@H]3CCCc4ccccc43)N2C1=O] | 41* |
| 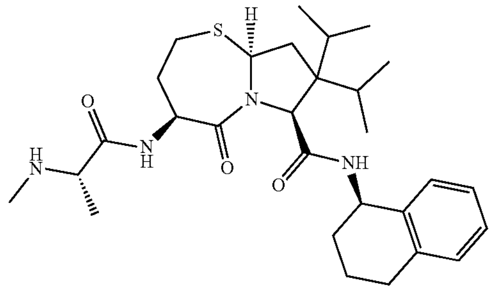 [SMILES: CN[C@@H](C)C(=O)N[C@H]1CCS[C@H]2CC(C(C)C)(C(C)C)[C@@H](C(=O)N[C@@H]3CCCc4ccccc43)N2C1=O] | 42* |
| 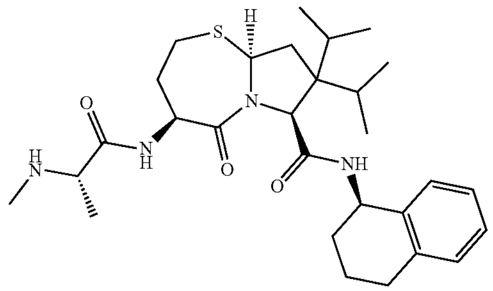 [SMILES: CN[C@@H](C)C(=O)N[C@H]1CCS[C@H]2CC(C(C)C)(C(C)C)[C@@H](C(=O)N[C@@H]3CCCc4ccccc43)N2C1=O] | 43* |
| 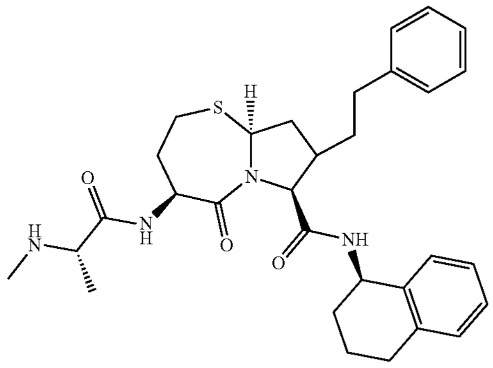 [SMILES: CN[C@@H](C)C(=O)N[C@H]1CCS[C@H]2CC(CCc3ccccc3)[C@@H](C(=O)N[C@@H]3CCCc4ccccc43)N2C1=O] | 44* |

TABLE A-continued
| Structure | Compound # |
|---|---|
| 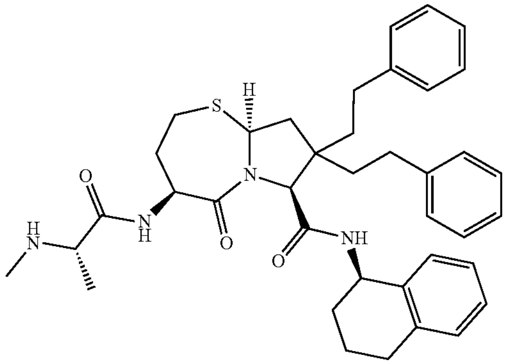 [SMILES: CN[C@@H](C)C(=O)N[C@H]1CCS[C@H]2CC(CCc3ccccc3)(CCc3ccccc3)[C@@H](C(=O)N[C@@H]3CCCc4ccccc43)N2C1=O] | 45* |
| 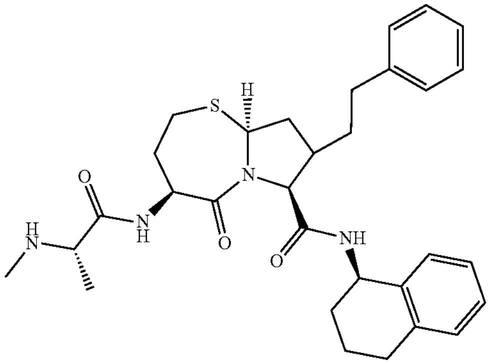 [SMILES: CN[C@@H](C)C(=O)N[C@H]1CCS[C@H]2CC(CCc3ccccc3)[C@@H](C(=O)N[C@@H]3CCCc4ccccc43)N2C1=O] | 46* |
| 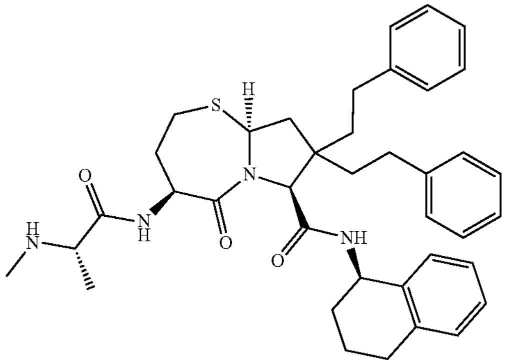 [SMILES: CN[C@@H](C)C(=O)N[C@H]1CCS[C@H]2CC(CCc3ccccc3)(CCc3ccccc3)[C@@H](C(=O)N[C@@H]3CCCc4ccccc43)N2C1=O] | 47* |
| 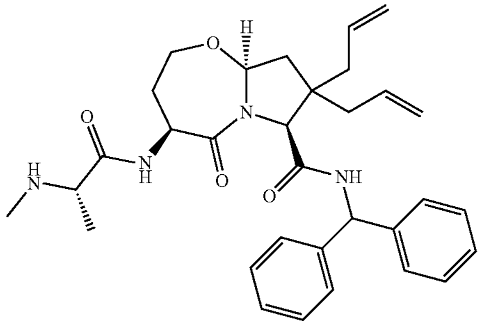 [SMILES: C=CCC1(CC=C)C[C@@H]2OCC[C@H](NC(=O)[C@H](C)NC)C(=O)N2[C@@H]1C(=O)NC(c1ccccc1)c1ccccc1] | 48* |

TABLE A-continued
| Structure | Compound # |
|---|---|
| 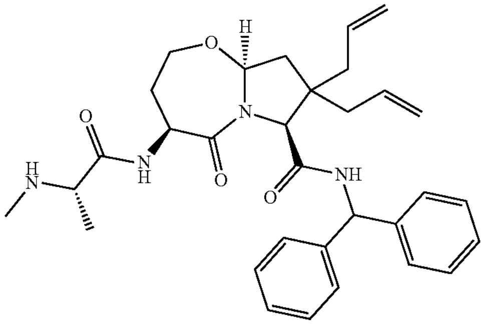 [SMILES: C=CCC1(CC=C)C[C@@H]2OCC[C@H](NC(=O)[C@H](C)NC)C(=O)N2[C@@H]1C(=O)NC(c1ccccc1)c1ccccc1] | 49* |
| 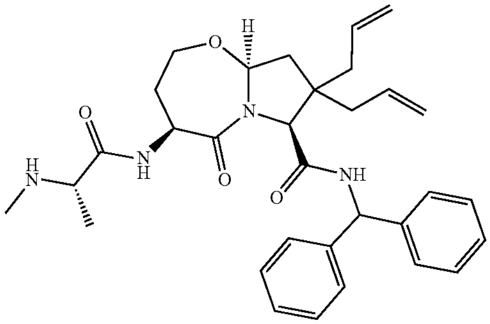 [SMILES: C=CCC1(CC=C)C[C@@H]2OCC[C@H](NC(=O)[C@H](C)NC)C(=O)N2[C@@H]1C(=O)NC(c1ccccc1)c1ccccc1] | 50* |
| 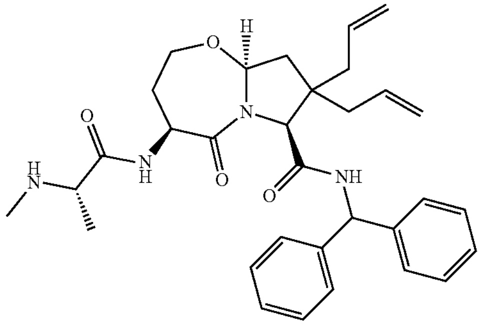 [SMILES: C=CCC1(CC=C)C[C@@H]2OCC[C@H](NC(=O)[C@H](C)NC)C(=O)N2[C@@H]1C(=O)NC(c1ccccc1)c1ccccc1] | 51* |
| 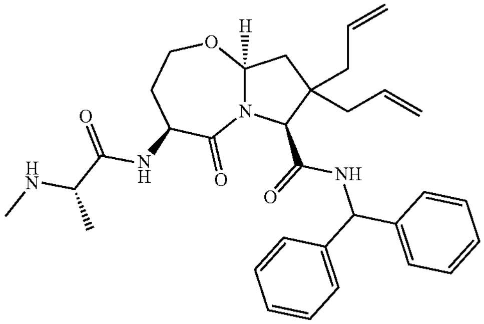 [SMILES: C=CCC1(CC=C)C[C@@H]2OCC[C@H](NC(=O)[C@H](C)NC)C(=O)N2[C@@H]1C(=O)NC(c1ccccc1)c1ccccc1] | 52* |

TABLE A-continued
| Structure | Compound # |
| --- | --- |
| 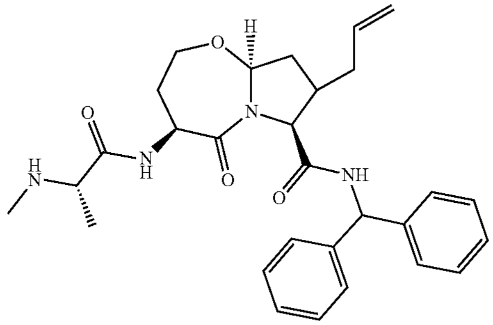 [SMILES: C=CCC1C[C@@H]2OCC[C@H](NC(=O)[C@H](C)NC)C(=O)N2[C@@H]1C(=O)NC(c1ccccc1)c1ccccc1] | 53** |
| 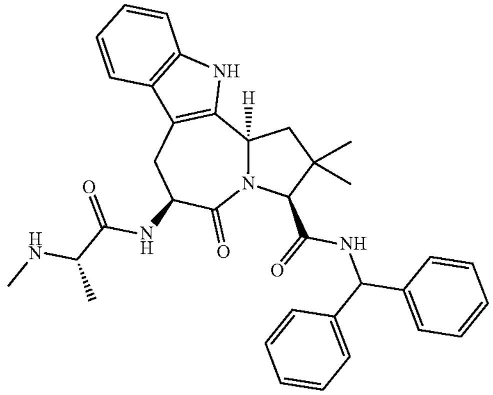 [SMILES: CN[C@@H](C)C(=O)N[C@H]1Cc2c([nH]c3ccccc23)[C@H]2CC(C)(C)[C@@H](C(=O)NC(c3ccccc3)c3ccccc3)N2C1=O] | 54* |
| 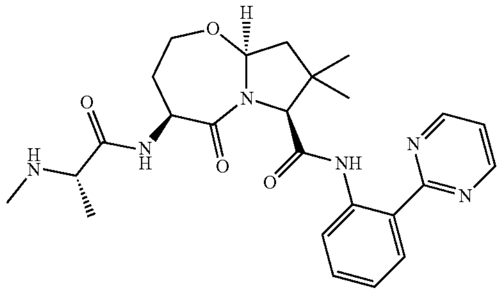 [SMILES: CN[C@@H](C)C(=O)N[C@H]1CCO[C@H]2CC(C)(C)[C@@H](C(=O)Nc3ccccc3-c3ncccn3)N2C1=O] | 55* |
| 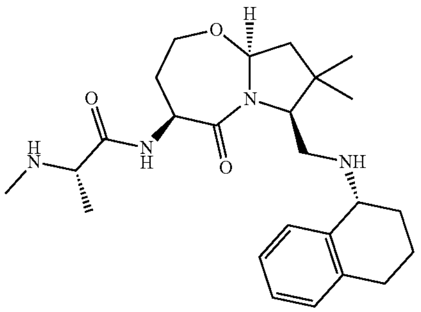 [SMILES: CN[C@@H](C)C(=O)N[C@H]1CCO[C@H]2CC(C)(C)[C@@H](CN[C@@H]3CCCc4ccccc43)N2C1=O] | 56* |

TABLE A-continued
| Structure | Compound # |
| --- | --- |
| 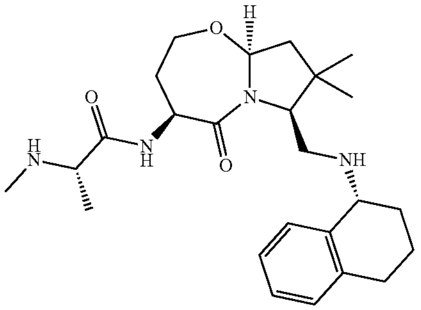 [SMILES: CN[C@@H](C)C(=O)N[C@H]1CCO[C@H]2CC(C)(C)[C@@H](CN[C@@H]3CCCc4ccccc43)N2C1=O] | 57* |
| 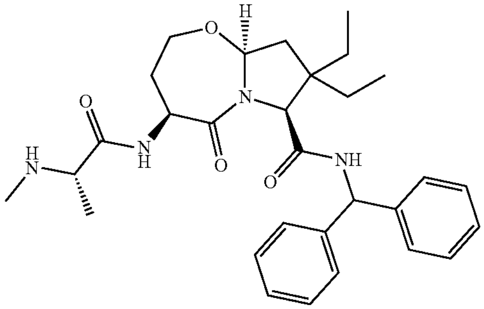 [SMILES: CCC1(CC)C[C@@H]2OCC[C@H](NC(=O)[C@H](C)NC)C(=O)N2[C@@H]1C(=O)NC(c1ccccc1)c1ccccc1] | 58* |
| 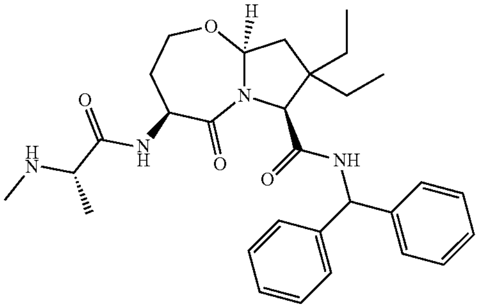 [SMILES: CCC1(CC)C[C@@H]2OCC[C@H](NC(=O)[C@H](C)NC)C(=O)N2[C@@H]1C(=O)NC(c1ccccc1)c1ccccc1] | 59* |
| 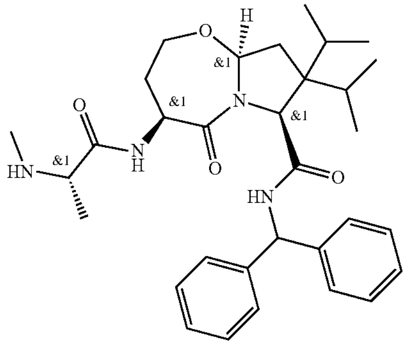 [SMILES: CN[C@@H](C)C(=O)N[C@H]1CCO[C@H]2CC(C(C)C)(C(C)C)[C@@H](C(=O)NC(c3ccccc3)c3ccccc3)N2C1=O] | 60* |

TABLE A-continued
| Structure | Compound # |
|---|---|
| 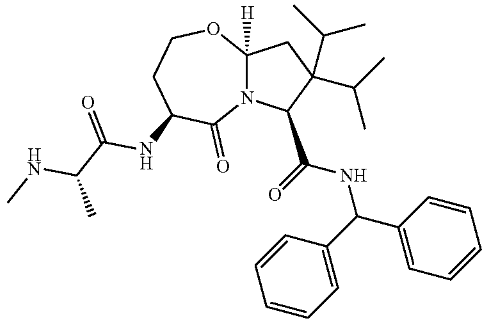 [SMILES: CN[C@@H](C)C(=O)N[C@H]1CCO[C@H]2CC(C(C)C)(C(C)C)[C@@H](C(=O)NC(c3ccccc3)c3ccccc3)N2C1=O] | 61* |
| 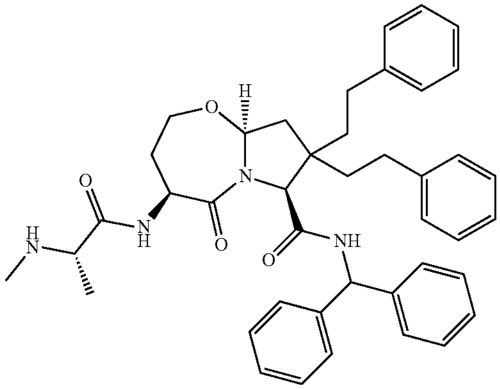 [SMILES: CN[C@@H](C)C(=O)N[C@H]1CCO[C@H]2CC(CCc3ccccc3)(CCc3ccccc3)[C@@H](C(=O)NC(c3ccccc3)c3ccccc3)N2C1=O] | 62* |
| 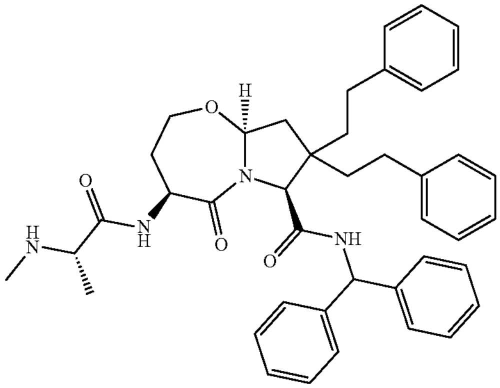 [SMILES: CN[C@@H](C)C(=O)N[C@H]1CCO[C@H]2CC(CCc3ccccc3)(CCc3ccccc3)[C@@H](C(=O)NC(c3ccccc3)c3ccccc3)N2C1=O] | 63* |
| 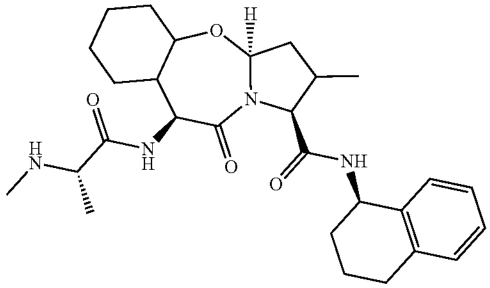 [SMILES: CN[C@@H](C)C(=O)N[C@@H]1C(=O)N2[C@H](CC(C)[C@H]2C(=O)N[C@@H]2CCCc3ccccc32)OC2CCCCC21] | 64* |

TABLE A-continued
| Structure | Compound # |
| --- | --- |
| 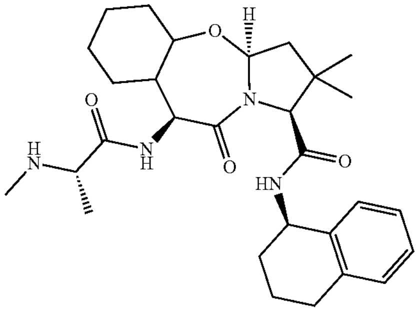 [SMILES: CN[C@@H](C)C(=O)N[C@@H]1C(=O)N2[C@H](CC(C)(C)[C@H]2C(=O)N[C@@H]2CCCc3ccccc32)OC2CCCCC21] | 65* |
| 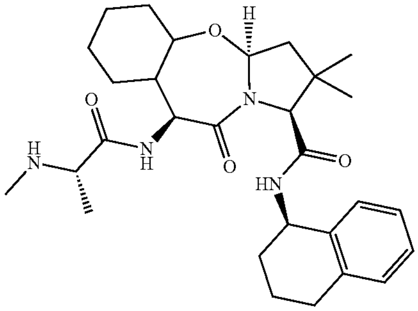 [SMILES: CN[C@@H](C)C(=O)N[C@@H]1C(=O)N2[C@H](CC(C)(C)[C@H]2C(=O)N[C@@H]2CCCc3ccccc32)OC2CCCCC21] | 66* |
| 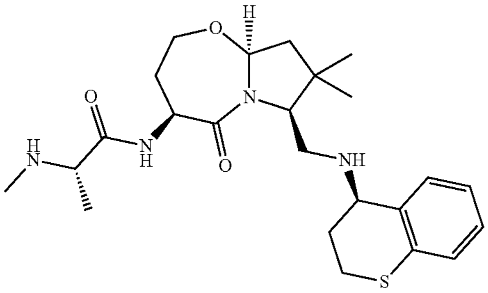 [SMILES: CN[C@@H](C)C(=O)N[C@H]1CCO[C@H]2CC(C)(C)[C@@H](CN[C@@H]3CCSc4ccccc43)N2C1=O] | 67* |
| 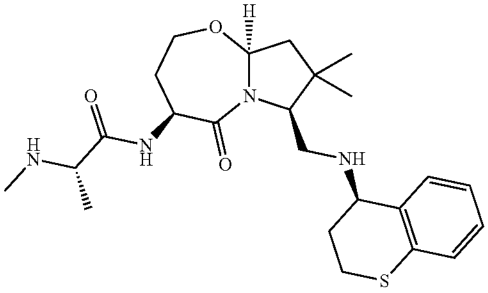 [SMILES: CN[C@@H](C)C(=O)N[C@H]1CCO[C@H]2CC(C)(C)[C@@H](CN[C@@H]3CCSc4ccccc43)N2C1=O] | 68* |
| 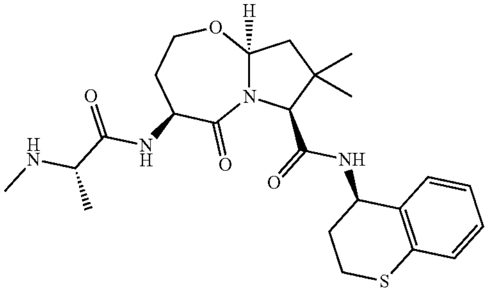 [SMILES: CN[C@@H](C)C(=O)N[C@H]1CCO[C@H]2CC(C)(C)[C@@H](C(=O)N[C@@H]3CCSc4ccccc43)N2C1=O] | 69* |

TABLE A-continued
| Structure | Compound # |
|---|---|
| 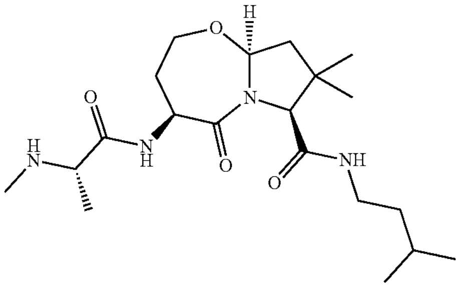 [SMILES: CN[C@@H](C)C(=O)N[C@H]1CCO[C@H]2CC(C)(C)[C@@H](C(=O)NCCC(C)C)N2C1=O] | 70* |
| 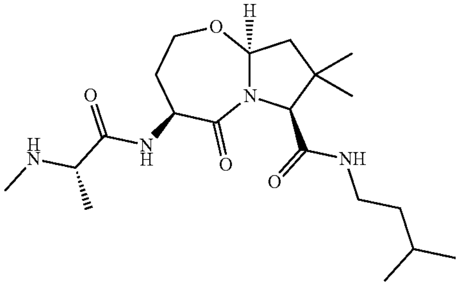 [SMILES: CN[C@@H](C)C(=O)N[C@H]1CCO[C@H]2CC(C)(C)[C@@H](C(=O)NCCC(C)C)N2C1=O] | 71* |
| 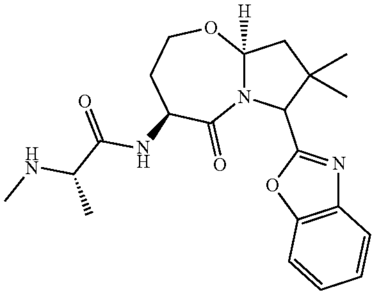 [SMILES: CN[C@@H](C)C(=O)N[C@H]1CCO[C@H]2CC(C)(C)C(c3nc4ccccc4o3)N2C1=O] | 72 |
| 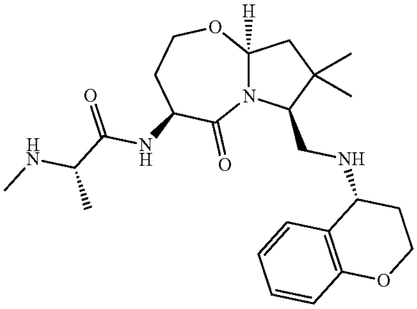 | 73 |
| 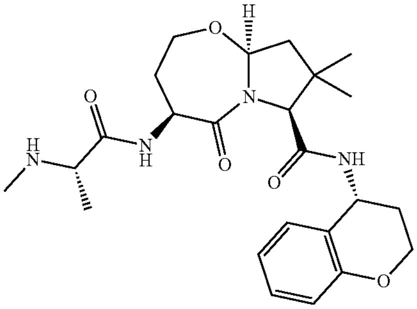 [SMILES: CN[C@@H](C)C(=O)N[C@H]1CCO[C@H]2CC(C)(C)[C@@H](C(=O)N[C@@H]3CCOc4ccccc43)N2C1=O] | 74 |

TABLE A-continued
| Structure | Compound # |
|---|---|
| 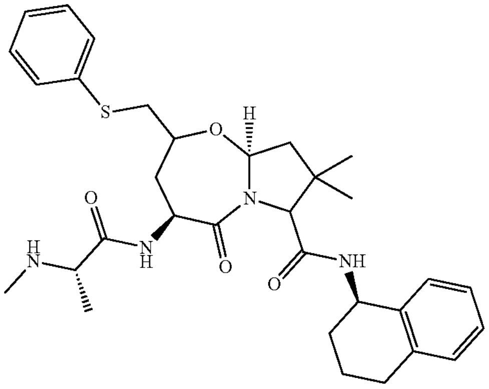 [SMILES: CN[C@@H](C)C(=O)N[C@H]1CC(CSc2ccccc2)O[C@H]2CC(C)(C)C(C(=O)N[C@@H]3CCCc4ccccc43)N2C1=O] | 75* |
| 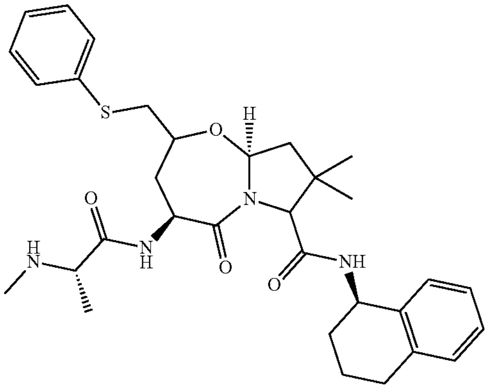 [SMILES: CN[C@@H](C)C(=O)N[C@H]1CC(CSc2ccccc2)O[C@H]2CC(C)(C)C(C(=O)N[C@@H]3CCCc4ccccc43)N2C1=O] | 76* |
| 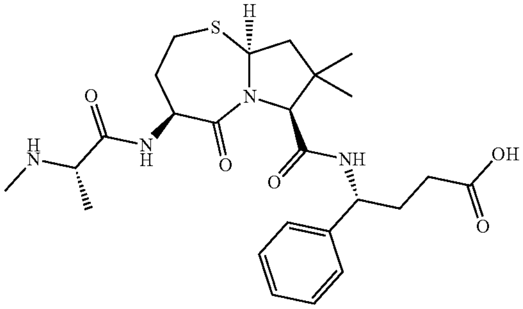 [SMILES: CN[C@@H](C)C(=O)N[C@H]1CCS[C@H]2CC(C)(C)[C@@H](C(=O)N[C@H](CCC(=O)O)c3ccccc3)N2C1=O] | 77 |
| 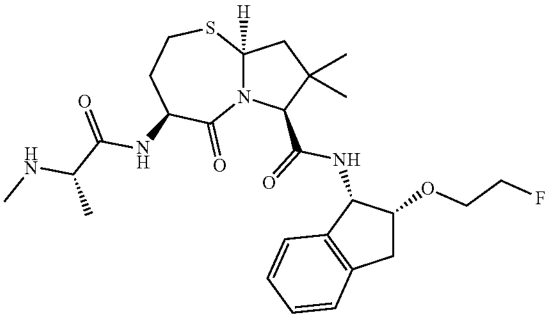 [SMILES: CN[C@@H](C)C(=O)N[C@H]1CCS[C@H]2CC(C)(C)[C@@H](C(=O)N[C@H]3c4ccccc4C[C@H]3OCCF)N2C1=O] | 78 |

TABLE A-continued
| Structure | Compound # |
| --- | --- |
| 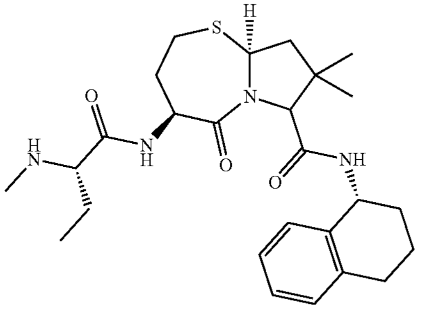 [SMILES: CC[C@H](NC)C(=O)N[C@H]1CCS[C@H]2CC(C)(C)C(C(=O)N[C@@H]3CCCc4ccccc43)N2C1=O] | 79 |
| 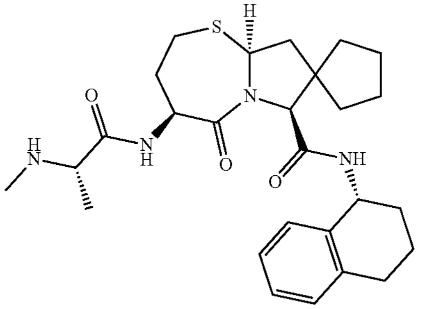 [SMILES: CN[C@@H](C)C(=O)N[C@H]1CCS[C@H]2CC3(CCCC3)[C@@H](C(=O)N[C@@H]3CCCc4ccccc43)N2C1=O] | 80 |
| 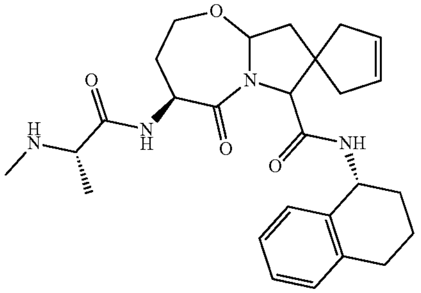 [SMILES: CN[C@@H](C)C(=O)N[C@H]1CCOC2CC3(CC=CC3)C(C(=O)N[C@@H]3CCCc4ccccc43)N2C1=O] | 81 |
| 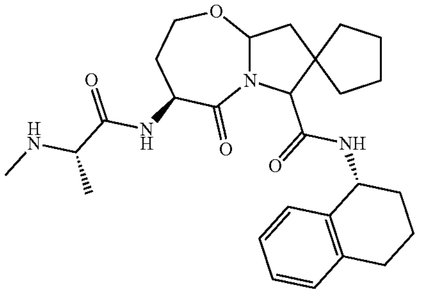 [SMILES: CN[C@@H](C)C(=O)N[C@H]1CCOC2CC3(CCCC3)C(C(=O)N[C@@H]3CCCc4ccccc43)N2C1=O] | 82 |
| 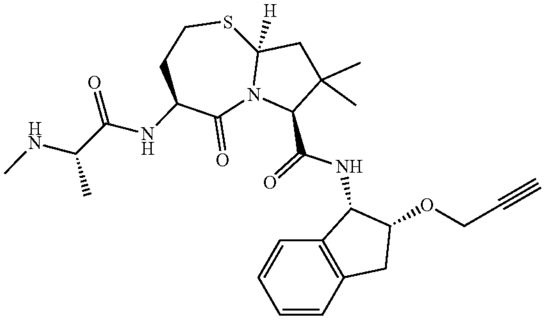 [SMILES: C#CCO[C@@H]1Cc2ccccc2[C@@H]1NC(=O)[C@H]1N2C(=O)[C@@H](NC(=O)[C@H](C)NC)CCS[C@H]2CC1(C)C] | 83 |

TABLE A-continued

| Structure | Compound # |
|---|---|
| 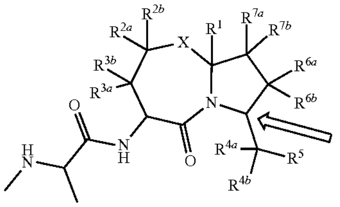 *stereochemistry assigned randomly **mixture of stereoisomers | |

Any combination of the groups described above or below for the various variables is contemplated herein. Throughout the specification, groups and substituents thereof are chosen by one skilled in the field to provide stable moieties and compounds.

Further Forms of Compounds Disclosed Herein

Isomers Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

In some embodiments, one isomer binds a target with higher affinity than another. In some embodiments, a mixture of isomers is preferable. In some embodiments, a compound described herein with unknown or undisclosed stereochemistry is a mixture of enantiomers or diastereomers. In some embodiments, an isomer disclosed as an (R) enantiomer may contain some portion of the (S) isomer as well. In some embodiments, a compound disclosed as an (R) isomer may contain up to 0.01%, 0.1%, 0.5%, 1%, 2%, 3%, 5%, 10%, 20%, 30%, 40%, 49% of the (S) isomer. In the preceding example, either isomer is interchangeable, e.g., a compound disclosed as an (S) isomer may contain any amount previously described of the (R) isomer as well. In some embodiments, a compound is isomerically pure. In some embodiments, a compound disclosed as a mixture of isomers may contain a given isomer in up to 99.9%, 99%, 98%, 97%, 95%, 90%, 80%, 70%, 60%, 50%, 40%, 30%, 20%, 10%, 5%, 3%, 2%, 1%, 0.5%, or 0.1% abundance relative to alternate isomers present in the mixture.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein, or a solvate, or stereoisomer thereof, include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this disclosure. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compound or a pharmaceutically acceptable salt, solvate, or stereoisomer thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefor react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, those compounds described herein which comprise a free acid group react with a suitable base, such as the hydroxide, carbonate, bicarbonate, or sulfate of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\ alkyl)_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

A synthetic route as outlined in Scheme 1 provides access compounds as described in Formula A-I, B-I, or C-I, in a highly efficient 3-step process. An initial Ugi 4-component reaction (4CR) enables efficient access to the fused 7-/5-membered scaffold as described herein. By stirring the carboxylic acid, aldehyde, isocyanide, and ammonia in 2,2,2,-trifluoroethanol (TFE) under microwave irradiation at 80° C. for 20 min, an intermediate product (not shown) is produced as a mixture of diastereomers. Subsequent treatment with trifluoroacetic acid (TFA) induces a reaction cascade resulting in Boc-deprotection and formation of the bicyclic ring structure shown in intermediates 1a and 1b. These combined transformations comprise step a in Scheme 1 below. The diastereomeric pair 1a and 1b are then separated by chromatography or other suitable methods (e.g., recrystallization), or are carried forward as a mixture of stereoisomers. In some instances, it is advantageous to carry forward with a crude mixture containing 1a and 1b without purification. The primary amines of 1a and 1b undergo a coupling reaction in step b with Boc-N-Me-Ala-OH to give a 1:1 mixture of diastereomers 1c and 1d, which are optionally purified by chromatography or other suitable methods. In some instances, purification is carried out using flash chromatography on silica gel. A final TFA deprotection (step c) gives the final compounds 1e and 1f. In some instances, overall yield for the four-step process involving a single purification step is 36-60%. The scheme as described extends to various alternatively-substituted aldehydes, carboxylic acids, or isocyanides, facilitating the synthesis of a broad range of compounds as disclosed herein.

Scheme 1

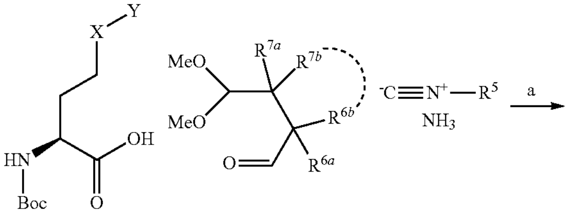

X=O, Y=H
X=S, Y=Trt

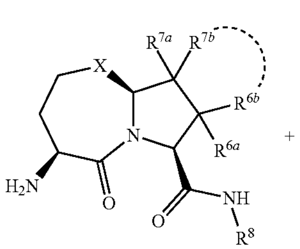

1a

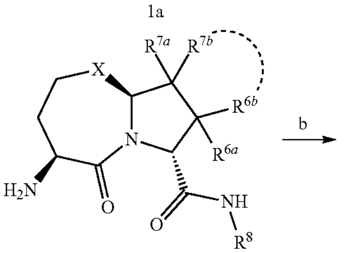

1b

-continued

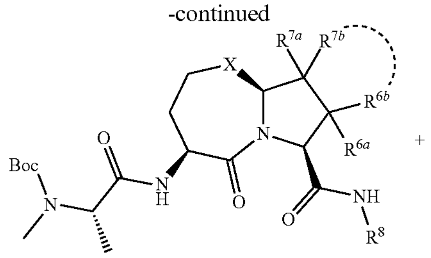

1c

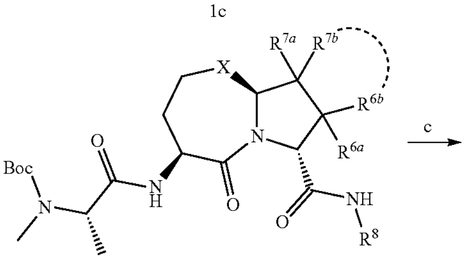

1c

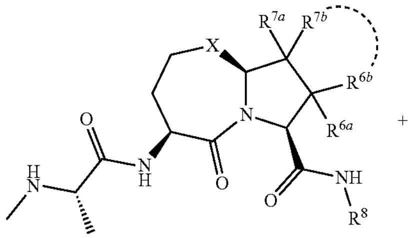

1e

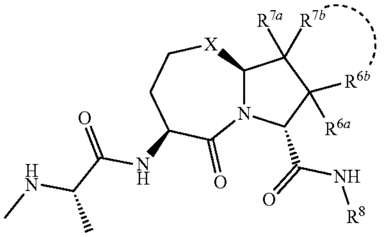

1f

In addition to the scaffolds outlined in Scheme 1, scaffolds featuring additional fused ring systems as described within Formula (A-I) or (C-I) can be accessed using an appropriately substituted carboxylic acid and/or aldehyde. Examples of some fused ring systems contemplated in the present disclosure, by way of non-limiting example, include those indicated in Scheme 2. Following a 4CR similar to that previously described in Scheme 1, followed by subsequent TFA deprotection/cyclization, a diastereomeric pair of compounds as indicated by intermediate 2 can be accessed. In step a, an appropriate carboxylic acid, aldehyde, isocyanide, and ammonia are stirred in TFE while heating under microwave irradiation (e.g., at 80° C. for 20 min). Following the 4CR, the intermediate (not shown) is treated with TFA to facilitate Boc deprotection and cyclization to achieve intermediate 2. In subsequent steps, as outlined in Scheme 1, the primary amine can be substituted and deprotected to achieve a compound as described within Formula (A-I) or (C-I). In many cases, the microwave reaction conditions can be replaced with continuous flow conditions, which mimics the efficient heating dynamics of microwave technology. For example, the first two steps (step a) can be performed in series without the need for purification. After collection of the intermediate 2 and a switch of solvent to THF, steps b and c as outlined in Scheme 1 can be executed to give final compounds as disclosed within Formula (A-I) or (C-I).

Scheme 2

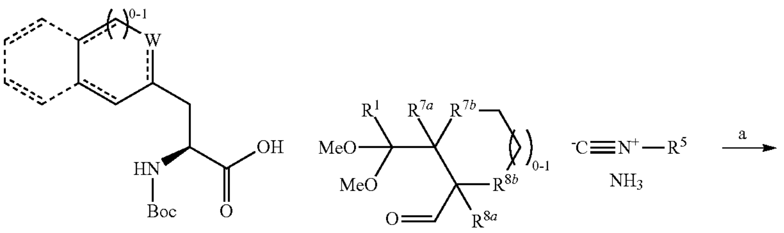

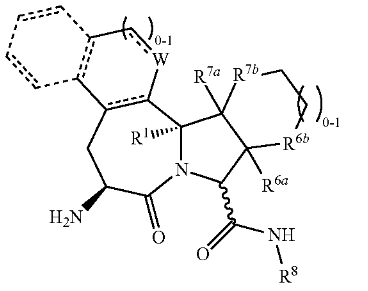

2

W = C or N

Conditions: (a) 1 eq carboxylic acid, 1.05 eq aldehyde, 1 eq isocyanide in TFE, μW heating at 80° C., 20 MIN; THEN 8-10 eq TFA, DCM, 32° C.

It will be understood that the reactions shown in Schemes 1-3 above are illustrative and are also applicable to synthesis of compounds of Formula II and III, and such disclosure is contemplated within the scope of embodiments described herein. Synthesis of compounds of Formula I, II, and III are also shown in further detail in the Chemistry Examples section.

Highlighted in Scheme 3 are synthetic routes to compounds featuring various amide isosteres. Using the valuable N-acylindole 6 allows the incorporation of a variety of functional groups at the region indicated in grey (Scheme 3).

The utility of 6 stems from its reactivity, which is similar to an ester and allows for hydride reduction to either the alcohol (using excess NaBH4) or aldehyde 8 (using 1 equivalent of NaBH4). Alkylation of the fully reduced alcohol provides access to ether derivatives 7. Chemistry has also been developed for the trifluoromethylation of carbonyls similar to 8 to construct $CF_3$-containing ether 9. The S-stereochemistry at the $CF_3$-containing stereocenter would be predicted based on the Felkin-Anh model. Reductive amination of aldehyde 8 affords the useful amine 10, from which a library of sulfonamides 11 are prepared.

Scheme 3

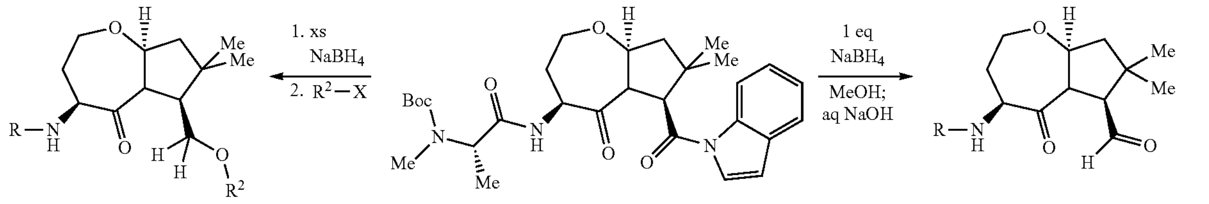

6

8

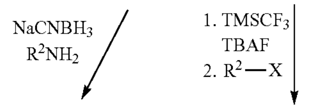

-continued

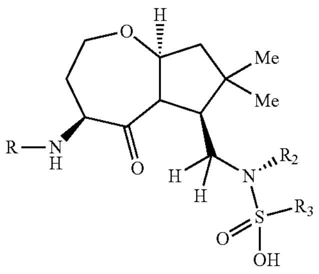

11

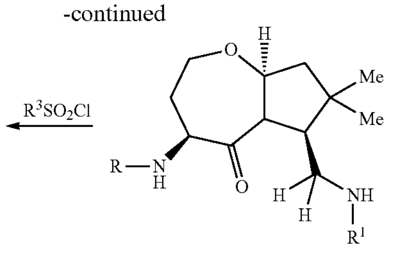

10

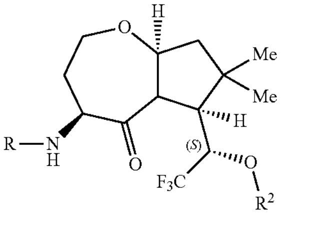

9

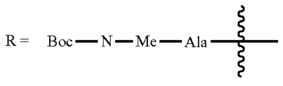

Scheme 4 details additional methods for functionalization of the region of the scaffold indicated in grey. The N-acylindole 6 is easily converted to the methyl ester 12 in basic methanol, from which the titanium-mediated Kulinkovich reaction can be used to access cyclopropyl alcohols. Formation of the sulfonate 13 followed by treatment with $MgBr_2$ affords the allyl bromide 14, which is a versatile intermediate. From here, a variety of different types of nucleophiles (alcohols, amines, thiols) are applied to access new chemical space. Tsuji-Trost conditions may also be employed for further activation of the allyl bromide with catalytic palladium. Synthesis of the nitrile 16 is achieved from aldehyde 8 using mild conditions (Scheme 4), and nitriles such as 16 are very reactive under Kulinkovich conditions (nitrile>ester>amide) to yield the cyclopropylamine. Subsequent treatment with a variety of potential electrophiles (alkyl halides, aryl halides, sulfonyl halides, acyl halides) gives derivatives 17. In order to perform the Kulinkovich reaction from a carboxamide, a modified strategy is adopted. Protection of amide 18 (made similarly to Scheme 5, but with Cbz instead of Boc) with the MTM group, followed by cyclopropylamine formation gives 19. Several deprotection reactions and a coupling with the alanine derivative provides new analogs such as 20 where the carboxamide carbonyl is replaced by a cyclopropyl group.

Scheme 4

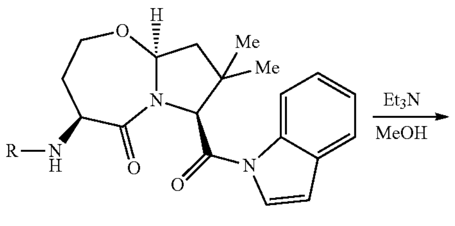

6

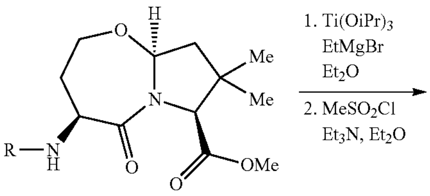

12

-continued

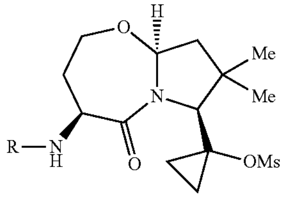

13

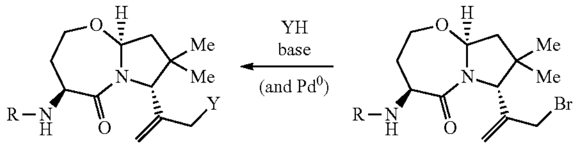

15 14

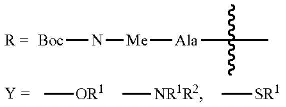

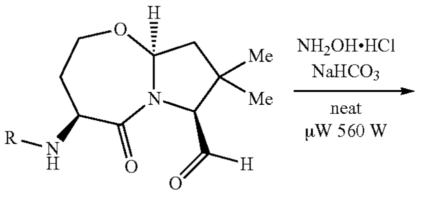

8

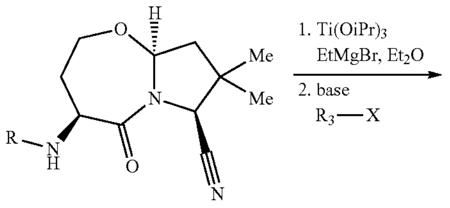

16

-continued

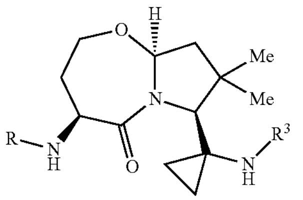

17

$R^3$ = alkyl, aryl, $SO_2R^4$, $R^4C{=}O$

Scheme 5

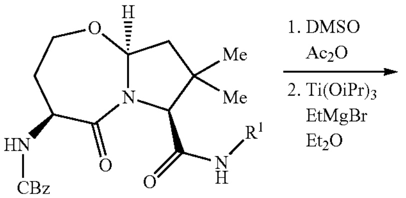

18

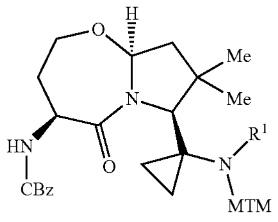

19

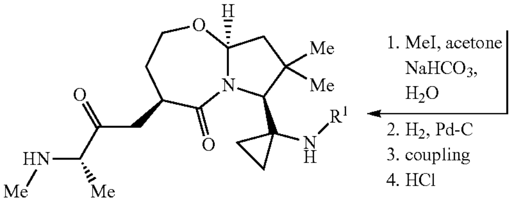

20

In Scheme 6, the 2-substituted indole derivative 23 can be synthesized by Fischer indole synthesis of ketone 21 with various phenylhydrazines 22. Isomer 24 may also form, but the silyl group helps direct enol formation to give preference to isomer 23. In either case, the silyl group cleaves under the acidic reaction conditions. Based on chemistry for a similarly activated acyl group, N-acylindole 6 undergoes displacement with the silyl Grignard reagent to give the ketone 21.

Scheme 6

6 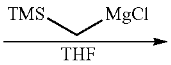

-continued

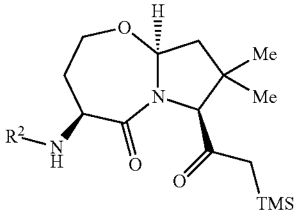

21

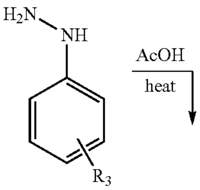

22

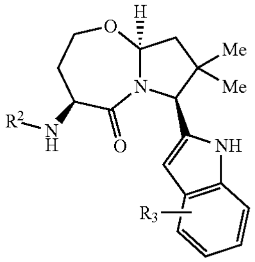

23

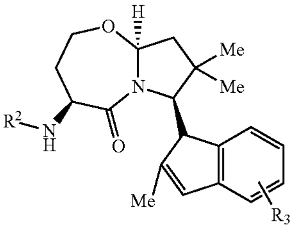

24

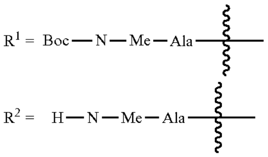

Although benzoxazole 28 and benzothiazole 29 can be accessed from aldehyde 8, a more efficient route via intermediate 27 by use of o-bromophenyl isocyanides 25 in the Ugi multicomponent reaction (Scheme 7). A copper-mediated coupling to form the benzoxazoles 28 and benzothiazoles 29 is then accomplished, giving the desired carboxamide isosteres.

Scheme 7

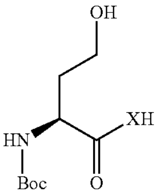

26

$NH_3$

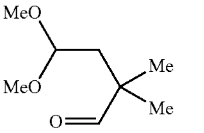

3

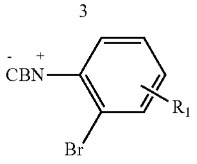

25

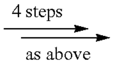

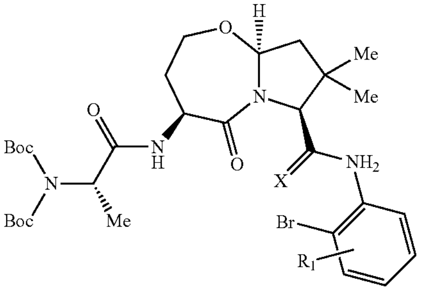

27

-continued

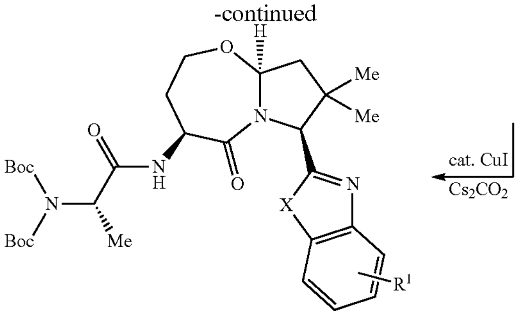

28: X = O
29: X = S

Administration and Pharmaceutical Composition

In general, the compounds of this invention will be administered in a therapeutically effective amount by any of the accepted modes of administration for agents that serve similar utilities. Therapeutically effective amounts of compound of Formula I, II, or III may range from about 0.01 to about 500 mg per kg patient body weight per day, which can be administered in single or multiple doses. Preferably, the dosage level will be about 0.1 to about 250 mg/kg per day; more preferably about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions are preferably provided in the form of tablets containing about 1.0 to about 1000 milligrams of the active ingredient, particularly about 1.0, 5.0, 10, 15, 20, 25, 50, 75, 100, 150, 200, 250, 300, 400, 500, 600, 750, 800, 900, and 1000 milligrams of the active ingredient. The actual amount of the compound of this invention, i.e., the active ingredient, will depend upon numerous factors such as the severity of the disease to be treated, the age and relative health of the subject, the potency of the compound being utilized, the route and form of administration, and other factors.

In general, compounds of this invention will be administered as pharmaceutical compositions by any one of the following routes: oral, systemic (e.g., intranasal, suppository, intrapulmonary), or parenteral (e.g., intramuscular, intravenous, intrathecal, or intraperitoneal) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, liposomes, exosomes, nanoparticles, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

In some embodiments, a pharmaceutical composition of the present disclosure comprises any one of the compounds as described herein, or pharmaceutically acceptable salt, solvate, diastereomeric mixture, or individual enantiomers thereof, and a pharmaceutically acceptable carrier. In some embodiments, a pharmaceutical composition of the present disclosure comprises any one of the compounds of Formula (A-I), (B-I), or (C-I), or pharmaceutically acceptable salt, solvate, diastereomeric mixture, or individual enantiomers thereof, and a pharmaceutically acceptable carrier.

The compositions are comprised of in general, a compound of Formula (A-I), (B-I), or (C-I) in combination with at least one pharmaceutically acceptable excipient. Acceptable excipients are non-toxic, aid administration, and do not adversely affect the therapeutic benefit of the compound of Formula (A-I), (B-I), or (C-I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt %) basis, from about 0.01-99.99 wt % of a compound of Formula (A-I), (B-I), or (C-I) based on the total formulation, with the balance being one or more suitable pharmaceutical excipients. Preferably, the compound is present at a level of about 1-80 wt %.

The compounds of the present invention may be used in combination with one or more other drugs in the treatment of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention also include those that contain one or more other active ingredients, in addition to a compound of the present invention.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound of the present invention. The weight ratio of the compound of the present invention to the second active ingredient may be varied and will depend upon the effective dose of each ingredient. Generally, an effective dose of each will be used.

In the case wherein the patient's status does improve, upon the doctor's discretion the administration of a compound described herein is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms.

Methods of Use

In some embodiments, described herein are methods of treating cancer in an individual in need thereof comprising administering a therapeutically effective amount of a melanoma inhibitor of apoptosis proteins (ML-IAP) antagonist. In some embodiments of a method of treating cancer, the ML-IAP antagonist is selective for ML-IAP over other inhibitor of apoptosis proteins (IAPs). In some embodiments of a method of treating cancer, the ML-IAP antagonist is at least 5-fold selective for ML-IAP over other IAPs. In some embodiments of a method of treating cancer, the ML-IAP antagonist is at least 10-fold selective for ML-IAP over other IAPs. In some embodiments of a method of treating cancer, the ML-IAP antagonist is at least 20-fold selective for ML-IAP over other IAPs. In some embodiments of a method of treating cancer, the ML-IAP antagonist is at least 30-fold selective for ML-IAP over other IAPs. In some embodiments of a method of treating cancer, the ML-IAP antagonist is at least 50-fold selective for ML-IAP over other IAPs. In some embodiments of a method of treating cancer, the ML-IAP antagonist is at least 100-fold selective for ML-IAP over other IAPs. In some embodiments of a method of treating cancer, the ML-IAP antagonist is at least 200-fold selective for ML-IAP over other IAPs.

In some embodiments of a method of treating cancer, the ML-IAP antagonist is at least 5-fold selective for ML-IAP BIR domain over XIAP BIR2/3 domains. In some embodiments of a method of treating cancer, the ML-IAP antagonist is at least 10-fold selective for ML-IAP BIR domain over XIAP BIR2/3 domains. In some embodiments of a method of treating cancer, the ML-IAP antagonist is at least 20-fold selective for ML-IAP BIR domain over XIAP BIR2/3 domains. In some embodiments of a method of treating cancer, the ML-IAP antagonist is at least 50-fold selective for ML-IAP BIR domain over XIAP BIR2/3 domains. In some embodiments of a method of treating cancer, the ML-IAP antagonist is at least 100-fold selective for ML-IAP BIR domain over XIAP BIR2/3 domains.

In some embodiments, described herein are methods for treating a disease or condition associated with the overexpression of ML-IAP in an individual, comprising administering a therapeutically effective amount of a compound described herein, or pharmaceutically acceptable salt, solvate, diastereomeric mixture, or individual enantiomers thereof, to the individual. In some embodiments, described herein are methods for treating a disease or condition associated with the overexpression of ML-IAP in an individual, comprising administering a therapeutically effective amount of a compound of Formula (A-I), (B-I), or (C-I), or pharmaceutically acceptable salt, solvate, diastereomeric mixture, or individual enantiomers thereof, to the individual. In some embodiments, the disease or condition is cancer. In some embodiments, the disease or condition is cancer.

In some embodiments, described herein are methods of inhibiting melanoma inhibitor of apoptosis protein (ML-IAP) with a compound as described herein. In some embodiments, described herein are methods of inhibiting melanoma inhibitor of apoptosis protein (ML-IAP) with a compound of Formula (A-I), (B-I), or (C-I).

In some embodiments, described herein are methods of treating cancer in an individual in need thereof comprising administering a therapeutically effective amount of a compound as described herein, or pharmaceutically acceptable salt, N-oxide, racemate, or stereoisomer thereof, to the individual. In some embodiments, described herein are methods of treating cancer in an individual in need thereof comprising administering a therapeutically effective amount of a compound of Formula (A-I), (B-I), or (C-I), or pharmaceutically acceptable salt, N-oxide, racemate, or stereoisomer thereof, to the individual.

In some embodiments of any one of the methods described herein, the cancer is a lung cancer. In some embodiments, the cancer is chemo-resistant, refractory, or relapsed. In some embodiments, the cancer is chemo-resistant. In some embodiments, the cancer is resistant to platinum-based chemotherapy. In some embodiments, the cancer is resistant to chemotherapy, targeted therapy, immunotherapy, adjuvant therapy, or anti-angiogenesis therapy. In some embodiments, the cancer is resistant to carboplatin, cisplatin, docetaxel, gemcitabine, nab-paclitaxel, paclitaxel, pemetrexed, vinorelbine, bevacizumab, ramucirumab, afatinib, dacomitinib, erlotinib, gefitinib, necitumumab, osimertinib, atezolizumab, durvalumab, nivolumab, or pembrolizumab. In some embodiments, the cancer is resistant to carboplatin or cisplatin. In some embodiments, the cancer is resistant to paclitaxel or nab-paclitaxel.

In some embodiments, the cancer is sensitized to radiation therapy, chemotherapy, targeted therapy, immunotherapy, adjuvant therapy, or anti-angiogenesis therapy. In some embodiments, the cancer is sensitized to radiation therapy. In some embodiments, the cancer is sensitized to chemotherapy. In some embodiments, the cancer is sensitized to targeted therapy. In some embodiments, the cancer is sensitized to immunotherapy. In some embodiments, the cancer is sensitized to adjuvant therapy. In some embodiments, the cancer is sensitized to anti-angiogenesis therapy. In some embodiments, the cancer is hypersensitized to chemotherapy. In some embodiments, chemo-resistance is reduced. In some embodiments, chemo-resistance is negated. In some embodiments, the cancer is sensitized to carboplatin, cisplatin, docetaxel, gemcitabine, nab-paclitaxel, paclitaxel, pemetrexed, vinorelbine, bevacizumab, ramucirumab, afatinib, dacomitinib, erlotinib, gefitinib, necitumumab, osimertinib, atezolizumab, durvalumab, nivolumab, or pembrolizumab. In some embodiments, the cancer is sensitized to carboplatin or cisplatin. In some embodiments, the cancer is sensitized to paclitaxel or nab-paclitaxel.

In some embodiments, the cancer is non-small cell lung cancer, adenocarcinoma, squamous cell carcinoma, adenosquamous carcinoma, sarcomatoid carcinoma, large cell carcinoma, or small cell lung cancer. In some embodiments, the cancer is non-small cell lung cancer. In some embodiments, the cancer is adenocarcinoma. In some embodiments, the cancer is squamous cell carcinoma. In some embodiments, the cancer is adenosquamous carcinoma. In some embodiments, the cancer is sarcomatoid carcinoma. In some embodiments, the cancer is large cell carcinoma. In some embodiments, the cancer is small cell lung cancer. In some embodiments, the non-small cell lung cancer is chemo-resistant. In some embodiments, the adenocarcinoma is chemo-resistant. In some embodiments, the squamous cell carcinoma is chemo-resistant. In some embodiments, the adenosquamous carcinoma is chemo-resistant. In some embodiments, the sarcomatoid carcinoma is chemo-resistant. In some embodiments, the large cell carcinoma is chemo-resistant. In some embodiments, the small cell lung cancer is chemo-resistant.

In some embodiments, a method as described herein comprises administering an additional therapeutic agent. In some embodiments, a method as described herein comprises administering at least two additional therapeutic agents. In some embodiments, the additional therapeutic agent is surgery, radiation therapy, chemotherapy, targeted therapy, immunotherapy, adjuvant therapy, anti-angiogenesis therapy, or pain therapy. In some embodiments, the additional therapeutic agent is chemotherapy, targeted therapy, immunotherapy, adjuvant therapy, or anti-angiogenesis therapy. In some embodiments, the additional therapeutic agent is surgery. In some embodiments, the additional therapeutic agent is radiation therapy. In some embodiments, the additional therapeutic agent is chemotherapy. In some embodiments, the additional therapeutic agent is targeted therapy. In some embodiments, the additional therapeutic agent is immunotherapy. In some embodiments, the additional therapeutic agent is adjuvant therapy. In some embodiments, the additional therapeutic agent is anti-angiogenesis therapy. In some embodiments, the additional therapeutic agent is pain therapy.

Also disclosed is a method of treating Human Immunodeficiency Virus (HIV) in a mammal comprising administering a therapeutically effective amount of a compound disclosed herein, or pharmaceutically acceptable salt, N-oxide, racemate, or stereoisomer thereof, to the individual.

Also disclosed is a method of reversing a latency of Human Immunodeficiency Virus (HIV) in a mammal comprising administering a therapeutically effective amount of a compound disclosed herein, or pharmaceutically acceptable salt, N-oxide, racemate, or stereoisomer thereof, to the individual. In some embodiments of a method of reversing a latency of Human Immunodeficiency Virus (HIV), the latency of HIV is reversed without activation of T cells. In some embodiments of a method of reversing a latency of Human Immunodeficiency Virus (HIV), the method further comprises administering an additional latency reversal agent, a killer agent, CarT, immunotherapy, neutralizing antibodies, or other agents. In some embodiments of a method of reversing a latency of Human Immunodeficiency Virus (HIV), the additional latency reversal agent is a histone deacetylase inhibitor (HDACi), a bromodomain and extra terminal domain inhibitors (BETi), or a Protein Kinase C (PKC) agonist.

Combination Therapy

In some embodiments, the additional therapeutic agent is carboplatin, cisplatin, docetaxel, gemcitabine, nab-paclitaxel, paclitaxel, pemetrexed, vinorelbine, bevacizumab, ramucirumab, afatinib, dacomitinib, erlotinib, gefitinib, necitumumab, osimertinib, atezolizumab, durvalumab, nivolumab, or pembrolizumab. In some embodiments, the additional therapeutic agent is carboplatin, cisplatin, docetaxel, gemcitabine, nab-paclitaxel, paclitaxel, or bevacizumab. In some embodiments, the additional therapeutic agent is carboplatin, cisplatin, or paclitaxel. In some embodiments, the additional therapeutic agent is carboplatin. In some embodiments, the additional therapeutic agent is cisplatin. In some embodiments, the additional therapeutic agent is gemcitabine. In some embodiments, the additional therapeutic agent is bevacizumab. In some embodiments, the additional therapeutic agent is vinorelbine.

In some embodiments, a pharmaceutical composition of the present disclosure comprises a selective melanoma inhibitor of apoptosis protein (ML-IAP) antagonist, at least one additional therapeutic agent used to treat cancer, and at least one excipient or carrier. In some embodiments, the pharmaceutical composition comprises at least two additional therapeutic agents used to treat cancer. In some embodiments, the pharmaceutical composition comprises at least three additional therapeutic agents used to treat cancer. In some embodiments, the additional therapeutic agents used to treat cancer is chemotherapy, targeted therapy, immunotherapy, adjuvant therapy, or anti-angiogenesis therapy. In some embodiments, the additional therapeutic agents used to treat cancer is carboplatin, cisplatin, docetaxel, gemcitabine, nab-paclitaxel, paclitaxel, pemetrexed, vinorelbine, bevacizumab, ramucirumab, afatinib, dacomitinib, erlotinib, gefitinib, necitumumab, osimertinib, atezolizumab, durvalumab, nivolumab, or pembrolizumab.

In some cases, a compound described herein is administered in combination with a second anti-cancer agent. Examples of anti-cancer agents for use in combination with a compound of Formula (A-I), (B-I), or (C-I) include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a compound of Formula (A-I), (B-I), or (C-I) include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of Formula (A-I), (B-I), or (C-I) include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B;

mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; $Ru_{11}$ retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of Formula (A-I), (B-I), or (C-I) include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a compound of Formula (A-I), (B-I), or (C-I) include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of Formula (A-I), (B-I), or (C-I) include, but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination a compound of Formula (A-I), (B-I), or (C-I) include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an irreversible EGFR tyrosine kinase inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin AI (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

In some cases, a compound described herein (e.g., a compound of Formula (A-I), (B-I), or (C-I)) is administered in combination with TNF-alpha and/or TNF-related apoptosis-inducing ligand (TRAIL). TRAIL shows homology to other members of the TNF-alpha family of proteins. In some cases, a compound described herein (e.g., a compound of Formula (A-I), (B-I), or (C-I)) is administered in combination with a TNF-alpha modulator and/or a TNF-alpha analogue (e.g., lenalidomide, revlimid, CC-5013; CC-4047, ACTIMID. Thalidomide and the like). In some cases, a compound described herein (e.g., a compound of Formula (A-I), (B-I), or (C-I)) is administered in combination with an adjuvant, hormone therapy, immunotherapy or any combination thereof.

In some cases, a compound described herein is administered in combination with antiretroviral therapy (ART). Examples of antiretroviral therapy (ART) for use in combination with a compound of Formula (A-I), (B-I), or (C-I) include Combivir, Kaletra, Aluvia, Trizivir, Epzicom, Kivexa, Triomune, Duovir-N, Truvada, Atripla, Complera, Eviplera, Stribild, Triumeq, Evotaz, Prezcobix, Rezolsta, Dutrebis, Genvoya, Odefsey, Descovy, Juluca, Symfi, Symfi Lo, Biktarvy, Cimduo, Symtuza, Delstrigo, and Dovato.

In some cases, a compound described herein is administered in combination with a latency reversal agent (LRA) with or without antiretroviral therapy (ART). Examples of latency reversal agent (LRA) for use in combination with a compound of Formula (A-I), (B-I), or (C-I) include histone deacetylase inhibitors (HDACi), bromodomain and extra terminal domain inhibitors (BETi), Protein Kinase C (PKC) agonists, activators of positive transcription elongation factor b (P-TEFb), Toll-like receptor (TLR) agonists, immune checkpoint inhibitors, tetraethylthiuram disulfide (Disulfiram), benzotriazole derivatives, quinolines, cytokines, methyltransferase inhibitors, and methylation inhibitors.

In some cases, a compound described herein is administered in combination with a killer agent, CarT, immunotherapy, neutralizing antibodies, or other agents. Additional latency reversal agents can be found in Stoszko et al., Curr Opin Virol. 2019 Jul. 16; 38:37-53 which is hereby incorporated by reference for such disclosures.

EXAMPLES

Chemical Synthesis

Reactions conducted under microwave irradiation were performed in a CEM Discover microwave reactor using either CEM 10 mL reaction vessels or a ChemGlass heavy wall pressure vessel (100 mL, 38 mmx 190 mm). Reaction progress was monitored by reverse-phase HPLC and/or thin-layer chromatography (TLC). Liquid chromatography-mass spectrometry was performed using either Waters or Shimadzu 2010EV LCMS instruments using water and acetonitrile or methanol doped with 0.1% formic acid. TLC was performed using silica gel 60 F254 pre-coated plates (0.25 mm). Flash chromatography was performed using silica gel (32-63 m particle size) or aluminum oxide (activated, basic, ~150 mesh size). Automated chromatographic purification was carried out using pre-packed silica or C18 cartridges (from RediSep and Luknova) and eluted using an ISCO Companion system. Reverse phase purifications were conducted using water and acetonitrile or methanol doped with 0.1% formic acid. All final product compounds were purified using one of these two chromatographic methods. Purity and characterization of compounds was established by a combination of TLC, liquid chromatography-mass spectroscopy (LC-MS) and Nuclear Magnetic Resonance (NMR) analytical techniques. $^{1}H$ and $^{13}C$ NMR spectra were obtained on a Joel 400 spectrometer at 400 MHz and 101 MHz, respectively. Chemical shifts are reported in δ (ppm) and were internally referenced to deuterated solvent signals.

LC-MS Conditions

HPLC-MS analyses were performed on a Waters ACQUITY UPLC with SQ mass detector and PDA eλ detector. The column used was a Phenomenex Kinetex C18 column (1.7 um, 2.1×50 mm). The mobile phase consisted of eluent A (water, 0.05% TFA) and eluent B ($CH_3CN$, 0.05% TFA), and the elution proceeded at 0.5 mL/min. The initial conditions were 90% A, then 90% A to 10% A linearly decreased within 1.75 min, then from 10% A to 90% A within 0.25 min. The total run time is 2 minutes.

General Isocyanide Synthesis

Synthesis of (R)—N-(1,2,3,4-tetrahydronaphthalen-1-yl)formamide (X-1)

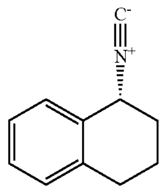

(R)—N-(1,2,3,4-tetrahydronaphthalen-1-yl)formamide (X-1). A solution of (R)-1,2,3,4-tetrahydronaphthalen-1-amine (67.9 mmol, 10 g, 1.0 eq) in ethyl formate (>10 eq, 100 mL) was refluxed at 80° C. for 40 hours. The mixture was concentrated to dryness and solubilized in a mixture of dichloromethane (100 mL) and triethylamine (50 mL, 5.0 eq). Phosphoryl trichloride (10 ml, 106 mmol, 1.6 eq) was added at 0° C. The mixture was stirred at 0° C. for 30 min then at 23° C. for 3 hours. The mixture was poured carefully in saturated aqueous sodium bicarbonate (700 mL), extracted with dichloromethane (3*300 mL), dried over sodium sulfate anhydrous, filtered and concentrated. The crude product was purified on silica gel chromatography (2-20% ethyl acetate in hexanes). Yield 7.2 g (67%) of an orange liquid. TLC-Rf=0.57 (15% ethyl acetate in hexanes). $^1$H NMR (400 MHz, CDCl3) δ 7.47-7.39 (m, 1H), 7.28-7.19 (m, 2H), 7.15-7.09 (m, 1H), 4.83 (t, 1H), 2.87 (dt, 1H), 2.76 (dt, 1H), 2.21-2.11 (m, 2H), 2.11-1.99 (m, 1H), 1.89-1.76 (m, 1H).

Synthesis of (isocyanomethylene)dibenzene (X-2)

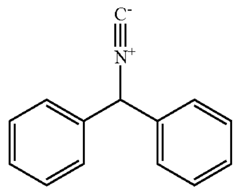

(isocyanomethylene)dibenzene (X-2). Follow synthesis of X-1. 10 g of an orange solid 95% yield. Rf=0.75 (15% ethyl acetate in hexanes). $^1$H NMR (400 MHz, $CDCl_3$) δ 7.40-7.32 (m, 10H), 5.91 (s, 1H).

Synthesis of 1-(2,2-dimethoxyethyl)-2-isocyanobenzene (X-3)

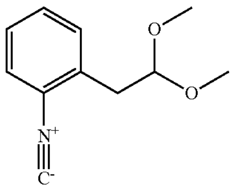

1-(2,2-dimethoxyethyl)-2-isocyanobenzene (X-3). To a solution of nitrotoluene (10 g, 1.0 eq) in dimethylformamide (160 mL, 0.5M) was added dimethylformamide diethylacetal (12.2 mL, 1.2 eq) and pyrrolidine (7.24 mL, 1.2 eq). The yellow reaction mixture was then stirred at 80° C. for 5 days. The mixture turned red. Water (500 mL) was added to the cooled reaction mixture at 23° C. and extracted with ethyl acetate (1*100 mL) and dichloromethane (2*200 mL). The combined organic layers were washed with water (1*100 mL) and brine (1*100 mL), dried over sodium sulfate anhydrous, filtered and concentrated. To the resulting oil (16.0 g, 1.0 eq) in methanol (160 mL, 0.5 M) was slowly added chlorotrimethylsilane (13.98 mL, 1.5 eq). The mixture was heated to 75° C. for 18 hours. The solvents were removed under vacuum. The resultant liquid was poured in a 5% citric acid (300 mL, aqueous solution) and extracted with ethyl acetate (3*100 mL). The combined organic layers were washed with a 1:1 mixture of saturated solution of sodium bicarbonate:brine (2*100 mL), dried over sodium sulfate anhydrous, filtered and concentrated to afford 15 g (97% yield) of a dark red oil. A sealed mixture of the oil and 10% Pd/C (2 g) in methanol (100 mL) flushed with nitrogen was placed under hydrogen atmosphere in a parr hydrogenator and stirred for 18 hours at 20 PSI. The mixture was then filtered through celite and concentrated. The crude intermediate was solubilized in ethyl formate (>10 eq, 30 mL) and refluxed at 80° C. for 40 hours. It was concentrated to dryness and solubilized in a mixture of dichloromethane (150 mL) and triethylamine (55 mL, 6.0 eq). Phosphoryl trichloride (9 ml, 1.5 eq) was added at 0° C. The mixture was stirred at 0° C. for 30 min then at 23° C. for 3 hours. The mixture was poured carefully in saturated aqueous sodium bicarbonate (700 mL), which was extracted with DCM (3*300 mL), dried over sodium sulfate anhydrous, filtered and concentrated. The crude was purified by column chromatography over silica gel (0-50% Dichloromethane in hexanes). 8.6 g of a stinky dark red oil (62% yield). TLC-Rf: 0.82 (30% ethyl acetate in hexanes).

General Synthesis of Aldehyde

Synthesis of 2-allyl-2-(2,2-dimethoxyethyl)pent-4-enenitrile (X-4a)

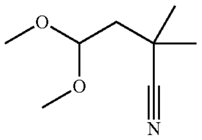

2-allyl-2-(2,2-dimethoxyethyl)pent-4-enenitrile (X-4a). To a stirred solution of 4,4-dimethoxybutanenitrile (4.0 g, 1.0 eq) in THF (60 mL, 0.5M) at −78° C. was slowly added 2.0M lithium diisoproprylamide (32.5 mL, 2.2 eq). After 30 min, iodomethane (4.83 mL, 2.5 eq) was added slowly at −78° C. The mixture was stirred at −78° C. for 1 h then stirred at r.t. for 18 hours. The mixture was carefully poured in a saturated aqueous solution of ammonium chloride (300 mL) and was extracted with DCM (3*200 mL), dried over sodium sulfate anhydrous, filtered and concentrated. The crude intermediate was purified by flash column chromatography over silica gel (20-100% dichloromethane in hexanes). 2.78 g (57%) of a slightly yellow liquid. Rf=0.42 (15% ethyl acetate in hexanes). $^1$H NMR (400 MHz, $CDCl_3$) δ 4.60 (t, 1H), 3.36 (s, 6H), 1.82 (d, 2H), 1.39 (s, 6H). LC-MS m/z: 157.70 (calcd:158.12 [M+H]+).

Synthesis of 1-(2,2-dimethoxyethyl)cyclopent-3-ene-1-carbonitrile (X-4b)

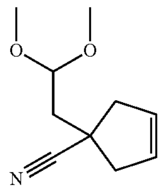

1-(2,2-dimethoxyethyl)cyclopent-3-ene-1-carbonitrile (X-4b). A nitrogen degassed solution of Grubbs 1 or Grubbs II (0.05 eq) in benzene (50 mL) was heated to 90° C. for 20 min. To the hot solution was added the crude 2-allyl-2-(2,2-dimethoxyethyl)pent-4-enenitrile (1 eq, 5 g, 23.89 mmol, synthesized following procedure X-4a using bromo-allyl) and the mixture was stirred under reflux for 14 hours. 0.05 eq of Grubbs catalyst was added again and the mixture stirred under reflux for a further 24 hours. The mixture was concentrated, and the product was purified by flash column chromatography over silica gel (0-20% ethyl acetate in hexanes). It afforded a colorless liquid (2.01 g, 46% yield). $^{1}$H NMR (400 MHz, $CDCl_3$) δ 5.68 (s, 2H), 4.63 (t, 1H), 3.38 (s, 6H), 2.89 (d, 2H), 2.60 (d, 2H), 1.98 (d, 2H). LC-MS m/z: 181.75 (calcd:182.12 [M+H]+).

Synthesis of 4,4-dimethoxy-2,2-dimethylbutanal (X-5a)

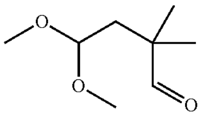

4,4-dimethoxy-2,2-dimethylbutanal (X-5a). The intermediate X-3a (2.78 g, 1.0 eq) was solubilized in DCM (50 mL) and cooled down to −78° C. 25% diisobutylaluminium hydride in hexanes (1.1 eq, 14 mL) was added and the mixture was stirred at −78° C. for 1 h, then at 0° C. for 1 hour. It was quenched with 20 mL of a saturated aqueous ammonium chloride and 30 mL of a saturated aqueous solution of Rochelle salt. The mixture was diluted with diethyl ether (100 mL) and brine (100 mL). It was warmed up to 23° C. and stirred vigorously for 1 h. The organic phase was separated, and the aqueous phase was extracted with dichloromethane (3*100 mL). The combined organic layers were washed with brine, dried over sodium sulfate anhydrous, filtered through a plug of silica gel and concentrated. The crude was purified by flash column chromatography over silica gel (0-100% dichloromethane in pentane): 2.00 g (45% yield) of a colorless liquid. Rf=0.39 (15% ethyl acetate in hexanes $^{1}$H NMR (400 MHz, $CDCl_3$) δ 9.38 (s, 1H), 4.34 (t, 1H), 3.29 (s, 6H), 1.84 (d, 2H), 1.06 (s, 6H).

Synthesis of 2-allyl-2-(2,2-dimethoxyethyl)pent-4-enal (X-5b)

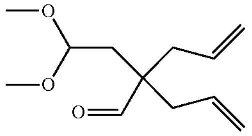

2-allyl-2-(2,2-dimethoxyethyl)pent-4-enal (X-5b). Followed the same procedure as X-4a and X-5a using bromo allyl. 90% yield. Also contains mono alkylated X-3c (<10%). The crude mixture of mono and bis alkylated was used in the next step without further purification. NMR of nitrile intermediate: $^{1}$H NMR (400 MHz, $CDCl_3$) δ 5.84 (ddt, 2H), 5.24 (dd, 2H), 5.20 (dd, 2H), 4.63 (t, 1H), 3.37 (s, 6H), 2.39 (dd, 4H), 1.84 (d, 2H). NMR of aldehyde X-5b: $^{1}$H NMR (400 MHz, $CDCl_3$) δ 9.61 (d, 1H), 5.78-5.66 (m, 1H), 5.14-5.05 (m, 3H), 4.41 (t, 1H), 3.32 (d, 3H), 3.31 (d, 3H), 2.57-2.47 (m, 1H), 2.47-2.31 (m, 2H), 2.27-2.16 (m, 1H), 2.05-1.95 (m, 1H), 1.90-1.82 (m, 1H), 1.79-1.70 (m, 1H). $^{13}$C NMR (400 MHz, $CDCl_3$) δ 203.88, 134.66, 117.88, 103.23, 53.89, 47.32, 33.53, 31.98. LC-MS m/z: 213.80 (calcd:213.15 [M+H]+).

Synthesis of 2,2-diethyl-4,4-dimethoxybutanal (X-5c)

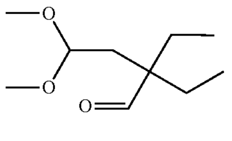

2,2-diethyl-4,4-dimethoxybutanal (X-5c). Followed the same procedure as X-4a and X-5a using iodoethane. 70% yield. Intermediate nitrile: $^{1}$H NMR (400 MHz, $CDCl_3$) δ 4.57 (t, 1H), 3.36 (s, 6H), 1.83 (d, 2H), 1.66 (tdt, 4H), 1.01 (t, 6H). NMR of aldehyde X-5c: $^{1}$H NMR (400 MHz, $CDCl_3$) δ 9.35 (s, 1H), 4.32 (t, 1H), 3.30 (s, 6H), 1.83 (d, 2H), 1.62 (dq, 2H), 1.45 (dq, 2H), 0.79 (t, 6H). LC-MS m/z: 156.60 (calcd: 157.12 [M-OMe]+).

Synthesis of 2,2-diisopropyl-4,4-dimethoxybutanal (X-5d)

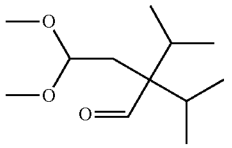

2,2-diisopropyl-4,4-dimethoxybutanal (X-5d). Followed the same procedure as X-4a and X-5a using 2-iodopropane. <10% yield. NMR of intermediate nitrile: $^{1}$H NMR (400 MHz, $CDCl_3$) δ 4.52 (t, 1H), 3.39 (s, 6H), 1.99 (hept, 2H), 1.74 (d, 2H), 1.08 (d, 6H), 0.99 (d, 6H). NMR of aldehyde X-5d: $^{1}$H NMR (400 MHz, $CDCl_3$) δ 9.55 (s, 1H), 4.57 (t, 1H), 3.29 (s, 6H), 2.12-2.02 (m, 2H), 1.89-1.83 (m, 2H), 0.91 (dd, 12H).

Synthesis of 4,4-dimethoxy-2,2-diphenethylbutanal (X-5e)

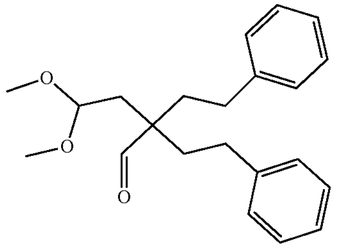 [SMILES: COC(CC(C=O)(CCc1ccccc1)CCc1ccccc1)OC]

4,4-dimethoxy-2,2-diphenethylbutanal (X-5e). Followed the same procedure as X-4a and X-5a using (2-iodoethyl) benzene. The mixture of mono and bis alkylated was used in the next step without further purification (880 mg, 54%).

NMR of Nitrile intermediate: $^1$H NMR (400 MHz, $CDCl_3$) δ 7.34-7.29 (m, 4H), 7.25-7.18 (m, 6H), 4.66 (t, 1H), 3.40 (s, 6H), 2.83-2.76 (m, 4H), 2.04 (d, 2H), 2.03-1.97 (m, 4H). NMR of aldehyde X-5e: $^1$H NMR (400 MHz, $CDCl_3$) δ 9.46 (s, 1H), 7.35-7.12 (m, 52H), 4.43 (t, 1H), 3.29 (s, 6H), 2.59-2.53 (m, 4H), 1.87-1.78 (m, 6H). LC-MS m/z: 341.95 (calcd: 341.21 [M+H]+).

Synthesis of 1-(2,2-dimethoxyethyl)cyclopent-3-ene-1-carbaldehyde (X-5f)

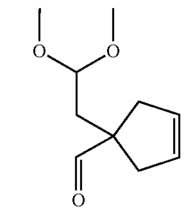

1-(2,2-dimethoxyethyl)cyclopent-3-ene-1-carbaldehyde (X-5f). Followed the synthesis of X-5a using X-4b. 2.0 g, 98% yield. $^1$H NMR (400 MHz, $CDCl_3$) δ 9.42 (s, 1H), 5.61 (s, 2H), 4.30 (t, 1H), 3.30 (s, 6H), 2.75 (d, 2H), 2.25 (d, 2H), 2.08 (d, 2H). LC-MS m/z: 185.80 (calcd: 185.12 [M+H]+).

Synthesis of 4-(dimethoxymethyl)nicotinaldehyde (X-5 g)

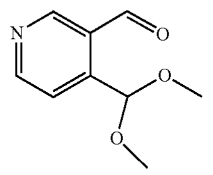

4-(dimethoxymethyl)nicotinaldehyde (X-5 g). P-toluenesulfonic acid (2.5 g, 1.2 eq) was added to a stirred solution of 3-bromopyridine-4-carboxyaldehyde (2.0 g, 1.0 eq) in 80 mL methanol and the mixture was heated to 75° C. The orange mixture turned red. After 4 hours the mixture was cooled to 23° C. and concentrated. 100 mL of saturated sodium bicarbonate was added to the crude and it was extracted with ethyl acetate (3*100 mL). The combined organic layers were washed with water (100 mL), brine (100 mL), dried over sodium sulfate anhydrous, filtered, concentrated and purified by column chromatography over silica gel using 0-50% ethyl acetate in hexanes. It afforded 3-bromo-4-(dimethoxymethyl)pyridine [1.5 g, 61% yield, TLC-Rf=0.3 in 15% ethyl acetate in hexanes, $^1$H NMR (400 MHz, $CDCl_3$) δ 8.72 (s, 1H), 8.53 (d, 1H), 7.52 (d, 1H), 5.50 (s, 1H), 3.38 (s, 6H)]. N-butyllithium was added dropwise to a solution of the latter in dry tetrahydrofuran (100 mL) at −75° C. The mixture turned deep orange. The mixture was stirred for 1 h then dimethylformamide (2.7 mL, 4.0 eq) was added dropwise. The mixture was removed from the cold bath and let warmed up to 23° C. for 5 hours. It was quenched with a saturated solution of ammonium chloride (100 mL) then neutralized with saturated sodium bicarbonate (100 mL) and extracted with ethyl acetate (3*100 mL). The combined organic layers were washed with brine (2*100 mL), dried over sodium sulfate anhydrous, filtered, concentrated and purified by column chromatography over silica gel (480 mg, 30% yield, TLC-Rf: 0.25 in 25% ethyl acetate in hexanes). $^1$H NMR (400 MHz, $CDCl_3$) δ 10.43 (s, 1H), 9.06 (s, 1H), 8.81 (d, 1H), 7.62 (d, 1H), 5.91 (s, 1H), 3.40 (s, 6H). LC-MS m/z: 181.75 (calcd: 182.08 [M+H]+).

Synthesis of (S)-2-((tert-butoxycarbonyl)amino)-3-(4-methoxyphenyl)propanoic acid (X-6)

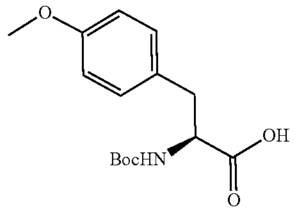 [SMILES: COc1ccc(C[C@H](NC(=O)OC(C)(C)C)C(=O)O)cc1]

(S)-2-((tert-butoxycarbonyl)amino)-3-(4-methoxyphenyl)propanoic acid (X-6). A mixture of (tert-butoxycarbonyl)-L-tyrosine (17.77 mmol, 1.0 eq), iodomethane (5 ml, 80 mmol, 4.5 eq) and potassium carbonate (37.3 mmol, 2.5 eq) was refluxed in acetone for 18 h. Then the mixture was concentrated, diluted with water at pH 2 and extracted with ethyl acetate. The combined organic layers were washed with a saturated solution of sodium bicarbonate, dried over anhydrous sodium sulfate, filtered and concentrated. It afforded 6.4 g of crude intermediate. This crude (6.4 g, 1.0 eq) was solubilized in methanol (50 mL) and 2M NaOH (45 mL, 5 eq) was added. The mixture was stirred at 40° C. for 3 hours. The mixture was acidified to pH 2 with 0.5M HCl and extracted with ethyl acetate (3*20 mL). The combined organic layers were dried over sodium sulfate anhydrous, filtered and concentrated. The crude oil was purified by flash column chromatography over silica gel to afford a colorless oil (5.1 g, 97% yield) that solidifies in the fridge at 5° C. $^1$H NMR (400 MHz, $CDCl_3$) δ 7.089 (d, J=8.24, 2H), 6.824 (d, J=8.70, 2H), 5.04-4.97 (bm, 1H), 4.58-4.50 (bm, 1H), 3.772 (s, 3H), 3.115 (dd, J=13.97, 5.50, 1H), 3.015 (dd, J=13.97, 5.50, 1H), 1.409 (s, 9H). LC-MS m/z: 317.85 (calcd:318.13 [M+Na]+).

Synthesis of (S)-2-((tert-butoxycarbonyl)amino)-3-(3-methoxyphenyl)propanoic acid (X-7)

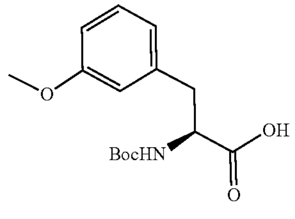 [SMILES: COc1cccc(C[C@H](NC(=O)OC(C)(C)C)C(=O)O)c1]

(S)-2-((tert-butoxycarbonyl)amino)-3-(3-methoxyphenyl)propanoic acid (X-7). Followed the procedure of X-6 using 3-hydroxy-L-phenylalanine. Obtained 600 mg (quantitative yield). $^1$H NMR (400 MHz, $CDCl_3$) δ 7.192 (t, J=7.56, 1H), 6.80-6.74 (m, 3H), 5.10-5.02 (bm, 1H), 4.61-4.53 (bm, 1H), 3.762 (s, 3H), 3.151 (dd, J=13.69, 5.50, 1H), 3.034 (dd, J=13.78, 6.33, 1H), 1.403 (s, 9H). LC-MS m/z: 317.85 (calcd: 318.13 [M+Na]+).

Synthesis of (2S)-2-((tert-butoxycarbonyl)amino)-2-((1S)-2-hydroxycyclohexyl)acetic acid (X-8)

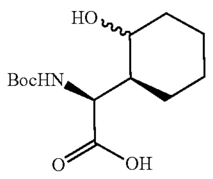

(2S)-2-((tert-butoxycarbonyl)amino)-2-((1S)-2-hydroxycyclohexyl)acetic acid (X-8). To a mixture of (2S)-2-((tert-butoxycarbonyl)amino)-2-(2-hydroxycyclohexyl)acetic acid (1.0 eq), which was synthesized following the patent literature: US20100048545A1, and 4-dimethylaminopyridine (0.1 eq) in tetrahydrofuran at 0° C. was added di-tert-butyl dicarbonate (1.1 eq). The mixture was stirred for 10 minutes at 0° C. then warmed up to 20° C. for 16 hours. The mixture was then concentrated, solubilized in methanol and sodium hydroxide was added (2M, 5 eq). The mixture was heated to 40° C. for 3 h. The reaction mixture was diluted with water (200 mL) then acidified to pH 2-3 with HCl 1M and extracted with ethyl acetate. The organics are combined, washed with saturated citric acid solution, dried over sodium sulfate anhydrous, filtered and concentrated. Crude: 370 mg. LC-MS m/z: 272.00 (calcd: 272.15 [M−H]—). $^1$H NMR (400 MHz, $CDCl_3$) δ 5.39 (d, 1H), 4.82 (dd, 1H), 4.43 (s, 1H), 4.03 (s, 1H), 3.53 (s, 1H), 3.23 (td, 1H), 2.02 (t, 3H), 1.92-1.56 (m, 7H), 1.50-1.42 (m, 18H), 1.40-1.13 (m, 6H), 1.13-0.96 (m, 1H).

Synthesis of (2S)-2-(((benzyloxy)carbonyl)amino)-4-hydroxy-5-(phenylthio)pentanoic acid (X-9)

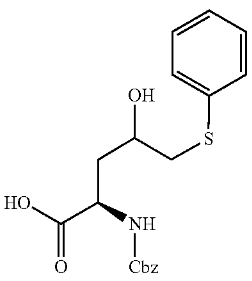 [SMILES: O=C(N[C@H](CC(O)CSc1ccccc1)C(=O)O)OCc1ccccc1]

(2S)-2-(((benzyloxy)carbonyl)amino)-4-hydroxy-5-(phenylthio)pentanoic acid (X-9). To a stirred solution of potassium tert-butoxide (2.0 eq) in tetrahydrofuran (100 mL), was added trimethylsulfoxonium iodide (2.0 eq, 1.761 g). The mixture was refluxed for 2 hours then cooled down to 0° C. A second mixture of 1,1'-carbonyldiimidazole (1.0 eq, 649 mg) and Z-L-Asp(OH)—OMe (1.0 eq, 1.293 g) was heated in tetrahydrofuran (0.1M) for 1 h at 40° C. The second mixture was cooled down to 0° C. before adding it to the first mixture at 0° C. The mixture was stirred at 0° C. for 1 h then warmed up to 23° C. for 1 hour. The reaction was quenched brine (200 mL) and extracted with ethyl acetate (3*100 mL). The combined organic layers were washed with brine (100 mL), dried over sodium sulfate anhydrous and concentrated to afford 1.6 g of crude intermediate. The crude (450 mg, 1.0 eq) was solubilized in acetonitrile (3 mL) and benzenethiol (139 mg, 1.0 eq). The reaction mixture was stirred at this temperature for 24 h then was concentrated. The crude was solubilized in methanol:tetrahydrofuran (20 mL, 1:1) at 0° C. was added sodium borohydride (0.6 eq-1 eq). The mixture was stirred at 0° C. for 30 min then warmed up to r.t for 2 hours. The mixture was quenched with a saturated solution of sodium bicarbonate (100 mL) and extracted with ethyl acetate (3*100 mL). The combined organic layers were dried over sodium sulfate anhydrous, filtered and concentrated. The crude was solubilized in a mixture of tetrahydrofuran:water (3:1, 40 mL) and sodium hydroxide was added (0.6 g, 5 eq). The mixture was stirred vigorously for 3 hours at 40° C. The mixture was quenched with 0.5M HCl (150 mL) and extracted with ethyl acetate (3*100 mL). The combined organic layers were dried over sodium sulfate anhydrous, filtered and concentrated. The crude was used in the next step without further purification. LC-MS m/z: 375.80 (calc'd 376.12 [M+H]+). $^1$H NMR (400 MHz, $CDCl_3$) δ 7.16-7.05 (m, 7H), 7.05-6.98 (m, 2H), 6.98-6.92 (m, 1H), 6.27 (s, 1H), 5.00 (d, 1H), 4.73 (d, 1H), 4.17 (s, 1H), 3.76 (s, 1H), 2.90 (d, 1H), 2.76 (d, 1H), 1.92 (s, 1H), 1.71 (s, 1H). $^{13}$C NMR (400 MHz, $CDCl_3$) δ 179.37, 157.50, 136.44, 136.41, 129.08, 128.97, 128.50, 127.98, 125.87, 68.09, 66.93, 54.29, 41.09, 40.30.

Amine Formation

Synthesis of (R)-thiochroman-4-aminium chloride (X-10)

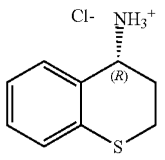

(R)-thiochroman-4-aminium chloride (X-10). A mixture of the thiochromanone (10 g, 60.9 mmol, 1.0 eq), (R)-2-methylpropane-2-sulfinamide (7.38 g, 60.9 mmol, 1.0 eq) and titanium tetraethoxide (27.8 g, 1.0 eq) was stirred under nitrogen at 70° C. for 30 min. The mixture, cooled to r.t., was diluted with ethyl acetate (250 mL) and 10 mL of brine. The mixture was stirred vigorously for 10 min. The mixture was filtered through celite and the filter cake was washed with ethyl acetate (300 mL). The solvents were removed under vacuum and the crude was solubilized in THF (0.3M) containing 2% water and cooled down to −50° C. Sodium borohydride (3.0 eq, 4.2 g) was added (3.0 eq) and the mixture was stirred at −50° C. for 1 h then at 23° C. for 2 hours. The solvents were removed under vacuum and the crude was purified by column chromatography (15-75% ethyl acetate in hexanes, the R enantiomer is the first to elute) to afford the pure (R)-2-methyl-N—((R)-thiochroman-4-yl)propane-2-sulfinamide [12 g, 72% yield, $^1$H NMR (400 MHz, $CDCl_3$) δ 7.32 (d, 1H), 7.16-7.08 (m, 2H), 7.07-7.01 (m, 1H), 4.61 (q, 1H), 3.26 (td, 1H), 3.18 (s, 1H), 2.80 (dt, 1H), 2.49-2.37 (m, 1H), 2.07-1.94 (m, 1H), 1.21 (s, 9H), $^{13}$C NMR (400 MHz, $CDCl_3$) δ 133.76, 132.69, 131.45, 128.50, 126.85, 124.75, 55.66, 50.99, 28.25, 22.70, 21.18] and the pure (R)-2-methyl-N—((S)-thiochroman-4-yl)propane-2-sulfinamide [3 g, 18% yield, $^1$H NMR (400 MHz, $CDCl_3$) δ 7.31 (ddt, 1H), 7.15-7.08 (m, 2H), 7.05-7.00 (m, 1H), 4.51 (ddd, 1H), 3.53 (d, 1H), 3.16 (ddd, 1H), 3.03-2.95 (m, 1H), 2.44 (dtd, 1H), 2.35 (ddt, 1H), 1.22 (s, 9H). The pure (R)-2-methyl-N—((R)-thiochroman-4-yl) propane-2-sulfinamide (2 g, 1 eq) was then solubilized in dioxane (1M) and 4 M HCl in dioxane (10 eq) was added slowly. The mixture was stirred for 14 hours at 23° C. Diethyl ether (to reach 0.1M) was added and the precipitate was filtrated, washed with diethyl ether (30 mL), collected and lyophilized in dioxane. 0.5 g (40% yield, white powder). $^{1}$H NMR (400 MHz, $CD_3OD$) δ 7.35 (ddd, 1H), 7.25 (ddd, 1H), 7.20-7.16 (m, 1H), 7.14 (td, 1H), 4.56 (t, 1H), 3.19 (ddd, 1H), 3.04 (ddd, 1H), 2.53-2.44 (m, 1H), 2.38-2.28 (m, 1H). $^{13}$C NMR (101 MHz, $CD_3OD$) δ 135.19, 131.29, 130.43, 128.77, 128.21, 125.64, 27.74, 21.90. LC-MS m/z: 163.80 (calcd: 164.05 [M−H]+).

Synthesis of (R)-chroman-4-aminium chloride (X-11)

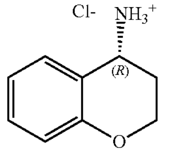

(R)-chroman-4-aminium chloride (X-11). Followed the synthesis of X-10 1.6 g (16% yield, tan powder). $^{1}$H NMR (400 MHz, $CD_3OD$) δ 7.38 (ddt, 1H), 7.29 (dddd, 1H), 7.00 (td, 1H), 6.89 (dd, 1H), 4.57 (t, 1H), 4.34-4.23 (m, 2H), 2.44-2.34 (m, 1H), 2.23-2.13 (m, 1H). $^{13}$C NMR (101 MHz, $CD_3OD$) δ 156.51, 131.83, 130.09, 122.16, 118.94, 118.84, 62.75, 46.00, 27.97. LC-MS m/z: 147.70 (calcd: 148.08 [M−H]+).

Synthesis of 2-(pyrimidin-2-yl)aniline (X-12)

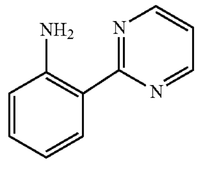 [SMILES: Nc1ccccc1-c1ncccn1]

2-(pyrimidin-2-yl)aniline (X-12). 2-Aminophenylboronic acid pinacol ester (1.5 g, 1.0 eq.), 2-bromopyrimidine (2.2 g, 2.0 eq), potassium carbonate (2.84 g, 3 eq) and Pd(dppf) (280 mg, 0.05 eq.) were mixed in DME/water (10 mL/1 mL) and refluxed for 20 h. 100 mL of 1M NaOH was added. It was extracted with DCM (3*30 mL), dried over sodium sulfate anhydrous, filtered through celite and concentrated. The product was purified by reverse phase silica gel (1.1 g, orange powder, 94% yield.). $^{1}$H NMR (400 MHz, $CDCl_3$): δ 8.78 (d, 2H), 8.44 (ddd, 1H), 7.24 (ddd, 1H), 7.10 (t, 1H), 6.78 (ddd, 1H), 6.74 (ddd, 1H), 6.26 (s, 2H). $^{13}$C NMR (101 MHz, $CDCl_3$): δ 166.29, 156.40, 148.81, 132.01, 130.97, 118.88, 117.50, 117.39, 117.15. LC-MS m/z: 172.10 (calcd: 172.09 [M+H]+).

Synthesis of (1S,2R)-2-(Prop-2-yn-1-yloxy)-2,3-dihydro-1H-inden-1-ammonium chloride (X-13)

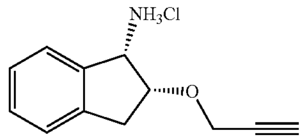

(1S,2R)-2-(Prop-2-yn-1-yloxy)-2,3-dihydro-1H-inden-1-ammonium chloride (X-13). Under $N_2$ atmosphere, tert-Butyl (1S,2R)-2-hydroxy-2,3-dihydro-1H-inden-1-ylcarbamate (2.50 g, 10.0 mmol, 1.00 eq.) was dissolved in dry DMF (20.0 mL) and the solution was cooled down to 0° C. Propargyl bromide in toluene (80%, 1.34 mL, 12.0 mmol, 1.20 eq.) was added. The resulting solution was treated in portions with powdered KOH (1.15 g, 420.6 mmol, 2.05 eq.) and stirring was continued at 0° C. After 1.5 h, water (40 mL) was added and the resulting mixture was extracted with ethyl acetate (4×40 mL). The combined organic layers were washed with water (2×40 mL) and brine (20 mL), dried over sodium sulfate anhydrous and concentrated. The residue was purified by flash column chromatography over silica gel (hexanes/ethyl acetate). It afforded tert-Butyl [(1S,2R)-2-(prop-2-yn-1-yloxy)-2,3-dihydro-1H-inden-1-yl]carbamate as a colorless solid, yield 2.29 g (79%). $R_f$=0.60 (25% ethyl acetate in hexanes). $^{1}$H NMR (400 MHz, $CDCl_3$) δ 7.35-7.30 (m, 1H), 7.25-7.19 (m, 3H), 5.27-5.03 (m, 2H), 4.48 (dq, 1H), 4.22 (dd, 2H), 3.09 (dd, 1H), 3.02 (dd, 1H), 2.43 (t, 1H), 1.51 (s, 9H). $^{13}$C NMR (101 MHz, $CDCl_3$) δ 156.27, 141.77, 139.43, 128.14, 127.21, 125.11, 124.51, 80.06, 79.74, 79.66, 74.65, 57.41, 57.17, 36.32, 28.56. LC-MS: m/z=287.90 (calcd. 288.16 [M+H]+). Tert-Butyl [(1S,2R)-2-(prop-2-yn-1-yloxy)-2,3-dihydro-1H-inden-1-yl]carbamate (100 mg, 0.348 mmol, 1.00 eq.) was treated with HCl in Dioxane (4 M, 2.61 mL, 30.0 eq.) at 20° C. After 2 h, all volatiles were removed under reduced pressure, the residue was transferred on a fritted funnel and washed with $Et_2O$. The remaining product was dried under reduced pressure. It afforded X-13 as a colorless solid, 71 mg (91%). $^{1}$H NMR (400 MHz, DMSO-$D_6$) δ 8.61 (s, 3H), 7.60 (d, 1H), 7.36-7.25 (m, 3H), 4.71 (s, 1H), 4.51 (q, 1H), 4.39-4.29 (m, 2H), 3.55 (t, 1H), 3.20-3.07 (m, 2H). $^{13}$C NMR (101 MHz, DMSO-$D_6$) δ 140.64, 137.06, 129.24, 126.87, 125.50, 125.15, 80.15, 78.34, 77.79, 57.08, 55.17, 35.80. LC-MS: m/z=188.05 (calcd. 188.11 [M+$H^+$]).

Synthesis of (1S,2R)-2-(2-Fluoroethoxy)-2,3-dihydro-1H-inden-1-ammonium chloride (X-14)

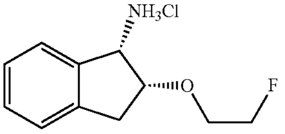

(1S,2R)-2-(2-Fluoroethoxy)-2,3-dihydro-1H-inden-1-ammonium chloride (X-14). Follow same procedure as X-13 using 2-fluoroethyl 4-methylbenzenesulfonate (315 mg, 1.44 mmol, 1.20 eq). It afforded the intermediate tert-butyl [(1S,2R)-2-(2-fluoroethoxy)-2,3-dihydro-1H-inden-1-yl] carbamate as a colorless solid, 250 mg (70%). $R_f$=0.41 (25% ethyl acetate in hexanes). $^1$H NMR (400 MHz, $CDCl_3$) δ 7.35-7.31 (m, 1H), 7.22 (d, 3H), 5.29-5.02 (m, 2H), 4.52 (dt, 2H), 4.33-4.28 (m, 1H), 3.78 (ddd, 2H), 3.04 (d, 2H), 1.50 (s, 9H). LC-MS: m/z=295.95 (calcd. 296.17 [M+H$^+$]). It afforded X-14 as a colorless solid, 123 mg (68%). $^1$H NMR (400 MHz, DMSO-$d_6$) δ 8.62 (s, 3H), 7.62 (d, 1H), 7.36-7.26 (m, 3H), 4.70 (t, 1H), 4.66-4.50 (m, 2H), 4.45-4.39 (m, 1H), 3.90-3.78 (m, 2H), 3.15-3.03 (m, 2H). $^{13}$C NMR (101 MHz, DMSO-$d_6$) δ 140.81, 137.17, 129.18, 126.82, 125.56, 125.17, 83.85, 82.20, 79.19, 69.19, 69.01, 55.12, 35.98. LC-MS: m/z=195.90 (calcd. 196.11 [M+H$^+$]).

Synthesis of tert-butyl ((S)-1-(((4S,7S,9aS)-7-(1H-indole-1-carbonyl)-8,8-dimethyl-5-oxooctahydropyrrolo[2,1-b][1,3]oxazepin-4-yl)amino)-1-oxopropan-2-yl)(methyl)carbamate (X-15)

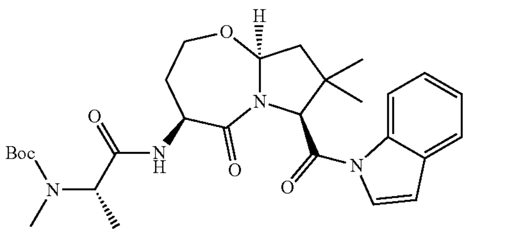 [SMILES: C[C@@H](C(=O)N[C@H]1CCO[C@H]2CC(C)(C)[C@@H](C(=O)n3ccc4ccccc43)N2C1=O)N(C)C(=O)OC(C)(C)C]

tert-butyl ((S)-1-(((4S,7S,9aS)-7-(1H-indole-1-carbonyl)-8,8-dimethyl-5-oxooctahydropyrrolo[2,1-b][1,3]oxazepin-4-yl)amino)-1-oxopropan-2-yl)(methyl)carbamate (X-15). Follow synthesis of X-1 using Boc-HSer-OH and X-3. The crude product was purified by flash column chromatography over silica gel to afford the pure diastereoisomer (second eluting isomer). $^1$H NMR (400 MHz, $CD_3OD$) δ 8.524 (d, J=8.24, 1H), 7.547 (d, J=8.24, 1H), 7.527 (d, J=3.66, 1H), 7.320 (td, J=8.46, 1.37, 1H), 7.259 (td, J=6.64, 1.37, 1H), 7.206 (broad singlet, 1H), 6.676 (d, J=3.66, 1H), 5.338 (t, J=6.41, 1H), 4.985 (s, 1H), 4.739 (q, J=7.33, 1H), 4.278 (dt, J=12.36, 3.21, 1H), 4.03-3.93 (m, 1H), 2.729 (s, 3H), 2.272 (dd, J=13.74, 6.41, 1H), 2.209 (dd, J=13.51, 6.87, 1H), 1.964 (d, J=5.50, 1H), 1.944 (d, J=5.50, 1H), 1.395 (s, 9H), 1.301 (d, J=7.33, 3H), 1.209 (s, 3H), 0.970 (s, 3H). $^{13}$C NMR (101 MHz, $CD_3OD$) δ 171.303, 171.179, 169.129, 135.786, 130.485, 125.356, 124.555, 124.164, 120.903, 117.042, 110.034, 89.162, 80.782, 70.827, 68.081, 53.236, 52.921, 50.624, 46.200, 40.488, 40.202, 32.460, 30.420, 29.314, 28.351, 23.526, 13.944. LC-MS m/z: 527.05 (calcd. 527.29 [M+H]+).

Synthesis of (4S,7S,9aS)-4-((S)-2-((tert-butoxycarbonyl)(methyl)amino)propanamido)-8,8-dimethyl-5-oxooctahydropyrrolo[2,1-b][1,3]oxazepine-7-carboxylic acid (X-16)

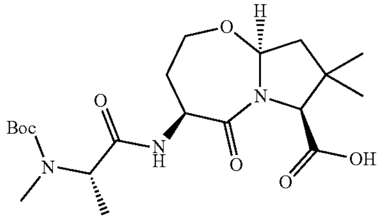

(4S,7S,9aS)-4-((S)-2-((tert-butoxycarbonyl)(methyl)amino)propanamido)-8,8-dimethyl-5-oxooctahydropyrrolo[2,1-b][1,3]oxazepine-7-carboxylic acid (X-16). To a solution of X-15 (250 mg, 0.475 mmol) in methanol (1M) was added 2M aqueous NaOH (to reach a 1M NaOH concentration). The mixture is stirred at 40° C. for 3-6 hours. The mixture was concentrated to dryness and purified by reverse phase silica gel. 89.1 mg (62% yield). LC-MS m/z: 428.00 (calcd. 428.24 [M+H]+). H NMR (400 MHz, $CDCl_3$) δ 7.31 (s, 1H), 5.23 (t, 1H), 4.73 (q, 1H), 4.22-4.13 (m, 2H), 3.99-3.88 (m, 1H), 2.80 (s, 3H), 2.19-2.12 (m, 1H), 2.02 (dd, 1H), 1.95 (dd, 2H), 1.46 (s, 9H), 1.35 (d, 3H), 1.19-1.12 (m, 6H).

Synthesis of tert-butyl ((S)-1-(((4S,7S,9aS)-7-formyl-8,8-dimethyl-5-oxooctahydropyrrolo[2,1-b][1,3]oxazepin-4-yl)amino)-1-oxopropan-2-yl)(methyl)carbamate (X-17)

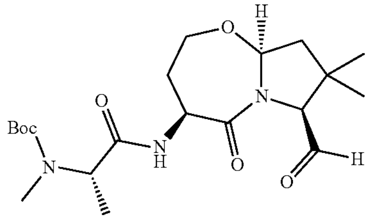

tert-butyl ((S)-1-(((4S,7S,9aS)-7-formyl-8,8-dimethyl-5-oxooctahydropyrrolo[2,1-b][1,3]oxazepin-4-yl)amino)-1-oxopropan-2-yl)(methyl)carbamate (X-17). To a solution of X-15 (1.0 eq, 500 mg) in tetrahydrofuran at −20° C. was added sodium borohydride (2 eq). The mixture was stirred at −20° C. for 30 min then at 23° C. for 18 hours. The mixture was quenched with water and sodium bicarbonate. It was extracted with ethyl acetate. The combined organic layers were washed with water, dried over sodium sulfate anhydrous, filtered and concentrated to afford the alcohol intermediate (176 mg, 46% yield, $^{13}$C NMR (101 MHz, $CD_3OD$) δ 172.13, 171.96, 88.71, 69.95, 68.01, 60.59, 52.50, 45.16, 37.88, 32.43, 29.72, 28.11, 27.30, 21.58). oxalyl chloride (2.0 eq) was solubilized in dry DCM then cooled down to −78° C. DMSO (4.0 eq) was added dropwise and the reaction was stirred for 10 min (at −78° C.). A solution of the alcohol (1.0 eq) in DCM was added dropwise and stirred for 15 min at −78° C. triethylamine (4.5 eq) was added at −78° C. and the mixture was stirred for 15 min at −78 C. The mixture was warmed up to 0° C. and stirred for a further 10 min. after completion (monitored by LCMS), ethyl acetate was added to the mixture. The organic phase was washed with Brine, dried over sodium sulfate, filtered and concentrated. 555B: 125.2 mg (31%). LC-MS m/z: 412.00 (calcd. 412.24 [M+H]+).

Synthesis of (4S,7S,9aS)-4-({(2S)-2-[(tert-Butoxycarbonyl)(methyl)amino]propanoyl}amino)-8,8-dimethyl-5-oxooctahydropyrrolo[2,1-b][1,3]thiazepine-7-carboxylic acid (X-18)

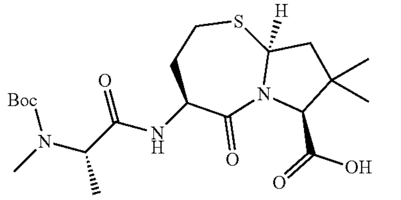

(4S,7S,9aS)-4-({(2S)-2-[(tert-Butoxycarbonyl)(methyl) amino]propanoyl}amino)-8,8-dimethyl-5-oxooctahydropyrrolo[2,1-b][1,3]thiazepine-7-carboxylic acid (X-18). Followed the same procedure as X-16 using N-(tert-butoxycarbonyl)-S-trityl-L-homocysteine instead of the homoserine. Before deprotection of the indole-convertible isocyanide, it afforded 2 isomers: the first undesired isomer as a yellow solid, 214 mg (14%). $R_f$=0.47 (50% ethyl acetate in hexanes). The second desired isomer as a yellow solid, 254 mg (17%). $R_f$=0.20 (50% ethyl acetate in hexanes). $^1$H NMR (400 MHz, $CDCl_3$) δ 8.57 (d, 1H), 7.59-7.55 (m, 2H), 7.37-7.27 (m, 3H), 6.70 (d, 1H), 5.26 (t, 1H), 5.09 (s, 1H), 4.71 (s), 4.61 (dd, 1H), 3.30 (ddd, 1H), 2.90 (ddd, 1H), 2.75 (s, 3H), 2.33-2.25 (m, 3H), 1.96 (q, 1H), 1.43 (s, 9H), 1.33 (d, 3H), 1.26-1.24 (m, 5H), 1.02 (s, 3H). LC-MS: m/z=565.26 (calcd. 565.25 [M+Na$^+$]). It was dissolved in methanol (3.0 mL) and aq. NaOH solution (1 M, 1.20 mL, 1.20 mmol, 5.00 eq.) was added. After the resulting mixture was stirred for 5 h at 32° C., the methanol was removed in vacuo. NaOH solution (1 M, 30 mL) and brine (10 mL) were added and washed with ethyl acetate (3*10 mL). The aqueous layer was acidified with HCl solution (3 M) to pH 2 and extracted with $CH_2Cl_2$ (3*20 mL). The combined $CH_2Cl_2$ layers were dried over sodium sulfate anhydrous and concentrated in vacuo. The residue was purified by fc (cyclohexane/ethyl acetate with 1% HCOOH). It afforded X-18 as a colorless solid, 56 mg (53%). $R_f$=0.52 (hexanes/ethyl acetate/formic acid 3:7:0.2, Ceric Ammonium Molybdate stain). $^1$H NMR (400 MHz, $CDCl_3$) δ 7.38 (s, 1H), 5.19 (t, 1H), 4.60 (q, 1H), 4.23 (d, 1H), 3.25 (ddd, 1H), 2.91-2.77 (m, 4H), 2.35-2.21 (m, 2H), 2.02 (dd, 1H), 1.93 (q, 1H), 1.46 (d, 9H), 1.35 (d, 3H), 1.21 (d, 3H), 1.17 (d, 3H). LC-MS m/z: 444.10 (calcd. 444.22 [M+H$^+$]).

Synthesis of (4'S,7'S,9a'S)-4'-((S)-2-((tert-butoxycarbonyl)(methyl)amino)propanamido)-5'-oxo-2',3',4',5',9',9a'-hexahydro-7'H-spiro[cyclopentane-1,8'-pyrrolo[2,1-b][1,3]thiazepin]-3-ene-7'-carboxylic acid (X-19)

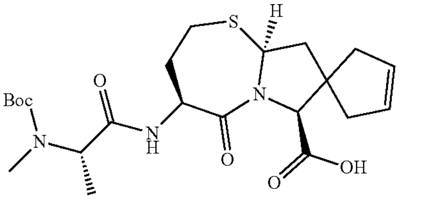 [SMILES: C[C@@H](C(=O)N[C@H]1CCS[C@H]2CC3(CC=CC3)[C@@H](C(=O)O)N2C1=O)N(C)C(=O)OC(C)(C)C]

(4'S,7'S,9a'S)-4'-((S)-2-((tert-butoxycarbonyl)(methyl) amino)propanamido)-5'-oxo-2',3',4',5',9',9a'-hexahydro-7'H-spiro[cyclopentane-1,8'-pyrrolo[2,1-b][1,3]thiazepin]-3-ene-7'-carboxylic acid. Follow synthesis of X-18 using X-5f. before the removal of the convertible isocyanide, it afforded two isomers. The first non-desired isomer as a brown solid, yield 37 mg (10%). $R_f$=0.33 (40% ethyl acetate in hexanes). The second desired isomer tert-butyl N-[(1S)-1-{[(4'S,7'S,9'aS)-7'-(1H-indole-1-carbonyl)-5'-oxo-3',4',5',7',9',9'a-hexahydro-2'H-spiro[cyclopentane-1,8'-pyrrolo[2,1-b][1,3]thiazepin]-3-en-4'-yl]carbamoyl}ethyl]-N-methylcarbamate as a brown solid, yield 86 mg (22%). $R_f$=0.21 (40% ethyl acetate in hexanes). $^1$H NMR (400 MHz, $CDCl_3$) δ 8.56 (d, 1H), 7.61 (d, 1H), 7.57 (d, 1H), 7.38-7.27 (m, 3H), 6.66 (t, 1H), 5.75-5.69 (m, 1H), 5.65-5.60 (m, 1H), 5.26-5.20 (m, 2H), 4.78-4.53 (m, 2H), 3.30 (dd, 1H), 2.93-2.85 (m, 1H), 2.76 (s, 3H), 2.63-2.50 (m, 2H), 2.42 (s, 2H), 2.33-2.18 (m, 3H), 1.95 (q, 1H), 1.44 (s, 9H), 1.34 (d, 3H). LC-MS: m/z=567.25 (calcd. 567.26 [M+H$^+$]).

The desired isomer (86 mg, 0.152 mmol, 1.00 eq.) was dissolved in methanol (1.84 mL) and aq. NaOH (1 M, 456 μL, 0.456 mmol, 3.00 eq.) was added. After the resulting mixture was stirred for 2 days at 40° C., the methanol was removed in vacuo. $Et_2O$ (10 mL) was added and washed with NaOH solution (1 M, 3×10 mL). After the combined NaOH layers were extracted with $Et_2O$ (2×10 mL), the aqueous layer was acidified with conc. HCl to pH Land extracted with $CH_2Cl_2$ (3×10 mL) and EtOAc (2×10 mL). The combined org. layers were dried ($Na_2SO_4$) and concentrated in vacuo. The residue was purified by fc (hexanes/ethyl acetate with 0.2% formic acid). It afforded (4'S,7'S,9'aS)-4'-(2-{[(tert-butoxy)carbonyl](methyl) amino}acetamido)-5'-oxo-3',4',5',7',9',9'a-hexahydro-2'H-spiro[cyclopentane-1,8'-pyrrolo[2,1-b][1,3]thiazepin]-3-ene-7'-carboxylic acid as a colorless solid, yield 48 mg (68%). $R_f$=0.46 (hexanes/ethyl acetate/formic acid 5:5:0.1, CAM stain). $^1$H NMR (400 MHz, $CDCl_3$) δ 7.40 (d, 1H), 5.74-5.68 (m, 1H), 5.66-5.60 (m, 1H), 5.19 (t, 1H), 4.63 (t, 2H), 4.46 (s, 1H), 3.25 (t, 1H), 2.85-2.76 (m, 4H), 2.73 (d, 1H), 2.50-2.42 (m, 1H), 2.36-2.22 (m, 4H), 2.20-2.11 (m, 1H), 1.93 (q, 1H), 1.45 (s, 9H), 1.34 (d, 3H). LC-MS m/z: 468.30 (calcd. 468.59 [M+H$^+$]).

Synthesis of (4S,9aS)-8,8-dimethyl-4-((S)-2-(methylamino)propanamido)-5-oxo-N—((R)-1,2,3,4-tetrahydronaphthalen-1-yl)octahydropyrrolo[2,1-b][1,3]thiazepine-7-carboxamide hydrochloride (Compound A)

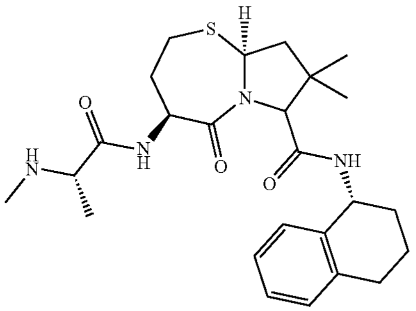 [SMILES: CN[C@@H](C)C(=O)N[C@H]1CCS[C@H]2CC(C)(C)C(C(=O)N[C@@H]3CCCc4ccccc43)N2C1=O]

In a sealed round bottom flask, X-1 (1.64 g, 1.0 eq) was added to a mixture of N-(tert-butoxycarbonyl)-S-trityl-L-homocysteine (5.0 g, 10.5 mmol, 1.0 eq), X-5a (1.8 g, 1.05 eq) and 7N ammonia (in methanol, 3.14 mL, 2.1 eq) in methanol (20 mL, 0.5M) at 0° C. The mixture was stirred at 40° C. for 17-41 hours. The mixture was concentrated and solubilized in a 2M HCl in dioxane solution (50 mL, 10 eq). The mixture was stirred for 2-4 hours at 40° C. The mixture was concentrated and quenched with saturated aqueous solution of sodium carbonate (300 mL). It was extracted with ethyl acetate (3*200 mL). The combined organic layers were washed with a solution of sodium bicarbonate (2*200 mL), dried over sodium sulfate anhydrous, filtered and concentrated to afford a crude oil. It was solubilized in tetrahydrofuran (0.5M) and cooled down to 0° C. To the solution was added Boc-N-Me-Alanine (1.0 eq), NMM (3.5 eq), HOBT (1.1 eq) then EDC.HCl (1.05 eq). The mixture was stirred at 0° C. for 30 min. the cold bath was removed and it was stirred at 23° C. for 18 hours. The mixture was quenched with saturated aqueous sodium bicarbonate (100 mL) and extracted with ethyl acetate (3*100 mL). The organic layers were combined, washed with brine, dried over sodium sulfate anhydrous, filtered and concentrated. The intermediate (1.0 eq, 1.3 mmol, 750 mg) was solubilized in methanol (3.0 mL) and 4M HCl in 1,4-Dioxane (3.0 mL) was added. The Mixture was stirred at 40° C. for 4 hours. The mixture was concentrated and purified by reverse phase HPLC (10-70% acetonitrile in water), then lyophilized from a water-dioxane mixture to afford the product as a powder. 559 mg, 8%, pink powder. $^1$H NMR (400 MHz, $CD_3OD$) δ 8.76 (d), 8.20 (d, 1H), 7.30 (d, 1H), 7.18-7.05 (m, 3H), 5.42 (t, 1H), 5.09 (q, 1H), 4.74 (d, 1H), 4.15 (s, 1H), 3.92 (q, 1H), 3.29-3.19 (m, 1H), 2.95-2.87 (m, 1H), 2.84-2.74 (m, 2H), 2.68 (s, 3H), 2.34-2.21 (m, 2H), 2.08-1.74 (m, 6H), 1.55 (d, 3H), 1.16 (s, 3H), 1.14 (s, 3H). $^{13}C$ NMR (101 MHz, $CD_3OD$) δ 172.32, 171.43, 169.24, 138.57, 137.39, 130.09, 129.79, 128.31, 127.11, 73.34, 61.87, 58.36, 54.47, 48.93, 47.33, 40.89, 33.65, 32.06, 31.81, 31.30, 30.10, 28.67, 23.90, 21.32, 16.26.

Example 1: Synthesis of (4S,7S,9aS)-8,8-dimethyl-4-((S)-2-(methylamino)propanamido)-5-oxo-N—((R)-1,2,3,4-tetrahydronaphthalen-1-yl)octahydropyrrolo[2,1-b][1,3]thiazepine-7-carboxamide 1,1-dioxide hydrochloride

1

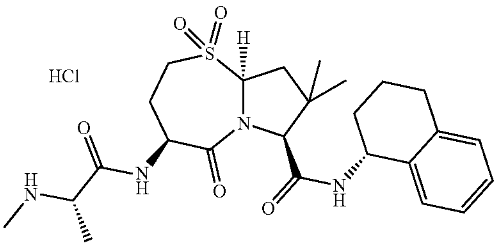

Followed the synthesis of compound A until after the Boc-Alanine coupling to get tert-butyl ((2S)-1-(((4S)-8,8-dimethyl-5-oxo-7-(((R)-1,2,3,4-tetrahydronaphthalen-1-yl) carbamoyl)octahydropyrrolo[2,1-b][1,3]thiazepin-4-yl) amino)-1-oxopropan-2-yl)(methyl)carbamate. This intermediate (1.0 eq, 0.4 mmol, 247 mg) in DCM (5 mL) at 0° C., was treated with MCPBA (2.0 eq). The mixture was stirred at 0° C. for 2 hours then concentrated and purified by flash column chromatography (50-100% ethyl acetate in hexanes). It was treated with aqueous HCl 3.0M (200 μL, 5 eq) at 40° C. for 3 hours then concentrated to afford 123 mg of 1.

Example 2 and 3: Synthesis of (3R, 6S,12bR)-2,2-dimethyl-6-((S)-2-(methylamino)propanamido)-5-oxo-N—((R)-1,2,3,4-tetrahydronaphthalen-1-yl)-1,2,3,5,6,7,12,12b-octahydropyrrolo[1',2':1,2]azepino[3,4-b]indole-3-carboxamide hydrochloride and (3S, 6S,12bR)-2,2-dimethyl-6-((S)-2-(methylamino)propanamido)-5-oxo-N—((R)-1,2,3,4-tetrahydronaphthalen-1-yl)-1,2,3,5,6,7,12,12b-octahydropyrrolo[1',2':1,2]azepino[3,4-b]indole-3-carboxamide hydrochloride

2

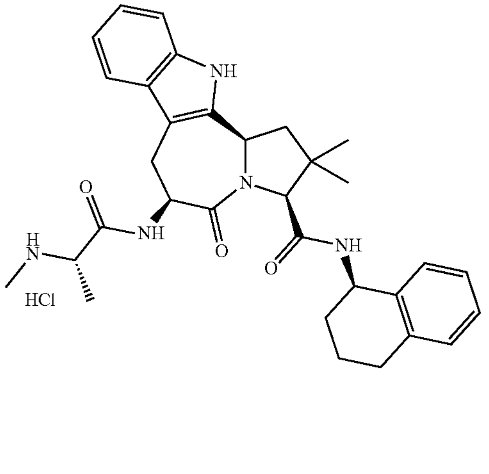

-continued

3

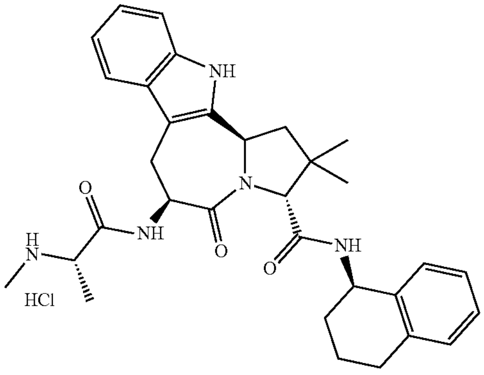

Followed the synthesis of Compound A using Boc-Trp-OH. Two isomers were separated: compound 2 (51.3 mg, 8% yield), compound 3 (34.1 mg, 10% yield). LCMS m/z: 542.20 (calcd. 542.30 [M+H]+).

Compound 2: $^1H$ NMR (400 MHz, $CD_3OD$) δ 7.38-7.33 (m, 2H), 7.31-6.87 (m, 13H), 5.76-5.65 (m, 1H), 5.27 (dd, 1H), 5.10 (p, 2H), 4.20 (s, 1H), 4.08 (q, 1H), 3.92-3.50 (m, 3H), 3.35 (s), 3.29 (dt, 1H), 2.96 (ddd, 1H), 2.73 (s, 3H), 2.01-1.72 (m, 9H), 1.57 (dd, 4H), 1.26 (d, 12H), 1.19 (d, 4H), 0.91 (s, 3H). $^{13}C$ NMR (101 MHz, $CD_3OD$) δ 196.03, 171.73, 169.39, 138.86, 138.78, 137.42, 136.46, 134.67, 130.24, 130.12, 129.98, 129.63, 128.38, 128.18, 127.07, 127.02, 122.79, 120.26, 118.49, 112.18, 107.91, 72.63, 68.31, 58.39, 55.90, 52.64, 45.57, 42.27, 41.49, 40.36, 31.90, 31.20, 30.71, 30.46, 30.27, 30.21, 30.02, 29.77, 29.45, 29.22, 29.11, 24.75, 24.46, 24.21, 21.13, 20.72, 16.45.

Compound 3: $^1H$ NMR (400 MHz, $CD_3OD$) δ 7.40-7.33 (m, 2H), 7.26 (dt, 1H), 7.23-6.99 (m, 8H), 6.86 (dd, 1H), 5.50 (dd, 1H), 5.16 (ddd, 1H), 4.27 (d, 1H), 4.08-3.97 (m, 1H), 3.70-3.58 (m, 1H), 3.30-3.22 (m, 1H), 3.05 (t, 1H), 2.71 (d, 4H), 2.60-2.37 (m, 5H), 1.65-1.59 (m, 5H), 1.28-1.26 (m, 4H), 1.20 (d, 3H). $^{13}C$ NMR (101 MHz, $CD_3OD$) δ 172.10, 171.35, 169.69, 138.14, 137.08, 136.79, 133.90, 129.96, 129.57, 128.93, 128.15, 126.98, 122.80, 120.20, 118.48, 112.28, 108.19, 101.15, 72.22, 58.38, 54.98, 52.44, 44.66, 40.87, 31.87, 30.93, 30.45, 30.26, 29.71, 28.37, 28.23, 24.22, 24.11, 20.80, 16.36.

Example 4: Synthesis of (4S)-4-((S)-2-(methylamino)propanamido)-5-oxo-N—((R)-1,2,3,4-tetrahydronaphthalen-1-yl)-2,3,4,5,7,11b-hexahydropyrido[4',3':3,4]pyrrolo[2,1-b][1,3]oxazepine-7-carboxamide dihydrochloride

4

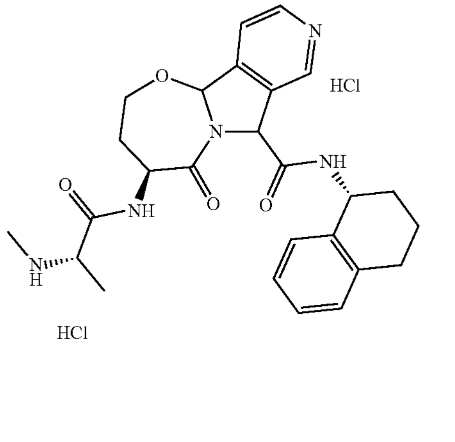

Followed the synthesis of compound A using Boc-HSer-OH and X-5 g. 27 mg (5% yield). LC-MS m/z: 239.10 (calcd. 239.63[M+H]$^{2+}$). $^{1}$H NMR (400 MHz, $CD_3OD$) δ 8.76-8.63 (m, 2H), 7.65 (d, 1H), 7.37 (dd, 1H), 7.24-7.07 (m, 4H), 6.86-6.59 (m, 1H), 5.82-5.58 (m, 1H), 5.14-5.02 (m, 1H), 4.61-4.25 (m, 1H), 3.76-3.57 (m, 1H), 2.82 (dd, 3H), 2.62 (dd, 3H), 2.07-1.90 (m, 4H), 1.82 (ddd, 2H), 1.63-1.47 (m, 4H). $^{13}$C NMR (101 MHz, $CD_3OD$) δ 173.27, 172.57, 169.96, 169.73, 150.79, 150.74, 150.70, 150.64, 150.43, 144.99, 144.82, 138.65, 137.28, 137.14, 133.19, 133.10, 130.35, 130.10, 130.05, 129.68, 129.66, 128.38, 128.31, 127.17, 127.15, 121.00, 120.90, 85.51, 85.46, 65.25, 64.76, 57.73, 57.00, 32.73, 32.48, 31.39, 31.31, 30.19, 30.16, 21.64, 21.52, 17.60, 16.46.

Example 5: Synthesis of (6S,11bR)—N-benzhydryl-9-methoxy-2,2-dimethyl-6-((S)-2-(methylamino) propanamido)-5-oxo-2,3,5,6,7,11b-hexahydro-1H-benzo[c]pyrrolo[1,2-a]azepine-3-carboxamide

5

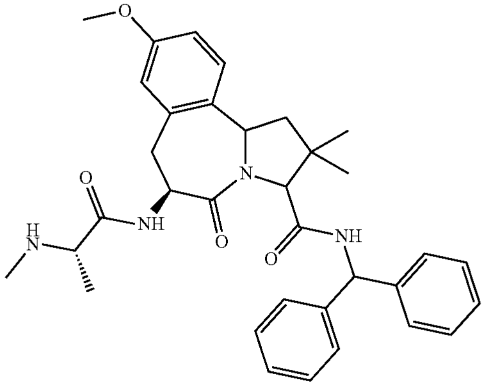

Follow synthesis of compound A using X-7 and X-2. 14 mg (10% yield), LC-MS m/z: 569.60 (calcd. 569.30[M+H]$^{+}$). $^{1}$H NMR (400 MHz, $CD_3OD$) δ 8.97 (d), 7.40-7.18 (m, 12H), 6.80 (dd, 1H), 6.74 (d, 1H), 6.27-6.21 (m, 1H), 5.44 (dd, 1H), 5.11 (dd, 1H), 4.27 (s, 1H), 3.77 (s, 3H), 3.74 (d, 1H), 3.39 (dd, 1H), 3.09 (dd, 1H), 2.65 (s, 3H), 2.55 (dd, 1H), 2.41 (dd, 1H), 2.00 (dq), 1.49 (d, 3H), 1.02 (s, 3H), 0.99 (s, 3H). $^{13}$C NMR (101 MHz, $CD_3OD$) δ 172.11, 172.00, 170.24, 160.28, 143.12, 142.78, 138.66, 131.01, 129.61, 129.32, 129.31, 129.26, 128.68, 128.56, 128.51, 128.11, 118.19, 117.44, 112.56, 72.66, 59.61, 58.63, 58.22, 55.70, 52.75, 43.17, 40.59, 37.48, 32.14, 29.18, 24.34, 16.71.

Example 6 and 33: (6S,11bR)—N-benzhydryl-10-methoxy-2,2-dimethyl-6-((S)-2-(methylamino)propanamido)-5-oxo-2,3,5,6,7,11b-hexahydro-1H-benzo[c]pyrrolo[1,2-a]azepine-3-carboxamide hydrochloride

6

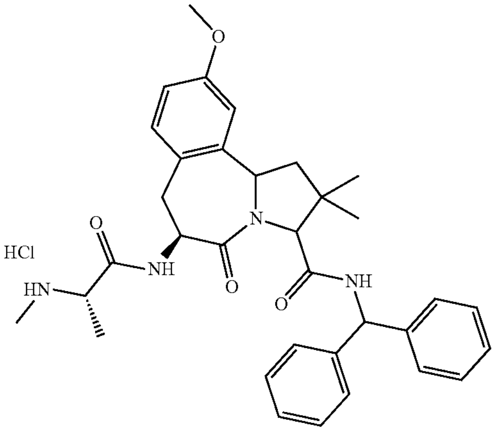

(6S,11bR)—N-benzhydryl-10-methoxy-2,2-dimethyl-6-((S)-2-(methylamino)propanamido)-5-oxo-2,3,5,6,7,11b-hexahydro-1H-benzo[c]pyrrolo[1,2-a]azepine-3-carboxamide hydrochloride (6). Followed the synthesis of compound A using X-6 and X-2. Two isomers isolated: compound 6 (20 mg), compound 33 (10 mg). LC-MS m/z: 569.25 (calcd. 569.3[M+H]+).

Compound 6: $^{1}$H NMR (400 MHz, $CD_3OD$) δ 8.44 (s, 2H), 8.06 (p), 7.38-7.07 (m, 17H), 6.88 (d, 1H), 6.80 (dt, 2H), 5.96 (ddt, 1H), 5.47-5.46 (m, 1H), 5.12 (dd), 5.07 (dd, 1H), 4.71 (d), 4.67 (d, 1H), 3.72-3.70 (m, 3H), 3.70-3.69 (m, 1H), 3.12-3.04 (m, 1H), 2.83 (ddd, 1H), 2.56-2.51 (m), 2.35 (d, 1H), 2.28 (d, 1H), 1.41 (ddd, 3H), 1.31-1.12 (m, 2H), 1.02 (d, 1H), 0.91 (d, 1H), 0.87 (d, 1H), 0.79 (d, 1H). $^{13}$C NMR (101 MHz, $CD_3OD$) δ 174.36, 173.83, 170.41, 169.81, 169.57, 160.18, 160.09, 140.56, 140.54, 139.83, 139.82, 131.52, 131.44, 130.37, 130.02, 129.81, 129.70, 129.59, 129.57, 129.54, 128.99, 128.97, 125.49, 125.45, 118.83, 118.76, 114.93, 114.84, 61.76, 61.72, 59.62, 59.58, 58.58, 58.52, 56.16, 55.95, 55.69, 55.66, 36.65, 36.51, 31.95, 31.92, 26.63, 26.60, 20.55, 20.44, 16.77, 16.74.

Compound 33: $^{1}$H NMR (400 MHz, $CD_3OD$) δ 8.50 (s, 1H), 7.40-7.09 (m, 14H), 6.92-6.67 (m, 2H), 6.26-6.07 (m, 1H), 5.60 (t), 5.50-5.48 (m), 5.37 (d), 5.20-5.02 (m, 1H), 4.37 (s), 4.32 (s), 4.28 (s), 4.20 (s), 3.79-3.68 (m, 4H), 3.45-3.40 (m, 1H), 3.22 (t), 3.19-2.94 (m, 1H), 2.90-2.68 (m, 1H), 2.48 (d), 2.38-2.25 (m, 2H), 2.24-2.11 (m), 2.09-1.88 (m, 1H), 1.42 (dd, 2H), 1.34-1.24 (m, 3H), 1.14-0.81 (m, 5H). $^{13}$C NMR (101 MHz, $CD_3OD$) δ 174.18, 173.97, 173.28, 172.88, 172.02, 171.99, 171.22, 160.45, 160.11, 160.08, 160.05, 143.11, 143.08, 143.00, 142.84, 142.82, 142.81, 142.77, 142.72, 131.77, 131.58, 131.47, 131.43, 131.30, 130.49, 130.27, 129.97, 129.66, 129.62, 129.61, 129.57, 129.50, 129.46, 129.44, 129.31, 129.30, 129.28, 129.08, 128.73, 128.63, 128.61, 128.56, 128.53, 128.51, 128.45, 128.35, 128.08, 128.01, 115.29, 114.93, 114.86, 114.79, 91.50, 90.57, 90.37, 71.81, 71.71, 71.52, 71.36, 58.65, 58.50, 58.37, 58.30, 58.23, 58.18, 55.74, 55.66, 55.62, 55.46, 54.92, 54.56, 54.30, 53.65, 53.49, 53.33, 45.32, 45.20, 43.47, 42.82, 41.45, 41.39, 41.06, 40.54, 40.41, 39.61, 38.62, 38.28, 38.06, 31.97, 31.91, 29.89, 29.74, 29.66, 24.97, 24.86, 24.57, 16.93, 16.82, 16.71.

Example 8 and 9: Synthesis of (6S,11bR)-9-methoxy-2,2-dimethyl-6-((S)-2-(methylamino)propanamido)-5-oxo-N—((R)-1,2,3,4-tetrahydronaphthalen-1-yl)-2,3,5,6,7,11b-hexahydro-1H-benzo[c]pyrrolo[1,2-a]azepine-3-carboxamide hydrochloride

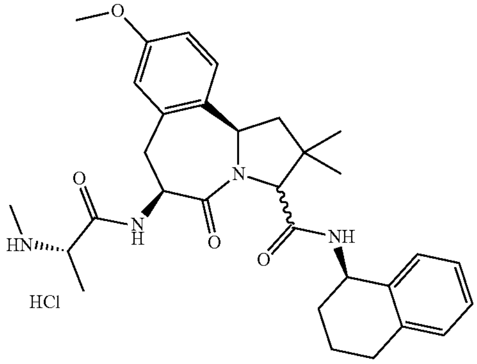 [SMILES: CN[C@@H](C)C(=O)N[C@H]1Cc2cc(OC)ccc2[C@H]2CC(C)(C)C(C(=O)N[C@@H]3CCCc4ccccc43)N2C1=O ; Cl]

Followed the synthesis of compound A using X-7. Two isomers were isolated: Compound 8 (17 mg, yellow solid, 25% yield), Compound 9 (47.2 mg, yellow solid, 50% yield). LC-MS m/z: 533.20 (calcd. 533.3[M+H]+).

Compound 8: $^1$H NMR (400 MHz, $CD_3OD$) δ 8.56 (d), 8.45 (d), 7.33 (d, 1H), 7.29-7.19 (m, 1H), 7.19-7.03 (m, 3H), 6.81 (d, 1H), 6.75 (s, 1H), 5.45 (t, 1H), 5.16-5.03 (m, 2H), 4.12 (s, 1H), 3.87-3.80 (m, 1H), 3.78 (d, 3H), 3.44 (dd, 1H), 3.04 (dd, 1H), 2.90-2.73 (m, 2H), 2.70 (s, 3H), 2.58 (dd, 1H), 2.42 (dd, 1H), 2.05-1.85 (m, 3H), 1.86-1.72 (m, 1H), 1.51 (d, 3H), 1.21 (s, 3H), 1.08 (s, 3H). $^{13}$C NMR (101 MHz, $CD_3OD$) δ 171.97, 171.61, 169.42, 160.44, 138.90, 138.88, 137.55, 130.98, 130.17, 129.99, 128.46, 128.20, 127.06, 117.44, 112.55, 73.20, 59.56, 58.48, 55.76, 53.24, 43.70, 40.22, 37.12, 31.93, 31.14, 30.27, 29.12, 24.59, 21.08, 16.37.

Compound 9: $^1$H NMR (400 MHz, $CD_3OD$) δ 8.19 (d), 7.34-7.00 (m, 7H), 6.99-6.90 (m, 1H), 6.80-6.75 (m, 1H), 6.74 (s, 1H), 6.29-6.24 (m, 1H), 5.35 (dd, 1H), 5.11-5.05 (m, 1H), 4.98-4.93 (m, 1H), 4.32 (s, 1H), 4.04 (dd, 1H), 3.89-3.81 (m, 2H), 3.80-3.75 (m, 5H), 3.44 (d, 1H), 3.40-3.33 (m, 1H), 3.17-3.10 (m, 2H), 2.90 (s, 2H), 2.76-2.68 (m, 5H), 2.57 (t, 1H), 2.31 (dd, 1H), 2.01-1.87 (m, 2H), 1.76 (td, 3H), 1.59-1.54 (m, 3H), 1.26 (d, 3H), 1.22-1.18 (m, 3H). $^{13}$C NMR (101 MHz, $CD_3OD$) δ 172.23, 172.14, 171.75, 169.60, 160.31, 159.62, 138.42, 138.40, 137.39, 137.36, 131.10, 130.86, 130.75, 130.52, 129.96, 129.61, 128.75, 128.15, 127.08, 116.93, 113.10, 107.67, 107.65, 103.50, 72.62, 72.58, 65.10, 58.54, 58.46, 55.74, 54.57, 52.34, 45.38, 43.91, 39.97, 36.61, 31.87, 31.22, 30.06, 28.24, 24.30, 21.38, 16.25.

Example 10 and 11: Synthesis of (6S,11bR)-10-methoxy-2,2-dimethyl-6-((S)-2-(methylamino)propanamido)-5-oxo-N—((R)-1,2,3,4-tetrahydronaphthalen-1-yl)-2,3,5,6,7,11b-hexahydro-1H-benzo[c]pyrrolo[1,2-a]azepine-3-carboxamide hydrochloride

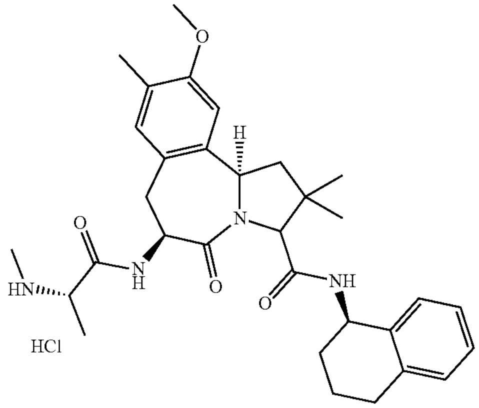

10, 11

Followed the synthesis of compound A using X-6. Two isomers were isolated: Compound 11 (5.8 mg, 5% yield), Compound 10 (9.9 mg, 10% yield). LC-MS m/z: 533.65 (calcd. 533.3[M+H]+).

Compound 11: $^1$H NMR (400 MHz, $CD_3OD$) δ 7.29-7.23 (m, 2H), 7.21-7.12 (m, 3H), 7.03-6.96 (m, 1H), 6.88-6.81 (m, 2H), 5.75-5.65 (m, 2H), 5.15 (dd, J=7.9, 1.2 Hz, 1H), 4.75 (d, J=1.2 Hz, 1H), 3.77-3.72 (m, 3H), 3.58-3.46 (m, 1H), 3.39-3.33 (m, 1H), 2.92-2.73 (m, 3H), 2.27 (s, 3H), 2.11-1.91 (m, 2H), 1.89-1.75 (m, 2H), 1.38 (d, J=6.7 Hz, 3H), 1.07 (s, 3H), 1.01 (s, 3H). $^{13}$C NMR (101 MHz, $CD_3OD$) δ 174.47, 169.94, 160.11, 140.16, 134.98, 131.45, 130.53, 130.41, 128.60, 128.54, 127.52, 124.86, 119.67, 114.85, 59.47, 58.88, 56.08, 55.67, 53.75, 38.31, 36.76, 30.24, 30.12, 26.52, 22.42, 20.73, 17.27.

Compound 10: $^1$H NMR (400 MHz, $CD_3OD$) δ 7.30-7.20 (m, 3H), 7.20-7.05 (m, 5H), 7.01-6.94 (m, 1H), 6.89-6.80 (m, 3H), 5.77 (dd, J=8.0, 1.1 Hz, 1H), 5.75-5.67 (m, 1H), 5.04 (dd, J=8.0, 1.1 Hz, 1H), 5.01-4.95 (m, 1H), 4.63 (d, J=1.1 Hz, 1H), 3.81-3.72 (m, 6H), 3.15 (dd, J=13.7, 6.5 Hz, 1H), 2.94-2.72 (m, 5H), 2.42 (s, 3H), 2.09-1.93 (m, 3H), 1.93-1.72 (m, 3H), 1.50 (d, J=6.6 Hz, 3H), 0.95 (s, 3H), 0.92 (s, 3H). $^{13}$C NMR (101 MHz, $CD_3OD$) δ 173.71, 169.60, 169.49, 160.19, 139.85, 135.48, 131.57, 130.48, 130.05, 128.58, 128.32, 127.51, 127.23, 125.17, 118.50, 114.95, 59.83, 58.49, 56.01, 55.70, 53.78, 39.01, 36.34, 31.84, 30.28, 29.54, 26.86, 22.74, 20.77, 16.60.

Example 12, 14, 13, and 15: Synthesis of (4S,9aS)-8,8-diallyl-4-((S)-2-(methylamino)propanamido)-5-oxo-N—((R)-1,2,3,4-tetrahydronaphthalen-1-yl) octahydropyrrolo[2,1-b][1,3]oxazepine-7-carboxamide hydrochloride (12, 14)

(4S,9aS)-8,8-allyl-4-((S)-2-(methylamino)propanamido)-5-oxo-N—((R)-1,2,3,4-tetrahydronaphthalen-1-yl)octahydropyrrolo[2,1-b][1,3]oxazepine-7-carboxamide hydrochloride (13, 15)

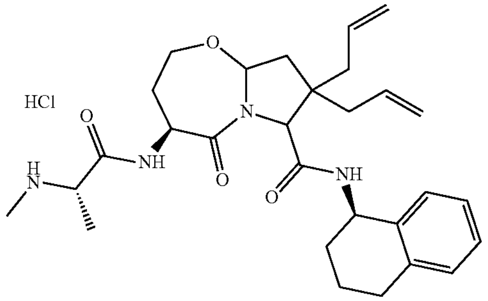

12, 14

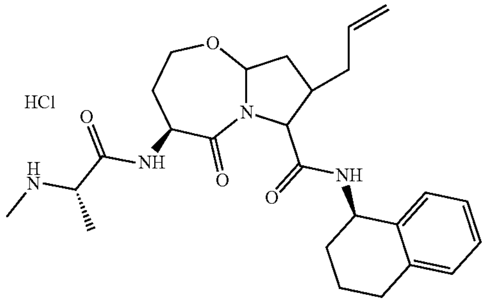

13, 15

Followed the synthesis of A using Boc-HSer-OH and X-5b. The monoalkylated compound 13 and compound 15 were side-products coming from unpurified X-5b. Four isomers separated or enriched: Compound 12 (11 mg), Compound 13 (4.0 mg, mono-allyl), Compound 14 (11.2 mg), Compound 15 (19.6 mg of mono-allyl). LC-MS m/z: 509.20 (calcd. 509.3[M+H]+), mono-alkylated: 469.15 (calcd. 469.3[M+H]+).

Compound 12: $^{1}H$ NMR (400 MHz, $CD_3OD$) δ 8.49 (d), 8.08 (d), 7.45 (s), 7.29 (d), 7.19-6.95 (m, 4H), 5.96-5.72 (m, 2H), 5.41 (d, 1H), 5.16-4.98 (m, 5H), 4.36 (d, 1H), 4.22-4.05 (m, 1H), 3.95 (d, 2H), 2.78 (q, 2H), 2.67 (s, 3H), 2.54 (dd,), 2.45-2.21 (m, 3H), 2.18-2.06 (m, 2H), 2.05-1.67 (m, 9H), 1.56 (d, 3H). $^{13}C$ NMR (101 MHz, $CD_3OD$) δ 172.65, 171.89, 171.76, 169.15, 138.79, 138.42, 137.43, 137.32, 135.18, 135.08, 135.00, 134.66, 130.11, 130.07, 129.99, 129.86, 129.70, 129.31, 128.33, 128.13, 127.10, 126.98, 119.59, 119.28, 118.84, 118.61, 90.84, 90.24, 71.61, 71.39, 70.34, 69.09, 58.45, 54.67, 54.07, 46.53, 46.33, 44.08, 43.86, 42.85, 42.29, 41.98, 40.11, 39.63, 34.56, 33.18, 32.22, 32.16, 31.15, 31.08, 30.22, 30.06, 21.29, 21.18, 16.49, 16.46.

Compound 14: $^{1}H$ NMR (400 MHz, $CD_3OD$) δ 8.08 (d, J=8.3 Hz, 1H), 7.29 (d, J=7.1 Hz, 1H), 7.13 (dq, J=14.0, 7.5 Hz, 3H), 5.94-5.76 (m, 2H), 5.42 (t, J=6.6 Hz, 1H), 5.16-5.04 (m, 5H), 4.32 (d, J=1.8 Hz, 1H), 4.10 (d, J=12.2 Hz, 1H), 4.01-3.87 (m, 2H), 2.88-2.72 (m, 2H), 2.68 (s, 3H), 2.40-2.25 (m, 2H), 2.17-2.05 (m, 4H), 2.01-1.93 (m, 4H), 1.91-1.74 (m, 5H), 1.58 (d, J=5.8 Hz, 3H). $^{13}C$ NMR (101 MHz, $CD_3OD$) δ 171.90, 171.50, 169.55, 138.45, 137.45, 135.02, 134.67, 130.12, 129.72, 128.34, 127.11, 119.58, 118.85, 90.21, 71.32, 69.10, 69.07, 58.42, 54.03, 49.64, 49.43, 49.21, 49.00, 48.79, 48.57, 48.36, 46.55, 43.86, 42.84, 40.13, 33.12, 31.96, 31.15, 30.05, 21.28, 16.38.

Compound 15: mixture of 3 isomers. $^{1}H$ NMR (400 MHz, $CD_3OD$) δ 8.38 (d), 8.25 (d), 8.11 (d), 7.48-7.40 (m), 7.30 (d), 7.23-7.02 (m, 4H), 5.90-5.74 (m, 1H), 5.46-5.33 (m, 1H), 5.15-4.99 (m, 3H), 4.48 (d, 1H), 4.13 (d, 1H), 4.05-3.86 (m, 2H), 2.87-2.72 (m, 2H), 2.68 (s, 3H), 2.56-2.28 (m, 2H), 2.17-2.05 (m, 2H), 2.02-1.71 (m, 8H), 1.65-1.47 (m, 3H). $^{13}C$ NMR (101 MHz, $CD_3OD$) δ 172.32, 172.04, 171.70, 169.63, 169.56, 169.21, 138.74, 138.49, 138.47, 137.69, 137.66, 137.54, 137.50, 137.40, 137.37, 137.32, 137.25, 136.76, 130.09, 130.07, 129.92, 129.85, 129.70, 128.29, 128.19, 128.16, 127.10, 127.05, 127.00, 117.62, 116.99, 116.88, 90.74, 90.45, 90.22, 71.32, 71.25, 67.45, 67.40, 65.20, 65.16, 64.94, 64.90, 58.41, 58.37, 54.24, 54.20, 54.15, 49.85, 41.49, 39.39, 39.35, 39.19, 39.15, 38.90, 37.95, 35.55, 35.44, 34.23, 33.44, 33.08, 31.91, 31.53, 31.51, 31.31, 31.29, 31.17, 31.15, 30.20, 30.09, 21.68, 21.36, 21.15, 16.45, 16.43, 16.40.

Examples 35-39: Synthesis of (4S,9aS)-8,8-diethyl-4-((S)-2-(methylamino)propanamido)-5-oxo-N—((R)-1,2,3,4-tetrahydronaphthalen-1-yl)octahydropyrrolo[2,1-b][1,3]thiazepine-7-carboxamide hydrochloride (35, 37, 38, 39)

(4S,9aS)-8,8-ethyl-4-((S)-2-(methylamino)propanamido)-5-oxo-N—((R)-1,2,3,4-tetrahydronaphthalen-1-yl)octahydropyrrolo[2,1-b][1,3]thiazepine-7-carboxamide hydrochloride (36)

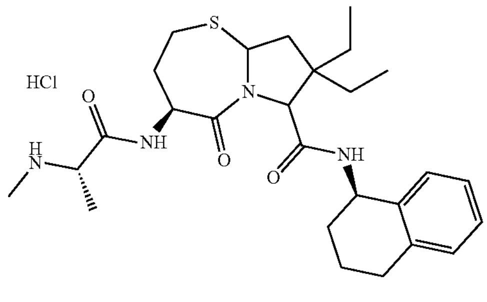

35, 37, 38, 39

36

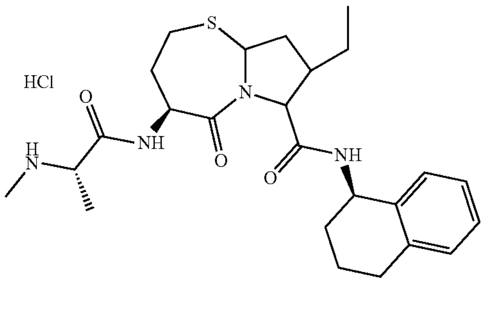

Followed the synthesis of A using X-5c. The monoalkylated compound 36 was a side-product coming from unpurified X-5c. Five isomers were separated or enriched with difficulty: (Compound 35, 10.4 mg), (Compound 36, 2.1 mg, mono-alkylated), (Compound 37, 3.0 mg), (Compound 38, 17.6 mg), (Compound 39, 1.0 mg). LC-MS m/z: 501.55 (calcd. 501.30[M+H]+), mono-alkylated LC-MS m/z: 473.45 (calcd. 473.3[M+H]+).

Compound 35: $^{1}$H NMR (400 MHz, $CD_3OD$) δ 8.62 (d), 8.52-8.39 (m, 2H), 7.33-7.26 (m), 7.20-7.03 (m, 4H), 5.48 (q, 1H), 5.40-5.33 (m), 5.07-4.99 (m, 1H), 4.79 (dd), 4.72 (dd, J=11.0, 1.9 Hz, 1H), 4.41-4.35 (m, 1H), 3.94-3.82 (m, 1H), 3.29-3.22 (m, 1H), 2.93-2.68 (m, 4H), 2.63 (d, 3H), 2.25 (ddt, 1H), 2.06-1.56 (m, 11H), 1.50 (d, 1H), 1.45 (d, 2H), 1.41-1.26 (m, 1H), 0.95-0.84 (m, 7H). $^{13}$C NMR (101 MHz, $CD_3OD$) δ 172.64, 172.55, 171.92, 169.49, 138.86, 137.42, 130.11, 129.94, 128.14, 127.01, 71.88, 63.40, 58.44, 55.17, 47.63, 44.81, 34.78, 33.17, 31.93, 30.99, 30.25, 29.98, 26.58, 21.17, 16.63, 9.22, 8.52, 8.49.

Compound 36 (mixture of at least 3 isomers (mono alkylated)): $^{1}$H NMR (400 MHz, $CD_3OD$) δ 8.40 (d,), 8.20 (d), 8.15 (d), 7.49-7.41 (m), 7.32-7.26 (m), 7.20-7.04 (m, 4H), 5.57-5.44 (m, 1H), 5.34 (t), 5.15-5.01 (m, 1H), 4.72 (dd), 4.55 (dd, 1H), 4.17 (d), 4.07 (d), 3.94-3.85 (m, 1H), 2.95-2.72 (m, 4H), 2.69-2.64 (m, 3H), 2.36-2.09 (m, 3H), 2.06-1.72 (m, 7H), 1.72-1.58 (m, 1H), 1.58-1.44 (m, 3H), 1.43-1.21 (m, 1H), 1.05-0.81 (m, 4H).

Compound 37 (mixture of mono and bis alkylate): $^{1}$H NMR (400 MHz, $CD_3OD$) δ 8.36 (s), 7.94 (d), 7.27 (d, 1H), 7.19-7.00 (m, 3H), 5.38-5.24 (m, 1H), 5.03 (d, 1H), 4.56-4.47 (m), 4.35 (s), 4.32-4.24 (m, 1H), 3.94-3.79 (m, 1H), 2.99-2.68 (m, 3H), 2.66-2.59 (m, 2H), 2.59-1.19 (m, 15H), 1.03-0.78 (m, 6H). $^{13}$C NMR (101 MHz, $CD_3OD$) δ 171.35, 170.00, 138.61, 137.38, 130.06, 129.96, 129.68, 128.43, 128.26, 127.11, 127.05, 72.24, 70.89, 62.01, 54.88, 49.71, 48.01, 43.94, 32.19, 32.07, 31.93, 31.69, 31.36, 30.13, 28.36, 26.15, 21.51, 9.17, 9.12, 8.42, 8.35.

Compound 38 (complex mixture of isomers mono and bis alkylated): $^{1}$H NMR (400 MHz, $CD_3OD$) δ 8.40 (s, 1H), 7.33-7.21 (m, 1H), 7.16-7.01 (m, 4H), 5.48-5.30 (m, 1H), 5.09-4.97 (m, 1H), 4.74-4.58 (m, 1H), 4.39-4.26 (m, 1H), 3.92-3.83 (m, 1H), 3.27-3.17 (m, 1H), 2.90-2.35 (m, 9H), 2.27-2.18 (m, 1H), 2.10-1.21 (m, 16H), 0.96-0.78 (m, 7H). $^{13}$C NMR (101 MHz, $CD_3OD$) δ 171.34, 171.21, 171.07, 170.59, 170.18, 170.02, 168.43, 168.19, 167.89, 167.57, 163.55, 137.53, 137.49, 137.24, 136.13, 136.00, 135.81, 128.97, 128.93, 128.79, 128.59, 128.49, 128.38, 127.20, 127.02, 126.82, 125.86, 125.80, 125.69, 125.67, 70.55, 70.14, 69.72, 62.06, 60.27, 59.94, 57.08, 57.04, 57.01, 54.08, 53.86, 53.10, 53.05, 48.41, 47.63, 46.53, 46.37, 46.34, 46.29, 43.52, 43.36, 43.11, 35.67, 33.44, 32.38, 31.85, 31.45, 30.99, 30.89, 30.54, 30.35, 30.05, 29.92, 29.69, 29.52, 28.94, 28.77, 28.67, 27.51, 27.20, 25.54, 25.27, 25.11, 20.00, 19.89, 19.77, 15.27, 15.23, 15.05, 8.02, 7.93, 7.86, 7.81, 7.31, 7.25, 7.21, 7.08.

Compound 39: mixture of three isomers bis-alkylated. $^{1}$H NMR (400 MHz, $CD_3OD$) δ 8.50 (s, 1H), 7.30-7.24 (m, 1H), 7.20-7.05 (m, 4H), 5.49-5.33 (m, 1H), 5.12-5.00 (m, 1H), 4.74-4.62 (m, 1H), 4.38-4.30 (m, 1H), 3.71 (q, 1H), 3.50-3.47 (m), 3.15-3.12 (m), 2.91-2.68 (m, 4H), 2.63-2.55 (m, 3H), 2.42 (dd, 1H), 2.24 (d, 1H), 2.04-1.75 (m, 7H), 1.73-1.58 (m, 2H), 1.51-1.27 (m, 6H), 0.96-0.82 (m, 7H).

Example 19, 21, and 20: Synthesis of (4S)-8,8-diethyl-4-((S)-2-(methylamino)propanamido)-5-oxo-N—((R)-1,2,3,4-tetrahydronaphthalen-1-yl)octahydropyrrolo[2,1-b][1,3]oxazepine-7-carboxamide hydrochloride (19, 21)

(4S)-8,8-ethyl-4-((S)-2-(methylamino)propanamido)-5-oxo-N—((R)-1,2,3,4-tetrahydronaphthalen-1-yl)octahydropyrrolo[2,1-b][1,3]oxazepine-7-carboxamide hydrochloride (20)

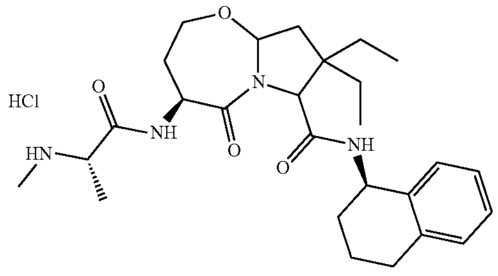

19, 21

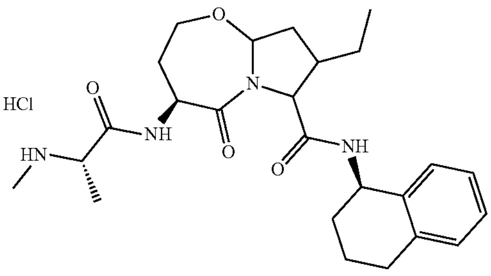

Followed the synthesis of compound A using Boc-HSer-OH and X-5c. The monoalkylated compound 20 is a side-product coming from unpurified X-5c. Three isomers isolated: Compound 19 (8.6 mg), Compound 20 (2.4 mg mono), Compound 21 (40.8 mg). LC-MS m/z: 485.20 (calcd. 485.3[M+H]+), mono LC-MS m/z: 457.10 (calcd. 457.3[M+H]+).

Compound 19: $^{1}$H NMR (400 MHz, $CD_3OD$) δ 7.49-7.43 (m, 1H), 7.20-7.05 (m, 4H), 6.00 (d), 5.78-5.69 (m), 5.57 (t), 5.47-5.32 (m, 1H), 5.15-4.93 (m, 1H), 4.79 (dd), 4.46-3.88 (m, 3H), 2.91-2.69 (m, 2H), 2.68 (d, 1H), 2.38-2.20 (m, 1H), 2.01-1.70 (m, 6H), 1.69-1.51 (m, 3H), 1.50-1.31 (m, 2H), 1.31-1.28 (m, 1H), 1.00-0.82 (m, 6H). $^{13}$C NMR (101 MHz, $CD_3OD$) δ 172.70, 172.14, 172.08, 171.89, 171.87, 170.16, 169.57, 169.17, 166.89, 142.54, 140.07, 138.95, 138.83, 138.49, 137.50, 137.48, 137.08, 134.97, 130.63, 130.23, 130.17, 130.14, 130.09, 130.00, 129.90, 129.75, 129.35, 128.75, 128.59, 128.35, 128.13, 127.83, 127.24, 127.10, 126.98, 113.22, 91.24, 91.00, 90.23, 71.52, 71.25, 70.88, 70.74, 69.41, 58.41, 58.39, 56.62, 54.76, 54.71, 54.19, 54.01, 47.28, 47.19, 44.36, 44.13, 44.08, 42.01, 34.50, 33.12, 32.14, 31.78, 31.24, 31.16, 31.11, 30.85, 30.25, 30.20, 30.17, 30.10, 29.36, 29.05, 28.67, 27.43, 26.67, 26.56, 26.40, 24.21, 22.47, 21.35, 21.20, 20.81, 20.61, 16.38, 9.28, 9.19, 9.03, 8.62, 8.53, 8.49.

Compound 20: $^{1}$H NMR (400 MHz, $CD_3OD$) δ 8.03 (d, J=8.4 Hz, 1H), 7.29-7.21 (m, 1H), 7.16-7.02 (m, 3H), 5.41 (t, J=6.6 Hz, 1H), 5.11-5.00 (m, 1H), 4.83 (s, 5H), 4.22 (s, 1H), 4.10-4.02 (m, 1H), 3.99-3.87 (m, 2H), 2.85-2.68 (m, 2H), 2.66 (s, 2H), 2.01 (s, 2H), 1.99-1.73 (m, 7H), 1.66-1.58 (m, 1H), 1.56 (d, J=7.0, 0.8 Hz, 3H), 1.45-1.37 (m, 2H), 1.36-1.26 (m, 1H), 0.92-0.78 (m, 6H). $^{13}$C NMR (101 MHz, $CD_3OD$) δ 170.75, 170.56, 168.28, 137.16, 136.20, 128.80, 128.43, 127.01, 125.81, 88.88, 69.94, 68.09, 57.08, 52.67, 47.66, 45.88, 42.82, 31.79, 30.55, 29.92, 28.78, 28.06, 25.35, 20.03, 15.12, 7.78, 7.28.

Example 22, 23, 24, 25, and 26: Synthesis of (4S, 9aS)-4-((S)-2-(methylamino)propanamido)-5-oxo-8, 8-diphenethyl-N—((R)-1,2,3,4-tetrahydronaphthalen-1-yl)octahydropyrrolo[2,1-b][1,3]oxazepine-7-carboxamide hydrochloride

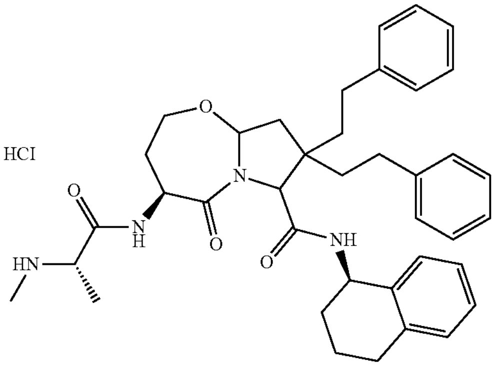

22,23,24,25,26

Followed the synthesis of compound A using Boc-HSer-OH and X-5e. Five isomers separated or enriched: Compound 22 (21.6 mg), Compound 23 (17.5 mg), Compound 24 (10.4 mg), Compound 25 (9.0 mg), Compound 26 (12.6 mg). LC-MS m/z:637.25 (calcd. 637.3[M+H]+).

Compound 22: 2 isomers. $^{1}$H NMR (400 MHz, $CD_3OD$) δ 8.61 (d), 8.13 (d), 7.36-6.98 (m, 13H), 6.82 (d), 6.70-6.64 (m), 5.54-5.43 (m, 1H), 5.14-4.93 (m, 2H), 4.59-4.44 (m, 1H), 4.29-4.10 (m, 1H), 4.03-3.90 (m, 2H), 2.85-2.70 (m, 4H), 2.68 (dd, 3H), 2.65-2.40 (m, 2H), 2.21-1.63 (m, 11H), 1.63-1.53 (m, 3H). $^{13}$C NMR (101 MHz, $CD_3OD$) δ 172.79, 172.17, 171.73, 171.56, 169.62, 169.18, 143.69, 143.62, 143.46, 143.24, 138.68, 138.40, 137.43, 137.16, 130.11, 130.10, 130.07, 129.99, 129.94, 129.65, 129.51, 129.42, 129.39, 129.35, 129.32, 129.30, 129.27, 128.34, 128.01, 127.14, 127.05, 127.03, 126.99, 126.88, 91.02, 90.16, 71.55, 71.29, 70.89, 69.82, 58.39, 54.83, 54.72, 54.04, 46.89, 45.36, 44.84, 40.08, 40.03, 38.09, 37.51, 34.59, 33.05, 31.98, 31.81, 31.80, 31.78, 31.64, 31.47, 31.19, 31.09, 30.19, 30.02, 21.06, 20.98, 16.39, 16.36.

Compound 23: 1H NMR (400 MHz, DMSO-d6) δ 8.25-8.12 (m, 2H), 7.36-7.12 (m, 13H), 7.12-7.01 (m, 2H), 5.60-5.48 (m, 1H), 4.99-4.70 (m, 2H), 4.34 (s, 1H), 4.04 (d, J=12.6 Hz, 1H), 3.88 (t, J=12.1 Hz, 1H), 2.99 (q, J=6.8 Hz, 1H), 2.79-2.57 (m, 6H), 2.36 (dd, J=13.4, 6.5 Hz, 1H), 2.25 (s, 3H), 2.08 (s, 2H), 2.02-1.43 (m, 13H), 1.14 (d, J=6.9 Hz, 3H). $^{13}$C NMR (101 MHz, DMSO-$D_6$) δ 173.56, 170.87, 168.58, 142.39, 142.17, 137.04, 136.95, 128.80, 128.49, 128.45, 128.36, 128.27, 128.24, 128.11, 126.90, 125.80, 125.77, 118.15, 88.14, 69.48, 67.60, 59.37, 51.47, 46.38, 44.89, 43.00, 38.04, 35.65, 34.36, 32.51, 30.16, 29.73, 29.63, 28.62, 19.38, 18.93.

Compound 24: $^{1}$H NMR (400 MHz, $CD_3OD$) δ 7.86 (d, J=5.0 Hz, 1H), 7.36-6.94 (m, 17H), 6.85-6.76 (m), 5.49 (q), 5.12-5.02 (m, 1H), 5.02-4.95 (m), 4.59-4.45 (m, 1H), 2.85-2.44 (m, 9H), 2.35 (dt, 1H), 2.04-2.02 (m, 3H), 2.02-1.57 (m, 11H), 1.31-1.24 (m, 1H). $^{13}$C NMR (101 MHz, $CD_3OD$) δ 176.43, 173.37, 173.30, 172.61, 171.53, 171.14, 170.90, 143.69, 143.59, 143.57, 138.75, 138.38, 137.41, 137.25, 137.12, 130.12, 130.10, 130.09, 130.02, 129.81, 129.57, 129.51, 129.47, 129.44, 129.42, 129.40, 129.37, 129.35, 129.33, 129.32, 129.25, 128.34, 128.24, 128.23, 127.19, 127.13, 127.10, 127.05, 127.02, 127.00, 126.97, 126.91, 118.14, 90.16, 82.97, 71.37, 69.72, 60.34, 53.47, 46.92, 44.85, 42.13, 42.06, 39.98, 38.69, 38.08, 37.50, 34.42, 33.49, 33.12, 32.91, 32.00, 31.90, 31.82, 31.48, 31.20, 31.09, 31.08, 30.15, 30.03, 21.10, 21.04, 20.83, 19.22.

Compound 25: $^{1}$H NMR (400 MHz, $CD_3OD$) δ 7.37-7.10 (m, 15H), 7.02 (dd, J=4.6, 1.2 Hz, 2H), 6.82 (d, J=7.8 Hz, 1H), 6.66 (dt, J=8.2, 4.2 Hz, 1H), 5.53-5.41 (m, 1H), 5.12-4.90 (m, 3H), 4.52 (s, 1H), 4.25-4.09 (m, 1H), 4.02-3.88 (m, 2H), 2.85-2.70 (m, 6H), 2.68 (s, 4H), 2.65-2.55 (m, 2H), 2.46 (dd, J=13.7, 7.0 Hz, 1H), 2.21-2.07 (m, 3H), 2.03 (s, 2H), 2.02-1.69 (m, 12H), 1.56 (d, J=7.0 Hz, 3H). $^{13}$C NMR (101 MHz, $CD_3OD$) δ 172.81, 171.74, 169.17, 143.71, 143.63, 138.69, 137.16, 130.11, 130.00, 129.95, 129.70, 129.65, 129.61, 129.53, 129.50, 129.42, 129.36, 129.32, 129.27, 128.02, 127.15, 127.06, 126.99, 126.89, 91.06, 71.56, 70.91, 58.42, 54.76, 46.92, 46.83, 45.37, 40.08, 38.11, 34.60, 31.99, 31.77, 31.66, 31.19, 30.19, 20.97, 16.32.

Example 28, 29, 31, 27, 30, and 32: Synthesis of (4S,9aS)-8,8-diallyl-4-((S)-2-(methylamino)propanamido)-5-oxo-N—((R)-1,2,3,4-tetrahydronaphthalen-1-yl)octahydropyrrolo[2,1-b][1,3]thiazepine-7-carboxamide hydrochloride (28, 29, 31)

(4S,9aS)-8,8-allyl-4-((S)-2-(methylamino)propanamido)-5-oxo-N—((R)-1,2,3,4-tetrahydronaphthalen-1-yl)octahydropyrrolo[2,1-b][1,3]thiazepine-7-carboxamide hydrochloride (27, 30, 32)

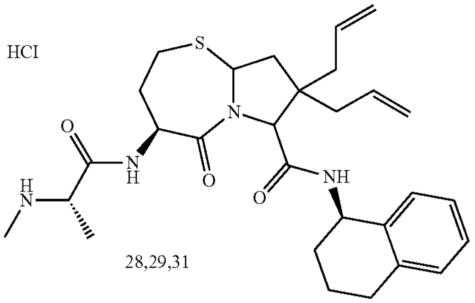

28,29,31

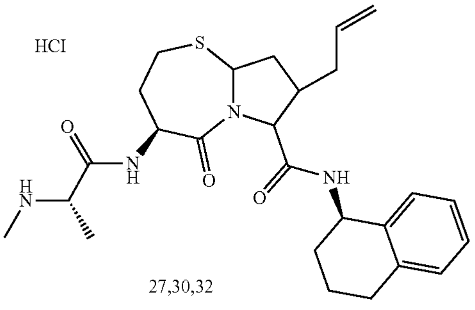

27,30,32

Follow synthesis of compound A using X-5b. The mono-alkylated compound 27, compound 30 and compound 32 were side-products coming from unpurified X-5b. 6 isomers were separated: Compound 27 (1.3 mg, mono-allyl), Compound 28 (2.4 mg), Compound 29 (4.6 mg), Compound 30 (2.4 mg mono), Compound 31 (3.0 mg), Compound 32 (5.0 mg mono). LC-MS m/z: 525.50 (calcd. 525.29[M+H]+), mono LC-MS m/z: 485.05 (calcd. 485.26[M+H]+).

Compound 27: $^{1}$H NMR (400 MHz, $CD_3OD$) δ 8.47 (s, 1H), 7.42-7.36 (m, 1H), 7.17-6.99 (m, 4H), 5.90-5.72 (m, 2H), 5.45 (dd, J=7.8, 4.0 Hz, 1H), 5.15-4.99 (m, 5H), 4.80-4.71 (m, 2H), 4.14 (d, J=6.4 Hz, 1H), 3.68 (q, J=7.2 Hz, 2H), 3.12-3.01 (m, 1H), 2.75 (dd, J=16.9, 9.7 Hz, 5H), 2.59-2.53 (m, 4H), 2.36-1.69 (m, 15H), 1.46 (dd, J=7.0, 1.8 Hz, 3H), 1.43-1.34 (m, 1H).

Compound 28: $^{1}$H NMR (400 MHz, $CD_3OD$) δ 8.49 (s, 1H), 7.29 (dd, J=6.5, 2.0 Hz, 1H), 7.20-7.05 (m, 5H), 5.96-5.77 (m, 3H), 5.38 (dd, 1H), 5.20-5.04 (m, 7H), 4.70 (dd, 1H), 4.41 (s, 1H), 4.27 (s), 3.74 (q, 1H), 2.90-2.72 (m, 5H), 2.60 (s, 3H), 2.57 (s, 1H), 2.46-2.34 (m, 3H), 2.29-1.74 (m, 15H), 1.53-1.44 (m, 4H). $^{13}$C NMR (101 MHz, $CD_3OD$) δ 172.35, 171.18, 138.57, 135.01, 134.61, 130.13, 129.81, 128.38, 127.13, 119.78, 118.96, 70.57, 61.81, 58.74, 54.31, 47.22, 46.91, 44.15, 42.13, 39.88, 33.55, 32.28, 31.17, 30.06, 27.65, 21.28, 16.80.

Compound 29: $^{1}$H NMR (400 MHz, $CD_3OD$) δ 8.51 (s, 1H), 7.34-7.26 (m), 7.18-7.03 (m, 4H), 5.98-5.77 (m, 2H), 5.56-5.34 (m, 1H), 5.21-5.00 (m, 5H), 4.72 (dd, 1H), 4.44 (d, 1H), 3.68 (q, 1H), 2.98-2.63 (m, 5H), 2.62-2.53 (m, 3H), 2.50-2.32 (m, 2H), 2.32-1.70 (m, 10H), 1.47 (t, 1H), 1.40 (d, 2H). $^{13}$C NMR (101 MHz, $CD_3OD$) δ 172.69, 171.56, 170.99, 138.88, 137.28, 135.12, 134.66, 130.12, 129.99, 128.18, 127.03, 119.69, 118.79, 78.96, 71.44, 63.33, 58.93, 55.03, 46.82, 44.42, 42.85, 39.71, 34.77, 33.18, 32.56, 30.98, 30.24, 21.13, 17.23.

Compound 30: $^{1}$H NMR (400 MHz, $CD_3OD$) δ 8.51 (s, 1H), 7.46-7.38 (m, 1H), 7.20-7.03 (m, 6H), 5.83 (ddt, 2H), 5.53-5.43 (m, 2H), 5.16-5.00 (m, 6H), 4.83-4.75 (m, 2H), 4.53 (d), 4.17 (d, 1H), 3.67 (q, J=6.8, 6.4 Hz, 2H), 2.95-2.67 (m, 7H), 2.65-2.51 (m, 7H), 2.50-1.73 (m, 20H), 1.47 (d, 3H), 1.39 (d, 1H). $^{13}$C NMR (101 MHz, $CD_3OD$) δ 171.99, 171.78, 138.80, 138.51, 137.66, 137.59, 136.67, 130.00, 128.26, 127.09, 117.83, 88.30, 68.26, 62.63, 58.92, 53.80, 41.99, 39.41, 37.67, 31.59, 31.51, 30.19, 21.58, 17.13.

Compound 31: $^{1}$H NMR (400 MHz, $CD_3OD$) δ 8.54-8.38 (m, 1H), 8.05-7.96 (m), 7.28 (dd, 1H), 7.19-7.04 (m, 3H), 7.01-6.92 (m), 6.86-6.82 (m), 5.96-5.78 (m, 2H), 5.46-5.32 (m, 1H), 5.18-5.03 (m, 5H), 4.70 (d, 1H), 4.41 (s, 1H), 3.76 (d, 1H), 3.49-3.44 (m, 1H), 2.91-2.71 (m, 4H), 2.61 (s, 3H), 2.41 (dd, 2H), 2.24 (d, 1H), 2.17 (d, 2H), 2.10 (dd, 1H), 2.04-1.72 (m, 7H), 1.50 (d, 3H). $^{13}$C NMR (101 MHz, $CD_3OD$) δ 172.33, 171.17, 138.56, 137.29, 135.00, 134.61, 130.13, 129.80, 128.77, 128.38, 127.12, 119.78, 118.96, 117.13, 70.58, 61.81, 58.69, 54.33, 47.22, 44.16, 42.13, 39.88, 33.53, 32.29, 32.22, 31.17, 30.07, 21.28, 16.72.

Compound 32: $^{1}$H NMR (400 MHz, $CD_3OD$) δ 8.48 (s, 2H), 7.44-7.22 (m, 1H), 7.22-6.99 (m, 8H), 5.91-5.68 (m, 2H), 5.55-5.40 (m, 1H), 5.15-4.97 (m, 6H), 4.79-4.43 (m, 3H), 4.23-4.11 (m, 1H), 3.75-3.59 (m, 3H), 2.98-1.66 (m, 38H), 1.51-1.33 (m, 6H).

Example 40, 41, 42, and 43: Synthesis of 4S,9aS)-8,8-diisopropyl-4-((S)-2-(methylamino)propanamido)-5-oxo-N—((R)-1,2,3,4-tetrahydronaphthalen-1-yl)octahydropyrrolo[2,1-b][1,3]thiazepine-7-carboxamide hydrochloride (40,41,42,43)

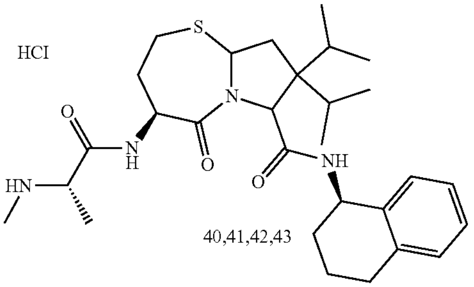 [SMILES: "HCI" ; CN[C@@H](C)C(=O)N[C@H]1CCSC2CC(C(C)C)(C(C)C)C(C(=O)N[C@@H]3CCCc4ccccc43)N2C1=O]

40,41,42,43

(Followed the synthesis of compound A using X-5d. Four isomers separated: Compound 40 (3.5 mg), Compound 41 (6.3 mg), Compound 42 (2.0 mg), Compound 43 (2.3 mg). LC-MS m/z: 529.55 (calcd. 529.32[M+H]+).

Compound 40: $^{1}$H NMR (400 MHz, $CD_3OD$) δ 8.44 (s, 2H), 8.03 (d, 1H), 7.31 (d), 7.21-7.05 (m, 6H), 5.36 (t, 1H), 5.31-5.25 (m), 5.11-4.99 (m, 2H), 4.61 (s), 4.57 (dd, 1H), 4.40 (s, 1H), 4.26 (dd,), 3.84 (q, J=6.9 Hz, 1H), 3.45-3.35 (m, 1H), 2.92-2.70 (m, 4H), 2.65-2.62 (m, 1H), 2.61 (s, 3H), 2.53 (dt, 1H), 2.32-2.21 (m, 1H), 2.10-1.71 (m, 13H), 1.50 (t, 1H), 1.46 (d, 3H), 1.10-0.89 (m, 19H). $^{13}$C NMR (101 MHz, $CD_3OD$) δ 172.14, 172.06, 171.86, 171.81, 171.70, 138.80, 137.27, 137.23, 130.37, 130.20, 130.06, 129.83, 128.49, 128.29, 127.08, 127.04, 72.02, 71.99, 70.67, 61.22, 58.38, 57.74, 53.94, 41.21, 34.56, 34.48, 32.13, 30.78, 30.10, 29.42, 27.66, 21.08, 21.01, 20.87, 20.73, 20.66, 20.42, 20.18, 16.96.

Compound 41: $^{1}$H NMR (400 MHz, $CD_3OD$) δ 8.47 (s, 1H), 8.20 (d, J=8.1 Hz, 1H), 7.30-7.25 (m, 1H), 7.20-7.06 (m, 3H), 5.37 (t, J=8.2 Hz, 1H), 5.10-4.99 (m, 1H), 4.66 (dd, J=11.2, 1.7 Hz, 1H), 4.51 (s, 1H), 3.79 (q, J=7.0 Hz, 1H), 2.85-2.71 (m, 3H), 2.68-2.62 (m, 1H), 2.62 (s, 3H), 2.26-2.18 (m, 1H), 2.10-1.77 (m, 9H), 1.50 (d, J=7.0 Hz, 3H), 1.07 (d, J=6.9 Hz, 3H), 1.03 (d, J=6.9 Hz, 3H), 0.99 (d, J=6.9 Hz, 3H), 0.96 (d, J=6.9 Hz, 3H). $^{13}$C NMR (101 MHz, $CD_3OD$) δ 172.09, 171.65, 170.17, 138.58, 137.14, 130.11, 129.99, 128.38, 127.08, 70.48, 63.18, 58.55, 54.34, 54.20, 49.71, 41.28, 34.38, 34.32, 33.33, 32.40, 32.06, 30.89, 30.07, 21.22, 20.87, 20.62, 20.26, 20.04, 16.57.

Compound 42: $^{1}$H NMR (400 MHz, $CD_3OD$) δ 8.52 (s, 1H), 8.20 (d), 7.87 (d, 1H), 7.28 (d), 7.22-7.05 (m, 4H), 5.46 (t, 1H), 5.37 (t), 5.02 (d, 1H), 4.63 (dd, 1H), 4.51 (d, 1H), 3.60 (dq, 1H), 3.49-3.47 (m), 2.79 (dt3H), 2.70-2.60 (m, 2H), 2.57 (d, 2H), 2.52 (d, 1H), 2.10-1.74 (m, 9H), 1.42 (td, 3H), 1.20-0.88 (m, 14H).

Compound 43: $^{1}$H NMR (400 MHz, $CD_3OD$) δ 8.58 (d), 8.47 (s, 1H), 8.20 (d), 7.39 (d), 7.28 (d), 7.20-7.04 (m, 4H), 5.50-5.34 (m, 1H), 5.19 (dd), 5.10-4.96 (m, 1H), 4.79-4.73 (m, 1H), 4.69-4.59 (m, 1H), 4.50 (d), 3.85-3.67 (m, 1H), 3.50-3.46 (m), 3.15-3.11 (m), 3.00 (s), 2.90-2.70 (m, 5H), 2.65-2.56 (m, 3H), 2.36-2.16 (m, 3H), 2.09-1.68 (m, 10H), 1.51-1.35 (m, 3H), 1.23-0.85 (m, 21H).

Example 45, 47, 44, and 46: Synthesis of (4S,9aS)-4-((S)-2-(methylamino)propanamido)-5-oxo-8,8-diphenethyl-N—((R)-1,2,3,4-tetrahydronaphthalen-1-yl)octahydropyrrolo[2,1-b][1,3]thiazepine-7-carboxamide hydrochloride (45, 47) and (4S,9aS)-4-((S)-2-(methylamino)propanamido)-5-oxo-8,8-phenethyl-N—((R)-1,2,3,4-tetrahydronaphthalen-1-yl)octahydropyrrolo[2,1-b][1,3]thiazepine-7-carboxamide hydrochloride (44, 46)

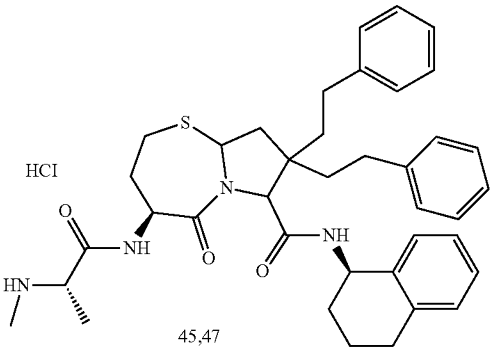

45,47

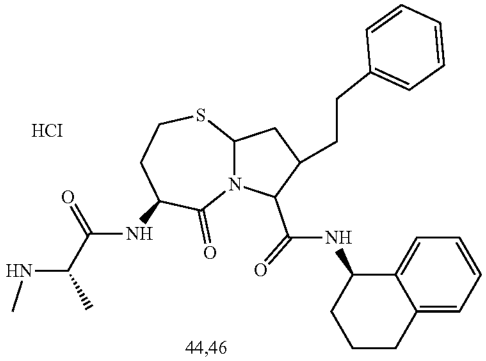

44,46

Followed the synthesis of compound A using X-5e. The monoalkylated compound 44 and compound 46 were side-products coming from unpurified X-5e. Four isomers were separated: Compound 44 (25 mg, mono), Compound 45 (7.8 mg), Compound 46 (2 mg, mono), Compound 47 (17.2 mg). LC-MS m/z: 653.90 (calcd. 653.35 [M+H]+), Mono:549.05 (calcd. 549.30 [M+H]+).

Compound 44: $^{1}H$ NMR (400 MHz, $CD_3OD$) δ 8.44 (s, 1H), 7.35-6.97 (m, 16H), 5.57-5.36 (m, 1H), 5.10-4.95 (m, 1H), 4.79-4.65 (m, 1H), 4.60-4.51 (m, 1H), 3.91-3.83 (m, 1H), 3.29-3.19 (m, 1H), 2.92-2.52 (m, 12H), 2.36-1.61 (m, 13H), 1.56-1.45 (m, 3H). $^{13}C$ NMR (101 MHz, $CD_3OD$) δ 172.75, 172.60, 172.50, 171.56, 171.30, 171.22, 169.76, 168.95, 143.51, 143.43, 143.24, 138.73, 138.51, 137.27, 137.15, 130.11, 129.95, 129.64, 129.60, 129.54, 129.52, 129.46, 129.37, 129.33, 129.29, 129.24, 129.17, 128.36, 128.03, 127.13, 127.07, 126.97, 72.03, 71.38, 63.45, 61.62, 61.41, 58.42, 58.39, 55.17, 54.44, 47.53, 47.27, 45.02, 40.59, 39.20, 37.28, 34.76, 33.49, 33.16, 32.22, 31.90, 31.85, 31.52, 31.45, 31.08, 30.19, 30.02, 21.21, 21.08, 20.99, 16.55, 16.38.

Compound 45: $^{1}H$ NMR (400 MHz, $CD_3OD$) δ 8.45 (s, 1H), 7.36-6.81 (m, 15H), 5.60-5.41 (m, 1H), 5.11-4.93 (m, 1H), 4.82-4.64 (m, 1H), 4.57-4.50 (m, 1H), 3.92-3.78 (m, 1H), 3.29-3.19 (m, 1H), 2.94-2.53 (m, 12H), 2.36-1.61 (m, 12H), 1.55-1.44 (m, 3H). $^{13}C$ NMR (101 MHz, $CD_3OD$) δ 172.79, 172.65, 172.53, 171.59, 171.24, 171.11, 170.15, 170.04, 169.06, 143.53, 143.51, 143.45, 143.42, 143.27, 143.16, 138.79, 138.74, 138.53, 137.28, 137.14, 136.99, 130.24, 130.12, 129.96, 129.87, 129.65, 129.60, 129.54, 129.52, 129.45, 129.39, 129.37, 129.34, 129.30, 129.17, 128.42, 128.36, 128.05, 127.15, 127.13, 127.09, 127.07, 127.01, 126.97, 71.75, 71.39, 61.65, 61.43, 58.57, 58.52, 54.44, 47.55, 47.41, 47.29, 45.03, 39.22, 37.30, 33.53, 32.23, 32.17, 31.98, 31.91, 31.46, 31.09, 30.03, 21.09, 20.94, 16.63, 16.49.

Compound 46: $^{1}H$ NMR (400 MHz, $CD_3OD$) δ 8.45 (s, 1H), 7.40-6.95 (m, 9H), 5.59-5.43 (m), 5.36-5.26 (m), 5.11-4.99 (m, 1H), 4.70-4.49 (m, 1H), 4.09 (d), 3.78 (dd, 1H), 2.94-2.64 (m, 7H), 2.65-2.58 (m, 3H), 2.54 (d, 1H), 2.23 (d, 3H), 2.03-1.61 (m, 7H), 1.53-1.40 (m, 3H).

Compound 47: $^{1}H$ NMR (400 MHz, $CD_3OD$) δ 8.46 (s, 1H), 7.37-6.98 (m, 16H), 6.85 (d, 1H), 6.76-6.66 (m, 1H), 5.53 (dd, 1H), 5.45 (dd), 5.07 (t), 4.98 (t, 1H), 4.79-4.70 (m, 1H), 4.56 (s, 1H), 4.53 (s), 3.89-3.81 (m, 1H), 2.93-2.65 (m, 9H), 2.64 (d, 3H), 2.61-2.53 (m, 1H), 2.37-2.22 (m, 2H), 2.18-1.59 (m, 12H), 1.55-1.44 (m, 3H). $^{13}C$ NMR (101 MHz, $CD_3OD$) δ 172.63, 172.52, 171.57, 171.23, 169.93, 169.61, 169.16, 143.51, 143.44, 143.41, 143.25, 138.74, 138.52, 137.27, 137.15, 130.11, 130.03, 129.95, 129.71, 129.65, 129.54, 129.52, 129.37, 129.33, 129.30, 129.17, 128.36, 128.04, 127.13, 127.09, 127.07, 126.97, 72.03, 71.38, 63.46, 61.63, 58.50, 58.45, 55.17, 54.44, 54.11, 47.54, 47.28, 45.75, 45.02, 40.59, 39.21, 37.86, 37.28, 34.77, 33.51, 33.17, 32.23, 31.97, 31.93, 31.90, 31.52, 31.45, 31.08, 30.19, 30.02, 21.09, 20.99, 16.63, 16.45.

Example 48, 49, 50, 51, 52, and 53: Synthesis of (4S)-8,8-diallyl-N-benzhydryl-4-((S)-2-(methylamino)propanamido)-5-oxooctahydropyrrolo[2,1-b][1,3]oxazepine-7-carboxamide hydrochloride (48, 49,50,51,52) and (4S)-8,8-allyl-N-benzhydryl-4-((S)-2-(methylamino)propanamido)-5-oxooctahydropyrrolo[2,1-b][1,3]oxazepine-7-carboxamide hydrochloride (53)

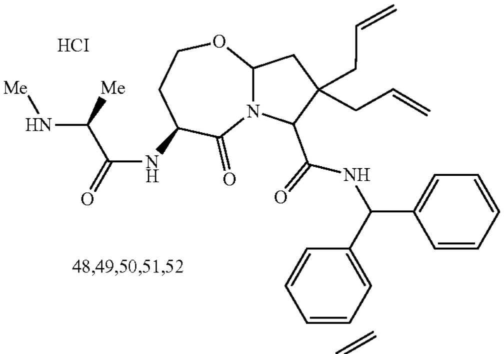

48,49,50,51,52

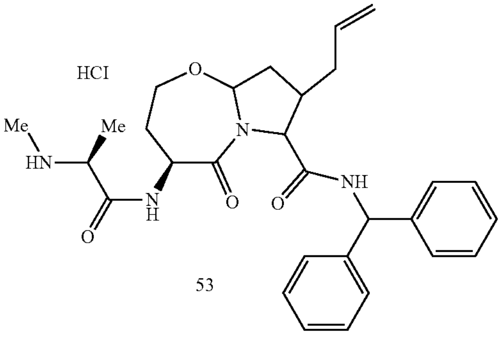

53

Followed the synthesis of compound A using X-5b and X-2. The monoalkylated compound 53 was a side-products coming from unpurified X-5b. 6 isomers were separated: Compound 48 (3.1 mg), Compound 49 (20.0 mg), Compound 50 (1.1 mg), Compound 51 (2.3 mg), Compound 52 (8 mg), Compound 53 (22.8 mg, mono). LC-MS m/z: 545.10 (calcd. 545.3 [M+H]+), mono-allyl: 505.45 (calcd. 505.3 [M+H]+).

Compound 48: $^1$H NMR (400 MHz, $CD_3OD$) δ 8.49 (s), 7.38-7.19 (m, 11H), 6.16 (s, 1H), 5.96-5.83 (m, 1H), 5.78-5.65 (m, 1H), 5.39 (d, J=7.0 Hz, 1H), 5.14-5.04 (m, 2H), 4.98-4.89 (m, 3H), 4.56 (s, 1H), 4.17 (dt, J=12.6, 3.2 Hz, 1H), 4.00-3.89 (m, 1H), 3.75 (q, J=6.9 Hz, 1H), 2.61 (s, 3H), 2.54 (dd, J=14.4, 6.9 Hz, 1H), 2.37-2.25 (m, 2H), 2.23-2.11 (m, 1H), 2.08-1.76 (m, 5H), 1.50 (d, J=7.0 Hz, 3H), 1.39-1.25 (m, 3H). $^{13}$C NMR (101 MHz, $CD_3OD$) δ 172.78, 172.07, 170.97, 142.70, 142.57, 135.11, 134.98, 129.56, 129.43, 129.25, 128.70, 128.57, 128.09, 119.25, 118.47, 90.93, 71.59, 70.08, 58.99, 58.45, 54.60, 46.62, 43.86, 42.20, 39.20, 34.59, 32.48, 17.17.

Compound 49: $^1$H NMR (400 MHz, $CD_3OD$) δ 8.51 (s), 8.39 (d), 7.40-7.19 (m, 11H), 6.19-6.11 (m, 1H), 5.96-5.65 (m, 2H), 5.54-5.36 (m, 1H), 5.17-4.91 (m, 6H), 4.48 (d, 1H), 4.21-4.05 (m, 1H), 3.97 (dtd, 1H), 3.84 (dq, 1H), 2.63 (s, 3H), 2.60-1.63 (m, 9H), 1.53 (dd, 3H). $^{13}$C NMR (101 MHz, $CD_3OD$) δ 172.70, 172.05, 171.53, 171.45, 170.51, 170.26, 142.81, 142.79, 142.77, 142.69, 142.55, 135.09, 134.98, 134.80, 134.58, 129.78, 129.66, 129.55, 129.41, 129.25, 128.72, 128.69, 128.64, 128.54, 128.38, 128.09, 119.69, 119.26, 118.79, 118.46, 90.89, 90.18, 71.58, 71.39, 70.06, 68.98, 68.95, 58.72, 58.69, 58.62, 58.58, 58.42, 54.63, 53.74, 47.02, 46.59, 44.06, 43.86, 42.88, 42.19, 39.97, 39.18, 34.53, 32.91, 32.17, 32.09, 16.88, 16.74.

Compound 50: $^1$H NMR (400 MHz, $CD_3OD$) δ 8.49 (s, 1H), 7.36-7.16 (m, 11H), 6.11 (s, 1H), 5.85-5.64 (m, 2H), 5.48 (t, J=6.5 Hz, 1H), 5.13-4.86 (m, 5H), 4.38 (s, 1H), 4.09-4.01 (m, 1H), 3.97 (td, J=12.7, 12.2, 2.3 Hz, 1H), 3.56 (q, J=6.9 Hz, 1H), 2.51 (s, 3H), 2.35 (dd, J=14.0, 7.0 Hz, 1H), 2.18 (dd, J=14.0, 7.0 Hz, 1H), 2.10 (d, J=7.3 Hz, 2H), 1.98 (dd, J=14.1, 6.0 Hz, 1H), 1.85-1.71 (m, 2H), 1.71-1.53 (m, 1H), 1.42 (d, J=6.9 Hz, 3H), 1.29 (d, J=16.1 Hz, 2H).

Compound 51: $^1$H NMR (400 MHz, $CD_3OD$) δ 8.52 (s, 1H), 7.39-7.19 (m, 11H), 6.15 (d, J=11.4 Hz, 1H), 5.90 (ddt, 1H), 5.83-5.66 (m, 1H), 5.50 (t), 5.40 (d, 1H), 5.15-4.91 (m, 4H), 4.56 (s, 1H), 4.41 (s), 4.16 (dt, 1H), 4.12-4.05 (m), 4.03-3.90 (m, 1H), 3.59 (q, 1H), 2.54 (d, 3H), 2.42-2.26 (m, 2H), 2.25-2.10 (m, 2H), 2.04-1.64 (m, 5H), 1.47-1.41 (m, 3H), 1.31 (d, J=15.7 Hz, 1H). $^{13}$C NMR (101 MHz, $CD_3OD$) δ 172.88, 172.19, 172.07, 142.69, 142.56, 135.11, 134.99, 134.82, 134.61, 129.78, 129.66, 129.56, 129.43, 129.25, 128.70, 128.57, 128.40, 128.09, 119.26, 118.46, 90.92, 90.21, 71.60, 70.07, 68.97, 59.45, 59.22, 58.64, 58.45, 54.47, 49.64, 49.43, 49.21, 49.00, 48.79, 48.57, 48.36, 47.03, 46.62, 43.86, 42.90, 42.21, 39.20, 34.62, 33.07, 17.78.

Compound 52: $^1$H NMR (400 MHz, $CD_3OD$) δ 8.53 (s, 1H), 7.40-7.19 (m, 11H), 6.13 (s, 1H), 5.89-5.64 (m, 3H), 5.50 (t, 1H), 5.21-4.91 (m, 7H), 4.59 (s), 4.41 (s, 1H), 4.12-3.94 (m, 2H), 3.55-3.46 (m, 1H), 2.50 (s, 3H), 2.44-1.96 (m, 9H), 1.89-1.55 (m, 4H), 1.42 (d, 3H), 1.31 (d, 2H), 0.90 (t, 1H).

Compound 53: 3 isomers: $^1$H NMR (400 MHz, $CD_3OD$) δ 8.41 (d), 7.42-7.14 (m, 13H), 6.18-6.12 (m, 1H), 5.79-5.63 (m, 1H), 5.50-5.37 (m, 1H), 5.07-4.94 (m, 2H), 4.61 (dd, 1H), 4.20-3.87 (m, 3H), 2.68-2.64 (m, 3H), 2.61-1.63 (m, 8H), 1.60-1.53 (m, 3H). $^{13}$C NMR (101 MHz, $CD_3OD$) δ 172.32, 172.25, 172.13, 171.77, 171.69, 171.16, 169.83, 169.81, 169.56, 143.02, 142.87, 142.84, 142.83, 142.72, 142.61, 137.11, 137.05, 136.61, 129.79, 129.76, 129.73, 129.61, 129.58, 129.57, 129.45, 129.39, 129.36, 129.33, 129.31, 128.82, 128.73, 128.69, 128.63, 128.61, 128.59, 128.58, 128.56, 128.44, 128.36, 128.31, 128.14, 117.69, 116.91, 116.81, 90.66, 90.47, 90.29, 71.37, 71.32, 71.24, 67.20, 64.92, 64.83, 58.54, 58.45, 58.42, 58.39, 58.27, 54.28, 54.09, 53.91, 41.60, 39.66, 39.56, 39.15, 39.01, 38.28, 35.39, 35.13, 34.16, 33.34, 32.90, 31.89, 31.86, 16.55, 16.50, 16.49.

Example 54: Synthesis of (6S)—N-benzhydryl-2,2-dimethyl-6-((S)-2-(methylamino)propanamido)-5-oxo-1,2,3,5,6,7,12,12b-octahydropyrrolo[1',2':1,2]azepino[3,4-b]indole-3-carboxamide hydrochloride

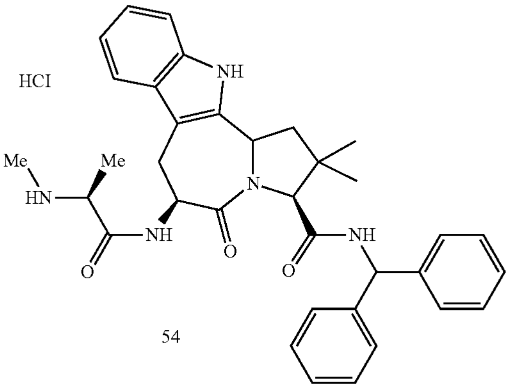 [SMILES: "HCI" ; CN[C@@H](C)C(=O)N[C@H]1Cc2c([nH]c3ccccc23)C2CC(C)(C)[C@@H](C(=O)NC(c3ccccc3)c3ccccc3)N2C1=O]

54

Followed the synthesis of compound A using Boc-Trp-OH and X-2. 18.4 mg. LC-MS m/z: 578.55 (calcd. 578.3 [M+H]+).

$^1$H NMR (400 MHz, DMSO-$d_6$) δ 10.93 (s, 1H), 8.99 (d, J=8.5 Hz, 1H), 8.59 (d, J=7.3 Hz, 1H), 8.28 (s, 1H), 7.38-7.21 (m, 15H), 7.11-7.04 (m, 1H), 7.02-6.94 (m, 1H), 6.14 (d, J=8.5 Hz, 1H), 5.67 (d, J=8.6 Hz, 1H), 5.08 (ddd, J=12.6, 7.3, 3.7 Hz, 1H), 4.32 (s, 1H), 3.33 (q, J=6.8 Hz, 1H), 3.18-3.10 (m, 1H), 2.77 (ddd, J=15.2, 12.5, 2.4 Hz, 1H), 2.37 (s, 3H), 1.26 (d, J=6.9 Hz, 3H), 0.90 (s, 3H), 0.79 (s, 3H). $^{13}$C NMR (101 MHz, DMSO-$D_6$) δ 172.05, 170.47, 169.56, 164.54, 142.33, 142.30, 134.74, 134.68, 128.44, 128.27, 128.15, 127.91, 127.34, 127.20, 126.94, 121.33, 118.94, 117.58, 111.29, 106.47, 70.22, 58.41, 56.00, 54.19, 50.15, 40.65, 40.02, 33.41, 28.42, 28.27, 23.77, 18.04.

Example 55: Synthesis of (4S,7S)-8,8-dimethyl-4-((S)-2-(methylamino)propanamido)-5-oxo-N-(2-(pyrimidin-2-yl)phenyl)octahydropyrrolo[2,1-b][1,3]oxazepine-7-carboxamide hydrochloride

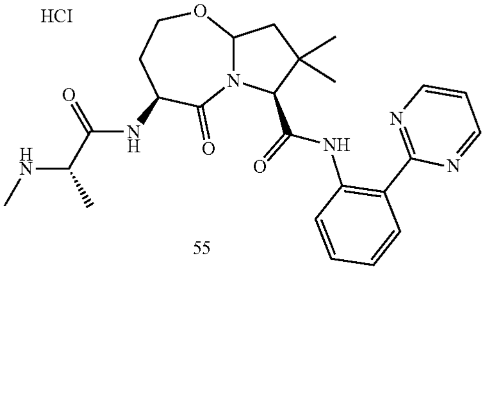 [SMILES: CN[C@@H](C)C(=O)N[C@H]1CCOC2CC(C)(C)[C@@H](C(=O)Nc3ccccc3-c3ncccn3)N2C1=O ; "HCI"]

55

To a mixture of X-16 (70 mg, 1.0 eq.), X-12 (1.0 eq), N-methylmorpholine (4.0 eq.) and HOBT.$H_2O$ (1.1 eq.) in THF (5 mL) at 0° C., was added EDC.HCl (1.05 eq.). The reaction mixture was stirred at 0° C. for 30 min then at 30° C. for 24 h. it was quenched with a saturated solution of sodium bicarbonate (30 mL) and extracted with ethyl acetate (3*20 mL). The combined organic layers were washed with brine (3*20 mL), dried over sodium sulfate anhydrous, filtered and concentrated. It afforded 20 mg of crude intermediate. The crude intermediate was solubilized in 4M HCl in 1,4-dioxane (1.0 mL). The mixture was stirred at 40° C. for 1 hours. The mixture was concentrated and purified by reverse phase HPLC (10-70% acetonitrile in water). 4.4 mg. LC-MS m/z: 481.00 (calcd. 481.2 [M+H]+).

$^1H$ NMR (400 MHz, $CD_3OD$) δ 8.95 (dd, J=4.9, 2.2 Hz, 2H), 8.53 (ddt, J=18.3, 8.5, 3.2 Hz, 2H), 7.52-7.45 (m, 1H), 7.45-7.40 (m, 1H), 7.29-7.19 (m, 2H), 5.48 (t, J=5.8 Hz, 1H), 4.25 (d, J=21.7 Hz, 2H), 4.10-3.94 (m, 2H), 3.74-3.55 (m, 3H), 3.36-3.34 (m, 1H), 2.97 (s, 1H), 2.57-2.50 (m, 4H), 1.55-1.50 (m, 1H), 1.49-1.45 (m, 1H), 1.43 (d, J=6.9 Hz, 3H), 1.29 (s, 2H), 1.26 (s, 3H), 1.10 (s, 3H).

Example 56 and 57: Synthesis of (S)—N-((4S,7S,9aS)-8,8-dimethyl-5-oxo-7-((((R)-1,2,3,4-tetrahydronaphthalen-1-yl)amino)methyl)octahydropyrrolo[2,1-b][1,3]oxazepin-4-yl)-2-(methylamino)propanamide dihydrochloride (56,57)

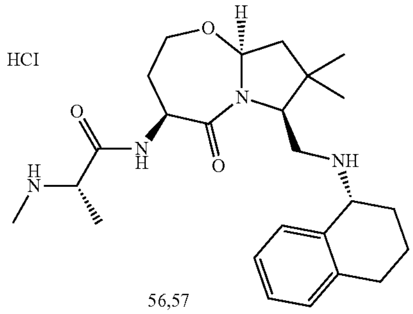 [SMILES: "HCI" ; CN[C@@H](C)C(=O)N[C@H]1CCO[C@H]2CC(C)(C)[C@@H](CN[C@@H]3CCCc4ccccc43)N2C1=O]

56,57

To a mixture of X-17 (1.0 eq, 123 mg) and (R)-1,2,3,4-tetrahydronaphthalen-1-amine (1.1 eq) in THF (0.2M) was added sodium cyanotrihydroborate (1.5 eq) at r.t. and the mixture was stirred for 3 hours. Water (3 mL) was added and the solvents were removed under vacuum. The crude intermediate was solubilized in dioxane (3.0 mL) and 4M HCl in 1,4-dioxane (3.0 mL) was added. The mixture was stirred at 40° C. for 4 hours. The mixture was concentrated and purified by reverse phase HPLC (10-70% acetonitrile in water).

Compound 57: 39.6 mg (40% yield). LC-MS m/z: 443.05 (calcd. 443.2 [M+H]+). $^1H$ NMR (400 MHz, $CD_3OD$) δ 7.61-7.56 (m), 7.51-7.42 (m, 1H), 7.37-7.19 (m, 4H), 5.41 (dd), 5.00 (dd), 4.59 (q, 1H), 4.55-4.50 (m), 4.13 (ddd), 4.06 (q), 3.97 (td), 3.79 (d), 3.70-3.61 (m, 1H), 3.61-3.53 (m), 2.97 (dt, 1H), 2.85 (ddd, 2H), 2.73-2.67 (m, 1H), 2.26-1.81 (m, 7H), 1.66 (dd, 1H), 1.46 (s, 1H), 1.45 (s, 2H), 1.43 (s, 1H), 1.17 (d, 2H). $^{13}C$ NMR (101 MHz, $CD_3OD$) δ 176.44, 169.87, 139.76, 139.71, 139.13, 132.89, 131.82, 131.57, 131.21, 131.10, 130.91, 130.70, 130.49, 130.45, 130.38, 129.93, 129.56, 127.69, 127.66, 127.57, 90.92, 73.53, 71.41, 67.21, 58.29, 57.63, 54.33, 54.25, 54.21, 50.20, 49.85, 49.39, 48.29, 46.45, 43.81, 40.53, 33.07, 31.91, 29.68, 29.49, 28.97, 27.09, 26.14, 26.11, 23.01, 19.89, 19.85, 19.53, 19.38, 18.95, 18.74, 18.70, 16.77.

Example 58 and 59: Synthesis of (4S)—N-benzhydryl-8,8-diethyl-4-((S)-2-(methylamino)propanamido)-5-oxooctahydropyrrolo[2,1-b][1,3]oxazepine-7-carboxamide hydrochloride

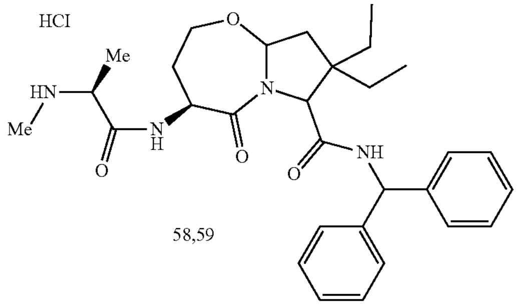 [SMILES: "HCI" ; CCC1(CC)CC2OCC[C@H](NC(=O)[C@H](C)NC)C(=O)N2C1C(=O)NC(c1ccccc1)c1ccccc1]

58,59

Followed the synthesis of compound A using Boc-HSer-OH, X-5c and X-2. It afforded two isomers: Compound 58 (28.9 mg), Compound 59 (78.3 mg). LC-MS m/z: 521.55 (calcd. 521.3 [M+H]+).

Compound 58: $^1H$ NMR (400 MHz, $CD_3OD$) δ 9.13 (d), 8.47-8.34 (m, 1H), 7.37-7.19 (m, 14H), 6.17 (d, 1H), 5.51 (t), 5.37 (d, 1H), 4.47 (s, 1H), 4.34 (s), 4.20-4.06 (m, 1H), 3.99-3.86 (m, 2H), 2.66 (s, 4H), 2.40 (dd), 2.22 (dd, 1H), 2.03-1.74 (m, 5H), 1.56-1.51 (m, 3H), 1.46-1.34 (m, 2H), 1.18-1.06 (m, 1H), 0.87 (t, 3H), 0.80-0.74 (m, 1H), 0.71 (t, 3H). $^{13}C$ NMR (101 MHz, $CD_3OD$) δ 172.64, 172.39, 172.16, 171.85, 169.85, 169.52, 142.82, 142.58, 129.75, 129.60, 129.55, 129.44, 129.21, 128.67, 128.65, 128.56, 128.47, 128.36, 128.08, 128.04, 90.99, 90.16, 71.52, 71.33, 70.53, 69.32, 58.65, 58.56, 58.44, 58.38, 58.32, 54.70, 53.76, 47.63, 47.36, 44.25, 43.97, 34.51, 32.88, 31.88, 31.86, 29.39, 29.13, 26.55, 26.08, 16.56, 16.51, 9.10, 8.88, 8.55.

Compound 59: $^1H$ NMR (400 MHz, $CD_3OD$) δ 8.40-8.31 (m, 1H), 7.37-7.19 (m, 12H), 6.16-6.10 (m, 1H), 5.50 (t, J=6.6 Hz, 1H), 4.92 (d, J=2.4 Hz, 1H), 4.33 (s, 1H), 4.12-4.04 (m, 1H), 4.03-3.94 (m, 1H), 3.90 (q, J=7.0 Hz, 1H), 2.66 (s, 3H), 2.40 (dd, J=13.8, 6.9 Hz, 1H), 1.93 (dd, J=13.9, 6.2 Hz, 1H), 1.82-1.76 (m, 1H), 1.75-1.63 (m, 1H), 1.59-1.54 (m, 3H), 1.50-1.38 (m, 3H), 1.13 (dq, J=14.6, 7.4 Hz, 1H), 0.86 (t, J=7.4 Hz, 3H), 0.77 (t, J=7.5 Hz, 3H). $^{13}C$ NMR (101 MHz, $CD_3OD$) δ 172.16, 171.86, 171.78, 169.80, 142.92, 142.82, 129.76, 129.61, 129.21, 128.69, 128.67, 128.48, 128.36, 90.18, 71.33, 69.34, 69.31, 58.68, 58.58, 58.42, 53.79, 47.65, 44.26, 32.90, 31.85, 29.40, 26.57, 16.48, 8.87, 8.54.

Example 60 and 61: Synthesis of (4S)—N-benzhydryl-8,8-diisopropyl-4-((S)-2-(methylamino)propanamido)-5-oxooctahydropyrrolo[2,1-b][1,3]oxazepine-7-carboxamide hydrochloride

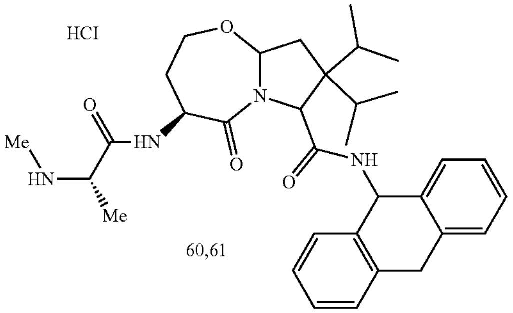 [SMILES: CN[C@@H](C)C(=O)N[C@H]1CCOC2CC(C(C)C)(C(C)C)C(C(=O)NC3c4ccccc4Cc4ccccc43)N2C1=O ; "HCI"]

60,61

Followed the synthesis of compound A using Boc-HSer-OH, X-5d and X-2. It afforded 2 Isomers: Compound 60 (4.7 mg), Compound 61 (7.7 mg). LC-MS m/z: 549.20 (calcd. 549.34 [M+H]+).

Compound 60: $^1$H NMR (400 MHz, $CD_3OD$) δ 8.49 (s, 1H), 7.38-7.16 (m, 13H), 6.22-6.11 (m, 1H), 5.35 (d, 1H), 4.81 (dd, 1H), 4.15 (dt, 1H), 3.97-3.88 (m, 1H), 3.79 (q, 1H), 2.62 (s, 2H), 2.47-2.36 (m, 1H), 2.28-2.13 (m, 2H), 1.99-1.81 (m, 3H), 1.74-1.63 (m, 1H), 1.54-1.44 (m, 3H), 1.09 (ddd, 6H), 1.03-0.83 (m, 10H), 0.82-0.70 (m, 3H). $^{13}$C NMR (101 MHz, $CD_3OD$) δ 173.04, 172.34, 170.56, 169.57, 142.77, 142.60, 129.69, 129.67, 129.65, 129.59, 129.42, 129.27, 129.14, 128.77, 128.66, 128.63, 128.61, 128.58, 128.47, 128.41, 128.28, 127.93, 91.27, 71.46, 70.80, 58.85, 58.53, 54.86, 53.06, 41.79, 35.54, 34.50, 33.52, 32.33, 21.71, 21.21, 20.98, 20.25, 17.09.

Compound 61: $^1$H NMR (400 MHz, $CD_3OD$) δ 8.46 (s, 1H), 8.33 (d), 7.38-7.19 (m, 11H), 6.13-6.07 (m, 1H), 5.47 (dd, 1H), 4.50 (s, 1H), 4.06-3.96 (m, 2H), 3.82 (q, 1H), 2.63 (s, 3H), 2.62-2.58 (m, 1H), 2.04-1.90 (m, 2H), 1.80-1.70 (m, 2H), 1.67-1.56 (m, 1H), 1.56-1.51 (m, 3H), 0.98-0.86 (m, 13H). $^{13}$C NMR (101 MHz, $CD_3OD$) δ 172.43, 172.36, 171.41, 170.32, 169.22, 142.91, 142.87, 142.70, 142.67, 129.75, 129.62, 128.72, 128.66, 128.52, 128.40, 90.92, 71.22, 69.70, 58.84, 58.74, 58.53, 54.17, 53.71, 41.15, 34.94, 34.03, 32.72, 32.01, 20.51, 20.39, 20.25, 16.67.

Example 62 and 63: Synthesis of (4S)—N-benzhydryl-4-((S)-2-(methylamino)propanamido)-5-oxo-8,8-diphenethyloctahydropyrrolo[2,1-b][1,3]oxazepine-7-carboxamide hydrochloride

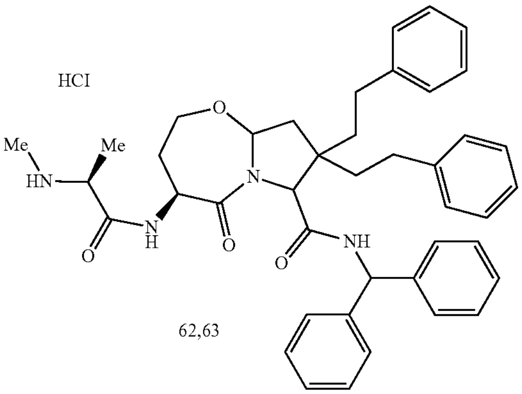 [SMILES: CN[C@@H](C)C(=O)N[C@H]1CCOC2CC(CCc3ccccc3)(CCc3ccccc3)C(C(=O)NC(c3ccccc3)c3ccccc3)N2C1=O ; "HCI"]

62,63

Followed the synthesis of compound A using Boc-HSer-OH, X-5e and X-2. It afforded two isomers: Compound 62 (17.0 mg), Compound 63 (25.3 mg). LC-MS m/z: 673.90 (calcd. 673.4 [M+H]+).

Compound 62: $^1$H NMR (400 MHz, DMSO-$d_6$) δ 9.09 (d, J=8.5 Hz, 1H), 8.35 (d, J=7.2 Hz, 1H), 8.24 (s, 1H), 7.33-7.14 (m, 18H), 7.14-7.09 (m, 4H), 6.99-6.93 (m, 2H), 6.09 (d, J=8.4 Hz, 1H), 5.49 (d, J=7.0 Hz, 1H), 4.78 (q, J=7.2 Hz, 1H), 4.61 (s, 1H), 4.03 (dt, J=12.4, 3.2 Hz, 1H), 3.94-3.85 (m, 1H), 3.20 (q, J=6.8 Hz, 1H), 2.78 (td, J=12.9, 6.6 Hz, 1H), 2.68-2.57 (m, 2H), 2.42 (td, J=13.0, 4.6 Hz, 1H), 2.33 (s, 3H), 2.30-2.22 (m, 1H), 2.05-1.82 (m, 4H), 1.81-1.68 (m, 3H), 1.37-1.24 (m, 2H), 1.22 (d, J=6.9 Hz, 3H). $^{13}$C NMR (101 MHz, DMSO-$D_6$) δ 172.27, 171.30, 168.98, 164.02, 142.48, 142.04, 141.79, 128.47, 128.41, 128.39, 128.35, 128.34, 128.25, 128.23, 128.19, 128.13, 128.08, 128.01, 127.70, 127.48, 127.14, 127.11, 126.93, 126.84, 125.73, 125.62, 88.74, 69.71, 68.71, 58.77, 55.79, 52.04, 44.98, 43.56, 38.64, 35.04, 33.56, 33.48, 30.21, 30.01, 18.36.

Compound 63: $^1$H NMR (400 MHz, DMSO-$d_6$) δ 9.09 (d), 8.65 (d,), 8.35-8.25 (m, 2H), 7.35-7.14 (m, 24H), 7.14-7.10 (m, 1H), 7.01-6.92 (m, 3H), 6.06 (d, 1H), 5.61 (t, J=6.6 Hz, 1H), 5.49 (d), 4.86 (ddd, 1H), 4.47 (s, 1H), 4.04 (dt, 1H), 3.95-3.83 (m, 1H), 3.20-3.12 (m, 1H), 2.79 (td, 4H), 2.41 (ddd, 2H), 2.33 (s, 1H), 2.28 (s, 3H), 2.05-1.83 (m, 2H), 1.80-1.59 (m, 5H), 1.58-1.45 (m, 1H), 1.44-1.25 (m, 1H), 1.21 (d, 1H), 1.18 (d, 3H). $^{13}$C NMR (101 MHz, DMSO-$D_6$) δ 172.48, 172.41, 171.33, 170.76, 168.99, 168.75, 164.34, 142.48, 142.34, 142.09, 142.05, 142.02, 141.79, 128.47, 128.41, 128.39, 128.36, 128.34, 128.25, 128.19, 128.13, 128.09, 128.09, 128.01, 128.01, 127.70, 127.49, 127.15, 127.12, 125.79, 125.62, 88.13, 69.50, 67.56, 58.58, 56.41, 51.50, 45.18, 44.99, 43.05, 38.08, 35.74, 33.70, 33.53, 32.18, 30.13, 29.77, 18.48, 18.27.

Example 64, 65, and 66: Synthesis of (1S,9S)-2,2-dimethyl-9-((S)-2-(methylamino)propanamido)-10-oxo-N—((R)-1,2,3,4-tetrahydronaphthalen-1-yl)dodecahydrobenzo[f]pyrrolo[2,1-b][1,3]oxazepine-1-carboxamide hydrochloride (64) and (1S,9S)-2,2-methyl-9-((S)-2-(methylamino)propanamido)-10-oxo-N—((R)-1,2,3,4-tetrahydronaphthalen-1-yl)dodecahydrobenzo[f]pyrrolo[2,1-b][1,3]oxazepine-1-carboxamide hydrochloride (65, 66)

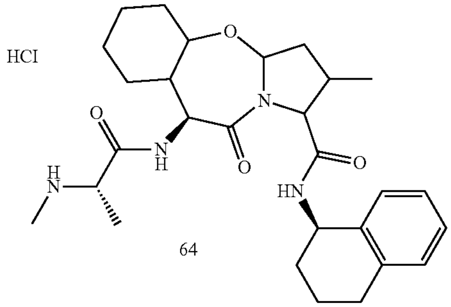

64

-continued

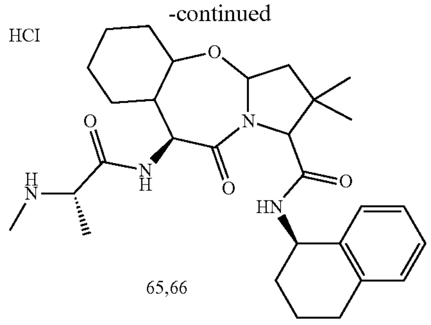

65,66

Followed the synthesis of compound A using X-8. It afforded three isomers: Compound 64 (6.0 mg mono), Compound 65 (21.5 mg), Compound 66 (12.8 mg). LC-MS m/z: 511.15 (calcd. 511.4[M+H]+), mono: 497.10 (calcd. 497.3[M+H]+).

Compound 64 (mixture of isomers): $^{1}H$ NMR (400 MHz, DMSO-$d_6$) δ 9.33-8.94 (m, 2H), 8.87 (d), 8.80 (d), 8.70 (d), 8.59 (d), 8.26-8.16 (m), 8.11 (s), 8.04-7.93 (m), 7.47 (d), 7.25-6.96 (m, 4H), 5.85-5.74 (m), 5.62-5.42 (m, 1H), 5.02-4.76 (m, 2H), 4.55-4.49 (m), 4.28-3.62 (m, 3H), 3.55-3.42 (m, 1H), 3.12 (d), 2.76-2.58 (m, 2H), 2.45-2.38 (m, 3H), 2.26-1.98 (m, 1H), 1.90-1.49 (m, 10H), 1.49-1.28 (m, 5H), 1.28-1.03 (m, 4H), 1.03-0.70 (m, 6H). $^{13}C$ NMR (101 MHz, DMSO-$D_6$) δ 170.87, 170.47, 170.38, 170.16, 170.04, 169.99, 169.27, 168.93, 168.86, 168.84, 168.82, 168.78, 168.70, 168.69, 168.33, 137.88, 137.76, 137.55, 137.51, 137.43, 137.39, 137.38, 129.33, 129.28, 129.25, 129.20, 129.09, 128.98, 128.94, 128.62, 127.72, 127.44, 127.41, 127.16, 127.12, 126.37, 126.36, 126.26, 126.20, 88.29, 87.76, 87.45, 87.44, 84.26, 83.84, 78.44, 78.33, 70.31, 70.09, 70.06, 69.66, 69.63, 61.05, 60.41, 56.77, 56.45, 56.42, 56.19, 55.43, 55.33, 47.28, 47.18, 47.02, 46.96, 46.93, 46.88, 46.75, 46.19, 46.18, 46.15, 46.14, 45.11, 44.13, 43.88, 42.93, 39.24, 39.09, 38.97, 38.40, 33.43, 31.46, 31.36, 31.22, 31.17, 30.59, 30.52, 30.38, 30.21, 30.20, 30.18, 29.47, 29.29, 29.15, 28.92, 27.46, 27.33, 25.84, 25.40, 24.91, 24.29, 24.22, 24.09, 21.23, 20.64, 20.34, 20.33, 20.20, 20.08, 16.71, 16.59, 16.53, 16.50, 16.44.

Example 67 and 68: Synthesis of (S)—N-((4S,7S,9aS)-8,8-dimethyl-5-oxo-7-((((R)-thiochroman-4-yl)amino)methyl)octahydropyrrolo[2,1-b][1,3]oxazepin-4-yl)-2-(methylamino)propanamide dihydrochloride

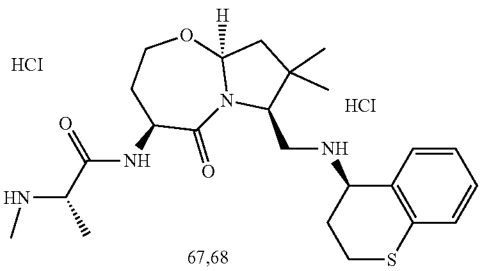

67,68

Followed the synthesis of compound 56 using X-10. It afforded two isomers: Compound 67 (2.5 mg, 15% yield), Compound 68 (2.3 mg, 14% yield). LC-MS m/z: 461.00 (calcd. 461.2 [M+H]+).

Compound 67: $^{1}H$ NMR (400 MHz, $CD_3OD$) δ 7.49 (dd, J=7.7, 1.4 Hz, 1H), 7.35-7.29 (m, 1H), 7.24 (dd, J=8.0, 1.4 Hz, 1H), 7.17 (td, J=7.4, 1.4 Hz, 1H), 5.38 (dd, J=6.9, 3.6 Hz, 1H), 4.99-4.90 (m, 1H), 4.64 (t, J=3.9 Hz, 1H), 4.12-4.04 (m, 1H), 4.00 (q, J=6.9 Hz, 1H), 3.93 (td, J=12.3, 2.2 Hz, 1H), 3.80 (d, J=9.5 Hz, 1H), 3.59 (d, J=13.2 Hz, 1H), 3.25 (dd, J=12.8, 3.6 Hz, 1H), 3.17-3.06 (m, 2H), 2.76 (dq, J=14.8, 3.9 Hz, 1H), 2.70 (s, 3H), 2.35-2.23 (m, 1H), 2.15 (dd, J=13.7, 6.8 Hz, 1H), 1.98-1.76 (m, 3H), 1.64 (d, J=7.0 Hz, 3H), 1.17 (s, 3H), 1.16 (s, 3H). $^{13}C$ NMR (101 MHz, $CD_3OD$) δ 176.38, 169.90, 135.96, 133.19, 131.37, 128.73, 127.64, 125.81, 90.85, 71.33, 66.78, 58.30, 56.70, 54.12, 46.32, 40.46, 32.90, 31.86, 27.20, 25.57, 22.97, 21.82, 16.76.

Compound 68: $^{1}H$ NMR (400 MHz, $CD_3OD$) δ 8.40 (s, 1H), 7.33 (dd, J=7.7, 1.5 Hz, 1H), 7.26-7.18 (m, 1H), 7.15 (dd, J=8.0, 1.5 Hz, 1H), 7.09 (td, J=7.4, 1.5 Hz, 1H), 5.35 (dd, J=7.0, 5.0 Hz, 1H), 4.92 (d, J=2.4 Hz, 1H), 4.18 (d, J=3.9 Hz, 1H), 4.08-4.00 (m, 1H), 3.93 (dd, J=12.0, 2.5 Hz, 1H), 3.88 (q, J=7.0 Hz, 1H), 3.80 (dd, J=8.3, 2.4 Hz, 1H), 3.25 (dd, J=12.6, 3.8 Hz, 1H), 3.02 (dt, J=12.8, 4.5 Hz, 1H), 2.90 (dd, J=12.5, 8.3 Hz, 1H), 2.66 (s, 3H), 2.52 (dq, J=13.4, 4.3 Hz, 1H), 2.18-2.07 (m, 2H), 1.94-1.75 (m, 3H), 1.57 (d, J=7.0 Hz, 3H), 1.11 (s, 3H), 1.08 (s, 3H). $^{13}C$ NMR (101 MHz, $CD_3OD$) δ 174.92, 170.37, 135.12, 132.43, 130.07, 128.22, 125.21, 90.48, 71.24, 67.17, 58.55, 56.43, 53.98, 46.30, 40.09, 33.37, 32.05, 28.26, 26.86, 22.98, 22.19, 16.83.

Example 69: Synthesis of (4S,7S,9aS)-8,8-dimethyl-4-((S)-2-(methylamino)propanamido)-5-oxo-N—((R)-thiochroman-4-yl)octahydropyrrolo[2,1-b][1,3]oxazepine-7-carboxamide hydrochloride

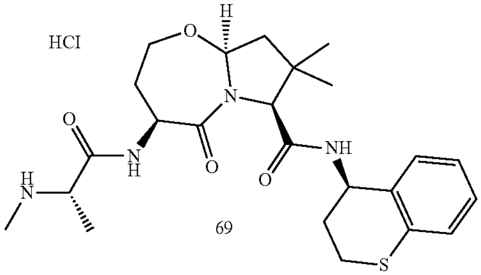 [SMILES: CN[C@@H](C)C(=O)N[C@H]1CCO[C@H]2CC(C)(C)[C@@H](C(=O)N[C@@H]3CCSc4ccccc43)N2C1=O ; "HCI"]

69

Followed the synthesis of compound 55 using X-10. 15 mg (70% yield). LC-MS m/z: 475.40 (calcd. 475.3 [M+H]+). $^{1}H$ NMR (400 MHz, $CD_3OD$) δ 8.51 (s, 1H), 7.31-7.24 (m, 1H), 7.17-6.94 (m, 3H), 5.45-5.39 (m, 1H), 5.10-5.04 (m, 1H), 4.08 (dd, J=3.7, 2.6 Hz, 2H), 3.92 (tt, J=12.1, 2.4 Hz, 1H), 3.80-3.69 (m, 1H), 3.08-2.95 (m, 2H), 2.62 (s, 1H), 2.58 (s, 2H), 2.34-2.23 (m, 1H), 2.18 (dd, J=13.4, 6.6 Hz, 1H), 2.13-1.98 (m, 2H), 1.97-1.87 (m, 1H), 1.87-1.75 (m, 1H), 1.49 (d, J=7.0 Hz, 2H), 1.45 (d, J=7.0 Hz, 1H), 1.09 (d, J=5.6 Hz, 6H). $^{13}C$ NMR (101 MHz, $CD_3OD$) δ 171.14, 171.01, 170.10, 170.09, 169.70, 169.56, 133.47, 133.43, 132.74, 132.69, 129.96, 129.88, 127.71, 127.69, 126.27, 126.25, 124.08, 124.05, 89.08, 70.35, 70.29, 69.99, 69.97, 57.46, 57.43, 52.78, 52.67, 46.95, 46.90, 45.66, 45.64, 38.85, 38.80, 31.93, 31.56, 31.07, 30.98, 28.42, 28.34, 28.01, 28.00, 22.91, 22.55, 22.52, 15.65, 15.58.

Example 70 and 71: Synthesis of (4S,7S,9aS)—N-isopentyl-8,8-dimethyl-4-((S)-2-(methylamino)propanamido)-5-oxooctahydropyrrolo[2,1-b][1,3]oxazepine-7-carboxamide hydrochloride (70, 71)

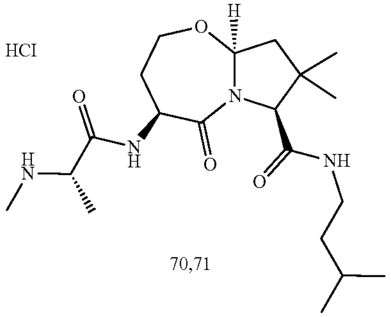 [SMILES: "HCI" ; CN[C@@H](C)C(=O)N[C@H]1CCO[C@H]2CC(C)(C)[C@@H](C(=O)NCCC(C)C)N2C1=O]

70,71

Followed the synthesis of compound 55 using 3-methylbutan-1-amine. It afforded 12 mg (60% yield). LC-MS m/z: 397.05 (calcd. 397.3 [M+H]+).

Compound 70: $^1$H NMR (400 MHz, $CD_3OD$) δ 5.49-5.43 (m, 1H), 4.24-4.16 (m, 1H), 4.04-3.93 (m, 2H), 3.71 (s, 1H), 3.29-3.15 (m, 2H), 2.60 (d, J=12.4 Hz, 3H), 2.21 (dd, J=13.1, 6.9 Hz, 1H), 2.10-1.96 (m, 2H), 1.89-1.79 (m, 1H), 1.70-1.58 (m, 1H), 1.51-1.36 (m, 5H), 1.12 (s, 3H), 1.06 (s, 3H), 0.97-0.87 (m, 7H). $^{13}$C NMR (101 MHz, $CD_3OD$) δ 172.36, 172.27, 172.19, 90.47, 71.84, 71.77, 71.38, 58.71, 54.15, 54.02, 49.64, 49.43, 49.21, 49.00, 48.79, 48.57, 48.36, 46.87, 46.84, 40.07, 40.04, 39.34, 38.65, 38.63, 33.21, 32.89, 32.35, 32.19, 29.33, 26.84, 24.08, 22.78, 22.75, 22.74, 16.83.).

Example 72: Synthesis of (2S)—N-((4S,9aS)-7-(benzo[d]oxazol-2-yl)-8,8-dimethyl-5-oxooctahydropyrrolo[2,1-b][1,3]oxazepin-4-yl)-2-(methylamino)propanamide hydrochloride

72

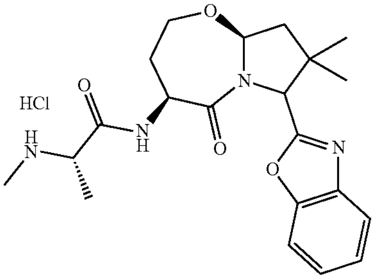

A mixture of ((benzyloxy)carbonyl)-L-homoserine (7.80 mmol) (2.00 g, 1 eq), 1-(2,2-dimethoxyethyl)-2-isocyanobenzene (7.80 mmol, 1.50 g), ammonia (1.115 ml, 7.80 mmol) and 4,4-dimethoxy-2,2-dimethylbutanal (7.80 mmol, 1.25 g) in 2,2,2-trifluoroethanol (8 mL) was heated at 80° C. under microwave irradiation. The mixture was then concentrated, diluted with 20 mL of dioxane and treated with HCl (4M in dioxane, 20 mL). It was concentrated again and diluted in methanol (50 mL) then sodium hydroxide (30 mL, 2M aqueous) was added. The mixture was stirred at 50° C. for 5 hours. The reaction was quenched with 2M HCl (60 mL) and extracted with ethyl acetate (3*100 mL). the combined organic layers were washed with 0.1M HCl (1*100 mL), brine (2*100 mL), dried over sodium sulfate anhydrous, filtered and concentrated to afford 3 g of crude (4S,9aS)-4-(((benzyloxy)carbonyl)amino)-8,8-dimethyl-5-oxooctahydropyrrolo[2,1-b][1,3]oxazepine-7-carboxylic acid. To a solution of this acid (200 mg, 0.531 mmol, 1.0 eq) and DMF (1 drop, catalytic) in DCM (3 mL) at 0° C. was added oxalyl chloride (56 uL, 1.2 eq). The mixture was stirred at 40° C. for 1 hour then 2-bromoaniline (183 mg, 1.063 mmol, 2.0 eq) was added followed by triethylamine (74 ul, 2.0 eq). The mixture was stirred at 23° C. for 3 hours. brine (50 mL) was added to the reaction mixture and the product was extracted with DCM (3*20 mL). The organic layers were dried over sodium sulfate anhydrous, filtered, concentrated and purified by column chromatography to afford: 209 mg (75% yield) of benzyl ((4S,9aS)-7-((2-bromophenyl)carbamoyl)-8,8-dimethyl-5-oxooctahydropyrrolo[2,1-b][1,3]oxazepin-4-yl)carbamate.

A mixture of the latter (200 mg, 0.377 mmol, 1.0 eq), cesium carbonate (67.9 mg, 1.131 mmol, 3.0 eq), 1,10-phenanthroline (13.59 mg, 0.075 mmol, 0.2 eq) and copper (I) iodide (7.18 mg, 0.038 mmol, 0.1 eq) in DME (2 mL) was heated in a microwave reactor at 120° C. for 30 min. The mixture was filtered through celite and the pad was washed with ethanol. The filtrate was concentrated to afford the crude intermediate: 260 mg. LC-MS mz: 450.00 (calcd. 450.2 [M+H]+). It was diluted in ethanol (5 mL) and 10% Pd/C (30 mg) was added. The mixture was purged with nitrogen then put under hydrogen atmosphere and stirred for 2 hours at 23° C. The reaction mixture was filtered through celite and concentrated. LC-MS m/z: 316.0 (calcd. 316.2 [M+H]+). To a solution of N-(tert-butoxycarbonyl)-N-methyl-L-alanine (153 mg, 0.755 mmol, 2.0 eq) in DCM (0.4M) was added oxalyl chloride (2.0 eq) followed by a drop of DMF. The mixture was stirred at 35° C. for 30 min. The mixture was concentrated to dryness and the residue was solubilized in DCM (0.4M). To this solution, the crude tert-butyl ((2S)-1-(((4S,9aS)-7-(benzo[d]oxazol-2-yl)-8,8-dimethyl-5-oxooctahydropyrrolo[2,1-b][1,3]oxazepin-4-yl)amino)-1-oxopropan-2-yl)(methyl)carbamate (1.0 eq, 189 mg) in DCM (0.5M) was added dropwise followed by diisopropyethylamine (4.0 eq, 260 uL)). The mixture was stirred at 35° C. for 2 hours then concentrated to dryness. LC-MS m/z: 400.90 (calcd. 401.3 [M+H]+). To the crude in dioxane (2 mL) was added 4.0M HCl in dioxane (2 mL). The mixture was stirred at 40° C. for 2 hours. The mixture was concentrated and purified by reverse phase silica gel. 50 mg (35% yield) LC-MS m/z: 401.0 (calcd. 401.3 [M+H]+).

$^1$H NMR (400 MHz, $CD_3OD$) δ 8.42 (s, 1H), 7.63-7.56 (m, 2H), 7.38-7.34 (m, 2H), 5.61 (d, J=6.8 Hz, 1H), 5.01-4.94 (m, 2H), 4.25-4.17 (m, 1H), 4.01 (ddd, J=14.0, 10.3, 2.0 Hz, 1H), 3.81 (q, J=7.0 Hz, 1H), 2.59 (s, 3H), 2.44 (dd, J=13.8, 6.9 Hz, 1H), 2.07-1.80 (m, 4H), 1.45 (s, 3H), 1.41 (d, J=7.0 Hz, 3H), 1.25 (d, J=3.7 Hz, 1H), 0.85 (d, J=1.9 Hz, 1H), 0.78 (s, 3H). $^{13}$C NMR (101 MHz, $CD_3OD$) δ 171.59, 168.32, 165.44, 150.46, 140.11, 125.31, 124.71, 119.17, 110.64, 89.96, 70.34, 66.12, 57.02, 53.34, 45.17, 40.76, 32.87, 30.46, 28.33, 22.88, 15.01.

Example 73: Synthesis of (S)—N-((4S,7S,9aS)-7-((((R)-chroman-4-yl)amino)methyl)-8,8-dimethyl-5-oxooctahydropyrrolo[2,1-b][1,3]oxazepin-4-yl)-2-(methylamino)propanamide dihydrochloride

73

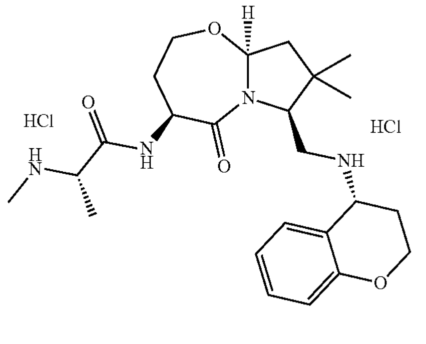

Followed the synthesis of compound 56 using X-11. 3.2 mg (20% yield). LC-MS m/z: 445.00 (calcd. 445.3 [M+H]+). $^{1}H$ NMR (400 MHz, $CD_3OD$) δ 8.25 (s, 1H), 7.50-7.44 (m, 1H), 7.37-7.22 (m, 1H), 7.00-6.93 (m, 1H), 6.90-6.84 (m, 1H), 5.41-5.27 (m, 1H), 4.97 (dd, J=11.8, 1.9 Hz, 1H), 4.56-4.49 (m, 1H), 4.36-4.20 (m, 2H), 4.11 (dddd, J=12.8, 6.5, 3.8, 2.8 Hz, 1H), 4.00-3.86 (m, 2H), 3.79-3.71 (m, 1H), 3.66-3.53 (m, 1H), 3.19 (dd, J=13.3, 9.2 Hz, 1H), 2.69-2.61 (m, 4H), 2.41-2.31 (m, 1H), 2.19-1.74 (m, 5H), 1.61 (d, J=7.0 Hz, 2H), 1.57-1.53 (m, 1H), 1.19-1.09 (m, 5H), 1.07-0.95 (m, 2H). $^{13}C$ NMR (101 MHz, $CD_3OD$) δ 177.78, 171.46, 158.23, 133.65, 132.36, 123.63, 123.50, 120.50, 119.52, 92.43, 91.54, 72.88, 72.70, 70.89, 68.86, 64.29, 59.85, 55.73, 55.58, 54.78, 47.90, 41.99, 40.63, 35.01, 34.61, 33.34, 28.63, 27.16, 24.41, 18.16, 17.87.

Example 74: Synthesis of (4S,7S,9aS)—N—((R)-chroman-4-yl)-8,8-dimethyl-4-((S)-2-(methylamino)propanamido)-5-oxooctahydropyrrolo[2,1-b][1,3]oxazepine-7-carboxamide hydrochloride

74

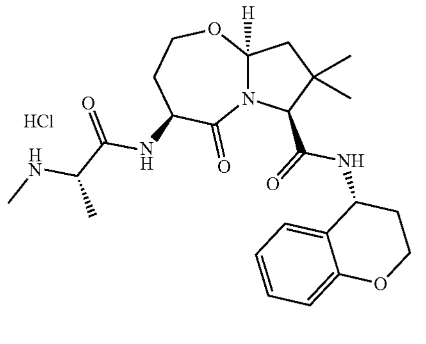

Followed the synthesis of 55 using X-11. It afforded 15 mg (65%). LC-MS m/z: 459.10 (calcd. 459.3 [M+H]+). $^{1}H$ NMR (400 MHz, $CD_3OD$) δ 8.30 (dd, J=16.7, 7.9 Hz, 1H), 7.27-7.21 (m, 1H), 7.13-7.08 (m, 1H), 6.87-6.79 (m, 1H), 6.77-6.71 (m, 1H), 5.43-5.36 (m, 1H), 5.12-5.03 (m, 1H), 4.85-4.81 (m, 1H), 4.26-4.06 (m, 4H), 4.04 (s, 1H), 3.97-3.81 (m, 2H), 2.66 (s, 1H), 2.63 (s, 2H), 2.21-1.91 (m, 6H), 1.86-1.73 (m, 1H), 1.53 (d, J=6.9 Hz, 2H), 1.48 (d, J=6.9 Hz, 1H), 1.09 (d, J=4.4 Hz, 6H). $^{13}C$ NMR (101 MHz, $CD_3OD$) δ 173.44, 172.92, 171.17, 157.66, 131.75, 131.25, 124.61, 122.81, 119.09, 91.69, 72.75, 72.51, 65.74, 59.69, 55.37, 48.23, 46.14, 41.28, 34.41, 33.06, 31.49, 30.48, 25.45, 17.74.

Example 75 and 76: Synthesis of rac-(4R)-8,8-dimethyl-4-((R)-2-(methylamino)propanamido)-5-oxo-2-((phenylthio)methyl)-N—((S)-1,2,3,4-tetrahydronaphthalen-1-yl)octahydropyrrolo[2,1-b][1,3]oxazepine-7-carboxamide hydrochloride (75, 76)

75,76

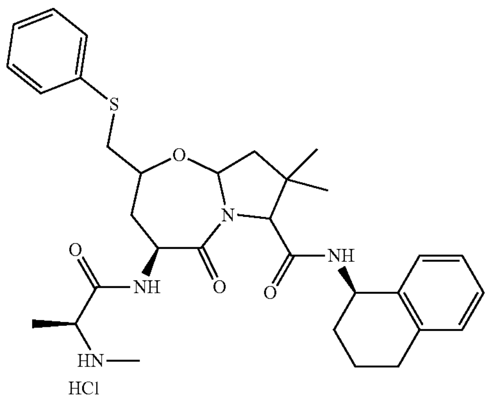

To a mixture of 4,4-dimethoxy-2,2-dimethylbutanal (0.493 g, 3.08 mmol), ammonia (7M in methanol, 0.600 ml, 4.20 mmol), X-9 (1.051 g, 2.8 mmol) in methanol at 0° C. was added X-1 (0.484 g, 3.08 mmol). The mixture was stirred at 0° C. for 10 min then at 40° C. for 24 hours. The mixture was concentrated, solubilized in dioxane (7 mL) and treated with HCl (4M in dioxane, 7 mL). The mixture was stirred at 40° C. for 1 hour. The mixture was quenched with a saturated aqueous solution of sodium bicarbonate (200 mL) and extracted with ethyl acetate (2*100 mL). The combined organic layers were washed with 0.5 M aqueous HCl (100 mL), brine (2*100 mL), dried over sodium sulfate anhydrous, filtered and concentrated. The crude (1.4 mmol, 879 mg) in tetrahydrofuran (3 mL) at 0° C., was treated with TBAF (5 eq, 1M in THF, 7 mmol). The mixture was then heated to 72° C. for 24 h. 5 mL of water was then added and the mixture was stirred for 30 min. The mixture was then cooled down to 23° C. and diluted with a saturated aqueous solution of sodium bicarbonate (50 mL). It was extracted with ethyl acetate (3*50 mL). The combined organic layers were washed with brine (2*50 mL), dried over sodium sulfate anhydrous, filtered and concentrated. To a mixture of latter crude, N-methylmorpholine (4.20 mmol, 0.462 mL), HOBT (0.236 g, 1.540 mmol) and N-(tert-butoxycarbonyl)-N-methyl-L-alanine (0.313 g, 1.540 mmol) in THF (14 mL) at 0° C. was added EDC.HCl (0.282 g, 1.470 mmol). The mixture was stirred at 0° C. for 30 min then warmed to 35° C. for 18 hours. The mixture was diluted with water (100 mL) and 0.1M HCl (10 mL). It was extracted with ethyl acetate (3*100 mL). The combined organic layers were washed with a saturated solution of sodium bicarbonate (1*100 mL), washed with brine (1*100 mL), dried over sodium sulfate anhydrous, filtered through a plug of silica gel (the plug was washed with 200 mL of ethyl acetate) and concentrated. The crude was used in the next step without further purification. To a solution of the crude (950 mg, 1.4 mmol) in dioxane (5 mL) was added 4M HCl in dioxane (10 eq). The mixture was stirred at 40° C. for 2 hours. The mixture was then concentrated to dryness. It afforded 400 mg of crude product. The product was purified by Dionex (15-50% acetonitrile in water). It afforded two fractions. Compound 75 (187 mg), Compound 76 (210 mg) overall yield of 25%. LC-MS m/z: 579.40 (calcd. 579.30 [M+H]+).

Compound 75: $^1$H NMR (400 MHz, DMSO-$d_6$) δ 8.17 (d, J=6.8 Hz, 1H), 7.99 (d, J=8.3 Hz, 1H), 7.33-7.23 (m, 5H), 7.20-7.02 (m, 7H), 5.48 (t, J=6.4 Hz, 1H), 4.92-4.85 (m, 1H), 4.77 (ddd, J=11.8, 6.9, 2.0 Hz, 1H), 4.00-3.93 (m, 2H), 3.52 (s, 1H), 3.00-2.87 (m, 4H), 2.68 (d, J=7.9 Hz, 2H), 2.19 (s, 3H), 2.06-1.99 (m, 2H), 1.80 (dt, J=12.5, 6.2 Hz, 3H), 1.70-1.63 (m, 2H), 1.47 (dt, J=13.5, 11.3 Hz, 1H), 1.09 (d, J=6.9 Hz, 3H), 0.97 (s, 3H), 0.96 (s, 3H). $^{13}$C NMR (101 MHz, DMSO-$D_6$) δ 174.04, 170.85, 168.92, 137.59, 137.48, 136.71, 129.54, 129.26, 129.15, 129.13, 127.39, 126.40, 87.88, 79.15, 69.91, 66.88, 59.82, 50.90, 47.13, 45.85, 40.96, 38.93, 38.36, 37.04, 34.81, 30.28, 29.21, 29.02, 24.08, 20.19, 19.43.

Compound 76: $^1$H NMR (400 MHz, DMSO-$d_6$) δ 8.15 (d, J=6.8 Hz, 1H), 8.11 (d, J=8.6 Hz, 1H), 7.38-7.19 (m, 5H), 7.19-6.94 (m, 7H), 5.48 (t, J=6.6 Hz, 1H), 4.89 (q, J=7.1 Hz, 1H), 4.80-4.70 (m, 1H), 4.11-3.91 (m, 3H), 3.08 (qd, J=14.0, 5.7 Hz, 2H), 3.01-2.91 (m, 1H), 2.66 (dq, J=10.7, 6.4, 4.5 Hz, 3H), 2.20 (dd, J=4.3, 0.9 Hz, 3H), 2.10-2.00 (m, 1H), 1.94 (d, J=13.6 Hz, 1H), 1.87-1.48 (m, 8H), 1.12 (s, 2H), 1.09 (dd, J=6.7, 3.5 Hz, 3H), 0.98-0.92 (m, 4H). $^{13}$C NMR (101 MHz, DMSO-$D_6$) δ 173.82, 171.20, 169.23, 137.73, 137.58, 137.10, 129.52, 129.42, 129.20, 128.87, 128.72, 127.15, 126.17, 88.43, 79.63, 71.36, 59.88, 51.07, 46.98, 45.95, 40.96, 39.16, 38.39, 34.89, 30.68, 30.32, 29.33, 24.84, 20.62, 19.39.

Example 77: Synthesis of (R)-4-((4S,7S,9aS)-8,8-dimethyl-4-((S)-2-(methylamino)propanamido)-5-oxooctahydropyrrolo[2,1-b][1,3]thiazepine-7-carboxamido)-4-phenylbutanoic acid hydrochloride

77

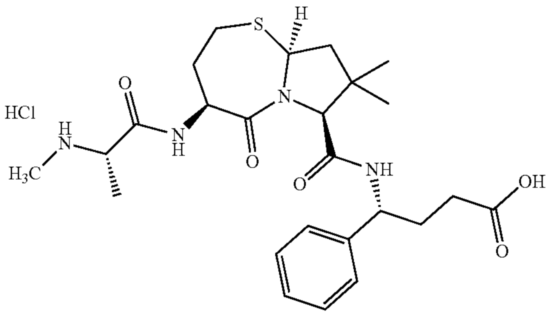

Under nitrogen atmosphere, N-Ethyl-N-(propan-2-yl)propan-2-amine (153 μL, 0.879 mmol, 3.00 eq.) and COMU® (157 mg, 0.366 mmol, 1.25 eq.) were added to a solution of X-18 (130 mg, 0.293 mmol, 1.00 eq.) dissolved in dry THF (2.4 mL) and stirred at rt. After 45 minutes, (1R)-4-methoxy-4-oxo-1-phenylbutan-1-ammonium chloride (80 mg, 0.352 mmol, 1.20 eq.) was added and stirring was continued for 22 h. Upon completion, ethyl acetate (30 mL) was added and washed with 1M NaOH (2*10 mL), 1M HCl (2*10 mL), water (10 mL) and brine (10 mL), dried over sodium sulfate anhydrous and concentrated in vacuo. The resulting residue was purified by flash column chromatography (hexanes/ethyl acetate). It afforded methyl (4R)-4-{[(4S,7S,9aS)-4-[(2S)-2-{[(tert-butoxy)carbonyl](methyl)amino}propanamido]-8,8-dimethyl-5-oxo-octahydropyrrolo[2,1-b][1,3]thiazepin-7-yl]formamido}-4-phenylbutanoate as a colorless solid, 123 mg (68%). $R_f$=0.30 (70% ethyl acetate in hexanes, Ceric Ammonium Molybdate stain). $^1$H NMR (400 MHz, $CD_3OD$) δ 8.15 (d, J=8.4 Hz, 1H), 7.39-7.31 (m, 4H), 7.28-7.22 (m, 1H), 5.46 (d, J=8.7 Hz, 1H), 4.95-4.89 (m, 1H), 4.67-4.61 (m, 1H), 4.20 (s, 1H), 3.65 (s, 3H), 3.35-3.31 (m, 1H), 2.91 (ddd, J=14.5, 4.9, 2.5 Hz, 1H), 2.85 (s, 3H), 2.37 (td, J=7.2, 1.4 Hz, 2H), 2.33-2.20 (m, 2H), 2.15-2.02 (m, 2H), 1.98-1.82 (m, 2H), 1.47 (s, 9H), 1.37 (d, J=7.2 Hz, 3H), 1.13 (s, 3H), 1.00 (s, 3H). $^{13}$C NMR (101 MHz, $CD_3OD$): δ (ppm)=174.91, 173.24, 172.79, 171.84, 143.26, 129.66, 128.46, 127.65, 81.82, 73.44, 61.87, 54.36, 54.14, 52.20, 47.10, 40.88, 33.74, 32.34, 31.74, 31.10, 28.78, 28.66, 23.80, 14.47. LC-MS m/z: 619.30 (calcd. 619.32 [M+H$^+$]). Lithium hydroxide solution (1 M, 250 μL, 0.250 mmol, 2.00 eq.) was added to the intermediate (77 mg, 0.125 mmol, 1.00 eq.) dissolved in THF (250 μL) at rt. The resulting emulsion was stirred at 40° C. for 16 h. Upon completion, ethyl acetate (30 mL) was added and washed with 1M HCl (10 mL), water (10 mL), brine (10 mL), dried over sodium sulfate anhydrous and concentrated in vacuo. The resulting residue was purified by flash column chromatography (hexanes/ethyl acetate/formic acid 0.2%). It afforded (4R)-4-{[(4S,7S,9aS)-4-[(2S)-2-{[(tert-butoxy)carbonyl](methyl)amino}propanamido]-8,8-dimethyl-5-oxo-octahydropyrrolo[2,1-b][1,3]thiazepin-7-yl]formamido}-4-phenylbutanoic acid as a colorless oil, yield 53 mg (70%). $R_f$=0.56 (hexanes/ethyl acetate/formic acid 1:9:0.1, Ceric Ammonium Molybdate stain). $^1$H NMR (400 MHz, $CD_3OD$) δ 8.14 (d,), 7.38-7.28 (m, 4H), 7.26-7.20 (m, 1H), 5.44 (t), 4.93-4.89 (m, 1H), 4.63 (d), 4.18 (s, 1H), 3.34-3.29 (m, 1H), 2.92-2.85 (m, 1H), 2.83 (s, 3H), 2.32 (td, 2H), 2.29-2.25 (m, 1H), 2.25-2.19 (m, 1H), 2.12-2.00 (m, 2H), 1.94-1.81 (m, 2H), 1.45 (s, 9H), 1.35 (d, 3H), 1.11 (s, 3H), 0.99 (s, 3H). $^{13}$C NMR (101 MHz, $CD_3OD$) δ 176.40, 173.26, 172.80, 143.41, 129.64, 128.41, 127.61, 73.47, 61.87, 54.41, 54.14, 47.12, 40.88, 33.77, 32.33, 31.83, 31.11, 28.80, 28.67, 23.82, 14.46. LC-MS m/z: 605.25 (calcd. 605.30 [M+H$^+$]). It (53 mg, 0.00873 mmol, 1.00 eq.) was treated with HCl in dioxane (4 M, 873 μL, 3.49 mmol, 40.0 eq.) at rt. After 2 h, all volatiles were removed under reduced pressure, the residue was transferred on a fritted funnel and washed with $Et_2O$ (3×1.5 mL). The remaining product was dried under reduced pressure. It afforded (R)-4-((4S,7S,9aS)-8,8-dimethyl-4-((S)-2-(methylamino)propanamido)-5-oxooctahydropyrrolo[2,1-b][1,3]thiazepine-7-carboxamido)-4-phenylbutanoic acid hydrochloride as a colorless solid, yield 24 mg (51%). $^1$H NMR (400 MHz, $CDOD_3$): δ (ppm)=8.15 (d, J=8.5 Hz, 1H), 7.39-7.20 (m, 5H), 5.46 (t, J=7.7 Hz, 1H), 4.91 (s, 3H), 4.75 (d, J=10.5 Hz, 1H), 4.18 (s, 1H), 3.96-3.85 (m, 1H), 3.33 (s, 2H), 2.94 (d, J=14.7 Hz, 1H), 2.67 (s, 3H), 2.41-2.21 (m, 4H), 2.15-1.95 (m, 3H), 1.87 (dd, J=13.1, 9.2 Hz, 1H), 1.54 (d, J=6.9 Hz, 3H), 1.14 (s, 3H), 0.99 (s, 3H). $^{13}$C NMR (101 MHz, $CDOD_3$) δ 173.60, 171.04, 170.41, 167.95, 141.89, 128.34, 127.17, 126.35, 72.15, 60.47, 57.01, 53.15, 53.06, 45.87, 39.57, 32.22, 31.44, 30.94, 30.48, 30.42, 27.45, 22.48, 14.95. LC-MS: m/z=505.10 (calcd. 505.25 [M+H$^+$]).

Example 78: Synthesis of (4S,7S,9aS)—N-((1S,2R)-2-(2-fluoroethoxy)-2,3-dihydro-1H-inden-1-yl)-8,8-dimethyl-4-((S)-2-(methylamino)propanamido)-5-oxooctahydropyrrolo[2,1-b][1,3]thiazepine-7-carboxamide hydrochloride

78

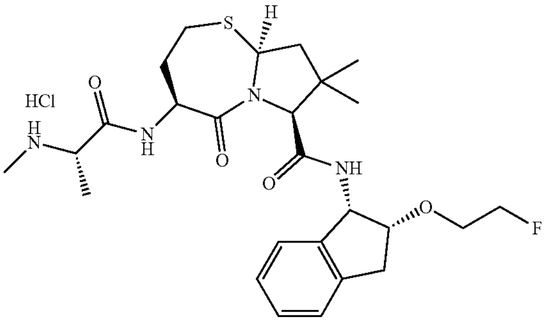

Followed the procedure of 55 using X-18 and X-14. It afforded (4S,7S,9aS)—N-((1S,2R)-2-(2-fluoroethoxy)-2,3-dihydro-1H-inden-1-yl)-8,8-dimethyl-4-((S)-2-(methylamino)propanamido)-5-oxooctahydropyrrolo[2,1-b][1,3]thiazepine-7-carboxamide hydrochloride as a colorless solid, yield 42 mg (47%). $^1$H NMR (400 MHz, $CD_3OD$) δ 8.71 (d), 7.96 (d, 1H), 7.34 (d, 1H), 7.27-7.17 (m, 3H), 5.52-5.42 (m, 2H), 4.75 (d, 1H), 4.62-4.55 (m, 1H), 4.46 (d, 1H), 4.36 (q, 1H), 4.25 (s, 1H), 3.94 (q, 1H), 3.80 (t, 1H), 3.74-3.71 (m, 1H), 3.31-3.27 (m, 1H), 3.11 (d, 2H), 2.91 (d, 1H), 2.68 (s, 3H), 2.37-2.22 (m, 2H), 2.08 (q, 1H), 1.81 (dd, 1H), 1.56 (d3H), 1.18-1.10 (m, 6H). $^{13}$C NMR (101 MHz, $CD_3OD$) δ 171.11, 170.81, 168.01, 141.05, 139.81, 128.06, 126.66, 124.81, 124.25, 83.73, 82.06, 80.86, 72.18, 68.99, 68.80, 60.47, 57.00, 55.49, 53.15, 45.88, 39.54, 36.08, 32.01, 31.04, 30.49, 27.48, 22.68, 15.01. LC-MS: m/z=521.15 (calcd. 521.26 [M+H$^+$]).

Example 79: Synthesis of (4S,7S,9aS)-8,8-dimethyl-4-((S)-2-(methylamino)butanamido)-5-oxo-N—((R)-1,2,3,4-tetrahydronaphthalen-1-yl)octahydropyrrolo[2,1-b][1,3]thiazepine-7-carboxamide hydrochloride

79

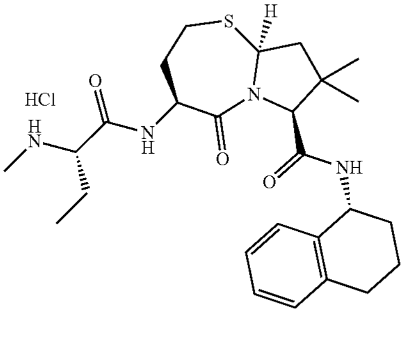

Followed the synthesis of X-18 using (2S)-2-{[(tert-butoxy)carbonyl](methyl)amino}butanoic acid to afford (4S,7S,9aS)-4-[(2S)-2-{[(tert-butoxy)carbonyl](methyl)amino}butanamido]-8,8-dimethyl-5-oxo-octahydropyrrolo[2,1-b][1,3]thiazepine-7-carboxylic acid as a colorless gum, yield 134 mg (69%). $R_f$=0.33 (hexanes/ethyl acetate/formic acid 4:6:0.1, CAM stain). $^1$H NMR (400 MHz, $CDCl_3$) δ 7.38 (d, J=36.3 Hz, 1H), 5.21 (t, J=7.0 Hz, 1H), 4.67-4.49 (m, 1H), 4.25 (s, 1H), 3.24 (t, J=12.9 Hz, 1H), 2.87-2.79 (m, 1H), 2.77 (s, 3H), 2.32-2.21 (m, 2H), 2.03-1.87 (m, 3H), 1.66 (s, 1H), 1.47 (s, 9H), 1.20 (s, 3H), 1.17 (s, 3H), 0.88 (t, J=7.4 Hz, 3H). $^{13}$C NMR (101 MHz, $CDCl_3$) δ 173.75, 171.06, 156.87, 80.73, 70.33, 61.36, 53.06, 46.34, 39.88, 33.24, 31.77, 30.27, 28.62, 28.46, 23.84, 21.44, 10.67. LC-MS: m/z=458.20 (calcd. 458.23 [M+H$^+$]).

Under nitrogen atmosphere, N-Ethyl-N-(propan-2-yl)propan-2-amine (76 μL, 0.437 mmol, 2.50 eq.) and COMU® (97 mg, 0.227 mmol, 1.30 eq.) were added to a solution of (4S,7S,9aS)-4-[(2S)-2-{[(tert-Butoxy)carbonyl](methyl)amino}butanamido]-8,8-dimethyl-5-oxo-octahydropyrrolo[2,1-b][1,3]thiazepine-7-carboxylic acid (80 mg, 0.175 mmol, 1.00 eq.) in dry THF (1.7 mL) at 0° C. After the reaction mixture was stirred for 30 min at 0° C., (R)-(−)-1,2,3,4-tetrahydro-1-naphthylamine (39 μL, 0.262 mmol, 1.50 eq.) was added and stirring was continued for 24 h at rt. Afterwards, all volatiles were removed under reduced pressure, the residue was dissolved in ethyl acetate (30 mL), washed with sat. $NaHCO_3$ solution (2*10 mL), 1M HCl (2*10 mL), water (10 mL) and brine (10 mL), dried ($Na_2SO_4$) and concentrated in vacuo. The residue was purified by flash column chromatography (hexanes/ethyl acetate). It afforded tert-butyl N-[(1S)-1-{[(4S,7S,9aS)-8,8-dimethyl-5-oxo-7-{[(1R)-1,2,3,4-tetrahydronaphthalen-1-yl]carbamoyl}-octahydropyrrolo[2,1-b][1,3]thiazepin-4-yl]carbamoyl}propyl]-N-methylcarbamate as a colorless resin, yield 81 mg (79%). $R_f$=0.30 (hexanes/ethyl acetate 5:5, Cerium(IV) sulfate stain). $^1$H NMR (400 MHz, $CDCl_3$) δ 1H NMR (400 MHz, CDCl3) δ 7.28-7.22 (m, 1H), 7.14 (d, J=3.9 Hz, 2H), 7.11-7.04 (m, 1H), 6.96 (d, J=17.3 Hz, 1H), 5.22-5.09 (m, 2H), 4.55-4.48 (m, 1H), 4.24 (s, 1H), 3.27 (t, J=14.0 Hz, 1H), 2.85-2.69 (m, 6H), 2.33-2.21 (m, 2H), 1.94-1.61 (m, 8H), 1.48 (s, 9H), 1.23 (s, 3H), 1.10 (s, 3H), 0.89 (t, J=6.1 Hz, 3H). $^{13}$C NMR (101 MHz, $CDCl_3$) δ 170.83, 170.06, 168.57, 137.36, 136.49, 129.19, 128.88, 127.32, 126.28, 80.52, 72.44, 60.90, 52.93, 47.56, 46.14, 39.87, 33.60, 31.92, 30.15, 29.22, 28.88, 28.43, 23.54, 19.92, 10.69. LC-MS: m/z=587.30 (calcd. 587.33 [M+H$^+$]). Tert-butyl N-[(1S)-1-{[(4S,7S,9aS)-8,8-dimethyl-5-oxo-7-{[(1R)-1,2,3,4-tetrahydronaphthalen-1-yl]carbamoyl}-octahydropyrrolo[2,1-b][1,3]thiazepin-4-yl]carbamoyl}propyl]-N-methylcarbamate (65 mg, 0.111 mmol, 1.00 eq.) was treated with HCl in dioxane (4 M, 1.11 mL, 4.45 mmol, 40.0 eq.) at rt. After 2 h, all volatiles were removed under reduced pressure, the residue was transferred on a fritted funnel and washed with $Et_2O$ (3×1.5 mL). The remaining product was dried under reduced pressure. It afforded 79 as a colorless solid, yield 42 mg (72%). $^1$H NMR (400 MHz, $CD_3OD$) δ 8.83 (d), 8.18 (d, 1H), 7.31 (d, 1H), 7.19-7.05 (m, 3H), 5.42 (t, 1H), 5.09 (d, 1H), 4.77 (d, 1H), 4.16 (s, 1H), 3.83 (d, 1H), 3.24 (d, 1H), 2.92 (d, 1H), 2.86-2.76 (m, 2H), 2.67 (s, 3H), 2.36-2.21 (m, 2H), 2.05-1.77 (m, 9H), 1.20-1.11 (m, 6H), 1.06 (t, 3H). $^{13}$C NMR (101 MHz, $CD_3OD$) δ 172.12, 171.55, 167.96, 138.54, 137.45, 130.07, 129.81, 128.30, 127.10, 73.39, 63.76, 61.86, 54.53, 47.39, 40.86, 33.72, 32.35, 32.06, 31.33, 30.10, 28.70, 24.84, 23.93, 21.33, 9.17. LC-MS: m/z=487.55 (calcd. 487.27 for $C_{26}H_{39}N_4O_3S^+$ [M+H$^+$]).

Example 80: Synthesis of (4'S,7'S,9a'S)-4'-((S)-2-(methylamino)propanamido)-5'-oxo-N—((R)-1,2,3,4-tetrahydronaphthalen-1-yl)hexahydro-7'H-spiro[cyclopentane-1,8'-pyrrolo[2,1-b][1,3]thiazepine]-7'-carboxamide hydrochloride

80

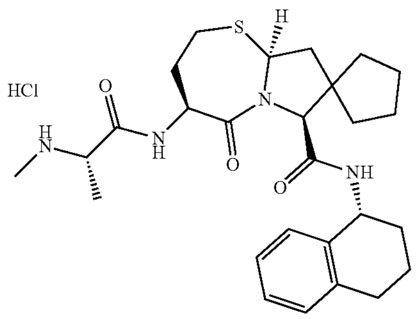

Under $N_2$ atmosphere, N-Ethyl-N-(propan-2-yl)propan-2-amine (78 µL, 0.447 mmol, 3.00 eq.) and COMU® (83 mg, 0.194 mmol, 1.30 eq.) were added to a solution of carboxylic acid X-19 (70 mg, 0.149 mmol, 1.00 eq.) in dry THF (1.2 mL). After the reaction mixture was stirred for 30 min, (R)-(−)-1,2,3,4-tetrahydro-1-naphthylamine (33 µL, 0.224 mmol, 1.50 eq.) was added and stirring was continued for 24 h at rt. Afterwards, all volatiles were removed under reduced pressure, the residue was dissolved in ethyl acetate (30 mL), washed with sat. $NaHCO_3$ solution (2×10 mL), HCl solution (1 M, 2×10 mL), water (10 mL) and brine (10 mL), the organic layer was dried ($Na_2SO_4$) and concentrated in vacuo. The crude was solubilized in methanol and palladium over carbon (10% w/w, 100 mg) was added. The mixture was put under hydrogen atmosphere and stirred for 24 hours. It was concentrated and the residue was purified by flash column chromatography (hexanes/ethyl acetate). It afforded tert-butyl N-[(1S)-1-{[(4'S,7'S,9'aS)-5'-oxo-7'-{[(1R)-1,2,3,4-tetrahydronaphthalen-1-yl]carbamoyl}-hexahydro-2'H-spiro[cyclopentane-1,8'-pyrrolo[2,1-b][1,3]thiazepin]-4'-yl]carbamoyl}ethyl]-N-methylcarbamate as a colorless resin, yield 34 mg (39%). $R_f$=0.48 (hexanes/ethyl acetate 6:4, Cerium(IV) sulfate stain). $^1$H NMR (400 MHz, $CDCl_3$) δ 1.34 (d, J=7.1 Hz, 3H), 1.47 (s, 9H), 1.49-1.88 (m, 12H), 2.00-2.07 (m, 2H), 2.25-2.37 (m, 2H), 2.70-2.85 (m, 6H), 3.26 (t, J=13.9 Hz, 1H), 4.31 (s, 1H), 4.52 (dd, J=10.8/6.1 Hz, 1H), 4.70 (s, broad, 1H), 5.04-5.11 (m, 1H), 5.19 (q, J=6.0/4.7 Hz, 1H), 7.00 (d, J=8.0 Hz, 1H), 7.05-7.17 (m, 3H), 7.23-7.28 (m, 1H), 7.39 (s, 1H). $^{13}$C NMR (101 MHz, $CDCl_3$) δ 14.0, 20.1, 23.8, 24.3, 28.4, 29.2, 30.2, 30.4, 31.9, 33.6, 39.6, 44.1, 47.5, 51.1, 52.9, 54.0, 60.9, 70.6, 126.2, 127.3, 128.8, 129.1, 137.3, 168.6, 170.7, 171.0. LC-MS: m/z=599.25 (calcd. 599.33 [M+H$^+$]). It was treated with 4M HCl (10 eq) at 40° C. for 2 hours then concentrated under vacuo to afford 80. LC-MS m/z: 499.15 (calcd. 499.27 [M+H$^+$]).

Example 81: Synthesis of (4'S)-4'-((S)-2-(methylamino)propanamido)-5'-oxo-N—((R)-1,2,3,4-tetrahydronaphthalen-1-yl)-2',3',4',5',9',9a'-hexahydro-7'H-spiro[cyclopentane-1,8'-pyrrolo[2,1-b][1,3]oxazepin]-3-ene-7'-carboxamide hydrochloride

81

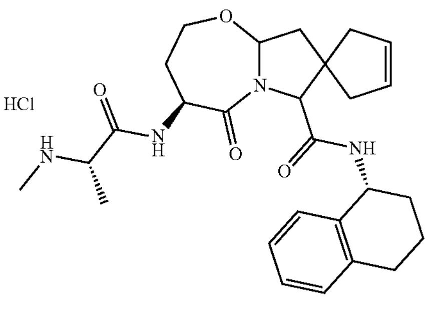

Followed the synthesis of compound A using X-5f. LC-MS m/z: 481.75 (calcd. 481.3 [M+H]+). $^1$H NMR (400 MHz, $CD_3OD$) δ 7.30-7.24 (m, 1H), 7.16-7.01 (m, 4H), 5.72-5.58 (m, 2H), 5.46-5.39 (m, 1H), 5.06 (td, J=5.5, 4.9, 3.0 Hz, 1H), 4.89 (ddd, J=11.8, 6.7, 2.0 Hz, 1H), 4.25 (s, 1H), 4.15-4.06 (m, 1H), 3.99-3.92 (m, 2H), 2.85-2.68 (m, 3H), 2.66 (s, 4H), 2.43-1.69 (m, 14H), 1.60-1.49 (m, 4H). $^{13}$C NMR (101 MHz, $CD_3OD$) δ 170.70, 170.26, 168.28, 137.15, 136.26, 129.31, 128.77, 128.35, 128.26, 126.98, 125.83, 88.89, 70.06, 69.13, 57.09, 52.84, 49.18, 48.59, 46.40, 44.76, 38.98, 31.93, 30.58, 30.06, 28.81, 20.16, 15.16.

Example 82: Synthesis of (4'S)-4'-((S)-2-(methylamino)propanamido)-5'-oxo-N—((R)-1,2,3,4-tetrahydronaphthalen-1-yl)hexahydro-7'H-spiro[cyclopentane-1,8'-pyrrolo[2,1-b][1,3]oxazepine]-7'-carboxamide hydrochloride

82

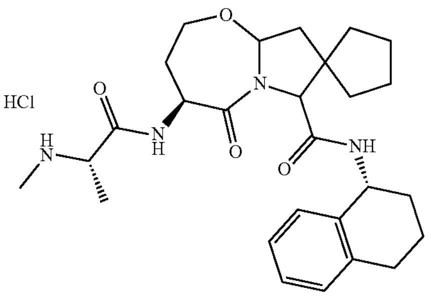

Followed the synthesis of compound 81 until it afforded the intermediate boc-protected: tert-butyl methyl((2S)-1-oxo-1-(((4'S)-5'-oxo-7'-(((R)-1,2,3,4-tetrahydronaphthalen-1-yl)carbamoyl)hexahydro-7'H-spiro[cyclopentane-1,8'-pyrrolo[2,1-b][1,3]oxazepin]-4'-yl)amino)propan-2-yl)carbamate. This intermediate (200 mg) was solubilized in methanol (5 ml) and Palladium over carbon (30 mg, 10% W/W, wet) was added. The mixture was flushed with nitrogen before being put under hydrogen atmosphere. The mixture was stirred under hydrogen atmosphere for 3-6 hours, filtered over celite. The celite plug was washed with methanol and the filtrate was concentrated. the crude was treated with HCl (10 eq, 4M in dioxane) for 2 hours at 30° C. than concentrated and purified by reverse phase silica gel C18. LC-MS m/z: 483.50 (calcd. 483.3 [M+H]+). $^{1}$H NMR (400 MHz, $CD_3OD$) δ 7.29-7.23 (m, 1H), 7.17-7.01 (m, 4H), 5.40 (t, 1H), 5.06 (t, 1H), 4.86 (dd, 1H), 4.14 (s, 1H), 4.13-4.06 (m, 1H), 3.98-3.87 (m, 2H), 2.87-2.68 (m, 3H), 2.66 (d, 3H), 2.29-2.21 (m, 1H), 2.12-2.02 (m, 1H), 2.02-1.92 (m, 2H), 1.89-1.67 (m, 10H), 1.54 (dd, 6H). $^{13}$C NMR (101 MHz, $CD_3OD$) δ 170.61, 170.56, 168.26, 137.16, 136.20, 128.75, 128.40, 126.97, 125.79, 89.04, 69.98, 68.78, 57.09, 52.80, 50.23, 48.55, 43.42, 39.20, 32.82, 31.84, 30.53, 30.08, 28.79, 23.36, 23.12, 20.10, 15.10.

Example 83: Synthesis of (2S)-1-{[(4S,7S,9aS)-8,8-Dimethyl-5-oxo-7-{[(1S,2R)-2-(prop-2-yn-1-yloxy)-2,3-dihydro-1H-inden-1-yl]carbamoyl}octahydropyrrolo[2,1-b][1,3]thiazepin-4-yl]amino}-N-methyl-1-oxopropan-2-ammonium chloride

83

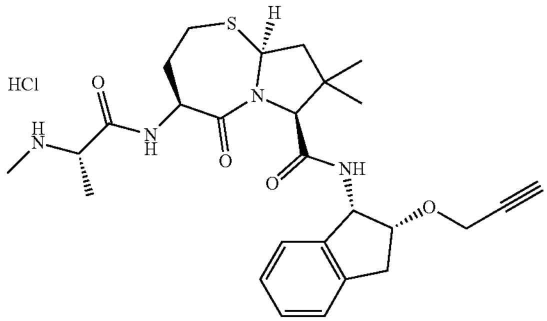

Followed the procedure of compound 55 using X-18 and X-13. It afforded (2S)-1-{[(4S,7S,9aS)-8,8-Dimethyl-5-oxo-7-{[(1S,2R)-2-(prop-2-yn-1-yloxy)-2,3-dihydro-1H-inden-1-yl]carbamoyl}octahydropyrrolo[2,1-b][1,3]thiazepin-4-yl]amino}-N-methyl-1-oxopropan-2-ammonium chloride as a colorless solid, yield 51 mg (50%). $^{1}$H NMR (400 MHz, $CD_3OD$) δ 8.00 (d, 1H), 7.32 (d, 1H), 7.26-7.17 (m, 3H), 5.52-5.40 (m, 2H), 4.75 (dd, 1H), 4.52 (td, 1H), 4.28-4.21 (m, 2H), 4.16 (dd, 1H), 3.94 (q, 1H), 3.37-3.28 (m, 4H), 3.16 (dd, 1H), 3.09 (dd, 1H), 2.96-2.87 (m, 2H), 2.68 (s, 3H), 2.34 (dd, 1H), 2.30-2.21 (m, 1H), 2.20-2.07 (m, 1H), 1.81 (dd, 1H), 1.55 (d, 3H), 1.19-1.12 (m, 6H). $^{13}$C NMR (101 MHz, $CD_3OD$) δ 172.36, 172.09, 169.23, 142.27, 140.97, 129.34, 127.99, 126.08, 125.45, 80.60, 80.40, 76.36, 73.57, 68.08, 61.68, 58.27, 57.57, 56.63, 54.40, 49.64, 49.43, 49.21, 49.00, 48.78, 48.58, 48.36, 47.23, 40.77, 37.18, 33.44, 32.38, 31.80, 28.90, 24.14, 16.34.

Example A

SKOV-3 cancer cell lines were treated with a test compound, either as a pure enantiomer or a mixture of stereoisomers, at a concentration of 10 μM. Cell viability was evaluated following treatment with a compound as disclosed in Table B. Viability of cancer cells following treatment is indicated according to the following legend:

A=0-25% viability B=26-50% viability C=>50% viability

TABLE B

| # | % viability after treatment with 10 micromolar of test compound (SKOV-3 cells) |
|---|---|
| 1 | C |
| 2 | B |
| 3 | C |
| 4 | C |
| 5 | C |
| 6 | B |
| 7 | B |
| 8 | B |
| 9 | A |
| 10 | B |
| 11 | B |
| 12 | B |
| 13 | B |
| 14 | A |
| 15 | B |
| 19 | B |
| 20 | B |
| 21 | A |
| 22 | A |
| 23 | B |
| 24 | B |
| 25 | B |
| 26 | C |
| 27 | B |
| 28 | B |
| 29 | A |
| 30 | B |
| 31 | B |
| 32 | A |
| 33 | B |
| 34 | C |
| 35 | A |
| 36 | B |
| 37 | B |
| 38 | A |
| 39 | B |
| 40 | C |
| 41 | A |
| 42 | C |
| 43 | C |
| 44 | A |
| 45 | A |
| 46 | B |
| 47 | A |
| 48 | C |
| 49 | B |
| 50 | B |
| 51 | B |
| 52 | B |
| 53 | B |
| 54 | C |
| 55 | C |
| 56 | C |
| 57 | C |
| 58 | B |
| 59 | A |
| 60 | A |
| 61 | B |
| 62 | C |
| 63 | C |
| 64 | A |
| 65 | A |
| 66 | A |
| 67 | B |
| 68 | C |
| 69 | A |
| 70 | C |
| 71 | NT |
| 72 | C |
| 73 | B |
| 74 | A |
| 75 | A |
| 76 | A |
| 77 | B |
| 78 | A |
| 79 | A |

TABLE B-continued

| # | % viability after treatment with 10 micromolar of test compound (SKOV-3 cells) |
|---|---|
| 80 | A |
| 81 | A |
| 82 | A |
| 83 | A |

Example B: Evaluation of Sensitization of Cancer Cells to Standard of Care Treatment As discussed herein, ML-IAP is upregulated in many tumors and is believed to underlie chemoresistance due to its ability to inhibit apoptosis in cancer cells. In order to assess the role of ML-IAP antagonists in cancer treatment, H460 lung cancer cells are treated with a standard of care treatment (e.g., vinorelbine) alone or in combination with a selective ML-IAP antagonist. Early data suggests that inhibition of ML-IAP should lead to increased sensitivity to chemotherapeutic agents inducing apoptosis. Data presented in FIG. 1 confirm this sensitizing effect in lung cancer cells with the clinically relevant anti-cancer agent vinorelbine (FIG. 1). The leftward shift in the dose dependent response (DDR) curve indicates a resensitization of lung cancer cells to the anti-cancer agent. Furthermore, TNF induction is absent following treatment with a compound described herein in breast cancer MDA-MB-231 cells. This effect provides a substantial advantage clinically as it avoids an inappropriate inflammatory response.

Example C: Fluorescence Polarization (FP) Assays

Compounds of the present disclosure were evaluated for potency and selectivity in a fluorescence polarization (FP) assay that measures inhibition of SMAC peptide binding to ML-IAP. To measure SMAC peptide binding, multi-well plate format FP assays based on the ability of SMAC peptides to bind the BIR domains of several IAPs are used to generate $IC_{50}$ and Ki values for analogues. The FP assays utilize plasmid constructs encoding various full length IAPs or fragments for expression as either GST or His6-fusion proteins in bacteria. Compounds are evaluated for activity against several members of the IAP family, including the BIR domains of XIAP, cIAP1 and cIAP2 in order to generate selectivity profiles of the compounds disclosed herein. These assays also enable the identification and characterization of potency profiles of ML-IAP binding.

The activity of the compounds disclosed herein were tested against XIAP-BIR3 as shown in Table C. Activity of the compounds are indicated according to the following legend:

A=<1 nM B=1-10 nM C=10-100 nM D=32 >100 nM

TABLE C

| Compound # | XIAP-BIR3 Ki [nM] |
|---|---|
| A | C |
| 38 | D |
| 65 | C |
| 80 | C |
| 81 | C |
| 82 | C |

Example D: Cell-Based Assays for ML-IAP Inhibitors & Combination Therapies

Compounds active in the FP assays are tested in several lung cancer cell lines including all those within the NCI 60 panel for community-wide data relevance. Compounds are evaluated for the capacity to induce apoptosis and to sensitize tumor cells to apoptosis induced by lung cancer relevant chemotherapeutic drugs irrespective of mechanism. For example, lung cancer SOC is often platinum-based chemotherapy (e.g. Carboplatin or Cisplatin) and a DNA damaging agent or mitotic tubule inhibitor. Various cancer cell lines are tested with these combinations in the presence and absence of ML-IAP inhibition. These in cellulo recapitulations of clinical regimens yield valuable potency and dosing information relevant to xenograft models.

Candidate compounds are tested in 384-well plates for effects on cell viability in the presence or absence of an appropriate conventional anticancer drug. Cell viability is indirectly monitored in the first instance using CellTiterGlo (Promega Corp., Madison, WI) (Table D). To determine if cell death is apoptotic, the induction of caspase activity is assessed utilizing the CaspaseGlo Assay system (Promega Corp., Madison, WI) (Table E). Cell viability is monitored 1 to 3 days after addition of compounds and conventional drugs. For drug combination studies, a concentration of cytotoxic anticancer drug is chosen that shows only marginal activity. A compound of any of the formulae as disclosed herein is evaluated in combination with said anticancer drug to determine which ML-IAP antagonist can sensitize most efficaciously. Select candidate compounds are tested in 14 point drug dose response (DDR) curves in a 384-well format in order to establish potency in combination with decreasing concentrations of lung cancer relevant drug regimens. Furthermore, checker-board titrations of a conventional drug and the candidate molecules are performed to search for synergy (using ISOBOLOGRAM analysis). Compounds and combinations as described herein are also tested for cytotoxicity against normal human cells (e.g. primary fibroblasts, lymphocytes, hepatocytes, epithelial and endothelial cells) using known methods.

In addition to efficacy testing the compounds described herein with lung cancer SOC chemotherapeutics, potential “off label” agents are also identified that are effective once inhibition of apoptosis is eliminated by a compound as described herein. Multiple lung cancer cells are screened against an Oncology Dose Library (ODL) of 120 FDA-approved anti-cancer and experimental agents alone and in combination with a compound described herein. Hits from this assay are tested in a 14-point drug dose response (DDR) analysis as described previously.

Cell viability was evaluated following treatment with a compound as disclosed in Table D. Viability of cancer cells following treatment is indicated according to the following legend:

A=<1 nM B=1-10 nM C=10-100 nM D=100-1000 nM E=>1000 nM

TABLE D

| Compound # | SKOV-3 $IC_{50}$ [nM] | OVCAR-4 $IC_{50}$ [nM] |
|---|---|---|
| A | B | B |
| 1 | E | E |
| 2 | E | E |
| 9 | D | D |
| 11 | E | E |

TABLE D-continued

| Compound # | SKOV-3 $IC_{50}$ [nM] | OVCAR-4 $IC_{50}$ [nM] |
|---|---|---|
| 14 | D | D |
| 15 | C | E |
| 21 | C | D |
| 29 | E | E |
| 32 | C | E |
| 36 | C | D |
| 38 | C | C |
| 41 | E | E |
| 44 | E | E |
| 45 | D | E |
| 55 | E | E |
| 56 | E | E |
| 65 | C | C |
| 69 | C | D |
| 70 | E | E |
| 74 | C | D |
| 75 | C | C |
| 79 | B | C |
| 80 | A | B |
| 81 | B | C |
| 82 | B | B |

The induction of caspase activities was tested with a compound as disclosed in Table E. The activities are indicated according to the following legend:

A=<1 nM B=1-10 nM C=10-100 nM D=>100 nM

TABLE E

| Compound # | Caspase 3/7 $EC_{50}$ [nM] (SKOV-3) | Caspase 3/7 $EC_{50}$ [nM] (OVCAR-4) | Caspase 9 $EC_{50}$ [nM] (SKOV-3) |
|---|---|---|---|
| A | B | B | A |
| 38 | B | B | B |
| 65 | B | B | B |
| 79 | B | B | B |
| 80 | A | A | A |
| 81 | B | B | B |
| 82 | B | B | B |

Example E: Evaluation of Selectivity for ML-IAP in an Orthogonal Biochemical/Biophysical Assay An isothermal calorimetry (ITC) assay is utilized to probe compound binding to ML-IAP and selectivity against the BIR domains of other IAPs. ITC is the gold standard against which other techniques are compared. ITC, however, is not only able to measure binding affinities but also the magnitude of different thermodynamic forces that determine the binding energy. Since different chemical functionalities contribute differently to the binding forces, the knowledge acquired by ITC also provides precise guidelines for optimization of drug candidates.

Example F: Pharmacokinetic Evaluation Using in vitro Absorption, Distribution, Metabolism, Excretion and Toxicity (ADME/T) and in vivo Pharmacokinetic (PK) Assays In vitro ADME/T and physicochemical profiling assays are employed to optimize the drug-like properties of analogues and to aid in the selection of compounds for further development. Aqueous solubility data are determined at pH 5.0, 6.2 and pH 7.4 with UV detection. Compounds with aqueous solubility>10 μg/mL are selected and advanced for further PK evaluation. Free plasma concentrations are determined using rapid equilibrium dialysis, which is the most quantitative method for determining levels of plasma protein binding. Membrane permeability data are determined using a parallel artificial membrane permeability assay (PAMPA). This in vitro method assesses the passive diffusion of compounds across a layer of specialized mixtures of phospholipids that mimic (a) the gut epithelium, and (b) brain capillary endothelial cells, the primary barrier to absorption into the brain.

Metabolic stability in human, mouse, and rat microsomes are also used to evaluate compounds described herein for drug-like properties. For microsomal assays, compounds are incubated in the presence of 1 mg/mL microsomes; the metabolites are quantitated using LC/MS methods. Cytochrome P450 (CYP450) isoform (CYP1A2, 2C9, 2D6, and 3A4) inhibition is determined in human liver microsomes. Inhibition of product formation for compound substrates is detected by luminescence using the isoform specific P450-glo assay (Promega, Madison, WI) over 10 concentrations of inhibitor and assessed at one time point (previously determined to be in the linear range for time and protein concentration). The $IC_{50}$ is analyzed by a four parameter logistic fit. Appropriate positive control inhibitors are used for each enzyme. Mechanism-based inhibition will be investigated where warranted using the established method.

Pharmacokinetic (PK) studies are performed in vivo in mice for compounds as described herein. Standard formulations are evaluated, including hydroxypropyl methylcellulose, carboxymethylcellulose, and polyethylene glycol. For intravenous studies, compounds are administered via indwelling catheters in jugular vein and samples collected from the carotid artery. These experiments provide basic pharmacokinetic parameters including peak plasma concentration (Cmax), bioavailability (% F), exposure (AUC), half-life (t½), clearance (CL), volume of distribution (Vd), and brain levels. To measure bioavailability, a compound as described herein is administered to three animals/group, both orally (10 mg/kg) and intravenously (1 mg/kg). Intraperitoneally administration is also assessed in order to determine both brain and plasma levels of compounds.

The compounds described herein were tested in vivo in mice to measure PK plasma exposure as shown in Table F. The PK plasma values are indicated according to the following legend:

i=<100 nM ii=100-500 nM iii=500-1000 nM iv=>1000 nM

TABLE F

| Compound # | PK plasma exposure at 1 h (IP, 10 mg/kg) |
|---|---|
| A | iii |
| 38 | iii |
| 65 | iii |
| 79 | iii |
| 80 | iii |
| 81 | iii |
| 82 | iv |

Example G1: Evaluation of Efficacy in Relevant Mouse Tumorigenic (Xenograft) Models of Lung Cancer A compound as described herein is tested in mouse xenograft models of lung cancer to determine in vivo efficacy. A suitable lung cancer cell line as well as a potent apoptosis inducing agent exhibiting synergy with the compounds described herein is used for a first-pass xenograft study to determine appropriate dosing ranges in vivo. The dosing parameters are applied to a parallel xenograft study utilizing a suitable patient-derived lung cancer sample (Mayo Clinic, Rochester, MN).

A dosing regimen is selected that will maintain inhibition of ML-IAP in tumor cells by using two approaches: immunoblotting for SMAC levels, which are modulated through the E3 ligase activity of ML-IAP and measurement of activation of the apoptotic pathway through an apoptosis specific assay. This method enables one to (a) determine the compound levels in blood that correlates with inhibition of ML-IAP in tumors, as well as (b) determine what level of inhibition is required for a significant reduction of tumor growth in vivo. Compounds are tested in mice bearing xenografts of lung cancer cells as described above. Tumor xenografts are established in a group of 16 nude mice [4 test groups of 4 animals: (Group 1) Control; (Groups 2-4) ML-IAP antagonist at three dosing ranges ($IC_{50}$, 10× $IC_{50}$ and maximum tolerated dose, respectively) based on PK data obtained as described previously]. The NCI60 panel viability data suggests that no significant single agent toxicity is to be expected, however a more detailed assessment is prudent and necessary. Studies are initiated when tumors grow to approximately 0.25 $mm^3$, a size that is visible on the flank, but small enough so that the tumor does not contain a substantial necrotic core. The time point of the blood draw is based on the data from ADME/T and PK assays as described previously. Compound levels in the tumor are determined after final dosing and the animals are sacrificed.

Example G2: Evaluation of Efficacy in Relevant Mouse Tumorigenic (Xenograft) Models of Ovarian Cancer A compound as described herein is tested in mouse xenograft models of ovarian cancer to determine in vivo efficacy. A suitable ovarian cancer cell line as well as a potent apoptosis inducing agent exhibiting synergy with the compounds described herein is used for a first-pass xenograft study to determine appropriate dosing ranges in vivo. The dosing parameters are applied to a parallel xenograft study utilizing a suitable patient-derived ovarian cancer sample.

A dosing regimen is selected that will maintain inhibition of ML-IAP in tumor cells by using two approaches: immunoblotting for SMAC levels, which are modulated through the E3 ligase activity of ML-IAP and measurement of activation of the apoptotic pathway through an apoptosis specific assay. This method enables one to (a) determine the compound levels in blood that correlates with inhibition of ML-IAP in tumors, as well as (b) determine what level of inhibition is required for a significant reduction of tumor growth in vivo. Compounds are tested in mice bearing xenografts of ovarian cancer cells as described above. Tumor xenografts are established in a group of 16 nude mice [4 test groups of 4 animals: (Group 1) Control; (Groups 2-4) ML-IAP antagonist at three dosing ranges ($IC_{50}$, 10× $IC_{50}$ and maximum tolerated dose, respectively) based on PK data obtained as described previously]. The NCI60 panel viability data suggests that no significant single agent toxicity is to be expected, however a more detailed assessment is prudent and necessary. Studies are initiated when tumors grow to approximately 0.25 $mm^3$, a size that is visible on the flank, but small enough so that the tumor does not contain a substantial necrotic core. The time point of the blood draw is based on the data from ADME/T and PK assays as described previously. Compound levels in the tumor are determined after final dosing and the animals are sacrificed.

Example G3: Evaluation of Efficacy in Relevant Mouse Tumorigenic (Xenograft) Models of Triple-Negative Breast Cancer A compound as described herein is tested in mouse xenograft models of triple-negative breast cancer to determine in vivo efficacy. A suitable triple-negative breast cancer cell line as well as a potent apoptosis inducing agent exhibiting synergy with the compounds described herein is used for a first-pass xenograft study to determine appropriate dosing ranges in vivo. The dosing parameters are applied to a parallel xenograft study utilizing a suitable patient-derived triple-negative breast cancer sample.

A dosing regimen is selected that will maintain inhibition of ML-IAP in tumor cells by using two approaches: immunoblotting for SMAC levels, which are modulated through the E3 ligase activity of ML-IAP and measurement of activation of the apoptotic pathway through an apoptosis specific assay. This method enables one to (a) determine the compound levels in blood that correlates with inhibition of ML-IAP in tumors, as well as (b) determine what level of inhibition is required for a significant reduction of tumor growth in vivo. Compounds are tested in mice bearing xenografts of triple-negative breast cancer cells as described above. Tumor xenografts are established in a group of 16 nude mice [4 test groups of 4 animals: (Group 1) Control; (Groups 2-4) ML-IAP antagonist at three dosing ranges ($IC_{50}$, 10× $IC_{50}$ and maximum tolerated dose, respectively) based on PK data obtained as described previously]. The NCI60 panel viability data suggests that no significant single agent toxicity is to be expected, however a more detailed assessment is prudent and necessary. Studies are initiated when tumors grow to approximately 0.25 $mm^3$, a size that is visible on the flank, but small enough so that the tumor does not contain a substantial necrotic core. The time point of the blood draw is based on the data from ADME/T and PK assays as described previously. Compound levels in the tumor are determined after final dosing and the animals are sacrificed.

Example H: Assessing Levels of Apoptosis

Four mice are used per dose for analysis by the TUNEL assay and immunoblotting for SMAC as well as ML-IAP levels. Animals are sacrificed 12 hours after treatment and the tumor resected on ice. The TUNEL assay is regarded as the "gold standard" in apoptosis detection and is performed as described in the scientific literature. Utilization of the TUNEL assay is well established for the determination of apoptosis levels in tissues. Resected tumor tissue is analyzed and the observed level of induction of apoptosis is correlated to SMAC levels and a reduction in tumor growth.

Example I: Quantifying SMAC Levels in Tumor Xenografts

The homogenate is further lysed with detergent and analyzed by SDS-PAGE/Western-blotting, allowing visualization of SMAC levels in the tumor tissue. This analysis shows at what level the inhibition of ML-IAP in vivo exhibits a pronounced effect on SMAC degradation through ubiquitination by the E3 ligase domain of ML-IAP.

Example J: Monitoring Potential Toxicities

The collected blood samples are further analyzed for levels of the liver enzymes alanine transaminase (ALT) and aspartate transaminase (AST) as a preliminary assessment of possible liver damage; levels are identified and compared to the control group utilizing ELISA based assays.

Example K1: Evaluation of Efficacy in Xenograft Models of Human Lung Cancer

The antitumor effects of selected compounds described herein are measured in orthotopic xenograft models using human lung cancer cell lines as well as a suitable patient-derived lung cancer sample. The study has four arms: control, test compound alone, treatment with a SOC therapy, and the combination of test compound and SOC therapy. Furthermore, two arms are used for the patient-derived xenograft (PDX) study, one arm for control and one arm with the physician recommended SOC for the original tumor. Power calculations are performed based on published results on xenograft growth for comparable lung cancer lines, which indicate that a group size of 8 animals is required to provide a robust statistical chance of detecting a reduction in tumor growth of 60%. Due to variance known to exist in in vivo studies, 10 animals are initially included in each arm. Animals are randomly divided into each cohort representing one study arm. Lung cancer cells (1×106) are injected into the dorsal region of BALB/c athymic nude mice. Tumors are allowed to grow to a size of approximately 100 $mm^3$ (which is a point just after which they are palpable) before the combination treatment is initiated. This ensures that the tumor has begun to grow in all animals that will be administered compound, and also reduces the statistical variability in measuring tumor growth. Moreover, by initiating dosing after substantial tumor growth in vivo, this better mimics the human clinical condition and aids in the assessment of tumor regression with statistical certainty. Each animal is treated with test compound or vehicle for approximately 2-3 weeks, at which time untreated xenografts typically grow to a size of 200 to 300 $mm^3$. Tumor volumes are measured three times a week at orthogonal angles to calculate tumor volumes, which are then used to calculate tumor-doubling time. Differences in tumor growth are considered significant if a p-value of less than 0.05 is observed with Students' t-test between test and control groups.

To monitor compound levels, blood samples are drawn once each week on half of the cohort (4-5 animals per group) at an appropriate time after dosing; blood levels are assessed during the treatment period. To detect toxicity (e.g., liver toxicity) related to the testing regimen, the collected blood samples are analyzed for ALT and AST levels as a preliminary assessment of possible liver damage. Levels identified are compared to the control group utilizing ELISA based assays.

Example K2: Evaluation of Efficacy in Xenograft Models of Human Ovarian Cancer

The antitumor effects of selected compounds described herein are measured in orthotopic xenograft models using human ovarian cancer cell lines as well as a suitable patient-derived ovarian cancer sample. The study has four arms: control, test compound alone, treatment with a SOC therapy, and the combination of test compound and SOC therapy. Furthermore, two arms are used for the patient-derived xenograft (PDX) study, one arm for control and one arm with the physician recommended SOC for the original tumor. Power calculations are performed based on published results on xenograft growth for comparable ovarian cancer lines, which indicate that a group size of 8 animals is required to provide a robust statistical chance of detecting a reduction in tumor growth of 60%. Due to variance known to exist in in vivo studies, 10 animals are initially included in each arm. Animals are randomly divided into each cohort representing one study arm. Ovarian cancer cells (1×106) are injected into the dorsal region of BALB/c athymic nude mice. Tumors are allowed to grow to a size of approximately 100 $mm^3$ (which is a point just after which they are palpable) before the combination treatment is initiated. This ensures that the tumor has begun to grow in all animals that will be administered compound, and also reduces the statistical variability in measuring tumor growth. Moreover, by initiating dosing after substantial tumor growth in vivo, this better mimics the human clinical condition and aids in the assessment of tumor regression with statistical certainty. Each animal is treated with test compound or vehicle for approximately 2-3 weeks, at which time untreated xenografts typically grow to a size of 200 to 300 $mm^3$. Tumor volumes are measured three times a week at orthogonal angles to calculate tumor volumes, which are then used to calculate tumor-doubling time. Differences in tumor growth are considered significant if a p-value of less than 0.05 is observed with Students' t-test between test and control groups.

To monitor compound levels, blood samples are drawn once each week on half of the cohort (4-5 animals per group) at an appropriate time after dosing; blood levels are assessed during the treatment period. To detect toxicity (e.g., liver toxicity) related to the testing regimen, the collected blood samples are analyzed for ALT and AST levels as a preliminary assessment of possible liver damage. Levels identified are compared to the control group utilizing ELISA based assays.

Example K3: Evaluation of Efficacy in Xenograft Models of Human Triple-Negative Breast Cancer The antitumor effects of selected compounds described herein are measured in orthotopic xenograft models using human triple-negative breast cancer cell lines as well as a suitable patient-derived triple-negative breast cancer sample. The study has four arms: control, test compound alone, treatment with a SOC therapy, and the combination of test compound and SOC therapy. Furthermore, two arms are used for the patient-derived xenograft (PDX) study, one arm for control and one arm with the physician recommended SOC for the original tumor. Power calculations are performed based on published results on xenograft growth for comparable triple-negative breast cancer lines, which indicate that a group size of 8 animals is required to provide a robust statistical chance of detecting a reduction in tumor growth of 60%. Due to variance known to exist in in vivo studies, 10 animals are initially included in each arm. Animals are randomly divided into each cohort representing one study arm. Triple-negative breast cancer cells (1×106) are injected into the dorsal region of BALB/c athymic nude mice. Tumors are allowed to grow to a size of approximately 100 $mm^3$ (which is a point just after which they are palpable) before the combination treatment is initiated. This ensures that the tumor has begun to grow in all animals that will be administered compound, and also reduces the statistical variability in measuring tumor growth. Moreover, by initiating dosing after substantial tumor growth in vivo, this better mimics the human clinical condition and aids in the assessment of tumor regression with statistical certainty. Each animal is treated with test compound or vehicle for approximately 2-3 weeks, at which time untreated xenografts typically grow to a size of 200 to 300 $mm^3$. Tumor volumes are measured three times a week at orthogonal angles to calculate tumor volumes, which are then used to calculate tumor-doubling time. Differences in tumor growth are considered significant if a p-value of less than 0.05 is observed with Students' t-test between test and control groups.

To monitor compound levels, blood samples are drawn once each week on half of the cohort (4-5 animals per group) at an appropriate time after dosing; blood levels are assessed during the treatment period. To detect toxicity (e.g., liver toxicity) related to the testing regimen, the collected blood samples are analyzed for ALT and AST levels as a preliminary assessment of possible liver damage. Levels identified are compared to the control group utilizing ELISA based assays.

Example L Validation of ML-IAP as a Target

Figure 2:
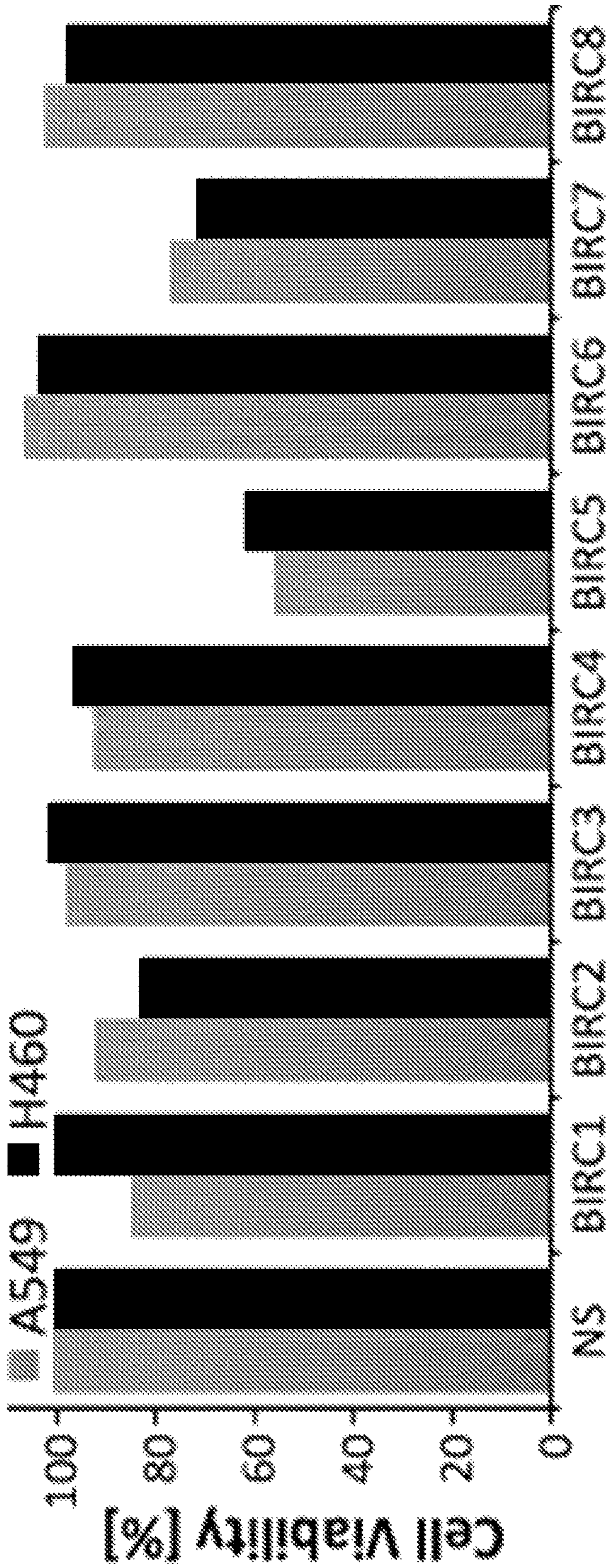
FIG. 2 illustrates the effects of gene ablation on cancer cell viability.

Several studies have presented evidence suggesting ML-IAP may be a viable target for combatting various forms of cancer. In an example, one such study found that siRNAs that ablate ML-IAP expression results in potent anti-tumor activity in models of human lung cancer. These findings are confirmed herein with a separate gene ablation study, wherein each member of the BIRC family is evaluated for its effects on cell viability of lung cancer cells. Ablation of expression of BIRC7, the gene for ML-IAP, shows a pronounced effect on cell viability of adenocarcinoma (A549) and non-small cell lung cancer (H460) cells (FIG. 2). Knock-down of BIRC1-4, BIRC6 or BIRC8 offers little to no impact on cell viability. BIRC5 (also known as survivin) shows a significant impact on cancer cell viability as well. However, in contrast to ML-IAP, survivin continues to play a physiological role even after development, making it a liability as a therapeutic target. These data show ML-IAP is a viable target in lung cancer cells and due to its lower liability compared to a similarly effective IAP (survivin), ML-IAP is validated as a therapeutic target in the treatment of cancer.

Example M: IAP Antagonists Reverses HIV-1 Latency

Figure 3:
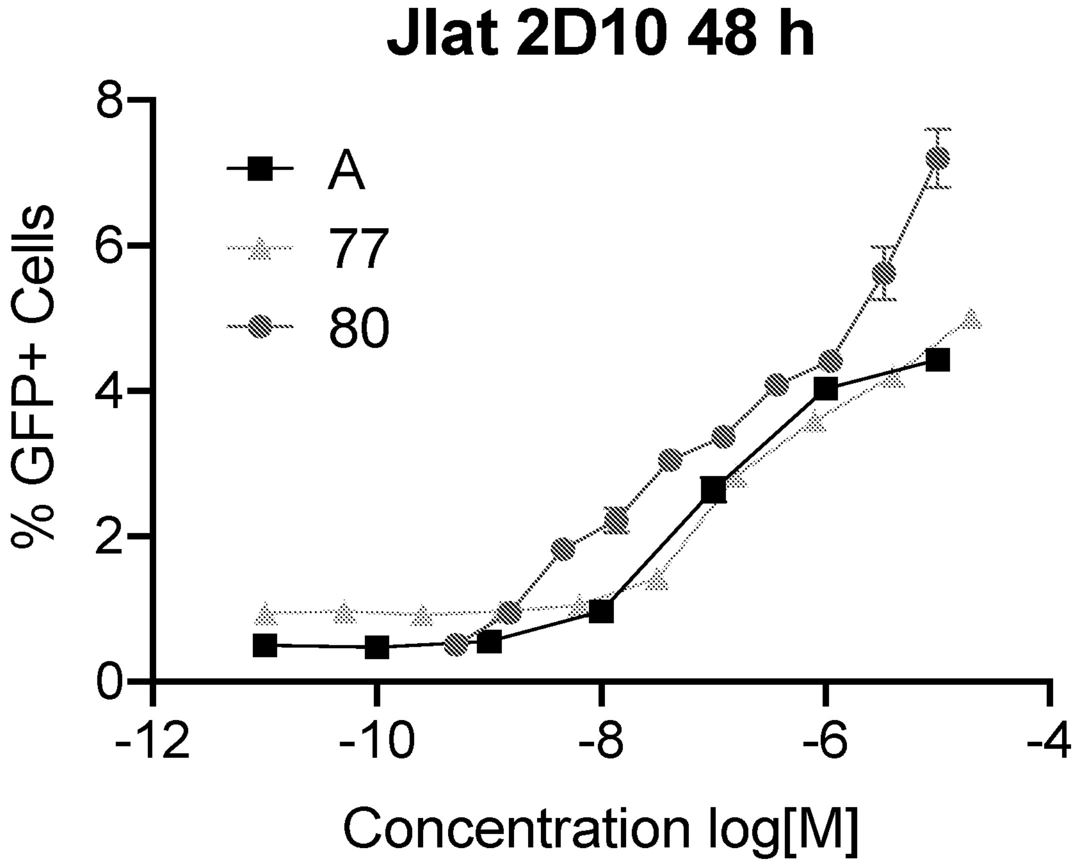
FIG. 3 illustrates IAP antagonists effect on reversing HIV-1 latency.

It has previously been demonstrated that latency reversal of HIV-1 can be promoted in in vitro and ex vivo systems through pharmacological manipulation of the non-canonical NF-kB pathway using the Smac mimetic compounds. SMAC mimetics modestly induced HIV-1 latency ex vivo in CD4+ T cells from ART-suppressed aviremic HIV-infected patients as a single agent. The activities of IAP antagonists in the latency infected Jurkat cell line 2D10 was examined (FIG. 3). Compounds for dose response assays, adjusted for equal DMSO concentrations, were spotted in 384-well plates and 2D10 cells were added to each well. After 48 h, GFP expression was analyzed. Latency reversal was assessed by measuring GFP expression by flow cytometry.

While preferred embodiments of the present technology have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound or pharmaceutically acceptable salt thereof, having the structure of Formula (A-III):

Formula (A-III)

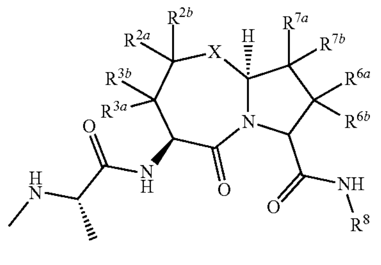

wherein,

X is $NR^A$, O, S, S(O), or $S(O)_2$;

$R^A$ is hydrogen;

$R^{2a}$, $R^{2b}$, $R^{3a}$, and $R^{3b}$ are each hydrogen;

$R^{6a}$ is —U;

$R^{6b}$ is —U;

—U is $C_1$-$C_6$alkyl;

or $R^{6a}$ and $R^{6b}$ together with the carbon atom to which they are attached form a saturated or partially saturated 3- to 7-membered cycloalkyl or a saturated or partially saturated 3- to 7-membered heterocycloalkyl;

$R^{7a}$ is hydrogen;

$R^{7b}$ is hydrogen;

$R^8$ is Z, $CH(Z)_2$, $CH_2CH(Z)_2$, $CH(C_1$-$C_6alkyl)Z$, or C(O)Z; and

Z is $C_3$-$C_{10}$cycloalkyl, 3- to 10-membered heterocycloalkyl, $C_6$-$C_{10}$aryl, or 5- to 10-membered heteroaryl; wherein each Z is optionally substituted with 1, 2, or 3 $C_1$-$C_4$alkyl, $C_1$-$C_4$haloalkyl, $C_1$-$C_4$alkoxy, $C_1$-$C_4$haloalkoxy, or 5- to 10-membered heteroaryl provided that when $R^{6a}$ and Rob are both $CH_3$ or when $R^{6a}$ and $R^{6b}$ together with the carbon atom to which they are attached form an unsubstituted cyclopentyl or unsubstituted cyclopentenyl, then $R^8$ is not

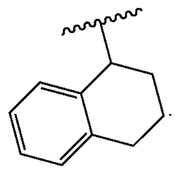 [SMILES: *C1CCCc2ccccc21]

2. The compound of claim 1, wherein X is O.

3. The compound of claim 1, wherein X is S or $S(O)_2$.

4. The compound of claim 1, wherein X is S.

5. The compound of claim 1, wherein X is $S(O)_2$.

6. The compound of claim 1, wherein X is $NR^A$.

7. The compound of claim 1, having the structure of Formula (A-IV-a), (A-IV-b), or (A-IV-c):

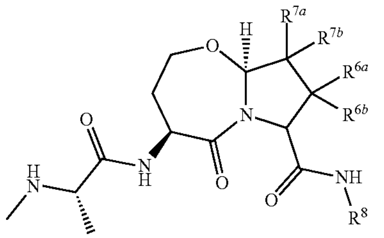

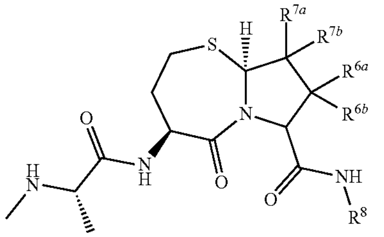

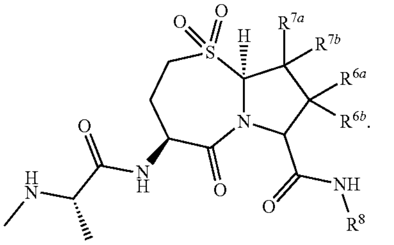

8. The compound of claim 1, wherein $R^{6a}$ and $R^{6b}$ together with the carbon atom to which they are attached form a saturated or partially saturated 3- to 7-membered cycloalkyl ring.

9. The compound of claim 8, wherein $R^{6a}$ and $R^{6b}$ together with the carbon atom to which they are attached form a saturated or partially saturated 3- to 5-membered cycloalkyl ring.

10. The compound of claim 1, wherein $R^{6b}$ is methyl, ethyl, 2-propenyl, or isopropyl.

11. The compound of claim 1, wherein $R^{6b}$ is methyl.

12. The compound of claim 1, wherein $R^{6a}$ and Rob are methyl.

13. The compound of claim 1, wherein $R^8$ is Z or $CH(Z)_2$.

14. The compound of claim 1, wherein $R^8$ is Z.

15. The compound of claim 1, wherein Z is $C_3$-$C_{10}$cycloalkyl or 3- to 10-membered heterocycloalkyl.

16. The compound of claim 1, wherein Z is $C_3$-$C_{10}$cycloalkyl.

17. The compound of claim 1, wherein $R^8$ is:

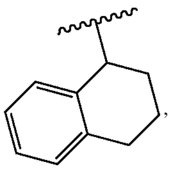,
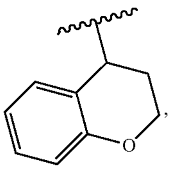,
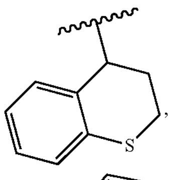,
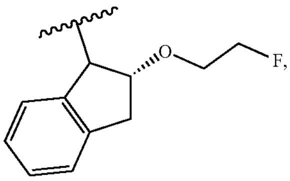, or
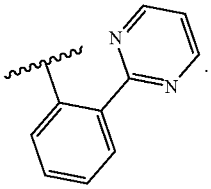.

18. A compound or pharmaceutically acceptable salt thereof, having the structure:

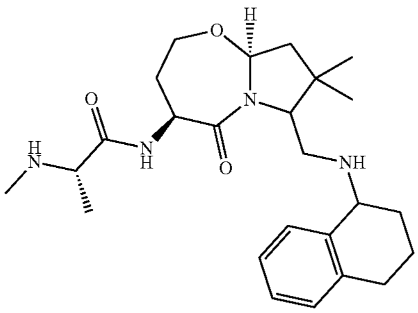,

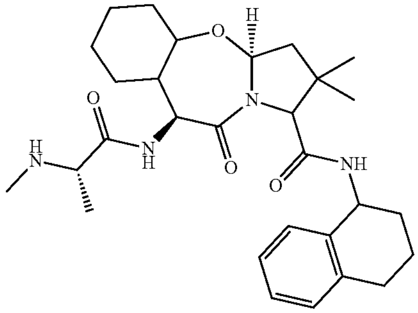,

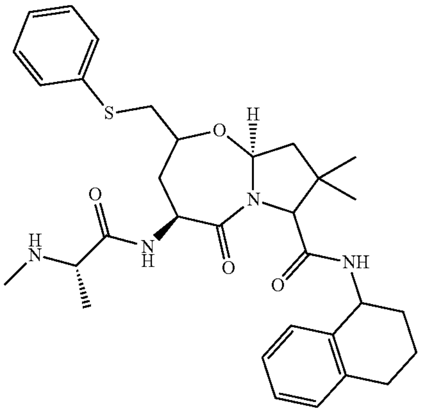,

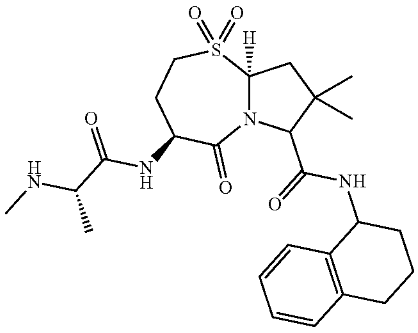,

-continued

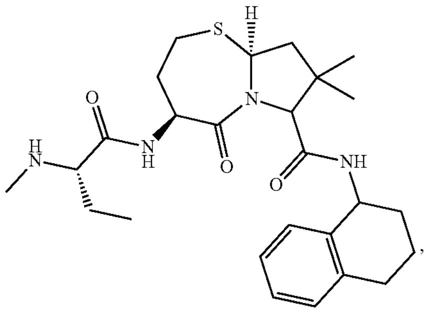

,

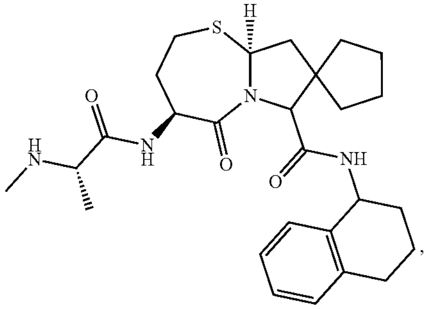

,

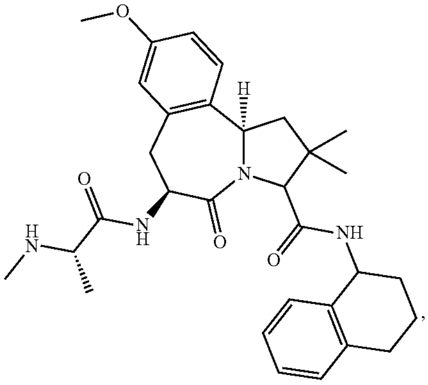

,

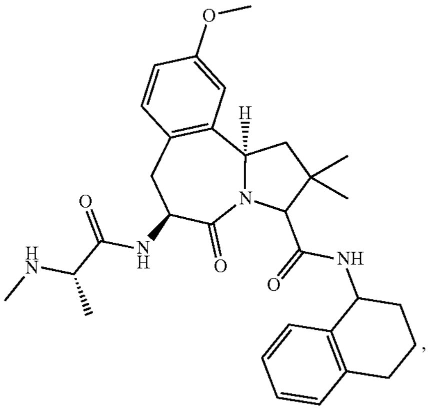

,

-continued

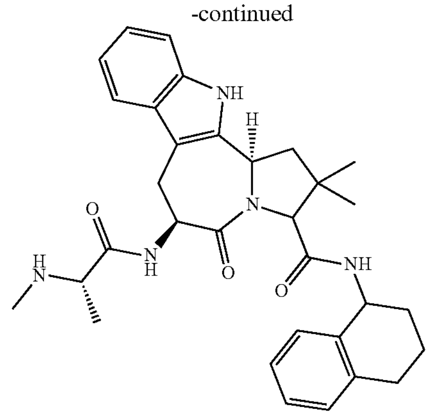

or

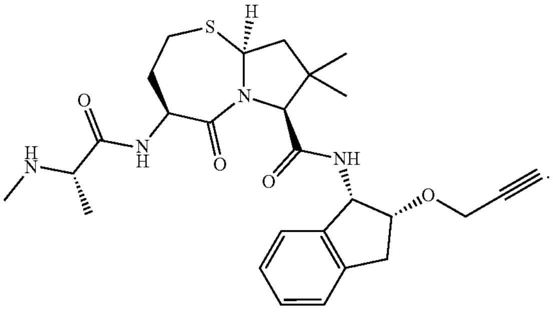

.

19. A pharmaceutical composition comprising a compound of claim 1, or pharmaceutically acceptable salt thereof, and a pharmaceutically acceptable carrier.

20. A method of treating cancer in an individual in need thereof comprising administering a therapeutically effective amount of a compound of claim 1, or pharmaceutically acceptable salt thereof, to the individual.

21. The compound of claim 18, having the structure:

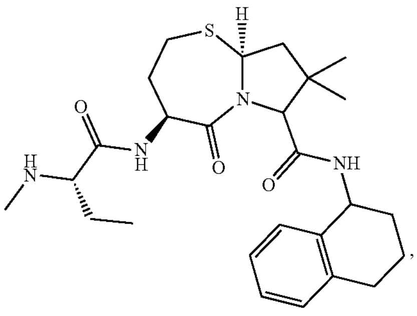 [SMILES: CC[C@H](NC)C(=O)N[C@H]1CCS[C@H]2CC(C)(C)C(C(=O)NC3CCCc4ccccc43)N2C1=O]

, or pharmaceutically acceptable salt thereof.

22. The compound of claim 18, having the structure:
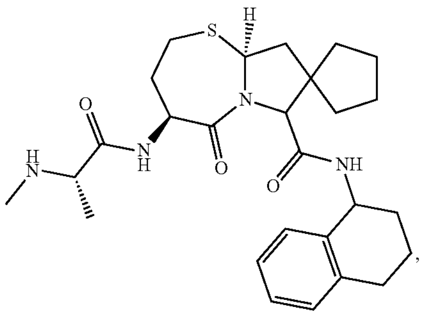 [SMILES: CN[C@@H](C)C(=O)N[C@H]1CCS[C@H]2CC3(CCCC3)C(C(=O)NC3CCCc4ccccc43)N2C1=O]
or pharmaceutically acceptable salt thereof.
* * * * *